(12) United States Patent
Seymour et al.

(10) Patent No.: US 10,610,606 B2
(45) Date of Patent: Apr. 7, 2020

(54) ADENO-ASSOCIATED VIRUS COMPOSITIONS FOR PAH GENE TRANSFER AND METHODS OF USE THEREOF

(71) Applicant: HOMOLOGY MEDICINES, INC., Bedford, MA (US)

(72) Inventors: Albert Barnes Seymour, Westborough, MA (US); Seemin Seher Ahmed, Worcester, MA (US); Jason Boke Wright, Concord, MA (US); Serena Nicole Dollive, Waltham, MA (US); Hillard Rubin, Northborough, MA (US)

(73) Assignee: HOMOLOGY MEDICINES, INC., Bedford, MA (US)

( * ) Notice: Subject to any disclaimer, the term of this patent is extended or adjusted under 35 U.S.C. 154(b) by 0 days.

(21) Appl. No.: 16/369,879

(22) Filed: Mar. 29, 2019

(65) Prior Publication Data

US 2019/0231901 A1 Aug. 1, 2019

Related U.S. Application Data

(63) Continuation of application No. PCT/US2019/016351, filed on Feb. 1, 2019.

(60) Provisional application No. 62/625,150, filed on Feb. 1, 2018.

(51) Int. Cl.
| | |
|---|---|
| *A61K 48/00* | (2006.01) |
| *C12N 15/864* | (2006.01) |
| *C12N 7/01* | (2006.01) |
| *C07K 14/015* | (2006.01) |
| *C12N 15/86* | (2006.01) |

(52) U.S. Cl.
CPC .......... *A61K 48/0066* (2013.01); *C12N 15/86* (2013.01); *C12N 2750/14143* (2013.01); *C12N 2750/14152* (2013.01); *C12N 2750/14171* (2013.01); *C12N 2830/32* (2013.01)

(58) Field of Classification Search
None
See application file for complete search history.

(56) References Cited

U.S. PATENT DOCUMENTS

| | | | |
|---|---|---|---|
| 5,252,479 A | 10/1993 | Srivastava | |
| 5,474,935 A | 12/1995 | Chatterjee et al. | |
| 5,589,377 A | 12/1996 | Lebkowski et al. | |
| 5,622,856 A | 4/1997 | Natsoulis | |
| 5,650,309 A | 7/1997 | Wong-Staal et al. | |
| 5,753,500 A | 5/1998 | Shenk et al. | |
| 5,780,447 A | 7/1998 | Nienhuis | |
| 5,895,759 A | 4/1999 | Strauss et al. | |
| 6,025,195 A | 2/2000 | Sandig et al. | |
| 6,153,436 A | 11/2000 | Hermonat et al. | |
| 6,156,303 A | 12/2000 | Russell et al. | |
| 6,180,613 B1 | 1/2001 | Kaplitt et al. | |
| 6,238,914 B1 | 5/2001 | Boyce | |
| 6,268,212 B1 | 7/2001 | Simonet | |
| 6,329,181 B1 | 12/2001 | Xiao et al. | |
| 6,338,962 B1 | 1/2002 | Boyce | |
| 6,387,670 B1 | 5/2002 | Leblois-Prehaud et al. | |
| 6,610,906 B1 | 8/2003 | Kurachi et al. | |
| 6,759,237 B1 | 7/2004 | Wilson et al. | |
| 6,919,209 B1 | 7/2005 | Chatterjee et al. | |
| 6,924,128 B2 | 8/2005 | Allen | |
| 6,936,243 B2 | 8/2005 | Snyder et al. | |
| 6,936,466 B2 | 8/2005 | Feldhaus | |
| 6,953,690 B1 | 10/2005 | Gao et al. | |
| 6,984,517 B1 | 1/2006 | Chiorini et al. | |
| 7,001,764 B2 | 2/2006 | Little et al. | |
| 7,022,519 B2 | 4/2006 | Gao et al. | |
| 7,056,502 B2 | 6/2006 | Hildinger et al. | |
| 7,091,029 B2 | 8/2006 | Hwang | |
| 7,094,604 B2 | 8/2006 | Snyder et al. | |
| 7,148,341 B2 | 12/2006 | Kleinschmidt et al. | |
| 7,157,571 B2 | 1/2007 | Wang et al. | |
| 7,172,893 B2 | 2/2007 | Rabinowitz et al. | |
| 7,179,903 B2 | 2/2007 | McArthur et al. | |
| 7,198,951 B2 | 4/2007 | Gao et al. | |
| 7,220,577 B2 | 5/2007 | Zolotukhin | |
| 7,235,393 B2 | 6/2007 | Gao et al. | |
| 7,259,151 B2 | 8/2007 | Arbetman et al. | |
| 7,282,199 B2 | 10/2007 | Gao et al. | |
| 7,351,813 B2 | 4/2008 | Miao et al. | |
| 7,465,583 B2 | 12/2008 | Sumulski et al. | |

(Continued)

FOREIGN PATENT DOCUMENTS

| | | |
|---|---|---|
| EP | 126544 A2 | 11/1984 |
| EP | 161788 A1 | 11/1985 |

(Continued)

OTHER PUBLICATIONS

Lochrie et al, Mutations on the External Surfaces of Adeno-Associated Virus Type 2 Capsids That Affect Transduction and Neutralization, J Vi, 2006, pp. 821-834.*

(Continued)

*Primary Examiner* — Maria Marvich
(74) *Attorney, Agent, or Firm* — Lathrop GPM LLP; Andrew T. Wilkins

(57) ABSTRACT

Provided herein are adeno-associated virus (AAV) compositions that can express a phenylalanine hydroxylase (PAH) polypeptide in a cell, thereby restoring the PAH gene function. Also provided are methods of use of the AAV compositions, and packaging systems for making the AAV compositions.

35 Claims, 23 Drawing Sheets

Specification includes a Sequence Listing.

(56) References Cited

U.S. PATENT DOCUMENTS

| | | |
|---|---|---|
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Engelhardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,617,548 B2 | 4/2017 | Chuah et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 2003/0129203 A1 | 7/2003 | Vega et al. |
| 2003/0130221 A1 | 7/2003 | High et al. |
| 2004/0086485 A1 | 5/2004 | Aguilar-Cordova et al. |
| 2004/0235174 A1 | 11/2004 | Grimm et al. |
| 2005/0112765 A1 | 5/2005 | Li et al. |
| 2009/0191597 A1 | 7/2009 | Sumulski et al. |
| 2009/0215879 A1 | 8/2009 | Diprimio et al. |
| 2010/0297084 A1 | 11/2010 | Bennett et al. |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0189225 A1 | 7/2013 | Voit et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0336245 A1 | 11/2014 | Mingozzi et al. |
| 2014/0359799 A1 | 12/2014 | Wang et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0238550 A1 | 8/2015 | McCown et al. |
| 2015/0315610 A1 | 11/2015 | Nishe et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0096182 A1* | 4/2016 | Storm .................. B02C 23/04 241/31 |
| 2016/0123990 A1 | 5/2016 | High et al. |
| 2016/0175365 A1 | 6/2016 | Golden |
| 2016/0229904 A1 | 8/2016 | Xiao et al. |
| 2017/0119906 A1 | 5/2017 | Riley |
| 2017/0326256 A1 | 11/2017 | Doering et al. |

FOREIGN PATENT DOCUMENTS

| | | |
|---|---|---|
| EP | 1497436 B1 | 1/2005 |
| WO | WO 1996/008560 A1 | 3/1996 |
| WO | WO 1998/009524 A1 | 3/1998 |
| WO | WO 1998/021349 A1 | 5/1998 |
| WO | WO 1998/027207 A1 | 6/1998 |
| WO | WO 1998/028417 A1 | 7/1998 |
| WO | WO 1999/003981 A1 | 1/1999 |
| WO | WO 1999018227 A1 | 4/1999 |
| WO | WO 1999/055564 A1 | 11/1999 |
| WO | WO 1999/064569 A1 | 12/1999 |
| WO | WO 2000/049160 A1 | 8/2000 |
| WO | WO 2001/036620 A2 | 5/2001 |
| WO | WO 2002/066611 A2 | 8/2002 |
| WO | WO 2003/087383 A1 | 10/2003 |
| WO | WO 2003/093436 A2 | 11/2003 |
| WO | WO 2005/111220 A2 | 11/2005 |
| WO | WO 2006/096815 A2 | 9/2006 |
| WO | WO 2007/019646 A1 | 2/2007 |
| WO | WO 2008/021140 A2 | 2/2008 |
| WO | WO 2009/000552 A2 | 12/2008 |
| WO | WO 2009/043936 A1 | 4/2009 |
| WO | WO 2009/130208 A1 | 10/2009 |
| WO | WO 2009/134681 A2 | 11/2009 |
| WO | WO 2010/124180 A1 | 10/2010 |
| WO | WO 2010/129021 A1 | 11/2010 |
| WO | WO 2011/012724 A1 | 2/2011 |
| WO | WO 2011038187 A1 | 3/2011 |
| WO | WO 2014/064277 A1 | 5/2014 |
| WO | WO 2014/089212 A1 | 6/2014 |
| WO | WO 2014/193716 A2 | 12/2014 |
| WO | WO 2015/061491 A1 | 4/2015 |
| WO | WO 2015/143177 A1 | 9/2015 |
| WO | WO 2015/164723 A1 | 10/2015 |
| WO | WO 2016/097218 A1 | 6/2016 |
| WO | WO 2016/097219 A1 | 6/2016 |
| WO | WO 2016/100575 A1 | 6/2016 |
| WO | WO 2016/146757 A1 | 9/2016 |
| WO | WO 2017/015154 A1 | 1/2017 |
| WO | WO 2017/100551 A1 | 6/2017 |
| WO | WO 2018/046737 A1 | 3/2018 |
| WO | WO 2018/126112 A1 | 7/2018 |
| WO | WO 2018/126116 A1 | 7/2018 |
| WO | WO 2018/129586 A1 | 7/2018 |
| WO | WO 2019/010091 A1 | 1/2019 |

OTHER PUBLICATIONS

Di Mattia et al, Structural Insight into the Unique Properties of Adeno-Associated Vims Serotype 9, JVi, 2012, pp. 6947-6958.*

Xie et al, Towards the atomic structure of tge Adeno-Assocaited Virus 2 capsid, IDR, 2000, p. 136.*

Adachi et al, Drawing a high-resolution functional map of adeno-associated virus capsid by massively parallel sequencing, Nature Communications, 2014, pp. 1-14.*

Lee et al, Adeno-Associated Virus (AAV) Vectors: Rational Design Strategies for Capsid Engineering, Curr Opin Biomed Eng. Sep. 2018 ; 7: 58-63.*

Hacein-Bey-Abina et al. (2008) "Insertional oncogenesis in 4 patients after retrovirus-mediated gene therapy of SCID-X1 ," J Clin Invest. 118(9):3132-42.

Kramer et al. (2003) "In vitro and in vivo comparative study of chimeric liver-specific promoters," Mol Therapy. 7:375-385.

Lu et al. (2013) "A mini-intronic plasmid (MIP): a novel robust transgene expression vector in vivo and in vitro," Mol Ther. 21(5):954-63.

Lu et al. (2017) "A 5' Noncoding Exon Containing Engineered Intron Enhances Transgene Expression from Recombinant AAV Vectors in vivo," Hum Gene Ther. 28(1):125-134.

(56) References Cited

OTHER PUBLICATIONS

Savy et al. (2017) "Impact of Inverted Terminal Repeat Integrity on rAAV8 Production Using the Baculovirus/Sf9 Cells System," Human Gene Therapy Methods. 28(5):277-289.
Sibley et al. (2016) "Lessons from non-canonical splicing," Nat Rev Gen. 17:407-21.
Yagi et al. (2011) "Complete restoration of phenylalanine oxidation in phenylketonuria mouse by a self-complementary adeno-associated virus vector," J Gene Med. 13:114-122.

\* cited by examiner

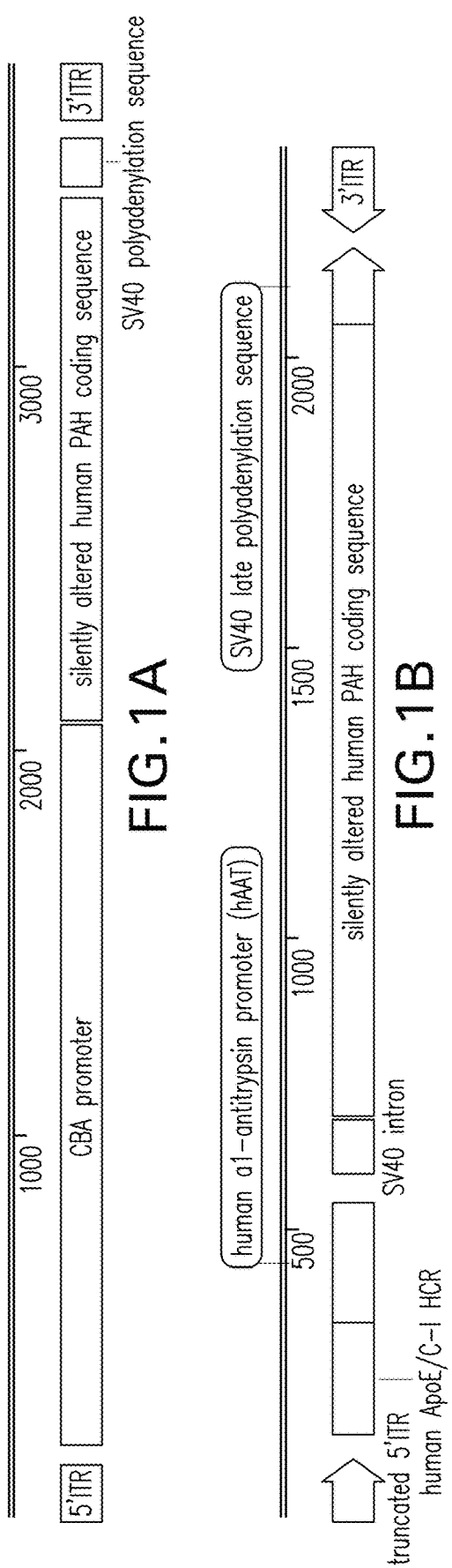
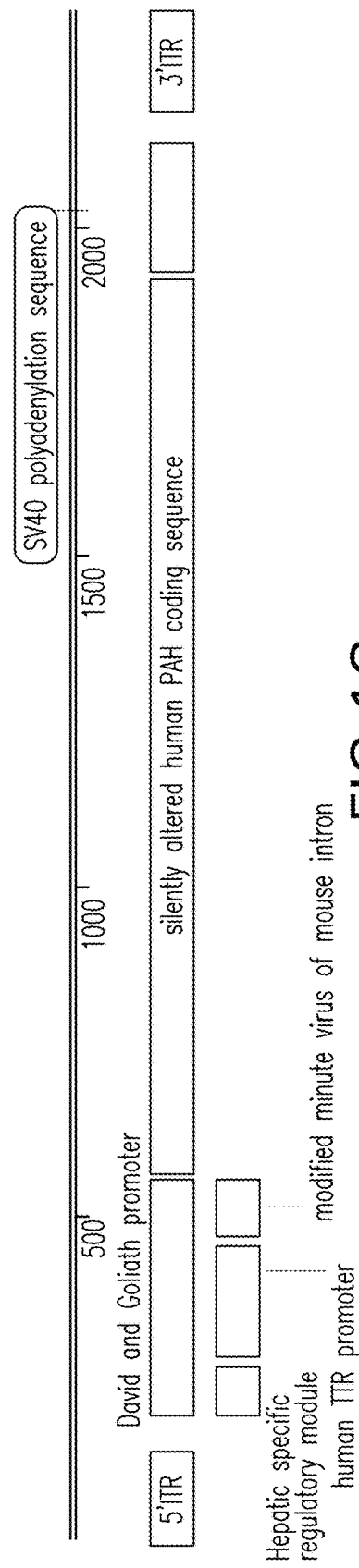
FIG.1A
FIG.1B
FIG.1C

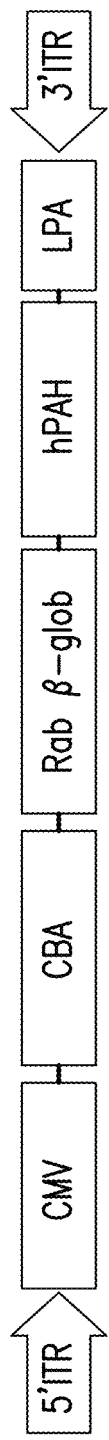
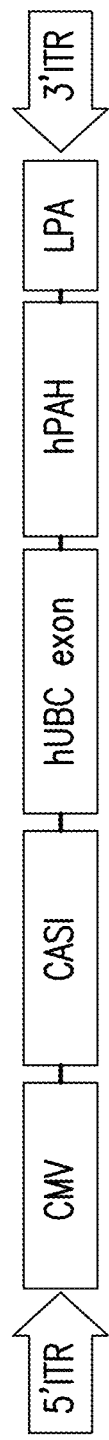
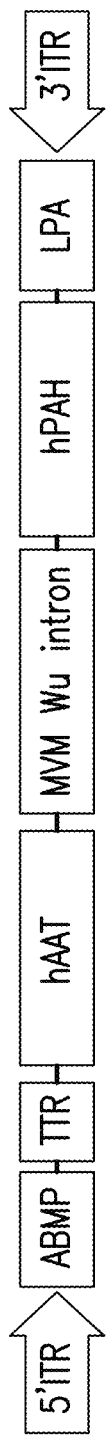
FIG.8A
FIG.8B
FIG.8C

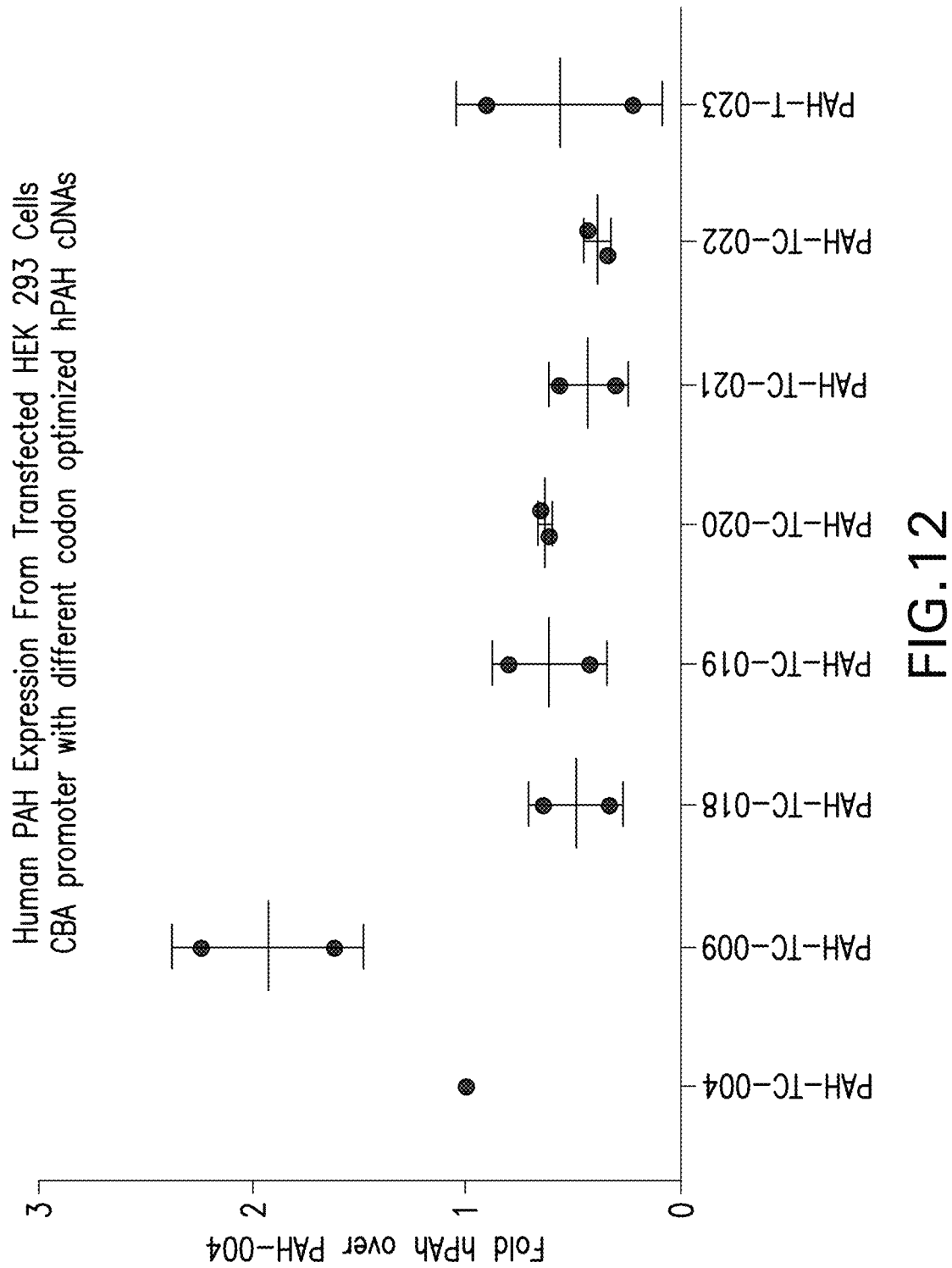

SEQUENCE LISTING

<160> NUMBER OF SEQ ID NOS: 92

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu

```
                    405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
```

```
              35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95
```

```
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510
```

```
Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Leu Thr Met Ala Ser Gly Gly Gly
    195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
```

```
                    565                 570                 575

Tyr Gly Gln Val Ala Thr Asn His Gln Ser Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Tyr Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
```

```
            195                 200                 205
Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620
```

-continued

```
Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Leu Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                    325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                    405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                    485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
            660                 665                 670
```

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
```

-continued

```
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
```

```
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
                450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Arg Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
```

```
Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

-continued

```
Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Arg Ala Tyr Asp
65                  70                  75                  80

Gln Gln Leu Lys Ala Gly Asp Asn Pro Tyr Leu Lys Tyr Asn His Ala
                85                  90                  95
```

```
Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
```

```
            515                 520                 525
Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Lys Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
```

-continued

```
            145                 150                 155                 160
        Lys Ser Gly Ala Gln Pro Ala Lys Lys Arg Leu Asn Phe Gly Gln Thr
                        165                 170                 175
        Gly Asp Thr Glu Ser Val Pro Asp Pro Gln Pro Ile Gly Glu Pro Pro
                        180                 185                 190
        Ala Ala Pro Ser Gly Val Gly Ser Leu Thr Met Ala Ser Gly Gly Gly
                        195                 200                 205
        Ala Pro Val Ala Asp Asn Asn Glu Gly Ala Asp Gly Val Gly Ser Ser
                        210                 215                 220
        Ser Gly Asn Trp His Cys Asp Ser Gln Trp Leu Gly Asp Arg Val Ile
        225                 230                 235                 240
        Thr Thr Ser Thr Arg Thr Trp Ala Leu Pro Thr Tyr Asn Asn His Leu
                        245                 250                 255
        Tyr Lys Gln Ile Ser Asn Ser Thr Ser Gly Gly Ser Ser Asn Asp Asn
                        260                 265                 270
        Ala Tyr Phe Gly Tyr Ser Thr Pro Trp Gly Tyr Phe Asp Phe Asn Arg
                        275                 280                 285
        Phe His Cys His Phe Ser Pro His Asp Trp Gln Arg Leu Ile Asn Asn
                        290                 295                 300
        Asn Trp Gly Phe Arg Pro Lys Arg Leu Asn Phe Lys Leu Phe Asn Ile
        305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Pro Phe Pro
                        355                 360                 365
        Ala Asp Val Phe Met Ile Pro Gln Tyr Gly Tyr Leu Thr Leu Asn Asp
                        370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Asn
        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Arg Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
```

```
Tyr Gly Gln Val Ala Thr Asn His Gln Ser Ala Gln Ala Gln Ala Gln
            580                 585                 590

Thr Gly Trp Val Gln Asn Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Met Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205
```

```
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
```

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 14
<211> LENGTH: 26
<212> TYPE: DNA
<213> ORGANISM: Artificial Sequence
<220> FEATURE:
<223> OTHER INFORMATION: splice acceptor

<400> SEQUENCE: 14
ctgacctctt ctcttcctcc cacagg                                        26

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

```
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Val Thr Gln Asn
                485                 490                 495
Asn Asn Ser Glu Phe Ala Trp Pro Arg Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
```

```
                610             615                 620
Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Arg Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
            50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

-continued

```
                245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Ala Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Arg Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
```

```
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
```

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Ile Ala Trp Pro Arg Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Cys Lys Ser Asn Asn Val Glu Phe Ala Val Asn Thr Glu Gly Val
705                 710                 715                 720
```

Tyr Ser Glu Pro Arg Pro Ile Gly Thr Arg Tyr Leu Thr Arg Asn Leu
            725                 730                 735

<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcct                                           145

<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc     120 gagcgcgcag agagggagtg gccaa                                           145

<210> SEQ ID NO 20
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20 ctctccccccc tgtcgcgttc gctcgctcgc tggctcgttt ggggggtgg cagctcaaag      60 agctgccaga cgacggccct ctggccgtcg ccccccaaa cgagccagcg agcgagcgaa     120
cgcgacaggg gggagagtgc cacactctca agcaagggg ttttgta                   167

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21
tacaaaacct ccttgcttga gagtgtggca ctctccccccc tgtcgcgttc gctcgctcgc    60
tggctcgttt ggggggtgg cagctcaaag agctgccaga cgacggccct ctggccgtcg    120 ccccccaaa cgagccagcg agcgagcgaa cgcgacaggg gggagag                   167

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

Met Pro Gly Phe Tyr Glu Ile Val Ile Lys Val Pro Ser Asp Leu Asp
1               5                   10                  15

-continued

```
Glu His Leu Pro Gly Ile Ser Asp Ser Phe Val Asn Trp Val Ala Glu
             20                  25                  30

Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Asp Phe Leu
     50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
             100                 105                 110

Arg Glu Lys Leu Ile Gln Arg Ile Tyr Arg Gly Ile Glu Pro Thr Leu
         115                 120                 125

Pro Asn Trp Phe Ala Val Thr Lys Thr Arg Asn Gly Ala Gly Gly Gly
 130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                 165                 170                 175

Ser Ala Cys Leu Asn Leu Thr Glu Arg Lys Arg Leu Val Ala Gln His
             180                 185                 190

Leu Thr His Val Ser Gln Thr Gln Glu Gln Asn Lys Glu Asn Gln Asn
         195                 200                 205

Pro Asn Ser Asp Ala Pro Val Ile Arg Ser Lys Thr Ser Ala Arg Tyr
 210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                 245                 250                 255

Ser Asn Ser Arg Ser Gln Ile Lys Ala Ala Leu Asp Asn Ala Gly Lys
             260                 265                 270

Ile Met Ser Leu Thr Lys Thr Ala Pro Asp Tyr Leu Val Gly Gln Gln
         275                 280                 285

Pro Val Glu Asp Ile Ser Ser Asn Arg Ile Tyr Lys Ile Leu Glu Leu
 290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                 325                 330                 335

Thr Thr Gly Lys Thr Asn Ile Ala Glu Ala Ile Ala His Thr Val Pro
             340                 345                 350

Phe Tyr Gly Cys Val Asn Trp Thr Asn Glu Asn Phe Pro Phe Asn Asp
         355                 360                 365

Cys Val Asp Lys Met Val Ile Trp Trp Glu Glu Gly Lys Met Thr Ala
 370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                 405                 410                 415

Ile Val Thr Ser Asn Thr Asn Met Cys Ala Val Ile Asp Gly Asn Ser
             420                 425                 430
```

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Cys Ile Phe Glu Gln
    610                 615                 620

<210> SEQ ID NO 23
<211> LENGTH: 452
<212> TYPE: PRT
<213> ORGANISM: Homo sapiens

<400> SEQUENCE: 23

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
        210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 24
<211> LENGTH: 1359
<212> TYPE: DNA
<213> ORGANISM: Homo sapiens

<400> SEQUENCE: 24

```
atgtccactg cggtcctgga aacccaggc ttgggcagga aactctctga ctttggacag    60
gaaacaagct atattgaaga caactgcaat caaaatggtg ccatatcact gatcttctca   120
ctcaaagaag aagttggtgc attggccaaa gtattgcgct tatttgagga gaatgatgta   180
aacctgaccc acattgaatc tagaccttct cgtttaaaga agatgagta tgaattttc    240 acccatttgg ataaacgtag cctgcctgct ctgacaaaca tcatcaagat cttgaggcat   300
gacattggtg ccactgtcca tgagctttca cgagataaga gaaagacac agtgccctgg   360 ttcccaagaa ccattcaaga gctggacaga tttgccaatc agattctcag ctatggagcg   420
gaactggatg ctgaccaccc tggttttaaa gatcctgtgt accgtgcaag acggaagcag   480
tttgctgaca ttgcctacaa ctaccgccat gggcagccca tccctcgagt ggaatacatg   540
gaggaagaaa agaaaacatg gggcacagtg ttcaagactc tgaagtcctt gtataaaacc   600
```

```
catgcttgct atgagtacaa tcacattttt ccacttcttg aaaagtactg tggcttccat      660
gaagataaca ttccccagct ggaagacgtt tctcaattcc tgcagacttg cactggtttc      720
cgcctccgac ctgtggctgg cctgctttcc tctcgggatt tcttgggtgg cctggccttc      780
cgagtcttcc actgcacaca gtacatcaga catggatcca agcccatgta tacccccgaa      840
cctgacatct gccatgagct gttgggacat gtgcccttgt tttcagatcg cagctttgcc      900
cagttttccc aggaaattgg ccttgcctct ctgggtgcac ctgatgaata cattgaaaag      960
ctcgccacaa tttactggtt tactgtggag tttgggctct gcaaacaagg agactccata     1020
aaggcatatg gtgctgggct cctgtcatcc tttggtgaat acagtactg cttatcagag      1080 aagccaaagc ttctccccct ggagctggag aagacagcca tccaaaatta cactgtcacg     1140
gagttccagc cctgtatta cgtggcagag agttttaatg atgccaagga gaaagtaagg      1200
aactttgctg ccacaatacc tcggcccttc tcagttcgct acgacccata cacccaaagg     1260
attgaggtct ggacaataca ccagcagctt aagattttgg ctgattccat taacagtgaa     1320
attggaatcc tttgcagtgc cctccagaaa ataaagtaa                           1359
```

<210> SEQ ID NO 25
<211> LENGTH: 1359
<212> TYPE: DNA
<213> ORGANISM: Artificial Sequence
<220> FEATURE:
<223> OTHER INFORMATION: Silently altered PAH coding sequence

<400> SEQUENCE: 25

```
atgtccaccg ctgtgctgga gaaccctggg ctggggagga aactgtcaga cttcgggcag       60
gagacttcat acattgagga taactgtaac cagaatggcg ccatctctct gatcttcagc      120
ctgaaggagg aagtgggcgc cctggcaaag gtgctgcgcc tgtttgagga aacgacgtg      180 aatctgaccc acatcgagtc ccggccttct agactgaaga aggacgagta cgagttcttt      240
acccacctgg ataagcggtc cctgccagcc ctgacaaaca tcatcaagat cctgaggcac      300
gacatcggag caaccgtgca cgagctgtct cgggacaaga gaaggatac cgtgccctgg      360 ttccctcgga caatccagga gctggataga tttgccaacc agatcctgtc ttacggagca      420
gagctggacg cagatcaccc tggcttcaag gacccagtgt atcgggcccg gagaaagcag      480
tttgccgata tcgcctacaa ttataggcac ggacagccaa tccctcgcgt ggagtatatg      540
gaggaggaga agaagacctg ggcacagtg ttcaagaccc tgaagagcct gtacaagaca      600
cacgcctgct acgagtataa ccacatcttc ccctgctgg agaagtattg ggctttcac      660 gaggacaata tccctcagct ggaggacgtg agccagttcc tgcagacctg cacaggcttt      720
aggctgaggc cagtggcagg actgctgagc tcccgggact cctgggagg actggccttc     780 agagtgtttc actgcaccca gtacatcagg cacggctcca gccaatgta tacaccagag      840 cccgacatct gtcacgagct gctgggccac gtgcccctgt ttagcgatag atccttcgcc      900
cagttttccc aggagatcgg actggcatct ctgggagcac ctgacgagta catcgagaag      960
ctggccacca tctattggtt cacagtggag tttggcctgt gcaagcaggg cgatagcatc     1020
aaggcctacg agcaggact gctgtctagc ttcggcgagc tgcagtattg tctgtccgag      1080
aagccaaagc tgctgcccct ggagctggag aagaccgcca tccagaacta caccgtgaca     1140
gagttccagc cctgtacta tgtggccgag tcttttaacg atgccaagga gaaggtgaga     1200
aatttcgccg ccacaatccc taggcccttc agcgtgcggt acgacccttA tacccagagg     1260
```

```
atcgaggtgc tggataatac acagcagctg aagatcctgg ctgactcaat caatagcgaa      1320
atcggaatcc tgtgctccgc cctgcagaaa atcaaatga                             1359

<210> SEQ ID NO 26
<211> LENGTH: 106
<212> TYPE: DNA
<213> ORGANISM: Artificial Sequence
<220> FEATURE:
<223> OTHER INFORMATION: truncated AAV2 5'ITR

<400> SEQUENCE: 26
ctgcgcgctc gctcgctcac tgaggccgcc cgggcaaagc ccgggcgtcg ggcgaccttt       60
ggtcgcccgg cctcagtgag cgagcgagcg cgcagagagg gagtgg                    106

<210> SEQ ID NO 27
<211> LENGTH: 143
<212> TYPE: DNA
<213> ORGANISM: Artificial Sequence
<220> FEATURE:
<223> OTHER INFORMATION: modified AAV2 3'ITR

<400> SEQUENCE: 27
aggaacccct agtgatggag ttggccactc cctctctgcg cgctcgctcg ctcactgagg       60
ccgggcgacc aaaggtcgcc cgacgcccgg gctttgcccg gcggcctca gtgagcgagc      120 gagcgcgcag agagggagtg gcc                                             143

<210> SEQ ID NO 28
<211> LENGTH: 1873
<212> TYPE: DNA
<213> ORGANISM: Artificial Sequence
<220> FEATURE:
<223> OTHER INFORMATION: CAG promoter

<400> SEQUENCE: 28
gatcttcaat attggccatt agccatatta ttcattggtt atatagcata aatcaatatt       60
ggctattggc cattgcatac gttgtatcta tatcataata tgtacattta tattggctca     120
tgtccaatat gaccgccatg ttggcattga ttattgacta gttattaata gtaatcaatt     180
acggggtcat tagttcatag cccatatatg gagttccgcg ttacataact acggtaaat      240 ggcccgcctg gctgaccgcc caacgacccc cgcccattga cgtcaataat gacgtatgtt     300
cccatagtaa cgccaatagg gactttccat tgacgtcaat gggtggagta tttacggtaa     360
actgcccact tggcagtaca tcaagtgtat catatgccaa gtccgccccc tattgacgtc     420
aatgacggta aatggcccgc ctggcattat gcccagtaca tgaccttacg gactttcct      480 acttggcagt acatctacgt attagtcatc gctattacca tggtcgaggt gagccccacg     540
ttctgcttca ctctccccat ctccccccc tccccacccc caattttgta tttatttatt      600
ttttaattat tttgtgcagc gatggggcg gggggggg ggggcgcgc gccaggcggg         660 gcggggcggg gcgaggggcg gggcggggcg aggcggagag tgcggcggc agccaatcag     720 agcggcgcgc tccgaaagtt cctttatg gcgaggcggc ggcggcggcg ccctataaa       780 aagcgaagcg cgcggcgggc gggagtcgct gcgacgctgc cttcgccccg tgccccgctc     840
cgccgccgcc tcgcgccgcc cgccccggct ctgactgacc gcgttactcc cacaggtgag     900
cgggcgggac ggcccttctc ctccgggctg taattagcgc ttggtttaat gacggcttgt     960
ttcttttctg tggctgcgtg aaagccttga ggggctccgg gagggccctt tgtgcggggg    1020
ggagcggctc ggggggtgcg tgcgtgtgtg tgtgcgtggg gagcgccgcg tgcggcccgc    1080
```

-continued

```
gctgcccggc ggctgtgagc gctgcgggcg cggcgcgggg ctttgtgcgc tccgcagtgt      1140
gcgcgagggg agcgcggccg ggggcggtgc cccgcggtgc ggggggggct gcagggggaa      1200
caaaggctgc gtgcggggtg tgtgcgtggg ggggtgagca ggggtgtgg gcgcggcggt       1260 cgggctgtaa ccccccctg caccccctc cccgagttgc tgagcacggc ccggcttcgg        1320
gtgcggggct ccgtacgggg cgtggcgcgg ggctcgccgt gccgggcggg gggtggcggc      1380
aggtgggggt gccgggcggg gcggggccgc ctcgggccgg ggagggctcg ggggaggggc      1440
gcggcggccc ccggagcgcc ggcggctgtc gaggcgcggc gagccgcagc cattgccttt      1500
tatggtaatc gtgcgagagg gcgcaggac ttcctttgtc ccaaatctgt gcggagccga      1560
aatctgggag gcgccgccgc accccctcta gcgggcgcgg ggcgaagcgg tgcggcgccg      1620
gcaggaagga aatgggcggg gagggccttc gtgcgtcgcc gcgccgccgt ccccttctcc      1680
ctctccagcc tcggggctgt ccgcgggggg acggctgcct tcggggggga cggggcaggg      1740
cggggttcgg cttctggcgt gtgaccgcg gctctagagc ctctgctaac catgttcatg      1800
ccttcttctt tttcctacag ctcctgggca acgtgctggt tattgtgctg tctcatcatt      1860
ttggcaaaga att                                                        1873
```

<210> SEQ ID NO 29
<211> LENGTH: 192
<212> TYPE: DNA
<213> ORGANISM: Homo sapiens

<400> SEQUENCE: 29

```
ccctaaaatg ggcaaacatt gcaagcagca acagcaaac acacagccct ccctgcctgc       60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gg                                                         192
```

<210> SEQ ID NO 30
<211> LENGTH: 205
<212> TYPE: DNA
<213> ORGANISM: Homo sapiens

<400> SEQUENCE: 30

```
aatgactcct ttcggtaagt gcagtggaag ctgtacactg cccaggcaaa gcgtccgggc       60
agcgtaggcg ggcgactcag atcccagcca gtggacttag cccctgtttg ctcctccgat     120
aactggggtg accttggtta atattcacca gcagcctccc ccgttgcccc tctggatcca     180
ctgcttaaat acggacgagg acagg                                           205
```

<210> SEQ ID NO 31
<211> LENGTH: 93
<212> TYPE: DNA
<213> ORGANISM: Simian virus 40

<400> SEQUENCE: 31

```
ctctaaggta aatataaaat ttttaagtgt ataatgtgtt aaactactga ttctaattgt       60
ttctctcttt tagattccaa cctttggaac tga                                   93
```

<210> SEQ ID NO 32
<211> LENGTH: 398
<212> TYPE: DNA
<213> ORGANISM: Artificial Sequence
<220> FEATURE:

```
<223> OTHER INFORMATION: pHMI-hPAH-TC-025 transcriptional regulatory
      region

<400> SEQUENCE: 32
ccctaaaatg ggcaaacatt gcaagcagca aacagcaaac acacagccct ccctgcctgc      60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct ccccgttgc     360 ccctctggat ccactgctta aatacggacg aggacagg                            398

<210> SEQ ID NO 33
<211> LENGTH: 72
<212> TYPE: DNA
<213> ORGANISM: Homo sapiens

<400> SEQUENCE: 33 ggggaggct gctggtgaat attaaccaag gtcaccccag ttatcggagg agcaaacagg      60
ggctaagtcc ac                                                          72

<210> SEQ ID NO 34
<211> LENGTH: 170
<212> TYPE: DNA
<213> ORGANISM: Homo sapiens

<400> SEQUENCE: 34
cgatgctcta atctctctag acaaggttca tatttgtatg ggttacttat tctctctttg      60
ttgactaagt caataatcag aatcagcagg tttgcagtca gattggcagg gataagcagc    120
ctagctcagg agaagtgagt ataaaagccc caggctggga gcagccatca                170

<210> SEQ ID NO 35
<211> LENGTH: 92
<212> TYPE: DNA
<213> ORGANISM: Artificial Sequence
<220> FEATURE:
<223> OTHER INFORMATION: modified MVM intron

<400> SEQUENCE: 35
aagaggtaag ggtttaaggg atggttggtt ggtgggtat taatgtttaa ttacctggag      60
cacctgcctg aaatcacttt ttttcaggtt gg                                   92

<210> SEQ ID NO 36
<211> LENGTH: 254
<212> TYPE: DNA
<213> ORGANISM: Artificial Sequence
<220> FEATURE:
<223> OTHER INFORMATION: pHMI-hPAH-TC-010 transcriptional regulatory
      region

<400> SEQUENCE: 36 ggggaggct gctggtgaat attaaccaag gtcaccccag ttatcggagg agcaaacagg      60
ggctaagtcc acctcgagcc atggcgatgc tctaatctct ctagacaagg ttcatatttg    120
tatgggttac ttattctctc tttgttgact aagtcaataa tcagaatcag caggtttgca    180
gtcagattgg cagggataag cagcctagct caggagaagt gagtataaaa gccccaggct    240
gggagcagcc atca                                                      254
```

<210> SEQ ID NO 37
<211> LENGTH: 592
<212> TYPE: DNA
<213> ORGANISM: Homo sapiens

<400> SEQUENCE: 37

```
gtaaatttta tggaatgtga atcataattc aattttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc cccttccaa  cccctcagtt cccatcctcc agcagctgtt tgtgtgctgc     360
ctctgaagtc cacactgaac aaacttcagc ctactcatgt ccctaaaatg ggcaaacatt     420
gcaagcagca aacagcaaac acacagccct ccctgcctgc tgaccttgga gctggggcag     480
aggtcagaga cctctctggg cccatgccac ctccaacatc cactcgaccc cttggaattt     540
cggtggagag gagcagaggt tgtcctggcg tggtttaggt agtgtgagag gg             592
```

<210> SEQ ID NO 38
<211> LENGTH: 423
<212> TYPE: DNA
<213> ORGANISM: Homo sapiens

<400> SEQUENCE: 38

```
gctctaaccc actctgatct cccagggcgg cagtaagtct tcagcatcag gcattttggg      60
gtgactcagt aaatggtaga tcttgctacc agtggaacag ccactaagga ttctgcagtg     120
agagcagagg gccagctaag tggtactctc ccagagactg tctgactcac gccacccct     180
ccaccttgga cacaggacgc tgtggttttct gagccaggta caatgactcc tttcggtaag     240
tgcagtggaa gctgtacact gcccaggcaa agcgtccggg cagcgtaggc gggcgactca     300
gatcccagcc agtggactta gcccctgttt gctcctccga taactggggt gaccttggtt     360
aatattcacc agcagcctcc cccgttgccc ctctggatcc actgcttaaa tacggacgag     420
gac                                                                   423
```

<210> SEQ ID NO 39
<211> LENGTH: 1021
<212> TYPE: DNA
<213> ORGANISM: Artificial Sequence
<220> FEATURE:
<223> OTHER INFORMATION: pHMI-hPAH-TC-011 transcriptional regulatory
      region

<400> SEQUENCE: 39

```
gtaaatttta tggaatgtga atcataattc aattttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc cccttccaa  cccctcagtt cccatcctcc agcagctgtt tgtgtgctgc     360
ctctgaagtc cacactgaac aaacttcagc ctactcatgt ccctaaaatg ggcaaacatt     420
gcaagcagca aacagcaaac acacagccct ccctgcctgc tgaccttgga gctggggcag     480
```

| | |
|---|---:|
| aggtcagaga cctctctggg cccatgccac ctccaacatc cactcgaccc cttggaattt | 540 |
| cggtggagag gagcagaggt tgtcctggcg tggtttaggt agtgtgagag ggcttaaggc | 600 |
| tctaacccac tctgatctcc cagggcggca gtaagtcttc agcatcaggc attttggggt | 660 |
| gactcagtaa atggtagatc ttgctaccag tggaacagcc actaaggatt ctgcagtgag | 720 |
| agcagagggc cagctaagtg gtactctccc agagactgtc tgactcacgc cacccctcc | 780 |
| accttggaca caggacgctg tggtttctga gccaggtaca atgactcctt tcggtaagtg | 840 |
| cagtggaagc tgtacactgc ccaggcaaag cgtccgggca gcgtaggcgg gcgactcaga | 900 |
| tcccagccag tggacttagc ccctgtttgc tcctccgata actggggtga ccttggttaa | 960 |
| tattcaccag cagcctcccc cgttgcccct ctggatccac tgcttaaata cggacgagga | 1020 |
| c | 1021 |

<210> SEQ ID NO 40
<211> LENGTH: 1168
<212> TYPE: DNA
<213> ORGANISM: Artificial Sequence
<220> FEATURE:
<223> OTHER INFORMATION: modified human EF-1alpha promoter

<400> SEQUENCE: 40

| | |
|---|---:|
| cgtgaggctc cggtgcccgt cagtgggcag agcgcacatc gcccacagtc cccgagaagt | 60 |
| tgggggagg ggtcggcaat tgaaccggtg cctagagaag gtggcgcggg gtaaactggg | 120 |
| aaagtgatgt cgtgtactgg ctccgccttt ttcccgaggg tggggagaa ccgtatataa | 180 |
| gtgcagtagt cgccgtgaac gttctttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacctggctc cagtacgtga ttcttgatcc cgagctggag ccaggggcgg | 360 |
| gccttgcgct ttaggagccc cttcgcctcg tgcttgagtt gaggcctggc ctgggcgctg | 420 |
| gggccgccgc gtgcgaatct ggtggcacct tcgcgcctgt ctcgctgctt tcgataagtc | 480 |
| tctagccatt taaaattttt gatgacctgc tgcgacgctt ttttttctggc aagatagtct | 540 |
| tgtaaatgcg ggccaggatc tgcacactgg tatttcggtt tttggggccg cgggcggcga | 600 |
| cggggcccgt gcgtcccagc gcacatgttc ggcgaggcgg ggcctgcgag cgcggccacc | 660 |
| gagaatcgga cggggggtagt ctcaagctgg ccggcctgct ctggtgcctg gcctcgcgcc | 720 |
| gccgtgtatc gccccgccct gggcggcaag gctggcccgg tcggcaccag ttgcgtgagc | 780 |
| ggaaagatgg ccgcttcccg gccctgctcc agggggctca aaatgggagga gcggcgctc | 840 |
| gggagagcgg gcgggtgagt cacccacaca aaggaaaggg gcctttccgt cctcagccgt | 900 |
| cgcttcatgt gactccacgg agtaccgggc gccgtccagg cacctcgatt agttctggag | 960 |
| cttttggagt acgtcgtctt taggttgggg ggagggggttt tatgcgatgg agtttcccca | 1020 |
| cactgagtgg gtggagactg aagttaggcc agcttggcac ttgatgtaat tctccttgga | 1080 |
| atttgcccctt tttgagtttg gatcttggtt cattctcaag cctcagacag tggttcaaag | 1140 |
| tttttttctt ccatttcagg tgtcgtga | 1168 |

<210> SEQ ID NO 41
<211> LENGTH: 1766
<212> TYPE: DNA
<213> ORGANISM: Artificial Sequence
<220> FEATURE:
<223> OTHER INFORMATION: pHMI-hPAH-TC-012 transcriptional regulatory
      region

<400> SEQUENCE: 41

```
gtaaatttta tggaatgtga atcataattc aatttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc ccccttccaa cccctcagtt cccatcctcc agcagctgtt tgtgtgctgc     360
ctctgaagtc cacactgaac aaacttcagc ctactcatgt ccctaaaatg ggcaaacatt     420
gcaagcagca aacagcaaac acacagccct ccctgcctgc tgaccttgga gctggggcag     480
aggtcagaga cctctctggg cccatgccac ctccaacatc cactcgaccc cttgaatttt     540
cggtggagag gagcagaggt tgtcctggcg tggtttaggt agtgtgagag ggcttaagcg     600
tgaggctccg gtgcccgtca gtgggcagag cgcacatcgc ccacagtccc cgagaagttg     660
gggggagggg tcggcaattg aaccggtgcc tagagaaggt ggcgcggggt aaactgggaa     720
agtgatgtcg tgtactggct ccgccttttt cccgagggtg ggggagaacc gtatataagt     780
gcagtagtcg ccgtgaacgt tctttttcgc aacgggtttg ccgccagaac acaggtaagt     840
gccgtgtgtg gttcccgcgg gcctggcctc tttacgggtt atggcccttg cgtgccttga     900
attacttcca cctggctcca gtacgtgatt cttgatcccg agctggagcc aggggcgggc     960
cttgcgcttt aggagcccct tcgcctcgtg cttgagttga ggcctggcct gggcgctggg    1020
gccgccgcgt gcgaatctgg tggcaccttc gcgcctgtct cgctgctttc gataagtctc    1080
tagccattta aaattttga tgacctgctg cgacgctttt tttctggcaa gatagtcttg    1140
taaatgcggg ccaggatctg cacactggta tttcggtttt tggggccgcg ggcggcgacg    1200
gggcccgtgc gtcccagcgc acatgttcgg cgaggcgggg cctgcgagcg cggccaccga    1260
gaatcggacg ggggtagtct caagctggcc ggcctgctct ggtgcctggc ctcgcgccgc    1320
cgtgtatcgc cccgccctgg gcggcaaggc tggcccggtc ggcaccagtt gcgtgagcgg    1380
aaagatggcc gcttcccggc cctgctccag ggggctcaaa atggaggacg cggcgctcgg    1440
gagagcgggc gggtgagtca cccacacaaa ggaaaggggc cttccgtcc tcagccgtcg     1500
cttcatgtga ctccacggag taccgggcgc cgtccaggca cctcgattag ttctggagct    1560
tttggagtac gtcgtcttta ggttgggggg aggggtttta tgcgatggag tttccccaca    1620
ctgagtgggt ggagactgaa gttaggccag cttggcactt gatgtaattc ccttggaat     1680
ttgcccttt tgagtttgga tcttggttca ttctcaagcc tcagacagtg gttcaaagtt     1740
tttttcttcc atttcaggtg tcgtga                                          1766
```

<210> SEQ ID NO 42
<211> LENGTH: 122
<212> TYPE: DNA
<213> ORGANISM: Simian virus 40

<400> SEQUENCE: 42

```
aacttgttta ttgcagctta taatggttac aaataaagca atagcatcac aaatttcaca      60
aataaagcat ttttttcact gcattctagt tgtggtttgt ccaaactcat caatgtatct     120
ta                                                                     122
```

<210> SEQ ID NO 43

<211> LENGTH: 133
<212> TYPE: DNA
<213> ORGANISM: Simian virus 40

<400> SEQUENCE: 43

```
tgctttattt gtgaaatttg tgatgctatt gctttatttg taaccattat aagctgcaat      60
aaacaagtta acaacaacaa ttgcattcat tttatgtttc aggttcaggg ggaggtgtgg     120
gaggtttttt aaa                                                        133
```

<210> SEQ ID NO 44

<400> SEQUENCE: 44

000

<210> SEQ ID NO 45
<211> LENGTH: 198
<212> TYPE: DNA
<213> ORGANISM: Simian virus 40

<400> SEQUENCE: 45

```
gatccagaca tgataagata cattgatgag tttggacaaa ccacaactag aatgcagtga      60
aaaaaatgct ttatttgtga aatttgtgat gctattgctt tatttgtaac cattataagc     120
tgcaataaac aagttaacaa caacaattgc attcatttta tgtttcaggt tcaggggag      180
gtgtgggagg ttttttaa                                                   198
```

<210> SEQ ID NO 46
<211> LENGTH: 3392
<212> TYPE: DNA
<213> ORGANISM: Artificial Sequence
<220> FEATURE:
<223> OTHER INFORMATION: pHMI-hPAH-TC-004 transfer genome

<400> SEQUENCE: 46

```
gatcttcaat attggccatt agccatatta ttcattggtt atatagcata atcaatatt       60
ggctattggc cattgcatac gttgtatcta tcataaata tgtacattta tattggctca      120
tgtccaatat gaccgccatg ttggcattga ttattgacta gttattaata gtaatcaatt     180
acggggtcat tagttcatag cccatatatg gagttccgcg ttacataact acggtaaat      240
ggcccgcctg gctgaccgcc caacgacccc cgcccattga cgtcaataat gacgtatgtt     300
cccatagtaa cgccaatagg gactttccat tgacgtcaat gggtggagta tttacggtaa     360
actgcccact tggcagtaca tcaagtgtat catatgccaa gtccgccccc tattgacgtc     420
aatgacggta aatggcccgc ctggcattat gcccagtaca tgaccttacg gactttcct      480
acttggcagt acatctacgt attagtcatc gctattacca tggtcgaggt gagccccacg     540
ttctgcttca ctctccccat ctccccccc tccccacccc caatttgtg tttattat        600
ttttaattat tttgtgcagc gatggggcg gggggggg gggcgcgc gccaggcggg          660
gcggggcggg gcgaggggcg gggcgggcg aggcggagag gtgcggcggc agccaatcag      720
agcggcgcgc tccgaaagtt ccttttatg gcgaggcggc ggcggcgcg gccctataaa        780
aagcgaagcg cgcggcgggc gggagtcgct gcgacgctgc cttcgccccg tgccccgctc      840
cgccgccgcc tcgcgccgcc cgccccggct ctgactgacc gcgttactcc cacaggtgag     900
cgggcgggac ggcccttctc ctccgggctg taattagcgc ttggtttaat gacggcttgt     960
ttcttttctg tggctgcgtg aaagccttga ggggctccgg gagggcccctt tgtgcggggg    1020
```

```
ggagcggctc gggggggtgcg tgcgtgtgtg tgtgcgtggg gagcgccgcg tgcggcccgc    1080
gctgcccggc ggctgtgagc gctgcgggcg cggcgcgggg ctttgtgcgc tccgcagtgt    1140
gcgcgagggg agcgcggccg ggggcggtgc cccgcggtgc gggggggggct gcgaggggaa    1200 caaaggctgc gtgcgggtg tgtgcgtggg ggggtgagca gggggtgtgg gcgcggcggt     1260
cgggctgtaa ccccccctg cacccccctc cccgagttgc tgagcacggc ccggcttcgg     1320
gtgcggggct ccgtacgggg cgtggcgcgg ggctcgccgt gccggcgggg gggtggcggc    1380
aggtgggggt gccgggcggg gcggggccgc ctcgggccgg ggagggctcg ggggaggggc    1440
gcggcggccc ccggagcgcc ggcggctgtc gaggcgcggc gagccgcagc cattgccttt    1500
tatggtaatc gtgcgagagg gcgcagggac ttcctttgtc ccaaatctgt gcggagccga    1560
aatctgggag gcgccgccgc accccctcta gcgggcgcgg ggcgaagcgg tgcgcgccg     1620 gcaggaagga aatgggcggg gagggccttc gtgcgtcgcc gcgccgccgt ccccttctcc    1680
ctctccagcc tcgggctgt ccgcgggggg acggctgcct tcgggggga cggggcaggg     1740 cggggttcgg cttctggcgt gtgaccggcg gctctagagc ctctgctaac catgttcatg    1800
ccttcttctt tttcctacag ctcctgggca acgtgctggt tattgtgctg tctcatcatt    1860
ttggcaaaga attccgccac catgtccacc gctgtgctgg agaaccctgg gctggggagg    1920
aaactgtcag acttcgggca ggagacttca tacattgagg ataactgtaa ccagaatggc    1980
gccatctctc tgatcttcag cctgaaggag gaagtgggcg ccctggcaaa ggtgctgcgc    2040
ctgtttgagg agaacgacgt gaatctgacc cacatcgagt cccggccttc tagactgaag    2100
aaggacgagt acgagttctt tacccacctg gataagcggt ccctgccagc cctgacaaac    2160
atcatcaaga tcctgaggca cgacatcgga gcaaccgtgc acgagctgtc tcgggacaag    2220
aagaaggata ccgtgccctg gttccctcgg acaatccagg agctggatag atttgccaac    2280
cagatcctgt cttacggagc agagctggac gcagatcacc ctggcttcaa ggacccagtg    2340
tatcgggccc ggagaaagca gtttgccgat atcgcctaca attataggca cggacagcca    2400
atccctcgcg tggagtatat ggaggaggag aagaagacct ggggcacagt gttcaagacc    2460
ctgaagagcc tgtacaagac acacgcctgc tacgagtata accacatctt ccccctgctg    2520
gagaagtatt gtggctttca cgaggacaat atccctcagc tggaggacgt gagccagttc    2580
ctgcagacct gcacaggctt taggctgagg ccagtggcag gactgctgag ctcccgggac    2640
ttcctgggag gactggcctt cagagtgttt cactgcaccc agtacatcag gcacggctcc    2700
aagccaatgt ataccaccga gcccgacatc tgtcacgagc tgctgggcca cgtgcccctg    2760
tttagcgata gatccttcgc ccagttttcc caggagatcg gactggcatc tctgggagca    2820
cctgacgagt acatcgagaa gctggccacc atctattggt tcacagtgga gtttggcctg    2880
tgcaagcagg gcgatagcat caaggcctac ggagcaggac tgctgtctag cttcggcgag    2940
ctgcagtatt gtctgtccga gaagccaaag ctgctgcccc tggagctgga gaagaccgcc    3000
atccagaact acaccgtgac agagttccag ccctgtact atgtggccga gtctttaac     3060 gatgccaagg agaaggtgag aaatttcgcc gccacaatcc ctaggcccct cagcgtgcgg    3120
tacgaccctt atcccagag gatcgagtg ctggataata cacagcagct gaagatcctg     3180
gctgactcaa tcaatagcga aatcggaatc ctgtgctccg ccctgcagaa aatcaaatga    3240
atcgattcta gagtcgagcc gcggactagt aacttgttta ttgcagctta taatggttac    3300
aaataaagca atagcatcac aaatttcaca aataaagcat ttttttcact gcattctagt    3360
tgtggtttgt ccaaactcat caatgtatct ta                                  3392
```

<210> SEQ ID NO 47
<211> LENGTH: 2042
<212> TYPE: DNA
<213> ORGANISM: Artificial Sequence
<220> FEATURE:
<223> OTHER INFORMATION: pHMI-hPAH-TC-025 transfer genome

<400> SEQUENCE: 47

```
ccctaaaatg ggcaaacatt gcaagcagca aacagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gggaatgact cctttcggta agtgcagtgg aagctgtaca ctgcccaggc     240
aaagcgtccg ggcagcgtag gcgggcgact cagatcccag ccagtggact tagcccctgt     300
ttgctcctcc gataactggg gtgaccttgg ttaatattca ccagcagcct ccccgttgc      360
ccctctggat ccactgctta atacggacg aggacagggc cctgtctcct cagcttcagg      420
caccaccact gacctgggac agtgaatcct ctaaggtaaa tataaaattt ttaagtgtat     480
aatgtgttaa actactgatt ctaattgttt ctctctttta gattccaacc tttggaactg     540
accgccacca tgtccaccgc tgtgctggag aaccctgggc tggggaggaa actgtcagac     600
ttcgggcagg agacttcata cattgaggat aactgtaacc agaatggcgc catctctctg     660
atcttcagcc tgaaggagga agtgggcgcc ctggcaaagg tgctgcgcct gtttgaggag     720
aacgacgtga atctgaccca catcgagtcc cggccttcta gactgaagaa ggacgagtac     780
gagttcttta cccacctgga taagcggtcc ctgccagccc tgacaaacat catcaagatc     840
ctgaggcacg acatcggagc aaccgtgcac gagctgtctc gggacaagaa gaaggatacc     900
gtgccctggt tccctcggac aatccaggag ctggatagat ttgccaacca gatcctgtct     960
tacggagcag agctggacgc agatcaccct ggcttcaagg acccagtgta tcgggcccgg    1020
agaaagcagt ttgccgatat cgcctacaat tataggcacg acagccaat ccctcgcgtg     1080
gagtatatgg aggaggagaa gaagacctgg ggcacagtgt tcaagaccct gaagagcctg    1140
tacaagacac acgcctgcta cgagtataac cacatcttcc ccctgctgga agtattgt      1200
ggctttcacg aggacaatat ccctcagctg gaggacgtga ccagttcct gcagacctgc     1260
acaggcttta ggctgagggc agtggcagga ctgctgagct cccgggactt cctgggagga    1320
ctggccttca gagtgtttca ctgcacccag tacatcaggc acggctccaa gccaatgtat    1380
acaccagagc ccgacatctg tcacgagctg ctggccacg tgcccctgtt tagcgataga    1440
tccttcgccc agtttttccca ggagatcgga ctggcatctc tgggagcacc tgacgagtac    1500
atcgagaagc tggccaccat ctattggttc acagtggagt ttggcctgtg caagcagggc    1560
gatagcatca aggcctacgg agcaggactg ctgtctagct tcggcgagct gcagtattgt    1620
ctgtccgaga gccaaagct gctgcccctg gagctggaga gaccgccat ccagaactac     1680
accgtgacag agttccagcc cctgtactat gtggccgagt cttttaacga tgccaaggag    1740
aaggtgagaa atttcgccgc cacaatccct aggcccttca gcgtgcggta cgacccttat    1800
acccagagga tcgaggtgct ggataataca cagcagctga gatcctggc tgactcaatc     1860
aatagcgaaa tcggaatcct gtgctccgcc ctgcagaaaa tcaaatgaat gctttatttg    1920
tgaaatttgt gatgctattg ctttatttgt aaccattata agctgcaata aacaagttaa    1980
caacaacaat tgcattcatt ttatgtttca ggttcagggg gaggtgtggg aggttttta    2040
```

| | |
|---|---:|
| aa | 2042 |

<210> SEQ ID NO 48
<211> LENGTH: 1927
<212> TYPE: DNA
<213> ORGANISM: Artificial Sequence
<220> FEATURE:
<223> OTHER INFORMATION: pHMI-hPAH-TC-010 transfer genome

<400> SEQUENCE: 48

| | | | | | |
|---|---|---|---|---|---:|
| gggggaggct | gctggtgaat | attaaccaag | gtcaccccag | ttatcggagg | agcaaacagg | 60 |
| ggctaagtcc | acctcgagcc | atggcgatgc | tctaatctct | ctagacaagg | ttcatatttg | 120 |
| tatgggttac | ttattctctc | tttgttgact | aagtcaataa | tcagaatcag | caggtttgca | 180 |
| gtcagattgg | cagggataag | cagcctagct | caggagaagt | gagtataaaa | gccccaggct | 240 |
| gggagcagcc | atcagctagc | gccggcaaga | ggtaagggtt | taagggatgg | ttggttggtg | 300 |
| gggtattaat | gtttaattac | ctggagcacc | tgcctgaaat | cacttttttt | caggttgggc | 360 |
| caccatgtcc | accgctgtgc | tggagaaccc | tgggctgggg | aggaaactgt | cagacttcgg | 420 |
| gcaggagact | tcatacattg | aggataactg | taaccagaat | ggcgccatct | ctctgatctt | 480 |
| cagcctgaag | gaggaagtgg | gcgccctggc | aaaggtgctg | cgcctgtttg | aggagaacga | 540 |
| cgtgaatctg | acccacatcg | agtcccggcc | ttctagactg | aagaaggacg | agtacgagtt | 600 |
| cttcacccac | ctggataagc | ggtccctgcc | agccctgaca | aacatcatca | agatcctgag | 660 |
| gcacgacatc | ggagcaaccg | tgcacgagct | gtctcgggac | aagaagaagg | ataccgtgcc | 720 |
| ctggttccct | cggacaatcc | aggagctgga | tagatttgcc | aaccagatcc | tgtcttacgg | 780 |
| agcagagctg | gacgcagatc | accctggctt | caaggaccca | gtgtatcggg | cccggagaaa | 840 |
| gcagtttgcc | gatatcgcct | acaattatag | gcacggacac | ccaatccctc | gcgtggagta | 900 |
| tatggaggag | gagaagaaga | cctggggcac | agtgttcaag | accctgaaga | gcctgtacaa | 960 |
| gacacacgcc | tgctacgagt | ataaccacat | cttccccctg | ctggagaagt | attgtggctt | 1020 |
| tcacgaggac | aatatccctc | agctggagga | cgtgagccag | ttcctgcaga | cctgcacagg | 1080 |
| ctttaggctg | aggccagtgg | caggactgct | gagctcccgg | gacttcctgg | gaggactggc | 1140 |
| cttcagagtg | tttcactgca | cccagtacat | caggcacggc | tccaagccaa | tgtatacacc | 1200 |
| agagcccgac | atctgtcacg | agctgctggg | ccacgtgccc | ctgtttagcg | atagatcctt | 1260 |
| cgcccagttt | tcccaggaga | tcggactggc | atctctggga | gcacctgacg | agtacatcga | 1320 |
| gaagctggcc | accatctatt | ggttcacagt | ggagtttggc | ctgtgcaagc | agggcgatag | 1380 |
| catcaaggcc | tacggagcag | gactgctgtc | tagcttcggc | gagctgcagt | attgtctgtc | 1440 |
| cgagaagcca | aagctgctgc | ccctggagct | ggagaagacc | gccatccaga | actacaccgt | 1500 |
| gacagagttc | cagcccctgt | actatgtggc | cgagtctttt | aacgatgcca | aggagaaggt | 1560 |
| gagaaatttc | gccgccacaa | tccctaggcc | cttcagcgtg | cggtacgacc | cttatcccca | 1620 |
| gaggatcgag | gtgctggata | tacacagca | gctgaagatc | ctggctgact | caatcaatag | 1680 |
| cgaaatcgga | atcctgtgct | ccgccctgca | gaaaatcaaa | tgaatcgtag | atccagacat | 1740 |
| gataagatac | attgatgagt | ttggacaaac | cacaactaga | atgcagtgaa | aaaaatgctt | 1800 |
| tatttgtgaa | atttgtgatg | ctattgcttt | atttgtaacc | attataagct | gcaataaaca | 1860 |
| agttaacaac | aacaattgca | ttcattttat | gtttcaggtt | cagggggagg | tgtgggaggt | 1920 |
| tttttaa | | | | | | 1927 |

<210> SEQ ID NO 49
<211> LENGTH: 2694
<212> TYPE: DNA
<213> ORGANISM: Artificial Sequence
<220> FEATURE:
<223> OTHER INFORMATION: pHMI-hPAH-TC-011

<400> SEQUENCE: 49

```
gtaaatttta tggaatgtga atcataattc aattttttcaa catgcgttag gagggacatt      60
tcaaactctt ttttacccta gactttccta ccatcaccca gagtatccag ccaggagggg     120
aggggctaga gacaccagaa gtttagcagg gaggagggcg tagggattcg gggaatgaag     180
ggatgggatt cagactaggg ccaggaccca gggatggaga gaaagagatg agagtggttt     240
gggggcttgg tgacttagag aacagagctg caggctcaga ggcacacagg agtttctggg     300
ctcaccctgc ccccttccaa cccctcagtt cccatcctcc agcagctgtt tgtgtgctgc     360
ctctgaagtc cacactgaac aaacttcagc ctactcatgt ccctaaaatg gcaaacatt      420
gcaagcagca aacagcaaac acacagccct ccctgcctgc tgaccttgga gctggggcag     480
aggtcagaga cctctctggg cccatgccac ctccaacatc cactcgaccc cttggaattt     540
cggtggagag gagcagaggt tgtcctggcg tggtttaggt agtgtgagag ggcttaaggc     600
tctaacccac tctgatctcc cagggcggca gtaagtcttc agcatcaggc attttggggt     660
gactcagtaa atggtagatc ttgctaccag tggaacagcc actaaggatt ctgcagtgag     720
agcagagggc cagctaagtg gtactctccc agagactgtc tgactcacgc cacccccctcc    780
accttggaca caggacgctg tggttttctga gccaggtaca atgactcctt tcggtaagtg    840
cagtggaagc tgtacactgc ccaggcaaag cgtccgggca gcgtaggcgg gcgactcaga    900
tcccagccag tggacttagc ccctgtttgc tcctccgata actggggtga ccttggttaa     960
tattcaccag cagcctcccc cgttgcccct ctggatccac tgcttaaata cggacgagga    1020
cgctagcgcc ggcaagaggt aagggtttaa gggatggttg gttggtgggg tattaatgtt    1080
taattacctg gagcacctgc ctgaaatcac ttttttttcag gttgggccac catgtccacc    1140
gctgtgctgg agaaccctgg gctggggagg aaactgtcag acttcgggca ggagacttca    1200
tacattgagg ataactgtaa ccagaatggc gccatctctc tgatcttcag cctgaaggag    1260
gaagtgggcg ccctggcaaa ggtgctgcgc ctgtttgagg agaacgacgt gaatctgacc    1320
cacatcgagt cccggccttc tagactgaag aaggacgagt cgagttcct tacccacctg    1380
gataagcggt ccctgccagc cctgacaaac atcatcaaga tcctgaggca cgacatcgga    1440
gcaaccgtgc acgagctgtc tcgggacaag aagaaggata ccgtgccctg gttccctcgg    1500
acaatccagg agctggatag atttgccaac cagatcctgt cttacggagc agagctggac    1560
gcagatcacc ctggcttcaa ggacccagtg tatcgggccc ggagaaagca gtttgccgat    1620
atcgcctaca attataggca cggacagcca atccctcgcg tggagtatat ggaggaggag    1680
aagaagacct ggggcacagt gttcaagacc ctgaagagcc tgtacaagac acacgcctgc    1740
tacgagtata accacatctt ccccctgctg gagaagtatt gtggctttca cgaggacaat    1800
atccctcagc tggaggacgt gagccagttc ctgcagacct gcacaggctt taggctgagg    1860
ccagtggcag gactgctgag ctcccgggac ttcctgggag actggccttt cagagtgttt    1920
cactgcaccc agtacatcag gcacggctcc aagccaatgt atacaccaga gcccgacatc    1980
tgtcacgagc tgctgggcca cgtgcccctg tttagcgata atccttcgc ccagttttcc    2040
caggagatcg gactggcatc tctgggagca cctgacgagt acatcgagaa gctggccacc    2100
```

| | | |
|---|---|---|
| atctattggt tcacagtgga gtttggcctg tgcaagcagg gcgatagcat caaggcctac | 2160 | |
| ggagcaggac tgctgtctag cttcggcgag ctgcagtatt gtctgtccga gaagccaaag | 2220 | |
| ctgctgcccc tggagctgga aagaccgcc atccagaact acaccgtgac agagttccag | 2280 | |
| cccctgtact atgtggccga gtcttttaac gatgccaagg agaaggtgag aaatttcgcc | 2340 | |
| gccacaatcc ctaggccctt cagcgtgcgg tacgacccett atcccagag gatcgaggtg | 2400 | |
| ctggataata cacagcagct gaagatcctg gctgactcaa tcaatagcga aatcggaatc | 2460 | |
| ctgtgctccg ccctgcagaa aatcaaatga atcgtagatc cagacatgat aagatacatt | 2520 | |
| gatgagtttg acaaaccac aactagaatg cagtgaaaaa aatgctttat ttgtgaaatt | 2580 | |
| tgtgatgcta ttgctttatt tgtaaccatt ataagctgca ataaacaagt taacaacaac | 2640 | |
| aattgcattc attttatgtt tcaggttcag ggggaggtgt gggaggtttt ttaa | 2694 | |

<210> SEQ ID NO 50
<211> LENGTH: 3335
<212> TYPE: DNA
<213> ORGANISM: Artificial Sequence
<220> FEATURE:
<223> OTHER INFORMATION: pHMI-hPAH-TC-012

<400> SEQUENCE: 50

| | | |
|---|---|---|
| gtaaatttta tggaatgtga atcataattc aattttttcaa catgcgttag gagggacatt | 60 | |
| tcaaactctt ttttacccta gactttccta ccatcaccca gagtatccag ccaggagggg | 120 | |
| aggggctaga gacaccagaa gtttagcagg gaggagggcg tagggattcg gggaatgaag | 180 | |
| ggatgggatt cagactaggg ccaggaccca gggatggaga gaaagagatg agagtggttt | 240 | |
| gggggcttgg tgacttagag aacagagctg caggctcaga ggcacacagg agtttctggg | 300 | |
| ctcaccctgc cccttccaa ccctcagtt cccatcctcc agcagctgtt tgtgtgctgc | 360 | |
| ctctgaagtc cacactgaac aaacttcagc ctactcatgt ccctaaaatg gcaaacatt | 420 | |
| gcaagcagca aacagcaaac acacagccct cctgcctgc tgaccttgga gctggggcag | 480 | |
| aggtcagaga cctctctggg cccatgccac ctccaacatc cactcgaccc cttggaattt | 540 | |
| cggtggagag gagcagaggt tgtcctggcg tggtttaggt agtgtgagag ggcttaagcg | 600 | |
| tgaggctccg gtgcccgtca gtgggcagag cgcacatcgc ccacagtccc cgagaagttg | 660 | |
| gggggagggg tcggcaattg aaccggtgcc tagagaaggc ggcgcggggt aaactgggaa | 720 | |
| agtgatgtcg tgtactggct ccgcctttt cccgagggtg ggggagaacc gtatataagt | 780 | |
| gcagtagtcg ccgtgaacgt tctttttcgc aacgggtttg ccgccagaac acaggtaagt | 840 | |
| gccgtgtgtg gttcccgcgg gcctggcctc tttacgggtt atggcccttg cgtgccttga | 900 | |
| attacttcca cctggctcca gtacgtgatt cttgatcccg agctggagcc aggggcgggc | 960 | |
| cttgcgcttt aggagcccct tcgcctcgtg cttgagttga ggcctggcct gggcgctggg | 1020 | |
| gccgccgcgt gcgaatctgg tggcaccttc gcgcctgtct cgctgctttc gataagtctc | 1080 | |
| tagccattta aaatttttga tgacctgctg cgacgctttt tttctggcaa gatagtcttg | 1140 | |
| taaatgcggg ccaggatctg cacactggta tttcggtttt tggggccgcg ggcggcgacg | 1200 | |
| gggcccgtgc gtcccagcgc acatgttcgg cgaggcgggg cctgcgagcg cggccaccga | 1260 | |
| gaatcggacg ggggtagtct caagctggcc ggcctgctct ggtgcctggc ctcgcgccgc | 1320 | |
| cgtgtatcgc cccgccctgg gcggcaaggc tggcccggtc ggcaccagtt gcgtgagcgg | 1380 | |
| aaagatggcc gcttccggc cctgctccag ggggctcaaa atggaggacg cggcgctcgg | 1440 | |
| gagagcgggc gggtgagtca cccacacaaa ggaaagggc cttccgtcc tcagccgtcg | 1500 | |

```
cttcatgtga ctccacggag taccgggcgc cgtccaggca cctcgattag ttctggagct    1560
tttggagtac gtcgtctttta ggttgggggg aggggtttta tgcgatggag tttccccaca    1620
ctgagtgggt ggagactgaa gttaggccag cttggcactt gatgtaattc tccttggaat    1680 ttgcccttt tgagtttgga tcttggttca ttctcaagcc tcagacagtg gttcaaagtt    1740
tttttcttcc atttcaggtg tcgtgagcca ccatgtccac cgctgtgctg agaaccctg     1800 ggctggggag gaaactgtca gacttcgggc aggagacttc atacattgag gataactgta    1860
accagaatgg cgccatctct ctgatcttca gcctgaagga ggaagtgggc gccctggcaa    1920
aggtgctgcg cctgtttgag gagaacgacg tgaatctgac ccacatcgag tcccggcctt    1980
ctagactgaa gaaggacgag tacgagttct tacccacct ggataagcgg tccctgccag     2040
ccctgacaaa catcatcaag atcctgaggc acgacatcgg agcaaccgtg cacgagctgt    2100
ctcgggacaa gaagaaggat accgtgccct ggttccctcg gacaatccag gagctggata    2160
gatttgccaa ccagatcctg tcttacggag cagagctgga cgcagatcac cctggcttca    2220
aggacccagt gtatcgggcc cggagaaagc agtttgccga tatcgcctac aattataggc    2280
acggacagcc aatccctcgc gtggagtata tggaggagga gaagaagacc tggggcacag    2340
tgttcaagac cctgaagagc ctgtacaaga cacacgcctg ctacgagtat aaccacatct    2400 tcccctgct ggagaagtat tgtggctttc acgaggacaa tatccctcag ctggaggacg     2460
tgagccagtt cctgcagacc tgcacaggct ttaggctgag gccagtggca ggactgctga    2520
gctcccggga cttcctggga ggactggcct tcagagtgtt tcactgcacc cagtacatca    2580
ggcacggctc caagccaatg tatacaccag agcccgacat ctgtcacgag ctgctgggcc    2640 acgtgccct gtttagcgat agatccttcg cccagttttc ccaggagatc ggactggcat    2700
ctctgggagc acctgacgag tacatcgaga agctggccac catctattgg ttcacagtgg    2760
agtttggcct gtgcaagcag ggcgatagca tcaaggccta cggagcagga ctgctgtcta    2820
gcttcggcga gctgcagtat tgtctgtccg agaagccaaa gctgctgccc ctggagctgg    2880
agaagaccgc catccagaac tacaccgtga cagagttcca gccctgtac tatgtggccg     2940 agtcttttaa cgatgccaag gagaaggtga gaaatttcgc cgccacaatc cctaggccct    3000
tcagcgtgcg gtacgaccct tatacccaga ggatcgaggt gctggataat acacagcagc    3060
tgaagatcct ggctgactca atcaatagcg aaatcggaat cctgtgctcc gccctgcaga    3120
aaatcaaatg aatcgtagat ccagacatga taagatacat tgatgagttt ggacaaacca    3180
caactagaat gcagtgaaaa aaatgcttta tttgtgaaat ttgtgatgct attgcttat     3240 ttgtaaccat tataagctgc aataaacaag ttaacaacaa caattgcatt cattttatgt    3300
ttcaggttca gggggaggtg tgggaggttt tttaa                                3335
```

<210> SEQ ID NO 51
<211> LENGTH: 3783
<212> TYPE: DNA
<213> ORGANISM: Artificial Sequence
<220> FEATURE:
<223> OTHER INFORMATION: pHMI-hPAH-TC-004 transfer genome (from 5' ITR to 3' ITR)

<400> SEQUENCE: 51

```
ttggccactc cctctctgcg cgctcgctcg ctcactgagg ccgggcgacc aaaggtcgcc       60
cgacgcccgg gctttgcccg gcggcctca gtgagcgagc gagcgcgcag agagggagtg       120
gccaactcca tcactagggg ttcctggagg ggtggagtcg tgacgtgaat tacgtcatag      180
```

```
ggttagggag gtcctgcaga tcttcaatat tggccattag ccatattatt cattggttat    240
atagcataaa tcaatattgg ctattggcca ttgcatacgt tgtatctata tcataatatg    300
tacatttata ttggctcatg tccaatatga ccgccatgtt ggcattgatt attgactagt    360
tattaatagt aatcaattac ggggtcatta gttcatagcc catatatgga gttccgcgtt    420
acataactta cggtaaatgg cccgcctggc tgaccgccca acgaccccg cccattgacg     480 tcaataatga cgtatgttcc catagtaacg ccaatagga ctttccattg acgtcaatgg     540
gtggagtatt tacggtaaac tgcccacttg gcagtacatc aagtgtatca tatgccaagt    600
ccgcccccta ttgacgtcaa tgacggtaaa tggcccgcct ggcattatgc ccagtacatg    660
accttacggg actttcctac ttggcagtac atctacgtat tagtcatcgc tattaccatg    720
gtcgaggtga gccccacgtt ctgcttcact ctccccatct cccccccctc ccacccccca    780
attttgtatt tatttatttt ttaattattt tgtgcagcga tggggggggg gggggggggg    840
gggcgcgcgc caggcggggc ggggcggggc gaggggcggg gcggggcgag gcggagaggt    900
gcggcggcag ccaatcagag cggcgcgctc cgaaagtttc cttttatggc gaggcggcgg    960
cggcggcggc cctataaaaa gcgaagcgcg cggcgggcgg gagtcgctgc gacgctgcct   1020
tcgccccgtg ccccgctccg ccgccgcctc gcgccgcccg ccccggctct gactgaccgc   1080
gttactccca caggtgagcg gcgggacgg cccttctcct ccgggctgta attagcgctt    1140
ggtttaatga cggcttgttt cttttctgtg gctgcgtgaa agccttgagg ggctccggga   1200
gggccctttg tgcgggggg agcggctcgg ggggtgcgtg cgtgtgtgtg tgcgtgggga    1260
gcgccgcgtg cggcccgcgc tgcccggcgg ctgtgagcgc tgcgggcgcg gcgcggggct   1320
ttgtgcgctc cgcagtgtgc gcgaggggag cgcggccggg ggcggtgccc cgcggtgcgg   1380 gggggctgc gaggggaaca aaggctgcgt gcggggtgtg tgcgtggggg ggtgagcagg    1440
gggtgtgggc gcggcggtcg ggctgtaacc ccccctgca ccccctccc cgagttgctg    1500 agcacggccc ggcttcgggt gcggggctcc gtacggggcg tggcgcgggg ctcgccgtgc   1560
cgggcggggg gtggcggcag gtggggtgc cgggcggggc ggggccgcct cgggccgggg    1620
agggctcggg ggaggggcgc ggcggccccc ggagcgccgg cggctgtcga ggcgcggcga   1680
gccgcagcca ttgccttta tggtaatcgt gcgagagggc gcaggggactt cctttgtccc   1740 aaatctgtgc ggagccgaaa tctgggaggc gccgccgcac cccctctagc gggcgcgggg   1800
cgaagcggtg cggcgccggc aggaaggaaa tgggcgggga gggccttcgt gcgtcgccgc   1860
gccgccgtcc ccttctccct ctccagcctc ggggctgtcc gcggggggac ggctgccttc   1920 ggggggacg gggcagggcg gggttcggct tctggcgtgt gaccggcggc tctagagcct    1980
ctgctaacca tgttcatgcc ttcttctttt tcctacagct cctgggcaac gtgctggtta   2040
ttgtgctgtc tcatcatttt ggcaaagaat tccgccacca tgtccaccgc tgtgctggag   2100
aaccctgggg tggggaggaa actgtcagac ttcgggcagg agacttcata cattgaggat   2160
aactgtaacc agaatggcgc catctctctg atcttcagcc tgaaggagga agtgggcgcc   2220
ctggcaaagg tgctgcgcct gtttgaggag aacgacgtga atctgaccca catcgagtcc   2280
cggccttcta gactgaagaa ggacgagtac gagttctta cccacctgga taagcggtcc   2340
ctgccagccc tgacaaacat catcaagatc ctgaggcacg acatcggagc aaccgtgcac   2400
gagctgtctc gggacaagaa gaaggatacc gtgcctggt tccctcggac aatccaggag   2460
ctggatagat ttgccaacca gatcctgtct tacggagcag agctggacgc agatcaccct   2520
```

```
ggcttcaagg acccagtgta tcgggcccgg agaaagcagt ttgccgatat cgcctacaat    2580
tataggcacg gacagccaat ccctcgcgtg gagtatatgg aggaggagaa gaagacctgg    2640
ggcacagtgt tcaagaccct gaagagcctg tacaagacac acgcctgcta cgagtataac    2700
cacatcttcc ccctgctgga gaagtattgt ggctttcacg aggacaatat ccctcagctg    2760
gaggacgtga gccagttcct gcagacctgc acaggcttta ggctgaggcc agtggcagga    2820
ctgctgagct cccgggactt cctgggagga ctggccttca gagtgtttca ctgcacccag    2880
tacatcaggc acggctccaa gccaatgtat acaccagagc ccgacatctg tcacgagctg    2940
ctgggccacg tgcccctgtt tagcgataga tccttcgccc agttttccca ggagatcgga    3000
ctggcatctc tgggagcacc tgacgagtac atcgagaagc tggccaccat ctattggttc    3060
acagtggagt ttggcctgtg caagcagggc gatagcatca aggcctacgg agcaggactg    3120
ctgtctagct tcggcgagct gcagtattgt ctgtccgaga gccaaagct gctgcccctg    3180 gagctggaga agaccgccat ccagaactac accgtgacag agttccagcc cctgtactat    3240
gtggccgagt cttttaacga tgccaaggag aaggtgagaa atttcgccgc cacaatccct    3300
aggcccttca gcgtgcggta cgaccctat acccagagga tcgaggtgct ggataataca    3360
cagcagctga agatcctggc tgactcaatc aatagcgaaa tcggaatcct gtgctccgcc    3420
ctgcagaaaa tcaaatgaat cgattctaga gtcgagccgc ggactagtaa cttgtttatt    3480
gcagcttata atggttacaa ataaagcaat agcatcacaa atttcacaaa taaagcattt    3540
ttttcactgc attctagttg tggtttgtcc aaactcatca atgtatctta ggtctagata    3600
cgtagataag tagcatggcg ggttaatcat taactacaag gaaccc ctag tgatggagtt    3660 ggccactccc tctctgcgcg ctcgctcgct cactgaggcc gggcgaccaa aggtcgcccg    3720
acgcccgggc tttgcccggg cggcctcagt gagcgagcga gcgcgcagag agggagtggc    3780
caa                                                                 3783
```

<210> SEQ ID NO 52
<211> LENGTH: 2356
<212> TYPE: DNA
<213> ORGANISM: Artificial Sequence
<220> FEATURE:
<223> OTHER INFORMATION: pHMI-hPAH-TC-025 transfer genome (from 5' ITR to 3' ITR)

<400> SEQUENCE: 52

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggaatt cacgcgtgga    120
tctgaattca attcacgcgt ggtacctccc taaaatgggc aaacattgca agcagcaaac    180
agcaaacaca cagccctccc tgcctgctga ccttggagct ggggcagagg tcagagacct    240
ctctgggccc atgccaccct caacatccac tcgacccctt ggaatttcgg tggagaggag    300
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactgggtg accttggtta    480 atattcacca gcagcctccc ccgttgcccc tctggatcca ctgcttaaat acggacgagg    540
acagggccct gtctcctcag cttcaggcac caccactgac ctgggacagt gaatcctcta    600 aggtaaaatat aaaattttta agtgtataat gtgttaaact actgattcta attgtttctc    660
tcttttagat tccaacccttt ggaactgacc gccaccatgt ccaccgctgt gctggagaac    720
```

-continued

```
cctgggctgg ggaggaaact gtcagacttc gggcaggaga cttcatacat tgaggataac      780
tgtaaccaga atggcgccat ctctctgatc ttcagcctga aggaggaagt gggcgccctg      840
gcaaaggtgc tgcgcctgtt tgaggagaac gacgtgaatc tgacccacat cgagtcccgg      900
ccttctagac tgaagaagga cgagtacgag ttctttaccc acctggataa gcggtccctg      960
ccagccctga caaacatcat caagatcctg aggcacgaca tcggagcaac cgtgcacgag     1020
ctgtctcggg acaagaagaa ggataccgtg ccctggttcc ctcggacaat ccaggagctg     1080
gatagatttg ccaaccagat cctgtcttac ggagcagagc tggacgcaga tcaccctggc     1140
ttcaaggacc cagtgtatcg ggcccggaga aagcagtttg ccgatatcgc ctacaattat     1200
aggcacggac agccaatccc tcgcgtggag tatatggagg aggagaagaa gacctggggc     1260
acagtgttca agaccctgaa gagcctgtac aagacacacg cctgctacga gtataaccac     1320
atcttccccc tgctggagaa gtattgtggc tttcacgagg acaatatccc tcagctggag     1380
gacgtgagcc agttcctgca gacctgcaca ggctttaggc tgaggccagt ggcaggactg     1440
ctgagctccc gggacttcct gggaggactg gccttcagag tgtttcactg cacccagtac     1500
atcaggcacg gctccaagcc aatgtataca ccagagcccg acatctgtca cgagctgctg     1560
ggccacgtgc cctgtttag cgatagatcc ttcgcccagt tttcccagga gatcggactg     1620
gcatctctgg gagcacctga cgagtacatc gagaagctgg ccaccatcta ttggttcaca     1680
gtggagtttg gcctgtgcaa gcagggcgat agcatcaagg cctacggagc aggactgctg     1740
tctagcttcg gcgagctgca gtattgtctg tccgagaagc caaagctgct gccctggag      1800 ctggagaaga ccgccatcca gaactacacc gtgacagagt ccagcccct gtactatgtg     1860 gccgagtctt ttaacgatgc caaggagaag gtgagaaatt cgccgccac aatccctagg     1920 cccttcagcg tgcggtacga cccttatacc cagaggatcg aggtgctgga taatacacag     1980
cagctgaaga tcctggctga ctcaatcaat agcgaaatcg gaatcctgtg ctccgccctg     2040
cagaaaatca aatgaatgct ttatttgtga aatttgtgat gctattgctt tatttgtaac     2100
cattataagc tgcaataaac aagttaacaa caacaattgc attcatttta tgtttcaggt     2160 tcaggggggag gtgtgggagg ttttttaaag catgctgggg agagatcgat ctgaggaacc     2220
cctagtgatg gagttggcca ctccctctct gcgcgctcgc tcgctcactg aggccgggcg     2280
accaaaggtc gcccgacgcc cgggctttgc ccgggcggcc tcagtgagcg agcgagcgcg     2340
cagagaggga gtggcc                                                    2356
```

<210> SEQ ID NO 53
<211> LENGTH: 2323
<212> TYPE: DNA
<213> ORGANISM: Artificial Sequence
<220> FEATURE:
<223> OTHER INFORMATION: pHMI-hPAH-TC-010 transfer genome (from 5' ITR to 3' ITR)

<400> SEQUENCE: 53

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctggagg ggtggagtcg tgacgtgaat tacgtcatag     180
ggttagggag gtcctgcagg gggaggctgc tggtgaatat taaccaaggt cacccccagtt    240 atcggaggag caaacagggg ctaagtccac ctcgagccat ggcgatgctc taatctctct     300
agacaaggtt catatttgta tgggttactt attctctctt tgttgactaa gtcaataatc     360
```

```
agaatcagca ggtttgcagt cagattggca gggataagca gcctagctca ggagaagtga      420
gtataaaagc cccaggctgg gagcagccat cagctagcgc cggcaagagg taagggttta      480
agggatggtt ggttggtggg gtattaatgt ttaattacct ggagcacctg cctgaaatca      540
cttttttcca ggttgggcca ccatgtccac cgctgtgctg gagaaccctg ggctggggag      600
gaaactgtca gacttcgggc aggagacttc atacattgag gataactgta accagaatgg      660
cgccatctct ctgatcttca gcctgaagga ggaagtgggc gccctggcaa aggtgctgcg      720
cctgtttgag gagaacgacg tgaatctgac ccacatcgag tcccggcctt ctagactgaa      780
gaaggacgag tacgagttct ttacccacct ggataagcgg tccctgccag ccctgacaaa      840
catcatcaag atcctgaggc acgacatcgg agcaaccgtg cacgagctgt ctcgggacaa      900
gaagaaggat accgtgccct ggttccctcg gacaatccag gagctggata gatttgccaa      960
ccagatcctg tcttacggag cagagctgga cgcagatcac cctggcttca aggacccagt     1020
gtatcgggcc cggagaaagc agtttgccga tatcgcctac aattataggc acggacagcc     1080
aatccctcgc gtggagtata tggaggagga gaagaagacc tggggcacag tgttcaagac     1140
cctgaagagc ctgtacaaga cacacgcctg ctacgagtat aaccacatct tcccctgct     1200
ggagaagtat tgtggctttc acgaggacaa tatccctcag ctggaggacg tgagccagtt     1260
cctgcagacc tgcacaggct ttaggctgag gccagtggca ggactgctga gctcccggga     1320
cttcctggga ggactggcct tcagagtgtt tcactgcacc cagtacatca ggcacggctc     1380
caagccaatg tataccaccag agcccgacat ctgtcacgag ctgctgggcc acgtgcccct     1440
gtttagcgat agatccttcg cccagttttc ccaggagatc ggactggcat ctctgggagc     1500
acctgacgag tacatcgaga agctggccac catctattgg ttcacagtgg agtttggcct     1560
gtgcaagcag ggcgatagca tcaaggccta cggagcagga ctgctgtcta gcttcggcga     1620
gctgcagtat tgtctgtccg agaagccaaa gctgctgccc ctggagctgg agaagaccgc     1680
catccagaac tacaccgtga cagagttcca gcccctgtac tatgtggccg agtcttttaa     1740
cgatgccaag gagaaggtga gaaatttcgc cgccacaatc cctaggccct tcagcgtgcg     1800
gtacgaccct tatcccaga ggatcgaggt gctggataat acacagcagc tgaagatcct     1860
ggctgactca atcaatagcg aaatcggaat cctgtgctcc gccctgcaga aaatcaaatg     1920
aatcgtagat ccagacatga taagatacat tgatgagttt ggacaaacca caactagaat     1980
gcagtgaaaa aaatgcttta tttgtgaaat ttgtgatgct attgctttat ttgtaaccat     2040
tataagctgc aataaacaag ttaacaacaa caattgcatt cattttatgt ttcaggttca     2100
gggggaggtg tgggaggttt tttaagcttg tttaaacgta cgtagataag tagcatggcg     2160
ggttaatcat taactacaag gaaccccctag tgatggagtt ggccactccc tctctgcgcg     2220
ctcgctcgct cactgaggcc gggcgaccaa aggtcgcccg acgcccgggc tttgcccggg     2280
cggcctcagt gagcgagcga gcgcgcagag agggagtggc caa                        2323
```

<210> SEQ ID NO 54
<211> LENGTH: 3090
<212> TYPE: DNA
<213> ORGANISM: Artificial Sequence
<220> FEATURE:
<223> OTHER INFORMATION: pHMI-hPAH-TC-011 transfer genome (from 5' ITR
    to 3' ITR)

<400> SEQUENCE: 54

```
ttggccactc cctctctgcg cgctcgctcg ctcactgagg ccgggcgacc aaaggtcgcc       60
```

```
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcagt aaattttatg gaatgtgaat cataattcaa ttttttcaaca    240 tgcgttagga gggacatttc aaactctttt ttaccctaga ctttcctacc atcacccaga    300
gtatccagcc aggaggggag gggctagaga caccagaagt ttagcaggga ggagggcgta    360
gggattcggg gaatgaaggg atgggattca gactagggcc aggacccagg gatggagaga    420
aagagatgag agtggtttgg gggcttggtg acttagagaa cagagctgca ggctcagagg    480
cacacaggag tttctgggct caccctgccc ccttccaacc cctcagttcc catcctccag    540
cagctgtttg tgtgctgcct ctgaagtcca cactgaacaa acttcagcct actcatgtcc    600
ctaaaatggg caaacattgc aagcagcaaa cagcaaacac acagccctcc ctgcctgctg    660
accttggagc tggggcagag gtcagagacc tctctgggcc catgccacct ccaacatcca    720 ctcgaccct tggaatttcg gtggagagga gcagaggttg tcctggcgtg gtttaggtag    780
tgtgagaggg cttaaggctc taacccactc tgatctccca gggcggcagt aagtcttcag    840
catcaggcat tttggggtga ctcagtaaat ggtagatctt gctaccagtg aacagccac    900 taaggattct gcagtgagag cagagggcca gctaagtggt actctcccag agactgtctg    960
actcacgcca cccctccac cttggacaca ggacgctgtg gtttctgagc caggtacaat    1020
gactcctttc ggtaagtgca gtggaagctg tacactgccc aggcaaagcg tccgggcagc    1080
gtaggcgggc gactcagatc ccagccagtg gacttagccc ctgtttgctc ctccgataac    1140
tggggtgacc ttggttaata ttcaccagca gcctcccccg ttgcccctct ggatccactg    1200
cttaaatacg gacgaggacg ctagcgccgg caagaggtaa gggtttaagg gatggttggt    1260
tggtggggta ttaatgttta attacctgga gcacctgcct gaaatcactt tttttcaggt    1320
tgggccacca tgtccaccgc tgtgctggag aaccctgggc tggggaggaa actgtcagac    1380
ttcgggcagg agacttcata cattgaggat aactgtaacc agaatggcgc catctctctg    1440
atcttcagcc tgaaggagga agtgggcgcc ctggcaaagg tgctgcgcct gttgaggag     1500 aacgacgtga atctgaccca catcgagtcc cggccttcta gactgaagaa ggacgagtac    1560
gagttcttta cccacctgga taagcggtcc ctgccagccc tgacaaacat catcaagatc    1620
ctgaggcacg acatcggagc aaccgtgcac gagctgtctc gggacaagaa gaaggatacc    1680
gtgccctggt tccctcggac aatccaggag ctggatagat tgccaaccag gatcctgtct    1740
tacggagcag agctggacgc agatcaccct ggcttcaagg acccagtgta tcgggcccgg    1800
agaaagcagt ttgccgatat cgcctacaat tataggcacg acagccaat ccctcgcgtg    1860 gagtatatgg aggaggagaa gaagacctgg ggcacagtgt tcaagaccct gaagagcctg    1920
tacaagacac acgcctgcta cgagtataac cacatcttcc ccctgctgga agtattgt    1980 ggctttcacg aggacaatat ccctcagctg gaggacgtga ccagttcct gcagacctgc    2040 acaggctttta ggctgaggcc agtggcagga ctgctgagct cccgggactt cctgggagga    2100
ctggccttca gagtgtttca ctgcacccag tacatcaggc acggctccaa gccaatgtat    2160
acaccagagc ccgacatctg tcacgagctg ctggcacg tgcccctgtt tagcgataga    2220
tccttcgccc agttttccca ggagatcgga ctggcatctc tgggagcacc tgacgagtac    2280
atcgagaagc tggccaccat ctattggttc acagtggagt ttggcctgtg caagcagggc    2340
gatagcatca aggcctacgg agcaggactg ctgtctagct tcggcgagct gcagtattgt    2400
ctgtccgaga agccaaagct gctgcccctg gagctggaga agaccgccat ccagaactac    2460
```

```
accgtgacag agttccagcc cctgtactat gtggccgagt cttttaacga tgccaaggag    2520
aaggtgagaa atttcgccgc cacaatccct aggcccttca gcgtgcggta cgacccttat    2580
acccagagga tcgaggtgct ggataataca cagcagctga agatcctggc tgactcaatc    2640
aatagcgaaa tcggaatcct gtgctccgcc ctgcagaaaa tcaaatgaat cgtagatcca    2700
gacatgataa gatacattga tgagtttgga caaaccacaa ctagaatgca gtgaaaaaaa    2760
tgctttattt gtgaaatttg tgatgctatt gctttatttg taaccattat aagctgcaat    2820
aaacaagtta acaacaacaa ttgcattcat tttatgtttc aggttcaggg ggaggtgtgg    2880
gaggtttttt aagcttgttt aaacgtacgt agataagtag catggcgggt taatcattaa    2940
ctacaaggaa cccctagtga tggagttggc cactccctct ctgcgcgctc gctcgctcac    3000
tgaggccggg cgaccaaagg tcgcccgacg cccgggcttt gcccgggcgg cctcagtgag    3060
cgagcgagcg cgcagagagg gagtggccaa                                    3090
```

<210> SEQ ID NO 55
<211> LENGTH: 3731
<212> TYPE: DNA
<213> ORGANISM: Artificial Sequence
<220> FEATURE:
<223> OTHER INFORMATION: pHMI-hPAH-TC-012 transfer genome (from 5' ITR to 3' ITR)

<400> SEQUENCE: 55

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180 ggttaggag gtcctgcagt aaattttatg gaatgtgaat cataattcaa tttttcaaca    240
tgcgttagga gggacatttc aaactctttt ttaccctaga cttctctacc atcacccaga    300
gtatccagcc aggaggggag gggctagaga caccagaagt ttagcaggga ggagggcgta    360
gggattcggg gaatgaaggg atgggattca gactagggcc aggacccagg gatggagaga    420
aagagatgag agtggtttgg gggcttggtg acttagagaa cagagctgca ggctcagagg    480
cacacaggag tttctgggct caccctgccc ccttccaacc cctcagttcc catcctccag    540
cagctgtttg tgtgctgcct ctgaagtcca cactgaacaa acttcagcct actcatgtcc    600
ctaaaatggg caaacattgc aagcagcaaa cagcaaacac acagccctcc ctgcctgctg    660
accttggagc tgggggcagag gtcagagacc tctctgggcc catgccacct ccaacatcca    720
ctcgacccct tggaatttcg gtggagagga gcagaggttg tcctggcgtg gtttaggtag    780
tgtgagaggc cttaagcgtg aggctccggt gcccgtcagt gggcagagcg cacatcgccc    840
acagtccccg agaagttggg gggagggggtc ggcaattgaa ccggtgccta gagaaggtgg    900
cgcggggtaa actgggaaag tgatgtcgtg tactggctcc gccttttccc cgagggtggg    960
ggagaaccgt atataagtgc agtagtcgcc gtgaacgttc ttttcgcaa cgggtttgcc   1020 gccagaacac aggtaagtgc cgtgtgtggt tcccgcgggc ctggcctctt tacgggttat   1080
ggcccttgcg tgccttgaat tacttccacc tggctccagt acgtgattct tgatcccgag   1140
ctggagccag ggcgggcct tgcgctttag gagcccttc gcctcgtgct tgagttgagg   1200
cctggcctgg gcgctgggc cgccgcgtgc gaatctggtg gcaccttcgc gcctgtctcg   1260
ctgctttcga taagtctcta gccatttaaa attttttgatg acctgctgcg acgctttttt   1320
tctggcaaga tagtcttgta aatgcgggcc aggatctgca cactggtatt tcggtttttg   1380
```

```
gggccgcggg cggcgacggg gcccgtgcgt cccagcgcac atgttcggcg aggcggggcc    1440
tgcgagcgcg gccaccgaga atcggacggg ggtagtctca agctggccgg cctgctctgg    1500
tgcctggcct cgcgccgccg tgtatcgccc cgccctgggc ggcaaggctg gcccggtcgg    1560
caccagttgc gtgagcggaa agatggccgc ttcccggccc tgctccaggg ggctcaaaat    1620
ggaggacgcg gcgctcggga gagcgggcgg gtgagtcacc cacacaaagg aaaggggcct    1680
ttccgtcctc agccgtcgct tcatgtgact ccacggagta ccgggcgccg tccaggcacc    1740
tcgattagtt ctggagcttt tggagtacgt cgtctttagg ttgggggggag gggttttatg    1800 cgatggagtt tccccacact gagtgggtgg agactgaagt taggccagct tggcacttga    1860
tgtaattctc cttggaattt gccctttttg agtttggatc ttggttcatt ctcaagcctc    1920
agacagtggt tcaaagtttt tttcttccat ttcaggtgtc gtgagccacc atgtccaccg    1980
ctgtgctgga gaaccctggg ctggggagga aactgtcaga cttcgggcag gagacttcat    2040
acattgagga taactgtaac cagaatggcg ccatctctct gatcttcagc ctgaaggagg    2100
aagtgggcgc cctggcaaag gtgctgcgcc tgtttgagga gaacgacgtg aatctgaccc    2160
acatcgagtc ccggccttct agactgaaga aggacgagta cgagttcttt acccacctgg    2220
ataagcggtc cctgccagcc ctgacaaaca tcatcaagat cctgaggcac gacatcggag    2280
caaccgtgca cgagctgtct cgggacaaga agaaggatac cgtgccctgg ttccctcgga    2340
caatccagga gctggataga tttgccaacc agatcctgtc ttacggagca gagctggacg    2400
cagatcaccc tggcttcaag gacccagtgt atcgggcccg gagaaagcag tttgccgata    2460
tcgcctacaa ttataggcac ggacagccaa tccctcgcgt ggagtatatg gaggaggaga    2520
agaagacctg gggcacagtg ttcaagaccc tgaagagcct gtacaagaca cacgcctgct    2580
acgagtataa ccacatcttc ccctgctgg agaagtattg tggctttcac gaggacaata    2640
tccctcagct ggaggacgtg agccagttcc tgcagacctg cacaggcttt aggctgaggc    2700
cagtggcagg actgctgagc tcccgggact tcctgggagg actggccttc agagtgtttc    2760
actgcaccca gtacatcagg cacgctccca gccaatgta tacaccagag cccgacatct    2820
gtcacgagct gctgggccac gtgccctgt ttagcgatag atccttcgcc cagttttccc    2880
aggagatcgg actggcatct ctgggagcac ctgacgagta catcgagaag ctggccacca    2940
tctattggtt cacagtggag tttggcctgt gcaagcaggg cgatagcatc aaggcctacg    3000
gagcaggact gctgtctagc ttcggcgagc tgcagtattg tctgtccgag aagccaaagc    3060 tgctgccct ggagctggag aagaccgcca tccagaacta caccgtgaca gagttccagc    3120
ccctgtacta tgtggccgag tcttttaacg atgccaagga gaaggtgaga aatttcgccg    3180
ccacaatccc taggccctc agcgtgcggt acgacctta cccagagg atcgaggtgc    3240 tggataatac acagcagctg aagatcctgg ctgactcaat caatagcgaa atcggaatcc    3300
tgtgctccgc cctgcagaaa atcaaatgaa tcgtagatcc agacatgata agatacattg    3360
atgagtttgg acaaaccaca actagaatgc agtgaaaaaa atgctttatt tgtgaaattt    3420
gtgatgctat tgctttattt gtaaccatta taagctgcaa taaacaagtt aacaacaaca    3480
attgcattca ttttatgttt caggttcagg ggaggtgtg gagggttttt taagcttgtt    3540
taaacgtacg tagataagta gcatggcggg ttaatcatta actacaagga acccctagtg    3600
atggagttgg ccactcctc tctgcgcgct cgctcgctca ctgaggccgg gcgaccaaag    3660
gtcgcccgac gcccgggctt tgcccgggcg gcctcagtga gcgagcgagc gcgcagagag    3720
```
ggagtggcca a                                                          3731

<210> SEQ ID NO 56
<211> LENGTH: 37
<212> TYPE: DNA
<213> ORGANISM: Artificial Sequence
<220> FEATURE:
<223> OTHER INFORMATION: 37 bp additional 3' ITR sequence from wtAAV2

<400> SEQUENCE: 56
gtagataagt agcatggcgg gttaatcatt aactaca                                37

<210> SEQ ID NO 57
<211> LENGTH: 180
<212> TYPE: DNA
<213> ORGANISM: Artificial Sequence
<220> FEATURE:
<223> OTHER INFORMATION: 3'ITR with additional 37 bp sequence

<400> SEQUENCE: 57
gtagataagt agcatggcgg gttaatcatt aactacaagg aaccccctagt gatggagttg        60 gccactccct ctctgcgcgc tcgctcgctc actgaggccg ggcgaccaaa ggtcgcccga       120
cgcccgggct ttgcccgggc ggcctcagtg agcgagcgag cgcgcagaga gggagtggcc       180

<210> SEQ ID NO 58
<211> LENGTH: 380
<212> TYPE: DNA
<213> ORGANISM: Artificial Sequence
<220> FEATURE:
<223> OTHER INFORMATION: CMV enhancer

<400> SEQUENCE: 58
ggcattgatt attgactagt tattaatagt aatcaattac ggggtcatta gttcatagcc        60
catatatgga gttccgcgtt acataactta cggtaaatgg cccgcctggc tgaccgccca       120 acgaccccg cccattgacg tcaataatga cgtatgttcc catagtaacg ccaatagggga       180 cttttccattg acgtcaatgg gtggagtatt tacggtaaac tgcccacttg gcagtacatc      240
aagtgtatca tatgccaagt ccgcccccta ttgacgtcaa tgacggtaaa tggcccgcct       300
ggcattatgc ccagtacatg accttacggg actttcctac ttggcagtac atctacgtat       360
tagtcatcgc tattaccatg                                                   380

<210> SEQ ID NO 59
<211> LENGTH: 1246
<212> TYPE: DNA
<213> ORGANISM: Artificial Sequence
<220> FEATURE:
<223> OTHER INFORMATION: CBA promoter

<400> SEQUENCE: 59
tcgaggtgag ccccacgttc tgcttcactc tccccatctc ccccccctcc ccacccccaa        60
ttttgtattt atttattttt taattatttt gtgcagcgat gggggcgggg ggggggggg       120 ggcgcgcgcc aggcggggcg ggcgggggcg aggggcgggg cggggcgagg cggagaggtg       180
cggcggcagc caatcagagc ggcgcgctcc gaaagtttcc ttttatggcg aggcggcggc       240
ggcggcggcc ctataaaaag cgaagcgcgc ggcgggcggg agtcgctgcg cgctgccttc       300
gccccgtgcc ccgctccgcc gccgcctcgc gccgcccgcc ccggctctga ctgaccgcgt       360
tactcccaca ggtgagcggg cgggacggcc cttctcctcc gggctgtaat tagcgcttgg       420
tttaatgacg gcttgttttct tttctgtggc tgcgtgaaag ccttgagggg ctccgggagg       480

| | |
|---|---|
| gcccttttgtg cggggggagc ggctcggggg gtgcgtgcgt gtgtgtgtgc gtggggagcg | 540 |
| ccgcgtgcgg ctccgcgctg cccggcggct gtgagcgctg cgggcgcggc gcggggcttt | 600 |
| gtgcgctccg cagtgtgcgc gaggggagcg cggccggggg cggtgccccg cggtgcgggg | 660 |
| ggggctgcga ggggaacaaa ggctgcgtgc ggggtgtgtg cgtgggggggg tgagcagggg | 720 |
| gtgtgggcgc gtcggtcggg ctgcaacccc ccctgcaccc ccctccccga gttgctgagc | 780 |
| acggcccggt tcgggtgcg gggctccgta cggggcgtgg cgcggggctc gccgtgccgg | 840 |
| gcggggggtg gcggcaggtg ggggtgccgg gcggggcggg gccgcctcgg gccggggagg | 900 |
| gctcggggga ggggcgcggc ggcccccgga gcgccgcgg ctgtcgaggc gcggcgagcc | 960 |
| gcagccattg cctttttatgg taatcgtgcg agagggcgca gggacttcct ttgtcccaaa | 1020 |
| tctgtgcgga gccgaaatct gggaggcgcc gccgcacccc ctctagcggg cgcggggcga | 1080 |
| agcggtgcgg cgccggcagg aaggaaatgg gcggggaggg ccttcgtgcg tcgccgcgcc | 1140 |
| gccgtcccct tctccctctc cagcctcggg gctgtccgcg ggggacggc tgccttcggg | 1200 |
| ggggacgggg cagggcgggg ttcggcttct ggcgtgtgac cggcgg | 1246 |

<210> SEQ ID NO 60
<211> LENGTH: 95
<212> TYPE: DNA
<213> ORGANISM: Artificial Sequence
<220> FEATURE:
<223> OTHER INFORMATION: rabbit beta-globin element

<400> SEQUENCE: 60

| | |
|---|---|
| cctctgctaa ccatgttcat gccttcttct tttcctaca gctcctgggc aacgtgctgg | 60 |
| ttattgtgct gtctcatcat tttggcaaag aattc | 95 |

<210> SEQ ID NO 61
<211> LENGTH: 3301
<212> TYPE: DNA
<213> ORGANISM: Artificial Sequence
<220> FEATURE:
<223> OTHER INFORMATION: pHMI-hPAH-TC-009 transfer genome

<400> SEQUENCE: 61

| | |
|---|---|
| tggcattgat tattgactag ttattaatag taatcaatta cggggtcatt agttcatagc | 60 |
| ccatatatgg agttccgcgt tacataactt acggtaaatg gcccgcctgg ctgaccgccc | 120 |
| aacgaccccc gcccattgac gtcaataatg acgtatgttc ccatagtaac gccaataggg | 180 |
| actttccatt gacgtcaatg ggtggagtat ttacggtaaa ctgcccactt ggcagtacat | 240 |
| caagtgtatc atatgccaag tccgccccct attgacgtca atgacggtaa atggcccgcc | 300 |
| tggcattatg cccagtacat gaccttacgg gactttccta cttggcagta catctacgta | 360 |
| ttagtcatcg ctattaccat ggtcgaggtg agccccacgt tctgcttcac tctccccatc | 420 |
| tcccccccct cccacccccc aattttgtat ttatttattt ttaattatt ttgtgcagcg | 480 |
| atgggggcgg gggggggggg gggcgcgcg ccaggcgggg cggggcgggg cgaggggcgg | 540 |
| ggcggggcga ggcggagagg tgcggcggca gccaatcaga gcggcgcgct ccgaaagttt | 600 |
| ccttttatgg cgaggcggcg gcggcggcgg ccctataaaa agcgaagcgc gcggcgggcg | 660 |
| ggagtcgctg cgcgctgcct tcgccccgtg cccgctccg ccgccgcctc gcgccgcccg | 720 |
| ccccggctct gactgaccgc gttactccca caggtgagcg gcgggacgg cccttctcct | 780 |
| ccgggctgta attagcgctt ggtttaatga cggcttgttt cttttctgtg gctgcgtgaa | 840 |

```
agccttgagg ggctccggga gggccctttg tgcgggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct tgtgcgctc cgcagtgtgc gcgaggggag cgcggccggg   1020
ggcggtgccc cgcggtgcgg gggggctgc gaggggaaca aaggctgcgt gcggggtgtg   1080
tgcgtggggg ggtgagcagg gggtgtgggc gcgtcggtcg ggctgcaacc ccccctgcac   1140
cccctcccc gagttgctga gcacggcccg gcttcgggtg cggggctccg tacgggcgt    1200
ggcgcgggc tcgccgtgcc gggcgggggg tggcggcagg tgggggtgcc gggcggggcg   1260
gggccgcctc gggccgggga gggctcgggg gaggggcgcg gcggccccg gagcgccggc    1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg gggggacgg ggcaggcgg ggttcggctt ctggcgtgtg   1620
accggcggct ctagagcctc tgctaaccat gttcatgcct tcttcttttt cctacagctc   1680
ctgggcaacg tgctggttat tgtgctgtct catcattttg gcaaagaatt ccgccaccat   1740
gtccaccgct gtgctggaga accctgggct ggggaggaaa ctgtcagact tcggcagga    1800
gacttcatac attgaggata actgtaacca gaatggcgcc atctctctga tcttcagcct   1860
gaaggaggaa gtgggcgccc tggcaaaggt gctgcgcctg tttgaggaga cgacgtgaa    1920
tctgacccac atcgagtccc ggccttctag actgaagaag gacgagtacg agttctttac   1980
ccacctggat aagcggtccc tgccagcccc tgacaaacatc atcaagatcc tgaggcacga   2040
catcggagca accgtgcacg agctgtctcg ggacaagaag aaggataccg tgccctggtt   2100
ccctcggaca atccaggagc tggatagatt tgccaaccag atcctgtctt acggagcaga   2160
gctgacgca gatcaccctg gcttcaagga cccagtgtat cgggcccgga gaaagcagtt   2220
tgccgatatc gcctacaatt ataggcacgg acagccaatc cctcgcgtgg agtatatgga   2280
ggaggagaag aagacctggg gcacagtgtt caagaccctg aagagcctgt acaagacaca   2340
cgcctgctac gagtataacc acatcttccc cctgctggag aagtattgtg ctttcacga    2400
ggacaatatc cctcagctgg aggacgtgag ccagttcctg cagacctgca caggcttta    2460
gctgaggcca gtggcaggac tgctgagctc ccgggacttc ctgggaggac tggccttcag   2520
agtgtttcac tgcacccagt acatcaggca cggctccaag ccaatgtata caccagagcc   2580
cgacatctgt cacgagctgc tgggccacgt gcccctgttt agcgatagat ccttcgccca   2640
gttttcccag gagatcggac tggcatctct gggagcacct gacgagtaca tcgagaagct   2700
ggccaccatc tattggttca cagtggagtt tggcctgtgc aagcagggcg atagcatcaa   2760
ggcctacgga gcaggactgc tgtctagctt cggcgagctg cagtattgtc tgtccgagaa   2820
gccaaagctg ctgcccctgg agctggagaa gaccgccatc cagaactaca ccgtgacaga   2880
gttccagccc ctgtactatg tggccgagtc tttaacgat gccaaggaga aggtgagaaa   2940
tttcgccgcc acaatcccta ggcccttcag cgtgcggtac gacccttata cccagaggat   3000
cgaggtgctg gataatacac agcagctgaa gatcctggct gactcaatca atagcgaaat   3060
cggaatcctg tgctccgccc tgcagaaaat caaatgaatc gtagatccag acatgataag   3120
atacattgat gagtttggac aaaccacaac tagaatgcag tgaaaaaat gctttatttg   3180
tgaaatttgt gatgctattg ctttatttgt aaccattata agctgcaata aacaagttaa   3240
```

```
caacaacaat tgcattcatt ttatgtttca ggttcagggg gaggtgtggg aggtttttta    3300
a                                                                   3301
```

<210> SEQ ID NO 62
<211> LENGTH: 3701
<212> TYPE: DNA
<213> ORGANISM: Artificial Sequence
<220> FEATURE:
<223> OTHER INFORMATION: pHMI-hPAH-TC-009 transfer genome

<400> SEQUENCE: 62

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcaga tctggcattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtccgcccc ctattgacgt    480
caatgacggt aaatggcccg cctggcatta tgcccagtac atgaccttac gggactttcc    540
tacttggcag tacatctacg tattagtcat cgctattacc atggtcgagg tgagccccac    600
gttctgcttc actctcccca tctcccccccc ctccccaccc ccaattttgt atttatttat    660
tttttaatta ttttgtgcag cgatggggc ggggggggg gggggcgcg cgccaggcgg      720 ggcggggcgg ggcgagggc ggggcggggc gaggcggaga ggtgcggcgg cagccaatca    780
gagcggcgcg ctccgaaagt ttcctttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg ggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca ggggtgtgg gcgcgtcggt   1320 cgggctgcaa cccccctgc accccctcc ccgagttgct gagcacggcc cggcttcggg   1380 tgcgggctc cgtacgggc gtggcgcggg gctcgccgtg ccgggcgggg ggtggcggca   1440
ggtgggggtg ccgggcgggg cggggccgcc tcgggccggg gagggctcgg ggagggggcg   1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca cccccctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggac ggggcagggc   1800 ggggttcggc ttctgcgtg tgaccggcgg ctctagagcc tctgctaacc atgttcatgc   1860
cttcttcttt ttcctacagc tcctgggcaa cgtgctggtt attgtgctgt ctcatcattt   1920
```

```
tggcaaagaa ttccgccacc atgtccaccg ctgtgctgga gaaccctggg ctggggagga    1980
aactgtcaga cttcgggcag gagacttcat acattgagga taactgtaac cagaatggcg    2040
ccatctctct gatcttcagc ctgaaggagg aagtgggcgc cctggcaaag gtgctgcgcc    2100
tgtttgagga gaacgacgtg aatctgaccc acatcgagtc ccggccttct agactgaaga    2160
aggacgagta cgagttcttt acccacctgg ataagcggtc cctgccagcc ctgacaaaca    2220
tcatcaagat cctgaggcac gacatcggag caaccgtgca cgagctgtct cgggacaaga    2280
agaaggatac cgtgccctgg ttccctcgga caatccagga gctggataga tttgccaacc    2340
agatcctgtc ttacggagca gagctggacg cagatcaccc tggcttcaag gacccagtgt    2400
atcgggcccg gagaaagcag tttgccgata tcgcctacaa ttataggcac ggacagccaa    2460
tccctcgcgt ggagtatatg gaggaggaga agaagacctg gggcacagtg ttcaagaccc    2520
tgaagagcct gtacaagaca cacgcctgct acgagtataa ccacatcttc ccctgctgg    2580 agaagtattg tggcttttcac gaggacaata tccctcagct ggaggacgtg agccagttcc    2640
tgcagacctg cacaggcttt aggctgaggc cagtggcagg actgctgagc tcccgggact    2700
tcctgggagg actggccttc agagtgtttc actgcaccca gtacatcagg cacggctcca    2760
agccaatgta taccagagag cccgacatct gtcacgagct gctgggccac gtgcccctgt    2820
ttagcgatag atccttcgcc cagttttccc aggagatcgg actggcatct ctgggagcac    2880
ctgacgagta catcgagaag ctggccacca tctattggtt cacagtggag tttggcctgt    2940
gcaagcaggg cgatagcatc aaggcctacg agcaggact gctgtctagc ttcggcgagc    3000
tgcagtattg tctgtccgag aagccaaagc tgctgcccct ggagctggag aagaccgcca    3060
tccagaacta caccgtgaca gagttccagc ccctgtacta tgtggccgag tcttttaacg    3120
atgccaagga gaaggtgaga aatttcgccg ccacaatccc taggcccttc agcgtgcggt    3180 acgacccta tacccagagg atcgaggtgc tggataatac acagcagctg aagatcctgg    3240
ctgactcaat caatagcgaa atcggaatcc tgtgctccgc cctgcagaaa atcaaatgaa    3300
tcgtagatcc agacatgata agatacattg atgagtttgg acaaaccaca actagaatgc    3360
agtgaaaaaa atgctttatt tgtgaaattt gtgatgctat tgctttattt gtaaccatta    3420
taagctgcaa taaacaagtt aacaacaaca attgcattca ttttatgttt caggttcagg    3480
gggaggtgtg ggaggttttt taagcttgtt taaacgtacg tagataagta gcatggcggg    3540
ttaatcatta actacaagga accctagtg atggagttgg ccactccctc tctgcgcgct    3600
cgctcgctca ctgaggccgg gcgaccaaag gtcgcccgac gcccgggctt tgcccgggcg    3660
gcctcagtga gcgagcgagc gcgcagagag ggagtggcca a               3701

<210> SEQ ID NO 63
<211> LENGTH: 1061
<212> TYPE: DNA
<213> ORGANISM: Artificial Sequence
<220> FEATURE:
<223> OTHER INFORMATION: CASI promoter region

<400> SEQUENCE: 63
tagggaggtc ctgcacgtta cataacttac ggtaaatggc ccgcctggct gaccgcccaa      60 cgaccccgc ccattgacgt caataatgac gtatgttccc atagtaacgc caatagggac     120
tttccattga cgtcaatggg tggagtattt acggtaaact gcccacttgg cagtacatca     180
agtgtatcat atgccaagta cgccccctat tgacgtcaat gacggtaaat ggcccgcctg     240
gcattatgcc cagtacatga ccttatggga ctttcctact tggcagtaca tctacgtatt     300
```

```
agtcatcgct attaccatgg tcgaggtgag ccccacgttc tgcttcactc tccccatctc      360 cccccctcc ccacccccaa ttttgtattt atttattttt taattatttt gtgcagcgat      420
gggggcgggg ggggggggg gcgcgcgcca ggcggggcgg ggcggggcga ggggcggggc      480
ggggcgaggc ggagaggtgc ggcggcagcc aatcagagcg gcgcgctccg aaagtttcct      540
tttatggcga ggcggcggcg gcggcggccc tataaaaagc gaagcgcgcg gcgggcggga      600
gtcgctgcgc gctgccttcg ccccgtgccc cgctccgccg ccgcctcgcg ccgcccgccc      660
cggctctgac tgaccgcgtt actaaaacag gtaagtccgg cctccgcgcc gggttttggc      720
gcctcccgcg ggcgccccc tcctcacggc gagcgctgcc acgtcagacg aagggcgcag      780
cgagcgtcct gatccttccg cccggacgct caggacagcg gcccgctgct cataagactc      840
ggccttagaa ccccagtatc agcagaagga catttttagga cgggacttgg gtgactctag      900
ggcactggtt ttctttccag agagcggaac aggcgaggaa aagtagtccc ttctcggcga      960
ttctgcggag ggatctccgt ggggcggtga acgccgatga tgcctctact aaccatgttc    1020
atgttttctt ttttttttcta caggtcctgg gtgacgaaca g                       1061

<210> SEQ ID NO 64
<211> LENGTH: 2630
<212> TYPE: DNA
<213> ORGANISM: Artificial Sequence
<220> FEATURE:
<223> OTHER INFORMATION: pHMI-hPAH-TC-013 transfer genome

<400> SEQUENCE: 64
tagggaggtc ctgcacgtta cataacttac ggtaaatggc ccgcctggct gaccgcccaa       60
cgacccccgc ccattgacgt caataatgac gtatgttccc atagtaacgc caatagggac      120
tttccattga cgtcaatggg tggagtattt acggtaaact gcccacttgg cagtacatca      180
agtgtatcat atgccaagta cgccccctat tgacgtcaat gacggtaaat ggcccgcctg      240
gcattatgcc cagtacatga ccttatggga ctttcctact tggcagtaca tctacgtatt      300
agtcatcgct attaccatgg tcgaggtgag ccccacgttc tgcttcactc tccccatctc      360 cccccctcc ccacccccaa ttttgtattt atttattttt taattatttt gtgcagcgat      420
gggggcgggg ggggggggg gcgcgcgcca ggcggggcgg ggcggggcga ggggcggggc      480
ggggcgaggc ggagaggtgc ggcggcagcc aatcagagcg gcgcgctccg aaagtttcct      540
tttatggcga ggcggcggcg gcggcggccc tataaaaagc gaagcgcgcg gcgggcggga      600
gtcgctgcgc gctgccttcg ccccgtgccc cgctccgccg ccgcctcgcg ccgcccgccc      660
cggctctgac tgaccgcgtt actaaaacag gtaagtccgg cctccgcgcc gggttttggc      720
gcctcccgcg ggcgccccc tcctcacggc gagcgctgcc acgtcagacg aagggcgcag      780
cgagcgtcct gatccttccg cccggacgct caggacagcg gcccgctgct cataagactc      840
ggccttagaa ccccagtatc agcagaagga catttttagga cgggacttgg gtgactctag      900
ggcactggtt ttctttccag agagcggaac aggcgaggaa aagtagtccc ttctcggcga      960
ttctgcggag ggatctccgt ggggcggtga acgccgatga tgcctctact aaccatgttc    1020
atgttttctt ttttttttcta caggtcctgg gtgacgaaca ggccaccatg tccaccgctg    1080
tgctggagaa ccctgggctg gggaggaaac tgtcagactt cgggcaggag acttcataca    1140
ttgaggataa ctgtaaccag aatggcgcca tctctctgat cttcagcctg aaggaggaag    1200
tgggcgccct ggcaaaggtg ctgcgcctgt ttgaggagaa cgacgtgaat ctgacccaca    1260
```

```
tcgagtcccg gccttctaga ctgaagaagg acgagtacga gttctttacc cacctggata    1320
agcggtccct gccagccctg acaaacatca tcaagatcct gaggcacgac atcggagcaa    1380
ccgtgcacga gctgtctcgg acaagaaga aggataccgt gccctggttc cctcggacaa     1440
tccaggagct ggatagattt gccaaccaga tcctgtctta cggagcagag ctggacgcag    1500
atcaccctgg cttcaaggac ccagtgtatc gggcccggag aaagcagttt gccgatatcg    1560
cctacaatta taggcacgga cagccaatcc ctcgcgtgga gtatatggag gaggagaaga    1620
agacctgggg cacagtgttc aagaccctga gagcctgta caagacacac gcctgctacg     1680
agtataacca catcttcccc ctgctggaga agtattgtgg cttttcacgag acaatatcc     1740 ctcagctgga ggacgtgagc cagttcctgc agacctgcac aggctttagg ctgaggccag    1800
tggcaggact gctgagctcc cgggacttcc tgggaggact ggccttcaga gtgtttcact    1860
gcacccagta catcaggcac ggctccaagc caatgtatac accagagccc gacatctgtc    1920
acgagctgct gggccacgtg cccctgttta gcgatagatc cttcgcccag ttttcccagg    1980
agatcggact ggcatctctg gagcacctg acgagtacat cgagaagctg gccaccatct    2040
attggttcac agtggagttt ggcctgtgca agcagggcga tagcatcaag gcctacggag    2100
caggactgct gtctagcttc ggcgagctgc agtattgtct gtccgagaag ccaaagctgc    2160
tgcccctgga gctggagaag accgccatcc agaactacac cgtgacagag ttccagcccc    2220
tgtactatgt ggccgagtct tttaacgatg ccaaggagag ggtgagaaat ttcgccgcca    2280
caatccctag gcccttcagc gtgcggtacg acccttatac ccagaggatc gaggtgctgg    2340
ataatacaca gcagctgaag atcctggctg actcaatcaa tagcgaaatc ggaatcctgt    2400
gctccgccct gcagaaaatc aaatgaatcg tagatccaga catgataaga tacattgatg    2460
agtttggaca aaccacaact agaatgcagt gaaaaaaatg ctttatttgt gaaatttgtg    2520
atgctattgc tttatttgta accattataa gctgcaataa acaagttaac aacaacaatt    2580
gcattcattt tatgtttcag gttcagggg aggtgtggga ggttttttaa                2630

<210> SEQ ID NO 65
<211> LENGTH: 3011
<212> TYPE: DNA
<213> ORGANISM: Artificial Sequence
<220> FEATURE:
<223> OTHER INFORMATION: pHMI-hPAH-TC-013 transfer genome

<400> SEQUENCE: 65
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag     180
ggttagggag gtcctgcacg ttacataact tacggtaaat ggcccgcctg gctgaccgcc     240
caacgacccc cgcccattga cgtcaataat gacgtatgtt cccatagtaa cgccaatagg     300
gactttccat tgacgtcaat gggtggagta tttacgtaa actgcccact ggcagtaca      360 tcaagtgtat catatgccaa gtacgcccc tattgacgtc aatgacggta aatggcccgc     420
ctggcattat gcccagtaca tgaccttatg gactttcct acttggcagt acatctacgt     480
attagtcatc gctattacca tggtcgaggt gagccccacg ttctgcttca ctctccccat     540
ctcccccccc tcccacccc caatttgta tttattat ttttaattat tttgtgcagc       600 gatggggcg ggggggggg ggggcgcgcg ccaggcgggg cggggcgggg cgaggggcgg      660
ggcggggcga ggcggagagg tgcggcggca gccaatcaga gcggcgcgct ccgaaagttt     720
```

```
ccttttatgg cgaggcggcg gcggcggcgg ccctataaaa agcgaagcgc gcggcgggcg      780
ggagtcgctg cgcgctgcct tcgccccgtg ccccgctccg ccgccgcctc gcgccgcccg      840
ccccggctct gactgaccgc gttactaaaa caggtaagtc cggcctccgc gccgggtttt      900
ggcgcctccc gcgggcgccc ccctcctcac ggcgagcgct gccacgtcag acgaagggcg      960
cagcgagcgt cctgatcctt ccgcccggac gctcaggaca gcggcccgct gctcataaga     1020
ctcggcctta aaccccagt atcagcagaa ggacatttta ggacgggact tgggtgactc     1080
tagggcactg gttttctttc cagagagcgg aacaggcgag gaaaagtagt cccttctcgg     1140
cgattctgcg gagggatctc cgtggggcgg tgaacgccga tgatgcctct actaaccatg     1200
ttcatgtttt cttttttttt ctacaggtcc tgggtgacga acaggccacc atgtccaccg     1260
ctgtgctgga aaccctgggg ctggggagga aactgtcaga cttcgggcag gagacttcat     1320
acattgagga taactgtaac cagaatggcg ccatctctct gatcttcagc ctgaaggagg     1380
aagtgggcgc cctggcaaag gtgctgcgcc tgtttgagga aacgacgtg aatctgaccc     1440 acatcgagtc ccggccttct agactgaaga aggacgagta cgagttcttt acccacctgg     1500
ataagcggtc cctgccagcc ctgacaaaca tcatcaagat cctgaggcac gacatcggag     1560
caaccgtgca cgagctgtct cgggacaaga agaaggatac cgtgccctgg ttccctcgga     1620
caatccagga gctggataga tttgccaacc agatcctgtc ttacggagca gagctggacg     1680
cagatcaccc tggcttcaag gacccagtgt atcgggcccg gagaaagcag tttgccgata     1740
tcgcctacaa ttataggcac ggacagccaa tccctcgcgt ggagtatatg gaggaggaga     1800
agaagacctg gggcacagtg ttcaagaccc tgaagagcct gtacaagaca cacgcctgct     1860
acgagtataa ccacatcttc ccctgctgg agaagtattg tggctttcac gaggacaata     1920
tccctcagct ggaggacgtg agccagttcc tgcagacctg cacaggcttt aggctgaggc     1980
cagtggcagg actgctgagc tcccgggact tcctgggagg actggccttc agagtgtttc     2040
actgcaccca gtacatcagg cacggctcca agccaatgta taccagagag cccgacatct     2100
gtcacgagct gctgggccac gtgccccctgt ttagcgatag atccttcgcc cagttttccc     2160
aggagatcgg actggcatct ctgggagcac ctgacgagta catcgagaag ctggccacca     2220
tctattggtt cacagtggag tttggcctgt gcaagcaggg cgatagcatc aaggcctacg     2280
gagcaggact gctgtctagc ttcggcgagc tgcagtattg tctgtccgag aagccaaagc     2340
tgctgcccct ggagctggag aagaccgcca tccagaacta caccgtgaca gagttccagc     2400
ccctgtacta tgtggccgag tcttttaacg atgccaagga gaaggtgaga aatttcgccg     2460
ccacaatccc taggcccttc agcgtgcggt acgacccctta tacccagagg atcgaggtgc     2520
tggataatac acagcagctg aagatcctgg ctgactcaat caatagcgaa atcggaatcc     2580
tgtgctccgc cctgcagaaa atcaaatgaa tcgtagatcc agacatgata agatacattg     2640
atgagtttgg acaaaccaca actagaatgc agtgaaaaaa atgctttatt tgtgaaattt     2700
gtgatgctat tgctttattt gtaaccatta taagctgcaa taaacaagtt aacaacaaca     2760
attgcattca ttttatgttt caggttcagg gggaggtgtg ggaggttttt taagcttgtt     2820
taaacgtacg tagataagta gcatggcggg ttaatcatta actacaagga acccctagtg     2880
atggagttgg ccactccctc tctgcgcgct cgctcgctca ctgaggccgg gcgaccaaag     2940
gtcgcccgac gcccgggctt tgcccggggcg gcctcagtga gcgagcgagc gcgcagagag     3000
ggagtggcca a                                                        3011
```

<210> SEQ ID NO 66
<211> LENGTH: 913
<212> TYPE: DNA
<213> ORGANISM: Artificial Sequence
<220> FEATURE:
<223> OTHER INFORMATION: hAAT promoter region

<400> SEQUENCE: 66

```
tagggaggtc ctgcacagaa ggggaggagg gggcagcagc tgtctgacca ctgttggtct      60
tgcaacttgt gtccccaggt taattttaa aaagcagtca aaagtccaag tggcccttgg     120
cagcatttac tctctctgtt tgctctggtt aataatctca ggagcacaaa cattcctgga     180
ggcaggagaa gaaatcaaca tcctggactt atcctctggg cctctcccca cccccaggat     240
tgtaactgaa atgcttcact ggtgctcctt ttgttttaag gcattggatc ttcatagcta     300
ctgatcgtgc ccaagcacac agtatctgca gcaaccactt aggcctccag gaatgtggtg     360
accattgacc ctaattcatt ccccttcatg gatcctatgt aaccatcctc caaaagagc     420
tttcgcaaac tcaaataaac acaggaaagg aagaccttct tatctttgag agtatatgtt     480
tagccctata gctctaaccc actctgatct cccagggcgg cagtaagtct tcagcatcag     540
gcattttggg gtgactcagt aaatggtaga tcttgctacc agtggaacag ccactaagga     600
ttctgcagtg agagcagagg gccagctaag tggtactctc ccagagactg tctgactcac     660
gccaccccct ccaccttgga cacaggacgc tgtggtttct gagccaggta caatgactcc     720
tttcggtaag tgcagtggaa gctgtacact gcccaggcaa agcgtccggg cagcgtaggc     780
gggcgactca gatcccagcc agtggactta gcccctgttt gctcctccga taactggggt     840
gaccttggtt aatattcacc agcagcctcc cccgttgccc ctctggatcc actgcttaaa     900
tacggacgag gac                                                        913
```

<210> SEQ ID NO 67
<211> LENGTH: 2600
<212> TYPE: DNA
<213> ORGANISM: Artificial Sequence
<220> FEATURE:
<223> OTHER INFORMATION: pHMI-hPAH-TC-017 transfer genome

<400> SEQUENCE: 67

```
tagggaggtc ctgcacagaa ggggaggagg gggcagcagc tgtctgacca ctgttggtct      60
tgcaacttgt gtccccaggt taattttaa aaagcagtca aaagtccaag tggcccttgg     120
cagcatttac tctctctgtt tgctctggtt aataatctca ggagcacaaa cattcctgga     180
ggcaggagaa gaaatcaaca tcctggactt atcctctggg cctctcccca cccccaggat     240
tgtaactgaa atgcttcact ggtgctcctt ttgttttaag gcattggatc ttcatagcta     300
ctgatcgtgc ccaagcacac agtatctgca gcaaccactt aggcctccag gaatgtggtg     360
accattgacc ctaattcatt ccccttcatg gatcctatgt aaccatcctc caaaagagc     420
tttcgcaaac tcaaataaac acaggaaagg aagaccttct tatctttgag agtatatgtt     480
tagccctata gctctaaccc actctgatct cccagggcgg cagtaagtct tcagcatcag     540
gcattttggg gtgactcagt aaatggtaga tcttgctacc agtggaacag ccactaagga     600
ttctgcagtg agagcagagg gccagctaag tggtactctc ccagagactg tctgactcac     660
gccaccccct ccaccttgga cacaggacgc tgtggtttct gagccaggta caatgactcc     720
tttcggtaag tgcagtggaa gctgtacact gcccaggcaa agcgtccggg cagcgtaggc     780
gggcgactca gatcccagcc agtggactta gcccctgttt gctcctccga taactggggt     840
```

```
gaccttggtt aatattcacc agcagcctcc cccgttgccc ctctggatcc actgcttaaa    900
tacggacgag gacgctagcg ccggcaagag gtaagggttt aagggatggt tggttggtgg    960
ggtattaatg tttaattacc tggagcacct gcctgaaatc actttttttc aggttggtta   1020
attaaggatc cgccaccatg tccaccgctg tgctggagaa ccctgggctg gggaggaaac   1080
tgtcagactt cgggcaggag acttcataca ttgaggataa ctgtaaccag aatggcgcca   1140
tctctctgat cttcagcctg aaggaggaag tgggcgccct ggcaaaggtg ctgcgcctgt   1200
ttgaggagaa cgacgtgaat ctgacccaca tcgagtcccg gccttctaga ctgaagaagg   1260
acgagtacga gttctttacc cacctggata gcggtccct gccagccctg acaaacatca    1320
tcaagatcct gaggcacgac atcggagcaa ccgtgcacga gctgtctcgg gacaagaaga   1380
aggataccgt gcctggttc cctcggacaa tccaggagct ggatagattt gccaaccaga   1440
tcctgtctta cggagcagag ctggacgcag atcaccctgg cttcaaggac ccagtgtatc   1500
gggcccggag aaagcagttt gccgatatcg cctacaatta taggcacgga cagccaatcc   1560
ctcgcgtgga gtatatggag gaggagaaga agacctgggg cacagtgttc aagaccctga   1620
agagcctgta caagacacac gcctgctacg agtataacca catcttcccc ctgctggaga   1680
agtattgtgg ctttcacgag gacaatatcc ctcagctgga ggacgtgagc cagttcctgc   1740
agacctgcac aggctttagg ctgaggccag tggcaggact gctgagctcc cgggacttcc   1800
tgggaggact ggccttcaga gtgtttcact gcacccagta catcaggcac ggctccaagc   1860
caatgtatac accagagccc gacatctgtc acgagctgct gggccacgtg cccctgttta   1920
gcgatagatc cttcgcccag ttttcccagg agatcggact ggcatctctg ggagcacctg   1980
acgagtacat cgagaagctg gccaccatct attggttcac agtggagttt ggcctgtgca   2040
agcagggcga tagcatcaag gcctacggag caggactgct gtctagcttc ggcgagctgc   2100
agtattgtct gtccgagaag ccaaagctgc tgcccctgga gctggagaag accgccatcc   2160
agaactacac cgtgacagag ttccagcccc tgtactatgt ggccgagtct tttaacgatg   2220
ccaaggagaa ggtgagaaat ttcgccgcca caatccctag gccccttcagc gtgcggtacg   2280 acccttatac ccagaggatc gaggtgctgg ataatacaca gcagctgaag atcctggctg   2340
actcaatcaa tagcgaaatc ggaatcctgt gctccgccct gcagaaaatc aaatgaatcg   2400
tagatccaga catgataaga tacattgatg agtttggaca aaccacaact agaatgcagt   2460
gaaaaaaatg ctttatttgt gaaatttgtg atgctattgc tttatttgta accattataa   2520
gctgcaataa acaagttaac aacaacaatt gcattcattt tatgtttcag gttcaggggg   2580
aggtgtggga ggttttttaa                                               2600
```

<210> SEQ ID NO 68
<211> LENGTH: 2981
<212> TYPE: DNA
<213> ORGANISM: Artificial Sequence
<220> FEATURE:
<223> OTHER INFORMATION: pHMI-hPAH-TC-017 transfer genome

<400> SEQUENCE: 68

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctggagg ggtggagtcg tgacgtgaat tacgtcatag    180
ggttagggag gtcctgcaca gaaggggagg aggggcagc agctgtctga ccactgttgg    240
```

```
tcttgcaact tgtgtcccca ggttaatttt taaaaagcag tcaaaagtcc aagtggccct    300
tggcagcatt tactctctct gtttgctctg gttaataatc tcaggagcac aaacattcct    360
ggaggcagga gaagaaatca acatcctgga cttatcctct gggcctctcc ccaccccag     420
gattgtaact gaaatgcttc actggtgctc cttttgtttt aaggcattgg atcttcatag    480
ctactgatcg tgcccaagca cacagtatct gcagcaacca cttaggcctc caggaatgtg    540
gtgaccattg accctaattc attcccttc atggatccta tgtaaccatc ctccaaaaag     600
agctttcgca aactcaaata aacacaggaa aggaagacct tcttatcttt gagagtatat    660
gtttagccct atagctctaa cccactctga tctcccaggg cggcagtaag tcttcagcat    720
caggcatttt ggggtgactc agtaaatggt agatcttgct accagtggaa cagccactaa    780
ggattctgca gtgagagcag agggccagct aagtggtact ctcccagaga ctgtctgact    840
cacgccaccc cctccacctt ggacacagga cgctgtggtt tctgagccag gtacaatgac    900
tcctttcggt aagtgcagtg gaagctgtac actgcccagg caaagcgtcc gggcagcgta    960
ggcgggcgac tcagatccca gccagtgac ttagcccctg tttgctcctc cgataactgg     1020
ggtgaccttg gttaatattc accagcagcc tcccccgttg ccctctgga tccactgctt     1080
aaatacggac gaggacgcta cgccggcaa gaggtaaggg tttaagggat ggttggttgg     1140
tggggtatta atgtttaatt acctggagca cctgcctgaa atcactttt ttcaggttgg     1200
ttaattaagg atccgccacc atgtccaccg ctgtgctgga accctggg ctggggagga     1260
aactgtcaga cttcgggcag gagacttcat acattgagga taactgtaac cagaatggcg    1320
ccatctctct gatcttcagc ctgaaggagg aagtgggcgc cctggcaaag gtgctgcgcc    1380
tgtttgagga gaacgacgtg aatctgaccc acatcgagtc ccggccttct agactgaaga    1440
aggacgagta cgagttcttt accccacctgg ataagcggtc cctgccagcc ctgacaaaca    1500
tcatcaagat cctgaggcac gacatcggag caaccgtgca cgagctgtct cgggacaaga    1560
agaaggatac cgtgccctgg ttccctcgga caatccagga gctggataga tttgccaacc    1620
agatcctgtc ttacggagca gagctggacg cagatcaccc tggcttcaag gacccagtgt    1680
atcgggcccg gagaaagcag tttgccgata tcgcctacaa ttataggcac ggacagccaa    1740
tccctcgcgt ggagtatatg gaggaggaga agaagacctg gggcacagtg ttcaagaccc    1800
tgaagagcct gtacaagaca cacgcctgct acgagtataa ccacatcttc ccctgctgg    1860
agaagtattg tggctttcac gaggacaata tccctcagct ggaggacgtg agccagttcc    1920
tgcagacctg cacaggcttt aggctgaggc cagtggcagg actgctgagc tcccgggact    1980
tcctgggagg actggccttc agagtgtttc actgcaccca gtacatcagg cacggctcca    2040
agccaatgta taccagagag cccgacatct gtcacgagct gctgggccac gtgcccctgt    2100
ttagcgatag atccttcgcc cagttttccc aggagatcgg actggcatct ctgggagcac    2160
ctgacgagta catcgagaag ctggccacca tctattggtt cacagtggag tttggcctgt    2220
gcaagcaggg cgatagcatc aaggcctacg agcaggact gctgtctagc ttcggcgagc    2280
tgcagtattg tctgtccgag aagccaaagc tgctgcccct ggagctggag aagaccgcca    2340
tccagaacta caccgtgaca gagttccagc ccctgtacta tgtggccgag tcttttaacg    2400
atgccaagga aaggtgaga aatttcgccg ccacaatccc taggcccttc agcgtgcggt    2460
acgacccta tacccagagg atcgaggtgc tggataatac acagcagctg aagatcctgg    2520
ctgactcaat caatagcgaa atcggaatcc tgtgctccgc cctgcagaaa atcaaatgaa    2580
tcgtagatcc agacatgata agatacattg atgagtttgg acaaaccaca actagaatgc    2640
```

```
agtgaaaaaa atgctttatt tgtgaaattt gtgatgctat tgctttattt gtaaccatta    2700
taagctgcaa taaacaagtt aacaacaaca attgcattca ttttatgttt caggttcagg    2760
gggaggtgtg ggaggttttt taagcttgtt taaacgtacg tagataagta gcatggcggg    2820
ttaatcatta actacaagga accccctagtg atggagttgg ccactccctc tctgcgcgct   2880
cgctcgctca ctgaggccgg gcgaccaaag gtcgcccgac gcccgggctt gcccgggcg    2940 gcctcagtga gcgagcgagc gcgcagagag ggagtggcca a                       2981
```

<210> SEQ ID NO 69
<211> LENGTH: 1359
<212> TYPE: DNA
<213> ORGANISM: Artificial Sequence
<220> FEATURE:
<223> OTHER INFORMATION: pHMI-hPAH-TC-018 PAH sequence

<400> SEQUENCE: 69

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tctttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300
gacatagggg caactgtaca tgaactgagt agagataaaa aaaagacac agtcccctgg      360 ttccccagga ccatccagga attggacagg tttgcaaacc agatactgag ctatggtgct     420
gagttggatg ctgatcaccc aggcttcaag gaccctgtgt acagagcaag gagaaagcag     480
tttgctgaca ttgcctacaa ttacaggcac ggccaaccca ttcctagagt cgagtacatg     540
gaagaagaga gaaaacctg gggcactgtc ttcaagaccc tgaagtcact gtacaagaca     600
catgcctgct atgaatacaa ccacatattt ccactcctag agaaatactg tggattccat     660
gaggacaata taccccaatt ggaggatgtc tcacagtttc tgcagacttg tacaggtttt     720
aggctgaggc cagtggctgg gcttctcagc agcagggact tcctgggtgg actggccttc     780 agggtgttc actgtacaca atacatcaga catggtagca aaccaatgta tactcctgaa      840
ccagacatct gccatgagct gcttgggcat gtgcctctgt tttcagacag gtcctttgct     900
cagttctcac aagagattgg gctagcttca ctggagctc cagatgagta tattgaaaaa     960
ctggcaacaa tttactggtt tacagtggag tttggacttt gtaagcaggg agactccatc    1020
aaggcctatg tgcaggatt gttgtcttcc tttgggaac tgcaatattg tctctctgaa      1080
aagcctaagt tgctaccact ggagcttgag aagactgcca ttcagaacta cacagtgact    1140
gaattccagc cctctacta tgttgcagag tctttcaatg atgccaagga aaaggttagg    1200
aactttgctg caacaatccc cagaccttc agtgtgaggt atgaccccta cactcagaga    1260
attgaagttc tggataacac ccagcagctg aaaattctgg cagatagtat caactctgag    1320
attggaatcc tgtgttctgc cctgcagaag atcaagtga                            1359
```

<210> SEQ ID NO 70
<211> LENGTH: 1359
<212> TYPE: DNA
<213> ORGANISM: Artificial Sequence
<220> FEATURE:
<223> OTHER INFORMATION: pHMI-hPAH-TC-019 PAH sequence

<400> SEQUENCE: 70

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tgtttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300 gacataggggg caactgtaca tgaactgagt agagataaaa aaaagagacac agtcccctgg    360 ttccccagga ccatccagga attggacagg tttgcaaacc agatactgag ctatggtgct     420
gagttggatg ctgatcaccc aggcttcaag gaccctgtgt acagagcaag agaaagcag      480 tttgctgaca ttgcctacaa ttacaggcac ggccaaccca ttcctagagt cgagtacatg     540
gaagaagaga agaaaacctg gggcactgtc ttcaagaccc tgaagtcact gtacaagaca     600
catgcctgct atgaatacaa ccacatattt ccactcctag agaaatactg tggattccat     660
gaggacaata taccccaatt ggaggatgtc tcacagtttc tgcagacttg tacaggtttt     720
aggctgaggc cagtggctgg gctcctcagc agcagggact tcctgggtgg actgccttt     780 cgagttttcc actgtactca gtatatcaga catggctcca agcctatgta taccccagaa     840
cctgacatct gccatgaact gcttgggcat gtgcctctct tttcagaccg ttcctttgcc     900
cagttttctc aggagattgg actagccagc ctaggtgcac cagatgagta cattgagaag     960
ttagcaacca tttactggtt cacagtggag ttcggtctct gcaagcaagg ggactcaata    1020
aaggcctatg gagcaggcct cctgtcaagt tttggagaac tccaatactg cctatctgag    1080
aagcctaaat tattacccct tggaactagaa aaaactgcaa tacagaacta cacagtgact    1140
gagtttcagc cactctacta tgtggcagag tcctttaatg atgccaaaga aaaggtccga    1200
aattttgctg caacaattcc caggcccttc tctgttcgct atgatccata cacccaaaga    1260
attgaagtcc tagataacac ccagcagctg aaaatcctgg cagacagtat caactctgaa    1320
attggaatcc tctgttctgc cctgcagaag atcaagtga                            1359
```

<210> SEQ ID NO 71
<211> LENGTH: 1359
<212> TYPE: DNA
<213> ORGANISM: Artificial Sequence
<220> FEATURE:
<223> OTHER INFORMATION: pHMI-hPAH-TC-020 PAH sequence

<400> SEQUENCE: 71

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tctttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300 gacataggggg caactgtaca tgaactgagt agagataaaa aaaagagacac agtcccctgg    360 ttccccagga ccatccagga attggacagg tttgcaaacc agatactgag ctatggtgct     420
gagttggatg ctgatcaccc aggcttcaag gaccctgtgt acagagcaag agaaagcag      480 tttgctgaca ttgcctacaa ttacaggcac ggccaaccca ttcctagagt cgagtacatg     540
gaagaagaga agaaaacctg gggcactgtc ttcaagaccc tgaagtcact gtacaagaca     600
catgcctgct atgaatacaa ccacatattt ccactcctag agaaatactg tggattccat     660
gaggacaata taccccaatt ggaggatgtc tcacagtttc tgcagacttg tacaggtttt     720
```

```
aggctgaggc cagtggctgg gcttctcagc agcagggact tcctgggtgg actggccttc    780
agggtgtttc actgtacaca atacatcaga catggtagca aaccaatgta tactcctgaa    840
ccagacatct gccatgagct gcttgggcat gtgcctctgt tcagcgacag aagctttgct    900
cagtttagcc aggagattgg gctggccagc ctgggcgccc tgatgagta tatcgagaaa     960 ctggccacaa tctactggtt cacagtggag ttcggcctgt gcaagcaggg cgactcaatc   1020
aaggcctatg gcgccggcct gctgagcagc ttcggcgaac tgcagtactg cctgagcgag   1080
aagcccaagc tgctgccact ggagctggag aaaaccgcca tccagaacta cacagtgaca   1140
gagttccagc ctctgtacta tgtggccgag agcttcaacg atgccaagga aaggtgagg    1200 aattttgccg ccactatccc caggccttc tccgtgagat atgacccta cacccagcga    1260 atcgaggtgc tggacaatac ccagcagctg aagatcctgg ccgattccat caactctgag   1320
atcggcattc tgtgtagcgc cctgcagaag attaagtga                           1359
```

<210> SEQ ID NO 72
<211> LENGTH: 1359
<212> TYPE: DNA
<213> ORGANISM: Artificial Sequence
<220> FEATURE:
<223> OTHER INFORMATION: pHMI-hPAH-TC-021 PAH sequence

<400> SEQUENCE: 72

```
atgtccactg ctgtgctgga gaacccaggc ctgggaagga agctgagtga ctttggccag     60
gagacctcct acatagagga caactgcaat cagaacgggg ccatcagcct gatcttcagc    120
cttaaagagg aggtaggcgc tctggcaaaa gtgctcagac tctttgagga gaatgatgtg    180
aatctcaccc acattgaatc caggcccagc agactcaaaa aggatgaata tgaattttc     240 acccacttgg acaaaaggtc cttacctgcc cttacaaata tcatcaaaat tttgagacat    300
gacatagggg caactgtaca tgaactgagt agagataaaa aaaagacac agtcccctgg    360 ttccccagga ccatacagga attggacagg tttgcaaacc agatactgag ctatggtgct    420
gaattggatg ctgatcaccc aggcttcaag gaccctgtgt acagagcacg aagaaagcag    480
tttgctgaca ttgcctacaa ttacaggcac ggccaaccca ttcctagagt cgagtacatg    540
gaagaagaaa agaaaaactg gggcactgtg ttcaagaccc tgaagtcact gtacaagaca    600
catgcctgct atgaatacaa ccacatattt ccactcctag agaaatactg tggattccat    660
gaggacaaca taccccaatt ggaggatgtg tcacagtttc tgcagacttg tacaggtttt    720
aggctgaggc cagtggcagg gcttctcagc agcagggact tcctgggtgg actggccttc    780
agggtgtttc actgtacaca gtacatcaga catggtagca aaccaatgta tactcctgaa    840
ccagacatct gccatgagct gcttgggcat gtgcctctgt tttcagacag gtcctttgct    900
caattctcac aggagattgg actagccagc ctaggtgcac cagatgagta cattgagaag    960
ttagcaacca tttactggtt cacagtggag ttcggccttt gcaagcaagg ggactcaata   1020
aaggcctatg gagcaggcct cctgtcaagt tttggagaac tacaatactg cctatctgag   1080
aagcctaaat tattcccctt ggaactagaa aaaactgcaa tacagaacta cacagtgact   1140
gagtttcagc cactctacta tgtggccgag tccttcaatg atgccaaaga aaaggtccga   1200
aattttgctg caacaattcc caggccttc tctgttcgct atgatcctta cacccaaaga    1260
attgaagtcc tagataacac ccagcagctg aagatcctgg ctgatagcat aaacagcgaa   1320
attggaatcc tctgttctgc cctgcagaag atcaagtga                          1359
```

<210> SEQ ID NO 73
<211> LENGTH: 1359
<212> TYPE: DNA
<213> ORGANISM: Artificial Sequence
<220> FEATURE:
<223> OTHER INFORMATION: pHMI-hPAH-TC-022 PAH sequence

<400> SEQUENCE: 73

```
atgtccactg ctgtgctgga gaacccaggc ctgggcagga agttgagtga ctttgggcag      60
gagacctcct acatagaaga caattgcaat cagaatgggg ccatctctct gatcttcagc     120
cttaaagagg aggtgggtgc tctggcaaaa gtgctcagac tctttgagga gaatgatgtg     180
aatctcaccc acattgaatc caggcccagc agactcaaaa aggatgaata tgaattcttc     240
acccacttgg acaaaaggtc cttacctgcc cttacaaata tcatcaaaat tttgagacat     300
gacataggg caactgtaca tgaactgagt agagataaaa aaaaagacac agtccctgg     360
ttccccagga ccatccagga attggacagg tttgcaaacc agatactgag ctatggtgct     420
gagttggatg ctgatcaccc aggcttcaag accctgtgt acagagcaag agaaagcag     480
tttgctgaca ttgcctacaa ttacaggcac ggccaaccca ttcctagagt cgagtacatg     540
gaagaagaga agaaacctg gggcactgtc ttcaagaccc tgaagtcact gtacaagaca     600
catgcctgct atgaatacaa ccacatattt ccactcctag agaaatactg tggattccat     660
gaggacaata taccccaatt ggaggatgtc tcacagtttc tgcagacttg tacaggtttt     720
aggctgaggc cagtggctgg gcttctcagc agcagggact tcctgggtgg actggccttt     780
cgagttttcc actgtactca gtatatcaga catggctcca gcccatgta taccccagaa     840
cctgacatct gccatgaact gcttgggcat gtgcctctgt tttcagaccg ttcctttgcc     900
cagttttctc aggagattgg actagccagc ctaggtgcac cagatgagta cattgagaag     960
ttagcaacca tttactggtt cacagtggag ttcggccttt gcaagcaagg ggactcaata    1020
aaggcctatg agcaggcct cctgtcaagt tttggagaac tacaatactg cctatctgag    1080
aagcctaaat tattacccct tggaactaga aaaactgcaa tacagaacta cacagtgact    1140
gagtttcagc cactctacta tgtggcagag tcctttaatg atgccaaaga aaaggtccga    1200
aattttgctg caacaattcc caggcctttc tctgttcgct atgatccata cacccaaaga    1260
attgaagtcc tagataacac ccagcagctg aaaatcctgg cagacagcat caactctgaa    1320
attggaatcc tctgttctgc cctgcagaag atcaagtga                           1359
```

<210> SEQ ID NO 74
<211> LENGTH: 2111
<212> TYPE: DNA
<213> ORGANISM: Artificial Sequence
<220> FEATURE:
<223> OTHER INFORMATION: pHMI-hPAH-TC-018 transfer genome

<400> SEQUENCE: 74

```
ccctaaaatg ggcaaacatt gcaagcagca acagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gggaatgact cctttcggta agtgcagtgg aagctgtaca ctgcccaggc     240
aaagcgtccg ggcagcgtag gcgggcgact cagatcccag ccagtggact tagcccctgt     300
ttgctcctcc gataactggg gtgacccttgg ttaatattca ccagcagcct ccccgcttgc     360
ccctctggat ccactgctta aatacggacg aggacagggc cctgtctcct cagcttcagg     420
```

```
caccaccact gacctgggac agtgaatcct ctaaggtaaa tataaaattt ttaagtgtat      480
aatgtgttaa actactgatt ctaattgttt ctctctttta gattccaacc tttggaactg      540
accgccacca tgtccactgc tgtgctggag aacccaggcc tgggcaggaa gttgagtgac      600
tttgggcagg agacctccta catagaagac aattgcaatc agaatggggc catctctctg      660
atcttcagcc ttaaagagga ggtgggtgct ctggcaaaag tgctcagact ctttgaggag      720
aatgatgtga atctcaccca cattgaatcc aggcccagca gactcaaaaa ggatgaatat      780
gaattcttca cccacttgga caaaaggtcc ttacctgccc ttacaaatat catcaaaatt      840
ttgagacatg atagggggc aactgtacat gaactgagta gagataaaaa aaaagacaca      900
gtcccctggt tccccaggac catccaggaa ttggacaggt ttgcaaacca gatactgagc      960
tatggtgctg agttggatgc tgatcaccca ggcttcaagg accctgtgta cagagcaagg     1020
agaaagcagt ttgctgacat tgcctacaat tacaggcacg ccaacccat tcctagagtc     1080 gagtacatgg aagaagagaa gaaaacctgg ggcactgtct tcaagaccct gaagtcactg     1140
tacaagacac atgcctgcta tgaatacaac cacatatttc cactcctaga aaatactgt     1200 ggattccatg aggacaatat accccaattg gaggatgtct cacagtttct gcagacttgt     1260 acaggttttta ggctgaggcc agtggctggg cttctcagca gcagggactt cctgggtgga     1320
ctggccttca gggtgtttca ctgtacacaa tacatcagac atggtagcaa accaatgtat     1380
actcctgaac cagacatctg ccatgagctg cttgggcatg tgcctctgtt ttcagacagg     1440
tcctttgctc agttctcaca agagattggg ctagcttcac tgggagctcc agatgagtat     1500
attgaaaaac tggcaacaat ttactggttt acagtggagt ttggactttg taagcaggga     1560
gactccatca aggcctatgg tgcaggattg ttgtcttcct ttggggaact gcaatattgt     1620
ctctctgaaa agcctaagtt gctaccactg gagcttgaga agactgccat tcagaactac     1680
acagtgactg aattccagcc cctctactat gttgcagagt cttttcaatga tgccaaggag     1740 aaggttagga actttgctgc aacaatcccc agaccttca gtgtgaggta tgaccctac     1800 actcagagaa ttgaagttct ggataacacc cagcagctga aaattctggc agatagtatc     1860
aactctgaga ttggaatcct gtgttctgcc ctgcagaaga tcaagtgact cgagatccag     1920
acatgataag atacattgat gagttttgga aaaccacaac tagaatgcag tgaaaaaaat     1980
gctttatttg tgaaatttgt gatgctattg ctttatttgt aaccattata agctgcaata     2040
aacaagttaa caacaacaat tgcattcatt ttatgtttca ggttcagggg gaggtgtggg     2100 aggttttttta a                                                        2111
```

<210> SEQ ID NO 75
<211> LENGTH: 2426
<212> TYPE: DNA
<213> ORGANISM: Artificial Sequence
<220> FEATURE:
<223> OTHER INFORMATION: pHMI-hPAH-TC-018 transfer genome

<400> SEQUENCE: 75

```
ctgcgcgctc gctcgctcac tgaggccgcc cgggcaaagc ccgggcgtcg gcgacctttt       60
ggtcgcccgg cctcagtgag cgagcgagcg cgcagagagg gagtggaatt cacgcgtgga      120
tctgaattca attcacgcgt ggtaccctcc taaaatgggc aaacattgca agcagcaaac      180
agcaaacaca cagccctccc tgcctgctga ccttggagct ggggcagagg tcagagacct      240
ctctgggccc atgccacctc caacatccac tcgaccccctt ggaatttcgg tggagaggag      300
```

```
cagaggttgt cctggcgtgg tttaggtagt gtgagagggg aatgactcct ttcggtaagt    360
gcagtggaag ctgtacactg cccaggcaaa gcgtccgggc agcgtaggcg ggcgactcag    420
atcccagcca gtggacttag cccctgtttg ctcctccgat aactggggtg accttggtta    480
atattcacca gcagcctccc ccgttgcccc tctggatcca ctgcttaaat acggacgagg    540
acagggccct gtctcctcag cttcaggcac caccactgac ctgggacagt gaatcctcta    600
aggtaaatat aaaattttta agtgtataat gtgttaaact actgattcta attgtttctc    660
tcttttagat tccaaccttt ggaactgacc gccaccatgt ccactgctgt gctggagaac    720
ccaggcctgg gcaggaagtt gagtgacttt gggcaggaga cctcctacat agaagacaat    780
tgcaatcaga atggggccat ctctctgatc ttcagcctta agaggaggt gggtgctctg     840
gcaaaagtgc tcagactctt tgaggagaat gatgtgaatc tcacccacat tgaatccagg    900
cccagcagac tcaaaaagga tgaatatgaa ttcttcaccc acttggacaa aggtccttac    960
cctgccctta caaatatcat caaaattttg acatgaca tagggcaac tgtacatgaa      1020
ctgagtagag ataaaaaaaa agacacagtc ccctggttcc ccaggaccat ccaggaattg    1080
gacaggtttg caaaccagat actgagctat ggtgctgagt tggatgctga tcacccaggc    1140
ttcaaggacc ctgtgtacag agcaaggaga aagcagtttg ctgacattgc ctacaattac    1200
aggcacggcc aacccattcc tagagtcgag tacatggaag aagagaagaa aacctggggc    1260
actgtcttca agaccctgaa gtcactgtac aagacacatg cctgctatga atacaaccac    1320
atatttccac tcctagagaa atactgtgga ttccatgagg acaatatacc ccaattggag    1380
gatgtctcac agtttctgca gacttgtaca ggttttaggc tgaggccagt ggctgggctt    1440
ctcagcagca gggacttcct gggtggactg gccttcaggg tgtttcactg tacacaatac    1500
atcagacatg gtagcaaacc aatgtatact cctgaaccag acatctgcca tgagctgctt    1560
gggcatgtgc ctctgttttc agacaggtcc tttgctcagt tctcacaaga gattgggcta    1620
gcttcactgg gagctccaga tgagtatatt gaaaaactgg caacaattta ctggtttaca    1680
gtggagtttg gactttgtaa gcagggagac tccatcaagg cctatggtgc aggattgttg    1740
tcttcctttg gggaactgca atattgtctc tctgaaaagc taagttgct accactggag      1800
cttgagaaga ctgccattca gaactacaca gtgactgaat tccagcccct ctactatgtt    1860
gcagagtctt tcaatgatgc caaggagaag gttaggaact ttgctgcaac aatccccaga    1920
cctttcagtg tgaggtatga ccctacact cagagaattg aagttctgga taacacccag       1980
cagctgaaaa ttctggcaga tagtatcaac tctgagattg gaatcctgtg ttctgccctg    2040
cagaagatca agtgactcga gatccagaca tgataagata cattgatgag tttggacaaa    2100
ccacaactag aatgcagtga aaaaatgct ttatttgtga aatttgtgat gctattgctt     2160
tatttgtaac cattataagc tgcaataaac aagttaacaa caacaattgc attcatttta    2220
tgtttcaggt tcaggggag gtgtgggagg tttttttaaag catgctgggg agagatcgat    2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                          2426
```

<210> SEQ ID NO 76
<211> LENGTH: 2111
<212> TYPE: DNA
<213> ORGANISM: Artificial Sequence
<220> FEATURE:
<223> OTHER INFORMATION: pHMI-hPAH-TC-019 transfer genome

<400> SEQUENCE: 76

```
ccctaaaatg ggcaaacatt gcaagcagca aacagcaaac acacagccct ccctgcctgc    60
tgaccttgga gctggggcag aggtcagaga cctctctggg cccatgccac ctccaacatc   120
cactcgaccc cttggaattt cggtggagag gagcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagccctgt   300
ttgctcctcc gataactggg gtgaccttgg ttaatattca ccagcagcct ccccgttgc   360
ccctctggat ccactgctta aatacggacg aggacagggc cctgtctcct cagcttcagg   420
caccaccact gacctgggac agtgaatcct ctaaggtaaa tataaaattt ttaagtgtat   480
aatgtgttaa actactgatt ctaattgttt ctctctttta gattccaacc tttgaactg   540
accgccacca tgtccactgc tgtgctggag aacccaggcc tgggcaggaa gttgagtgac   600
tttgggcagg agacctccta catagaagac aattgcaatc agaatggggc catctctctg   660
atcttcagcc ttaaagagga ggtgggtgct ctggcaaaag tgctcagact gtttgaggag   720
aatgatgtga atctcacccca cattgaatcc aggcccagca gactcaaaaa ggatgaatat   780
gaattcttca cccacttgga caaaaggtcc ttacctgccc ttacaaatat catcaaaatt   840
ttgagacatg ataggggc aactgtacat gaactgagta gagataaaaa aaaagacaca   900
gtcccctggt tccccaggac catccaggaa ttggacaggt ttgcaaacca gatactgagc   960
tatggtgctg agttggatgc tgatcaccca ggcttcaagg accctgtgta cagagcaagg  1020
agaaagcagt ttgctgacat tgcctacaat tacaggcacg ccaacccat tcctagagtc  1080
gagtacatgg aagaagagaa gaaaacctgg ggcactgtct tcaagaccct gaagtcactg  1140
tacaagacac atgcctgcta tgaatacaac cacatatttc cactcctaga gaaatactgt  1200
ggattccatg aggacaatat accccaattg gaggatgtct cacagtttct gcagacttgt  1260
acaggttttta ggctgaggcc agtggctggg ctcctcagca gcagggactt cctgggtgga  1320
ctggcctttc gagttttcca ctgtactcag tatatcagac atggctccaa gcctatgtat  1380
accccagaac ctgacatctg ccatgaactg cttgggcatg tgcctctctt ttcagaccgt  1440
tcctttgccc agttttctca ggagattgga ctagccagcc taggtgcacc agatgagtac  1500
attgagaagt tagcaaccat ttactggttc acagtggagt tcggtctctg caagcaaggg  1560
gactcaataa aggcctatgg agcaggcctc ctgtcaagtt ttggagaact ccaatactgc  1620
ctatctgaga agcctaaatt attacccttg gaactagaaa aaactgcaat acagaactac  1680
acagtgactg agtttcagcc actctactat gtggcagagt cctttaatga tgccaaagaa  1740
aaggtccgaa attttgctgc aacaattccc aggccccttct ctgttcgcta tgatccatac  1800
acccaaagaa ttgaagtcct agataacacc cagcagctga aaatcctggc agacagtatc  1860
aactctgaaa ttggaatcct ctgttctgcc ctgcagaaga tcaagtgact cgagatccag  1920
acatgataag atacattgat gagtttggac aaaccacaac tagaatgcag tgaaaaaaat  1980
gctttatttg tgaaatttgt gatgctattg ctttatttgt aaccattata agctgcaata  2040
aacaagttaa caacaacaat tgcattcatt ttatgtttca ggttcagggg gaggtgtggg  2100
aggttttta a                                                        2111
```

<210> SEQ ID NO 77
<211> LENGTH: 2426
<212> TYPE: DNA

<213> ORGANISM: Artificial Sequence
<220> FEATURE:
<223> OTHER INFORMATION: pHMI-hPAH-TC-019 transfer genome

<400> SEQUENCE: 77

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga     120
tctgaattca attcacgcgt ggtacctccc taaaatgggc aaacattgca agcagcaaac     180
agcaaacaca cagccctccc tgcctgctga ccttggagct ggggcagagg tcagagacct     240
ctctgggccc atgccacctc caacatccac tcgaccccctt ggaatttcgg tggagaggag     300
cagaggttgt cctggcgtgg tttaggtagt gtgagagggg aatgactcct ttcggtaagt     360
gcagtggaag ctgtacactg cccaggcaaa gcgtccgggc agcgtaggcg ggcgactcag     420
atcccagcca gtggacttag cccctgtttg ctcctccgat aactggggtg accttggtta     480
atattcacca gcagcctccc ccgttgcccc tctggatcca ctgcttaaat acggacgagg     540
acagggccct gtctcctcag cttcaggcac caccactgac ctgggacagt gaatcctcta     600
aggtaaatat aaaatttta agtgtataat gtgttaaact actgattcta attgtttctc     660
tcttttagat tccaaccttt ggaactgacc gccaccatgt ccactgctgt gctggagaac     720
ccaggcctgg gcaggaagtt gagtgacttt gggcaggaga cctcctacat agaagacaat     780
tgcaatcaga atggggccat ctctctgatc ttcagcctta agaggaggt gggtgctctg     840
gcaaaagtgc tcagactgtt tgaggagaat gatgtgaatc tcacccacat tgaatccagg     900
cccagcagac tcaaaaagga tgaatatgaa ttcttcaccc acttggacaa aggtccctta     960
cctgccctta caaatatcat caaaattttg agacatgaca taggggcaac tgtacatgaa    1020
ctgagtagag ataaaaaaaa agacacagtc ccctggttcc ccaggaccat ccaggaattg    1080
gacaggtttg caaaccagat actgagctat ggtgctgagt tggatgctga tcacccaggc    1140
ttcaaggacc ctgtgtacag agcaaggaga aagcagtttg ctgacattgc ctacaattac    1200
aggcacggcc aacccattcc tagagtcgag tacatggaag aagagaagaa aacctggggc    1260
actgtcttca gaccctgaa gtcactgtac aagacacatg cctgctatga atacaaccac    1320
atatttccac tcctagagaa atactgtgga ttccatgagg acaatatacc ccaattggag    1380
gatgtctcac agtttctgca gacttgtaca ggttttaggc tgaggccagt ggctgggctc    1440
ctcagcagca gggacttcct gggtggactg gcctttcgag ttttccactg tactcagtat    1500
atcagacatg gctccaagcc tatgtatacc ccagaacctg acatctgcca tgaactgctt    1560
gggcatgtgc ctctctttc agaccgttcc tttgcccagt tttctcagga gattggacta    1620
gccagcctag tgcaccaga tgagtacatt gagaagttag caaccattta ctggttcaca    1680
gtggagttcg gtctctgcaa gcaaggggac tcaataaagg cctatggagc aggcctcctg    1740
tcaagttttg gagaactcca atactgccta tctgagaagc taaattatt acccttggaa    1800
ctagaaaaaa ctgcaataca gaactacaca gtgactgagt ttcagccact ctactatgtg    1860
gcagagtcct ttaatgatgc caagaaaag gtccgaaatt tgctgcaac aattcccagg    1920
cccttctctg ttcgctatga tccatacacc caaagaattg aagtcctaga taacacccag    1980
cagctgaaaa tcctggcaga cagtatcaac tctgaaattg aatcctctg ttctgccctg    2040
cagaagatca agtgactcga gatccagaca tgataagata cattgatgag tttggacaaa    2100
ccacaactag aatgcagtga aaaaaatgct ttatttgtga aatttgtgat gctattgctt    2160
tatttgtaac cattataagc tgcaataaac aagttaacaa caacaattgc attcattta    2220
```

```
tgtttcaggt tcaggggagg gtgtgggagg tttttaaag catgctgggg agagatcgat    2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                       2426

<210> SEQ ID NO 78
<211> LENGTH: 2111
<212> TYPE: DNA
<213> ORGANISM: Artificial Sequence
<220> FEATURE:
<223> OTHER INFORMATION: pHMI-hPAH-TC-020 transfer genome

<400> SEQUENCE: 78
ccctaaaatg ggcaaacatt gcaagcagca aacagcaaac acacagccct ccctgcctgc     60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct ccccgttgc     360 ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctctttta gattccaacc tttggaactg    540
accgccacca tgtccactgc tgtgctggag aacccaggcc tgggcaggaa gttgagtgac    600
tttgggcagg agacctccta catagaagac aattgcaatc agaatgggc catctctctg    660 atcttcagcc ttaaagagga ggtgggtgct ctggcaaaag tgctcagact cttttgaggag    720 aatgatgtga atctcaccca cattgaatcc aggcccagca gactcaaaaa ggatgaatat    780
gaattcttca cccacttgga caaaaggtcc ttacctgccc ttacaaatat catcaaaatt    840
ttgagacatg acatagggc aactgtacat gaactgagta gagataaaaa aaaagacaca    900
gtcccctggt tccccaggac catccaggaa ttggacaggt ttgcaaacca gatactgagc    960
tatggtgctg agttggatgc tgatcaccca ggcttcaagg accctgtgta cagagcaagg   1020
agaaagcagt ttgctgacat tgcctacaat tacaggcacg ccaacccat tcctagagtc    1080 gagtacatgg aagaagagaa gaaaacctgg ggcactgtct tcaagaccct gaagtcactg   1140
tacaagacac atgcctgcta tgaatacaac cacatatttc cactcctaga gaatactgt    1200 ggattccatg aggacaatat accccaattg gaggatgtct cacagtttct gcagacttgt   1260
acaggtttta ggctgaggcc agtggctggg cttctcagca gcagggactt cctgggtgga    1320
ctggccttca ggggtgtttca ctgtacacaa tacatcagac atggtagcaa accaatgtat   1380
actcctgaac cagacatctg ccatgagctg cttgggcatg tgcctctgtt cagcgacaga    1440
agctttgctc agtttagcca ggagattggg ctggccagcc tgggcgcccc tgatgagtat    1500
atcgagaaac tggccacaat ctactggttc acagtggagt tcggcctgtg caagcagggc   1560
gactcaatca aggcctatgg cgccggcctg ctgagcagct tcggcgaact gcagtactgc   1620
ctgagcgaga gcccaagct gctgccactg gagctggaga aaaccgccat ccagaactac    1680
acagtgacag agtccagcc tctgtactat gtggccgaga gcttcaacga tgccaaggag   1740
aaggtgagga atttttgccgc cactatcccc aggcctttct ccgtgagata tgaccctac    1800
```

| acccagcgaa tcgaggtgct ggacaatacc cagcagctga agatcctggc cgattccatc | 1860 |
| aactctgaga tcggcattct gtgtagcgcc ctgcagaaga ttaagtgact cgagatccag | 1920 |
| acatgataag atacattgat gagtttggac aaaccacaac tagaatgcag tgaaaaaaat | 1980 |
| gctttatttg tgaaatttgt gatgctattg ctttatttgt aaccattata agctgcaata | 2040 |
| aacaagttaa caacaacaat tgcattcatt ttatgtttca ggttcagggg gaggtgtggg | 2100 |
| aggttttta a | 2111 |

<210> SEQ ID NO 79
<211> LENGTH: 2426
<212> TYPE: DNA
<213> ORGANISM: Artificial Sequence
<220> FEATURE:
<223> OTHER INFORMATION: pHMI-hPAH-TC-020 transfer genome

<400> SEQUENCE: 79

| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggaatt cacgcgtgga | 120 |
| tctgaattca attcacgcgt ggtacctccc taaaatgggc aaacattgca agcagcaaac | 180 |
| agcaaacaca cagccctccc tgcctgctga ccttggagct ggggcagagg tcagagacct | 240 |
| ctctgggccc atgccacctc caacatccac tcgacccctt ggaatttcgg tggagaggag | 300 |
| cagaggttgt cctggcgtgg tttaggtagt gtgagagggg aatgactcct ttcggtaagt | 360 |
| gcagtggaag ctgtacactg cccaggcaaa gcgtccgggc agcgtaggcg ggcgactcag | 420 |
| atcccagcca gtgacttag ccctgttg ctcctccgat aactgggtg accttggtta | 480 |
| atattcacca gcagcctccc ccgttgcccc tctggatcca ctgcttaaat acggacgagg | 540 |
| acagggccct gtctcctcag cttcaggcac accactgac ctgggacagt gaatcctcta | 600 |
| aggtaaatat aaaattttta agtgtataat gtgttaaact actgattcta attgtttctc | 660 |
| tcttttagat tccaaccttt ggaactgacc gccaccatgt ccactgctgt gctggagaac | 720 |
| ccaggcctgg gcaggaagtt gagtgacttt gggcaggaga cctcctacat agaagacaat | 780 |
| tgcaatcaga tggggccat ctctctgatc ttcagcctta agaggaggt gggtgctctg | 840 |
| gcaaaagtgc tcagactctt tgaggagaat gatgtgaatc tcacccacat tgaatccagg | 900 |
| cccagcagac tcaaaaagga tgaatatgaa ttcttcaccc acttggacaa aaggtcctta | 960 |
| cctgccctta caaatatcat caaaattttg agacatgaca taggggcaac tgtacatgaa | 1020 |
| ctgagtagag ataaaaaaaa agacacagtc ccctggttcc ccaggaccat ccaggaattg | 1080 |
| gacaggtttg caaaccagat actgagctat ggtgctgagt tggatgctga tcacccaggc | 1140 |
| ttcaaggacc ctgtgtacag agcaaggaga aagcagtttg ctgacattgc ctacaattac | 1200 |
| aggcacggcc aacccattcc tagagtcgag tacatggaag aagagaagaa acctggggc | 1260 |
| actgtcttca gaccctgaa gtcactgtac aagacacatg cctgctatga atacaaccac | 1320 |
| atatttccac tcctagagaa atactgtgga ttccatgagg acaatatacc ccaattggag | 1380 |
| gatgtctcac agtttctgca gacttgtaca ggttttaggc tgaggccagt ggctgggctt | 1440 |
| ctcagcagca gggacttcct gggtggactg gccttcaggg tgtttcactg tacacaatac | 1500 |
| atcagacatg gtagcaaacc aatgtatact cctgaaccag acatctgcca tgagctgctt | 1560 |
| gggcatgtgc ctctgttcag cgacagaagc tttgctcagt ttagccagga gattgggctg | 1620 |
| gccagcctgg gcgcccctga tgagtatatc gagaaactgg ccacaatcta ctggttcaca | 1680 |
| gtggagttcg gcctgtgcaa gcagggcgac tcaatcaagg cctatggcgc cggcctgctg | 1740 |

```
agcagcttcg gcgaactgca gtactgcctg agcgagaagc ccaagctgct gccactggag    1800
ctggagaaaa ccgccatcca gaactacaca gtgacagagt tccagcctct gtactatgtg    1860
gccgagagct tcaacgatgc caaggagaag gtgaggaatt tgccgccac tatccccagg     1920 cctttctccg tgagatatga cccctacacc cagcgaatcg aggtgctgga caataccag    1980 cagctgaaga tcctggccga ttccatcaac tctgagatcg gcattctgtg tagcgccctg    2040
cagaagatta agtgactcga gatccagaca tgataagata cattgatgag tttgacaaa    2100 ccacaactag aatgcagtga aaaaaatgct ttatttgtga aatttgtgat gctattgctt    2160
tatttgtaac cattataagc tgcaataaac aagttaacaa caacaattgc attcatttta    2220
tgtttcaggt tcaggggag gtgtgggagg ttttttaaag catgctgggg agagatcgat     2280
ctgaggaacc cctagtgatg gagttggcca ctccctctct gcgcgctcgc tcgctcactg    2340
aggccgggcg accaaaggtc gcccgacgcc cgggctttgc ccgggcggcc tcagtgagcg    2400
agcgagcgcg cagagaggga gtggcc                                         2426

<210> SEQ ID NO 80
<211> LENGTH: 2111
<212> TYPE: DNA
<213> ORGANISM: Artificial Sequence
<220> FEATURE:
<223> OTHER INFORMATION: pHMI-hPAH-TC-021 transfer genome

<400> SEQUENCE: 80
ccctaaaatg gcaaacatt gcaagcagca aacagcaaac acacagccct ccctgcctgc    60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagccctgt    300 ttgctcctcc gataactggg gtgaccttgg ttaatattca ccagcagcct ccccgttgc    360 ccctctggat ccactgctta aatacgacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctctttta gattccaacc tttggaactg    540
accgccacca tgtccactgc tgtgctggag aaccccaggcc tgggaaggaa gctgagtgac    600
tttggccagg agacctccta catagaggac aactgcaatc agaacggggc catcagcctg    660
atcttcagcc ttaaagagga ggtaggcgct ctggcaaaag tgctcagact cttttgaggag    720 aatgatgtga atctcaccca cattgaatcc aggcccagca gactcaaaaa ggatgaatat    780
gaatttttca cccacttgga caaaggtcc ttacctgccc ttacaaatat catcaaaatt    840
ttgagacatg acatagggc aactgtacat gaactgagta gagataaaaa aaagacaca    900 gtcccctggt tccccaggac catacaggaa ttggacaggt tgcaaaacca gatactgagc    960
tatggtgctg aattggatgc tgatcaccca ggcttcaagg accctgtgta cagagcacga    1020
agaaagcagt ttgctgacat tgcctacaat tacaggcacg ccaacccat tcctagagtc    1080 gagtacatgg aagaagaaaa gaaaacctgg ggcactgtgt tcaagaccct gaagtcactg    1140
tacaagacac atgcctgcta tgaatacaac cacatatttc cactcctaga gaaatactgt    1200
ggattccatg aggacaacat accccaattg gaggatgtgt cacagtttct gcagacttgt    1260
acaggtttta ggctgaggcc agtggcaggg cttctcagca gcaggacttt cctgggtgga    1320
```

```
ctggccttca gggtgtttca ctgtacacag tacatcagac atggtagcaa accaatgtat   1380
actcctgaac cagacatctg ccatgagctg cttgggcatg tgcctctgtt ttcagacagg   1440
tcctttgctc aattctcaca ggagattgga ctagccagcc taggtgcacc agatgagtac   1500
attgagaagt tagcaaccat ttactggttc acagtggagt tcggcctttg caagcaaggg   1560
gactcaataa aggcctatgg agcaggcctc ctgtcaagtt ttggagaact acaatactgc   1620
ctatctgaga agcctaaatt attacccttg gaactagaga aaactgcaat acagaactac   1680
acagtgactg agtttcagcc actctactat gtggccgagt ccttcaatga tgccaaagaa   1740
aaggtccgaa attttgctgc aacaattccc aggcctttct ctgttcgcta tgatccttac   1800
acccaaagaa ttgaagtcct agataacacc cagcagctga agatcctggc tgatagcata   1860
aacagcgaaa ttggaatcct ctgttctgcc ctgcagaaga tcaagtgact cgagatccag   1920
acatgataag atacattgat gagtttggac aaaccacaac tagaatgcag tgaaaaaaat   1980
gctttatttg tgaaatttgt gatgctattg ctttatttgt aaccattata agctgcaata   2040
aacaagttaa caacaacaat tgcattcatt ttatgtttca ggttcagggg gaggtgtggg   2100
aggttttta a                                                        2111

<210> SEQ ID NO 81
<211> LENGTH: 2426
<212> TYPE: DNA
<213> ORGANISM: Artificial Sequence
<220> FEATURE:
<223> OTHER INFORMATION: pHMI-hPAH-TC-021 transfer genome

<400> SEQUENCE: 81
ctgcgcgctc gctcgctcac tgaggccgcc cgggcaaagc ccgggcgtcg ggcgaccttt     60
ggtcgcccgg cctcagtgag cgagcgagcg cgcagagagg gagtggaatt cacgcgtgga   120
tctgaattca attcacgcgt ggtacctccc taaaatgggc aaacattgca agcagcaaac   180
agcaaacaca cagcccctcc tgcctgctga ccttggagct ggggcagagg tcagagacct   240
ctctgggccc atgccacctc caacatccac tcgacccctt ggaatttcgg tggagaggag   300
cagaggttgt cctggcgtgg tttaggtagt gtgagagggg aatgactcct ttcggtaagt   360
gcagtggaag ctgtacactg cccaggcaaa gcgtccgggc agcgtaggcg ggcgactcag   420
atcccagcca gtggacttag cccctgtttg ctcctccgat aactgggtg accttggtta    480
atattcacca gcagcctccc ccgttgcccc tctggatcca ctgcttaaat acggacgagg   540
acagggccct gtctcctcag cttcaggcac caccactgac ctgggacagt gaatcctcta   600
aggtaaatat aaaattttta agtgtataat gtgttaaact actgattcta attgtttctc   660
tcttttagat tccaaccttt ggaactgacc gccaccatgt ccactgctgt gctggagaac   720
ccaggcctgg gaaggaagct gagtgacttt ggccaggaga cctcctacat agaggacaac   780
tgcaatcaga acggggccat cagcctgatc ttcagcctta agaggaggt aggcgctctg    840
gcaaaagtgc tcagactctt tgaggagaat gatgtgaatc tcacccacat tgaatccagg   900
cccagcagac tcaaaaagga tgaatatgaa ttttcaccc acttggacaa aaggtcctta   960
cctgccctta caaatatcat caaaatttg agacatgaca taggggcaac tgtacatgaa   1020
ctgagtagag ataaaaaaaa agacacagtc ccctggttcc ccaggaccat acaggaattg   1080
gacaggtttg caaaccagat actgagctat ggtgctgaat tggatgctga tcacccaggc   1140
ttcaaggacc ctgtgtacag agcacgaaga aagcagtttg ctgacattgc ctacaattac   1200
aggcacggcc aacccattcc tagagtcgag tacatggaag aagaaagaa aacctggggc   1260
```

```
actgtgttca agaccctgaa gtcactgtac aagacacatg cctgctatga atacaaccac   1320
atatttccac tcctagagaa atactgtgga ttccatgagg acaacatacc ccaattggag   1380
gatgtgtcac agtttctgca gacttgtaca ggttttaggc tgaggccagt ggcagggctt   1440
ctcagcagca gggacttcct gggtggactg gccttcaggg tgtttcactg tacacagtac   1500
atcagacatg gtagcaaacc aatgtatact cctgaaccag acatctgcca tgagctgctt   1560
gggcatgtgc ctctgttttc agacaggtcc tttgctcaat tctcacagga gattggacta   1620
gccagcctag gtgcaccaga tgagtacatt gagaagttag caaccattta ctggttcaca   1680
gtggagttcg gcctttgcaa gcaaggggac tcaataaagg cctatggagc aggcctcctg   1740
tcaagttttg gagaactaca atactgccta tctgagaagc taaattatt accttggaa    1800 ctagagaaaa ctgcaataca gaactacaca gtgactgagt tcagccact ctactatgtg    1860 gccgagtcct tcaatgatgc caagaaaag gtccgaaatt tgctgcaac aattcccagg     1920 cctttctctg ttcgctatga tccttacacc caaagaattg aagtcctaga taacacccag   1980
cagctgaaga tcctggctga tagcataaac agcgaaattg gaatcctctg ttctgccctg   2040
cagaagatca agtgactcga gatccagaca tgataagata cattgatgag tttggacaaa   2100
ccacaactag aatgcagtga aaaaaatgct ttatttgtga aatttgtgat gctattgctt   2160
tatttgtaac cattataagc tgcaataaac aagttaacaa caacaattgc attcatttta   2220
tgtttcaggt tcagggggag gtgtgggagg ttttttaaag catgctgggg agagatcgat   2280
ctgaggaacc cctagtgatg gagttggcca ctccctctct gcgcgctcgc tcgctcactg   2340
aggccgggcg accaaaggtc gcccgacgcc cgggctttgc ccgggcggcc tcagtgagcg   2400
agcgagcgcg cagagaggga gtggcc                                        2426
```

<210> SEQ ID NO 82  
<211> LENGTH: 2111  
<212> TYPE: DNA  
<213> ORGANISM: Artificial Sequence  
<220> FEATURE:  
<223> OTHER INFORMATION: pHMI-hPAH-TC-022 transfer genome

<400> SEQUENCE: 82

```
ccctaaaatg gcaaacatt gcaagcagca aacagcaaac acacagccct cctgcctgc      60 tgaccttgga gctggggcag aggtcagaga cctctctggg cccatgccac ctccaacatc   120
cactcgaccc cttggaattt cggtggagag gagcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagcccctgt   300
ttgctcctcc gataactggg gtgaccttgg ttaatattca ccagcagcct ccccgttgc    360 ccctctggat ccactgctta aatacggacg aggacagggc cctgtctcct cagcttcagg   420
caccaccact gacctgggac agtgaatcct ctaaggtaaa tataaaattt ttaagtgtat   480
aatgtgttaa actactgatt ctaattgttt ctctctttta gattccaacc tttggaactg   540
accgccacca tgtccactgc tgtgctggag aacccaggcc tgggcaggaa gttgagtgac   600
tttgggcagg agacctccta catagaagac aattgcaatc agaatgggc catctctctg   660 atcttcagcc ttaaagagga ggtgggtgct ctggcaaaag tgctcagact cttttgaggag  720 aatgatgtga atctcaccca cattgaatcc aggcccagca gactcaaaaa ggatgaatat   780
gaattcttca cccacttgga caaaaggtcc ttacctgccc ttacaaatat catcaaaatt   840
```

```
ttgagacatg acatagggc aactgtacat gaactgagta gagataaaaa aaaagacaca    900
gtccctggt tccccaggac catccaggaa ttggacaggt ttgcaaacca gatactgagc    960
tatggtgctg agttggatgc tgatcaccca ggcttcaagg accctgtgta cagagcaagg   1020
agaaagcagt ttgctgacat tgcctacaat tacaggcacg ccaacccat tcctagagtc    1080
gagtacatgg aagaagagaa gaaaacctgg ggcactgtct tcaagaccct gaagtcactg   1140
tacaagacac atgcctgcta tgaatacaac cacatatttc cactcctaga gaaatactgt   1200
ggattccatg aggacaatat accccaattg gaggatgtct cacagtttct gcagacttgt   1260
acaggtttta ggctgaggcc agtggctggg cttctcagca gcaggactt cctgggtgga    1320
ctggcctttc gagttttcca ctgtactcag tatatcagac atggctccaa gcccatgtat   1380
accccagaac ctgacatctg ccatgaactg cttgggcatg tgcctctgtt ttcagaccgt   1440
tcctttgccc agttttctca ggagattgga ctagccagcc taggtgcacc agatgagtac   1500
attgagaagt tagcaaccat ttactggttc acagtggagt tcggcctttg caagcaaggg   1560
gactcaataa aggcctatgg agcaggcctc ctgtcaagtt ttggagaact acaatactgc   1620
ctatctgaga agcctaaatt attacccttg gaactagaaa aaactgcaat acagaactac   1680
acagtgactg agtttcagcc actctactat gtggcagagt cctttaatga tgccaaagaa   1740
aaggtccgaa attttgctgc aacaattccc aggccttct ctgttcgcta tgatccatac    1800
acccaaagaa ttgaagtcct agataacacc cagcagctga aatcctggc agacagcatc    1860
aactctgaaa ttggaatcct ctgttctgcc ctgcagaaga tcaagtgact cgagatccag   1920
acatgataag atacattgat gagtttggac aaaccacaac tagaatgcag tgaaaaaat    1980
gctttatttg tgaaatttgt gatgctattg ctttatttgt aaccattata agctgcaata   2040
aacaagttaa caacaacaat tgcattcatt ttatgtttca ggttcagggg gaggtgtggg   2100
aggttttta a                                                         2111
```

<210> SEQ ID NO 83
<211> LENGTH: 2426
<212> TYPE: DNA
<213> ORGANISM: Artificial Sequence
<220> FEATURE:
<223> OTHER INFORMATION: pHMI-hPAH-TC-022 transfer genome

<400> SEQUENCE: 83

```
ctgcgcgctc gctcgctcac tgaggccgcc cgggcaaagc ccgggcgtcg ggcgacctt      60
ggtcgcccgg cctcagtgag cgagcgagcg cgcagagagg gagtggaatt cacgcgtgga   120
tctgaattca attcacgcgt ggtacctccc taaaatgggc aaacattgca agcagcaaac   180
agcaaacaca cagccctccc tgcctgctga ccttggagct ggggcagagg tcagagacct   240
ctctgggccc atgccacctc caacatccac tcgaccctt ggaatttcgg tggagaggag    300
cagaggttgt cctggcgtgg tttaggtagt gtgagagggg aatgactcct ttcggtaagt   360
gcagtggaag ctgtacactg cccaggcaaa gcgtccgggc agcgtaggcg ggcgactcag   420
atcccagcca gtggacttag cccctgtttg ctcctccgat aactggggtg accttggtta   480
atattcacca gcagcctccc ccgttgcccc tctggatcca ctgcttaaat acggacgagg   540
acagggccct gtctcctcag cttcaggcac caccactgac ctgggacagt gaatcctcta   600
aggtaaatat aaaattttta agtgtataat gtgttaaact actgattcta attgtttctc   660
tcttttagat tccaaccttt ggaactgacc gccaccatgt ccactgctgt gctggagaac   720
ccaggcctgg gcaggaagtt gagtgacttt gggcaggaga cctcctacat agaagacaat   780
```

```
tgcaatcaga atggggccat ctctctgatc ttcagcccta aagaggaggt gggtgctctg    840
gcaaaagtgc tcagactctt tgaggagaat gatgtgaatc tcacccacat tgaatccagg    900
cccagcagac tcaaaaagga tgaatatgaa ttcttcaccc acttggacaa aaggtcctta    960
cctgccctta caaatatcat caaaattttg agacatgaca taggggcaac tgtacatgaa   1020
ctgagtagag ataaaaaaaa agacacagtc ccctggttcc ccaggaccat ccaggaattg   1080
gacaggtttg caaaccagat actgagctat ggtgctgagt tggatgctga tcacccaggc   1140
ttcaaggacc ctgtgtacag agcaaggaga aagcagtttg ctgacattgc ctacaattac   1200
aggcacggcc aacccattcc tagagtcgag tacatggaag aagagaagaa acctggggc    1260 actgtcttca agaccctgaa gtcactgtac aagacacatg cctgctatga atacaaccac   1320
atatttccac tcctagagaa atactgtgga ttccatgagg acaatatacc ccaattggag   1380
gatgtctcac agtttctgca gacttgtaca ggttttaggc tgaggccagt ggctgggctt   1440
ctcagcagca gggacttcct gggtggactg gcctttcgag ttttccactg tactcagtat   1500
atcagacatg gctccaagcc catgtatacc ccagaacctg acatctgcca tgaactgctt   1560
gggcatgtgc ctctgttttc agaccgttcc tttgcccagt tttctcagga gattggacta   1620
gccagcctag gtgcaccaga tgagtacatt gagaagttag caaccattta ctggttcaca   1680
gtggagttcg gcctttgcaa gcaaggggac tcaataaagg cctatggagc aggcctcctg   1740
tcaagttttg gagaactaca atactgccta tctgagaagc taaattatt acccttggaa    1800 ctagaaaaaa ctgcaataca gaactacaca gtgactgagt ttcagccact ctactatgtg   1860
gcagagtcct ttaatgatgc caagaaaag gtccgaaatt ttgctgcaac aattcccagg    1920
cctttctctg ttcgctatga tccatacacc caaagaattg aagtcctaga taacacccag   1980
cagctgaaaa tcctggcaga cagcatcaac tctgaaattg gaatcctctg ttctgccctg   2040
cagaagatca agtgactcga gatccagaca tgataagata cattgatgag tttggacaaa   2100
ccacaactag aatgcagtga aaaaatgct ttatttgtga aatttgtgat gctattgctt    2160
tatttgtaac cattataagc tgcaataaac aagttaacaa caacaattgc attcatttta   2220
tgtttcaggt tcaggggag gtgtgggagg ttttttaaag catgctgggg agagatcgat    2280
ctgaggaacc cctagtgatg gagttggcca ctccctctct gcgcgctcgc tcgctcactg   2340
aggccgggcg accaaaggtc gcccgacgcc cgggctttgc ccgggcggcc tcagtgagcg   2400
agcgagcgcg cagagaggga gtggcc                                       2426
```

<210> SEQ ID NO 84
<211> LENGTH: 2111
<212> TYPE: DNA
<213> ORGANISM: Artificial Sequence
<220> FEATURE:
<223> OTHER INFORMATION: pHMI-hPAH-TC-023 transfer genome

<400> SEQUENCE: 84

```
ccctaaaatg gcaaacatt gcaagcagca acagcaaac acacagccct ccctgcctgc      60
tgaccttgga gctggggcag aggtcagaga cctctctggg cccatgccac ctccaacatc   120
cactcgaccc cttggaattt cggtggagag gagcagaggt tgtcctggcg tggtttaggt   180
agtgtgagag gggaatgact cctttcggta agtgcagtgg aagctgtaca ctgcccaggc   240
aaagcgtccg ggcagcgtag gcgggcgact cagatcccag ccagtggact tagcccctgt    300
ttgctcctcc gataactggg gtgaccttgg ttaatattca ccagcagcct cccccgttgc   360
```

| | |
|---|---|
| ccctctggat ccactgctta aatacggacg aggacagggc cctgtctcct cagcttcagg | 420 |
| caccaccact gacctgggac agtgaatcct ctaaggtaaa tataaaattt ttaagtgtat | 480 |
| aatgtgttaa actactgatt ctaattgttt ctctctttta gattccaacc tttggaactg | 540 |
| accgccacca tgtccactgc ggtcctggaa aacccaggct tgggcaggaa actctctgac | 600 |
| tttggacagg aaacaagcta tattgaagac aactgcaatc aaaatggtgc catatcactg | 660 |
| atcttctcac tcaaagaaga agttggtgca ttggccaaag tattgcgctt atttgaggag | 720 |
| aatgatgtaa acctgaccca cattgaatct agaccttctc gtttaaagaa agatgagtat | 780 |
| gaattttca cccatttgga taaacgtagc ctgcctgctc tgacaaacat catcaagatc | 840 |
| ttgaggcatg acattggtgc cactgtccat gagctttcac gagataagaa gaaagacaca | 900 |
| gtgccctggt tcccaagaac cattcaagag ctggacagat tgccaatca gattctcagc | 960 |
| tatggagcgg aactggatgc tgaccaccct ggttttaaag atcctgtgta ccgtgcaaga | 1020 |
| cggaagcagt ttgctgacat tgcctacaac taccgccatg ggcagcccat ccctcgagtg | 1080 |
| gaatacatgg aggaagaaaa gaaaacatgg ggcacagtgt tcaagactct gaagtccttg | 1140 |
| tataaaaccc atgcttgcta tgagtacaat cacatttttc cacttcttga aaagtactgt | 1200 |
| ggcttccatg aagataacat tccccagctg gaagacgttt ctcaattcct gcagacttgc | 1260 |
| actggtttcc gcctccgacc tgtggctggc ctgctttcct ctcgggattt cttgggtggc | 1320 |
| ctggccttcc gagtcttcca ctgcacacag tacatccagac atggatccaa gcccatgtat | 1380 |
| acccccgaac ctgacatctg ccatgagctg ttgggacatg tgccttgtt ttcagatcgc | 1440 |
| agctttgccc agttttccca ggaaattggc cttgcctctc tgggtgcacc tgatgaatac | 1500 |
| attgaaaagc tcgccacaat ttactggttt actgtggagt ttgggctctg caaacaagga | 1560 |
| gactccataa aggcatatgg tgctgggctc ctgtcatcct ttggtgaatt acagtactgc | 1620 |
| ttatcagaga agccaaagct tctccccctg gagctggaga agacagccat ccaaaattac | 1680 |
| actgtcacgg agtccagcc cctgtattac gtggcagaga gttttaatga tgccaaggag | 1740 |
| aaagtaagga actttgctgc cacaatacct cggcccttct cagttcgcta cgacccatac | 1800 |
| acccaaagga ttgaggtctt ggacaatacc cagcagctta agattttggc tgattccatt | 1860 |
| aacagtgaaa ttggaatcct ttgcagtgcc ctccagaaaa taaagtaact cgagatccag | 1920 |
| acatgataag atacattgat gagtttggac aaaccacaac tagaatgcag tgaaaaaaat | 1980 |
| gctttatttg tgaaatttgt gatgctattg ctttatttgt aaccattata agctgcaata | 2040 |
| aacaagttaa caacaacaat tgcattcatt ttatgtttca ggttcagggg gaggtgtggg | 2100 |
| aggtttttta a | 2111 |

<210> SEQ ID NO 85
<211> LENGTH: 2426
<212> TYPE: DNA
<213> ORGANISM: Artificial Sequence
<220> FEATURE:
<223> OTHER INFORMATION: pHMI-hPAH-TC-023 transfer genome

<400> SEQUENCE: 85

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggaatt cacgcgtgga | 120 |
| tctgaattca attcacgcgt ggtacctccc taaatgggc aaacattgca agcagcaaac | 180 |
| agcaaacaca cagccctccc tgcctgctga ccttggagct ggggcagagg tcagagacct | 240 |
| ctctgggccc atgccacctc caacatccac tcgacccctt ggaatttcgg tggagaggag | 300 |

```
cagaggttgt cctggcgtgg tttaggtagt gtgagagggg aatgactcct ttcggtaagt      360
gcagtggaag ctgtacactg cccaggcaaa gcgtccgggc agcgtaggcg ggcgactcag      420
atcccagcca gtggacttag cccctgtttg ctcctccgat aactggggtg accttggtta      480
atattcacca gcagcctccc ccgttgcccc tctggatcca ctgcttaaat acggacgagg      540
acagggccct gtctcctcag cttcaggcac caccactgac ctgggacagt gaatcctcta      600
aggtaaatat aaaatttta agtgtataat gtgttaaact actgattcta attgtttctc      660
tcttttagat tccaaccttt ggaactgacc gccaccatgt ccactgcggt cctggaaaac      720
ccaggcttgg gcaggaaact ctctgacttt ggacaggaaa caagctatat tgaagacaac      780
tgcaatcaaa atggtgccat atcactgatc ttctcactca agaagaagt tggtgcattg       840 gccaaagtat tgcgcttatt tgaggagaat gatgtaaacc tgacccacat tgaatctaga      900
ccttctcgtt taaagaaaga tgagtatgaa ttttcaccc atttggataa acgtagcctg       960
cctgctctga caaacatcat caagatcttg aggcatgaca ttggtgccac tgtccatgag     1020
ctttcacgag ataagaagaa agacacagtg ccctggttcc caagaaccat tcaagagctg     1080
gacagatttg ccaatcagat tctcagctat ggagcggaac tggatgctga ccaccctggt     1140
tttaaagatc ctgtgtaccg tgcaagacgg aagcagtttg ctgacattgc ctacaactac     1200
cgccatgggc agcccatccc tcgagtggaa tacatggagg aagaaaagaa acatggggc      1260 acagtgttca agactctgaa gtccttgtat aaaacccatg cttgctatga gtacaatcac     1320 attttttccac ttcttgaaaa gtactgtggc ttccatgaag ataacattcc ccagctggaa    1380
gacgtttctc aattcctgca gacttgcact ggtttccgcc tccgacctgt ggctggcctg     1440 cttttcctctc gggatttctt gggtggcctg gccttccgag tcttccactg cacacagtac     1500
atcagacatg gatccaagcc catgtatacc cccgaacctg acatctgcca tgagctgttg     1560
ggacatgtgc ccttgttttc agatcgcagc tttgcccagt tttcccagga aattggcctt     1620
gcctctctgg gtgcacctga tgaatacatt gaaaagctcg ccacaattta ctggtttact     1680
gtggagtttg ggctctgcaa acaaggagac tccataaagg catatggtgc tgggctcctg     1740
tcatcctttg gtgaattaca gtactgctta tcagagaagc caaagcttct cccctggag      1800 ctggagaaga cagccatcca aaattacact gtcacggagt tccagccct gtattacgtg     1860 gcagagagtt ttaatgatgc caaggagaaa gtaaggaact tgctgccac aatacctcgg     1920 cccttctcag ttcgctacga cccatacacc caaaggattg aggtcttgga cataccccag     1980
cagcttaaga ttttggctga ttccattaac agtgaaattg gaatcctttg cagtgccctc    2040
cagaaaataa agtaactcga gatccagaca tgataagata cattgatgag tttggacaaa     2100
ccacaactag aatgcagtga aaaaaatgct ttatttgtga aatttgtgat gctattgctt     2160
tatttgtaac cattataagc tgcaataaac aagttaacaa caacaattgc attcattta      2220 tgtttcaggt tcaggggggg gtgtggaagg tttttaaag catgctgggg agagatcgat     2280
ctgaggaacc cctagtgatg gagttggcca ctccctctct cgcgctcgc tcgctcactg     2340 aggccgggcg accaaaggtc gcccgacgcc cgggctttgc ccgggcggcc tcagtgagcg    2400
agcgagcgcg cagagaggga gtggcc                                          2426
```

<210> SEQ ID NO 86
<211> LENGTH: 2042
<212> TYPE: DNA
<213> ORGANISM: Artificial Sequence
<220> FEATURE:

<223> OTHER INFORMATION: pHMI-01004 transfer genome

<400> SEQUENCE: 86

```
ccctaaaatg ggcaaacatt gcaagcagca aacagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag gggaatgact cctttcggta agtgcagtgg aagctgtaca ctgcccaggc     240
aaagcgtccg ggcagcgtag gcgggcgact cagatcccag ccagtggact tagcccctgt     300
ttgctcctcc gataactggg gtgaccttgg ttaatattca ccagcagcct cccccgttgc     360
ccctctggat ccactgctta aatacggacg aggacagggc cctgtctcct cagcttcagg     420
caccaccact gacctgggac agtgaatcct ctaaggtaaa tataaaattt ttaagtgtat     480
aatgtgttaa actactgatt ctaattgttt ctctcttta gattccaacc tttggaactg      540
accgccacca tgtccaccgc tgtgctggag aaccctgggc tggggaggaa actgtcagac     600
ttcgggcagg agacttcata cattgaggat aactgtaacc agaatggcgc catctctctg     660
atcttcagcc tgaaggagga agtgggcgcc ctggcaaagg tgctgcgcct gtttgaggag     720
aacgacgtga atctgaccca catcgagtcc cggccttcta gactgaagaa ggacgagtac     780
gagttcttta cccacctgga taagcggtcc ctgccagccc tgacaaacat catcaagatc     840
ctgaggcacg acatcggagc aaccgtgcac gagctgtctc gggacaagaa gaaggatacc     900
gtgccctggt tccctcggac aatccaggag ctggatagat tgccaaccag atcctgtct      960
tacggagcag agctggacgc agatcaccct ggcttcaagg acccagtgta tcgggcccgg    1020
agaaagcagt ttgccgatat cgcctacaat tataggcacg acagccaat ccctcgcgtg     1080
gagtatatgg aggaggagaa gaagacctgg ggcacagtgt tcaagaccct gaagagcctg    1140
tacaagacac acgcctgcta cgagtataac cacatcttcc ccctgctgga gaagtattgt    1200
ggctttcacg aggacaatat ccctcagctg gaggacgtga gccagttcct gcagacctgc    1260
acaggctttta ggctgagggc agtggcagga ctgctgagct cccgggactt cctgggagga    1320
ctggccttca gagtgtttca ctgcacccag tacatcaggc acggctccaa gccaatgtat    1380
acaccagagc ccgacatctg tcacgagctg ctgggccacg tgcccctgtt tagcgataga    1440
tccttcgccc agttttccca ggagatcgga ctggcatctc tgggagcacc tgacgagtac    1500
atcgagaagc tggccaccat ctattggttc acagtggagt ttggcctgtg caagcagggc    1560
gatagcatca aggcctacgg agcaggactg ctgtctagct tcggcgagct gcagtattgt    1620
ctgtccgaga agccaaagct gctgcccctg gagctggaga agaccgccat ccagaactac    1680
accgtgacag agttccagcc cctgtactat gtggccgagt cttttaacga tgccaaggag    1740
aaggtgagaa atttcgccgc cacaatccct aggcccttca gcgtgcggta cgacccttat    1800
acccagagga tcgaggtgct ggataataca cagcagctga agatcctggc tgactcaatc    1860
aatagcgaaa tcggaatcct gtgctccgcc ctgcagaaaa tcaaatgaat gctttatttg    1920
tgaaatttgt gatgctattg ctttatttgt aaccattata agctgcaata aacaagttaa    1980
caacaacaat tgcattcatt ttatgtttca ggttcagggg gaggtgtggg aggttttta     2040
aa                                                                   2042
```

<210> SEQ ID NO 87
<211> LENGTH: 2356
<212> TYPE: DNA
<213> ORGANISM: Artificial Sequence
<220> FEATURE:
<223> OTHER INFORMATION: pHMI-01004 transfer genome

<400> SEQUENCE: 87

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga     120
tctgaattca attcacgcgt ggtacctccc taaaatgggc aaacattgca agcagcaaac     180
agcaaacaca cagccctccc tgcctgctga ccttggagct ggggcagagg tcagagacct     240
ctctgggccc atgccacctc caacatccac tcgaccccct tggaatttcg tggagaggag     300
cagaggttgt cctggcgtgg tttaggtagt gtgagagggg aatgactcct ttcggtaagt     360
gcagtggaag ctgtacactg cccaggcaaa gcgtccgggc agcgtaggcg ggcgactcag     420
atcccagcca gtggacttag cccctgtttg ctcctccgat aactggggtg accttggtta     480
atattcacca gcagcctccc ccgttgcccc tctggatcca ctgcttaaat acggacgagg     540
acagggccct gtctcctcag cttcaggcac caccactgac ctgggacagt gaatcctcta     600
aggtaaatat aaaattttta agtgtataat gtgttaaact actgattcta attgtttctc     660
tcttttagat tccaaccttt ggaactgacc gccaccatgt ccaccgctgt gctggagaac     720
cctgggctgg ggaggaaact gtcagacttc gggcaggaga cttcatacat tgaggataac     780
tgtaaccaga atggcgccat ctctctgatc ttcagcctga aggaggaagt gggcgccctg     840
gcaaaggtgc tgcgcctgtt tgaggagaac gacgtgaatc tgacccacat cgagtcccgg     900
ccttctagac tgaagaagga cgagtacgag ttctttaccc acctggataa gcggtccctg     960
ccagccctga caaacatcat caagatcctg aggcacgaca tcggagcaac cgtgcacgag    1020
ctgtctcggg acaagaagaa ggataccgtg ccctggttcc ctcggacaat ccaggagctg    1080
gatagatttg ccaaccagat cctgtcttac ggagcagagc tggacgcaga tcaccctggc    1140
ttcaaggacc cagtgtatcg ggcccggaga aagcagtttg ccgatatcgc ctacaattat    1200
aggcacggac agccaatccc tcgcgtggag tatatggagg aggagaagaa gacctggggc    1260
acagtgttca gaccctgaa gagcctgtac aagacacacg cctgctacga gtataaccac    1320
atcttccccc tgctggagaa gtattgtggc tttcacgagg acaatatccc tcagctggag    1380
gacgtgagcc agttcctgca gacctgcaca ggctttaggc tgaggccagt ggcaggactg    1440
ctgagctccc gggacttcct gggaggactg gccttcagag tgtttcactg cacccagtac    1500
atcaggcacg gctccaagcc aatgtataca ccagagcccg acatctgtca cgagctgctg    1560
ggccacgtgc ccctgtttag cgatagatcc ttcgcccagt tttcccagga gatcggactg    1620
gcatctctgg gagcacctga cgagtacatc gagaagctgg ccaccatcta ttggttcaca    1680
gtggagtttg gcctgtgcaa gcagggcgat agcatcaagg cctacggagc aggactgctg    1740
tctagcttcg gcgagctgca gtattgtctg tccgagaagc caaagctgct gccctggag    1800
ctggagaaga ccgccatcca gaactacacc gtgacagagt tccagccct gtactatgtg    1860
gccgagtctt ttaacgatgc caaggagaag gtgagaaatt tcgccgccac aatccctagg    1920
cccttcagcg tgcggtacga cccttatacc cagaggatcg aggtgctgga taatacacag    1980
cagctgaaga tcctggctga ctcaatcaat agcgaaatcg gaatcctgtg ctccgccctg    2040
cagaaaatca aatgaatgct ttatttgtga aatttgtgat gctattgctt tatttgtaac    2100
cattataagc tgcaataaac aagttaacaa caacaattgc attcatttta tgtttcaggt    2160
tcaggggag gtgtgggagg ttttttaaag catgctgggg agagatcgat ctgaggaacc    2220
```

```
cctagtgatg gagttggcca ctccctctct gcgcgctcgc tcgctcactg aggccgggcg   2280
accaaaggtc gcccgacgcc cgggctttgc ccgggcggcc tcagtgagcg agcgagcgcg   2340
cagagaggga gtggcc                                                  2356

<210> SEQ ID NO 88
<211> LENGTH: 5041
<212> TYPE: DNA
<213> ORGANISM: Artificial Sequence
<220> FEATURE:
<223> OTHER INFORMATION: pHMI-01004 full sequence

<400> SEQUENCE: 88
agaaaaactc atcgagcatc aaatgaaatt gcaatttatt catatcagga ttatcaatac     60
catatttttg aaaaagccgt ttctgtaatg aaggagaaaa ctcaccgagg cagttccata    120
ggatggcaag atcctggtat cggtctgcga ttccgactcg tccaacatca atacaaccta    180
ttaatttccc ctcgtcaaaa ataaggttat caagtgagaa atcaccatga gtgacgactg    240
aatccggtga gaatggcaaa agtttatgca tttctttcca gacttgttca acaggccagc    300
cattacgctc gtcatcaaaa tcactcgcat caaccaaacc gttattcatt cgtgattgcg    360
cctgagcgag gcgaaatacg cgatcgctgt taaaaggaca attacaaaca ggaatcgagt    420
gcaaccggcg caggaacact gccagcgcat caacaatatt ttcacctgaa tcaggatatt    480
cttctaatac ctggaacgct gttttttccgg ggatcgcagt ggtgagtaac catgcatcat    540
caggagtacg gataaaatgc ttgatggtcg aagtggcat aaattccgtc agccagttta    600
gtctgaccat ctcatctgta acatcattgg caacgctacc tttgccatgt ttcagaaaca    660
actctggcgc atcgggcttc ccatacaagc gatagattgt cgcacctgat tgcccgacat    720
tatcgcgagc ccatttatac ccatataaat cagcatccat gttggaattt aatcgcggcc    780
tcgacgtttc ccgttgaata tggctcatat tcttcctttt tcaatattat tgaagcattt    840
atcagggtta ttgtctcatg agcggataca tatttgaatg tatttagaaa aataaacaaa    900
taggggtcag tgttacaacc aattaaccaa ttctgaacat tatcgcgagc ccatttatac    960
ctgaatatgg ctcataacac cccttgtttg cctggcggca gtagcgcggt ggtcccacct   1020 gacccccatgc cgaactcaga agtgaaacgc cgtagcgccg atggtagtgt ggggactccc   1080
catgcgagag tagggaactg ccaggcatca aataaaacga aaggctcagt cgaaagactg   1140
ggcctttcgc ccaaaccata tgattgacat gctagtttta cgattaccgt tcatcgccct   1200
gcgcgctcgc tcgctcactg aggccgcccg gcaaagccc gggcgtcggg cgacctttgg   1260
tcgcccggcc tcagtgagcg agcgagcgcg cagagaggga gtggaattca cgcgtggatc   1320
tgaattcaat tcacgcgtgg tacctcccta aatgggcaa acattgcaag cagcaaacag   1380
caaacacaca gccctccctg cctgctgacc ttggagctgg gcagaggtc agagacctct   1440 ctgggcccat gccacctcca acatccactc gacccttgg aatttcggtg agaggagca   1500 gaggttgtcc tggcgtggtt taggtagtgt gagagggaa tgactccttt cggtaagtgc   1560
agtggaagct gtacactgcc caggcaaagc gtccgggcag cgtaggcggg cgactcagat   1620
cccagccagt ggacttagcc cctgtttgct cctccgataa ctggggtgac cttggttaat   1680
attcaccagc agcctccccc gttgcccctc tggatccact gcttaaatac ggacgaggac   1740
agggccctgt ctcctcagct tcaggcacca ccactgacct gggacagtga atcctctaag   1800
gtaaatataa aattttttaag tgtataatgt gttaaactac tgattctaat tgtttctctc   1860
ttttagattc caacctttgg aactgaccgc caccatgtcc accgctgtgc tggagaaccc   1920
```

```
tgggctgggg aggaaactgt cagacttcgg gcaggagact tcatacattg aggataactg    1980
taaccagaat ggcgccatct ctctgatctt cagcctgaag gaggaagtgg gcgccctggc    2040
aaaggtgctg cgcctgtttg aggagaacga cgtgaatctg acccacatcg agtcccggcc    2100
ttctagactg aagaaggacg agtacgagtt ctttacccac ctggataagc ggtccctgcc    2160
agccctgaca acatcatca agatcctgag gcacgacatc ggagcaaccg tgcacgagct    2220
gtctcgggac aagaagaagg ataccgtgcc ctggttccct cggacaatcc aggagctgga    2280
tagatttgcc aaccagatcc tgtcttacgg agcagagctg gacgcagatc accctggctt    2340
caaggaccca gtgtatcggg cccggagaaa gcagtttgcc gatatcgcct acaattatag    2400
gcacggacag ccaatccctc gcgtggagta tatggaggag gagaagaaga cctggggcac    2460
agtgttcaag accctgaaga gcctgtacaa gacacacgcc tgctacgagt ataaccacat    2520
cttccccctg ctggagaagt attgtggctt tcacgaggac aatatccctc agctggagga    2580
cgtgagccag ttcctgcaga cctgcacagg ctttaggctg aggccagtgg caggactgct    2640
gagctcccgg gacttcctgg aggactggc cttcagagtg tttcactgca cccagtacat    2700
caggcacggc tccaagccaa tgtatacacc agagcccgac atctgtcacg agctgctggg    2760
ccacgtgccc ctgtttagcg atagatcctt cgcccagttt tcccaggaga tcggactggc    2820
atctctggga gcacctgacg agtacatcga gaagctggcc accatctatt ggttcacagt    2880
ggagtttggc ctgtgcaagc agggcgatag catcaaggcc tacggagcag gactgctgtc    2940
tagcttcggc gagctgcagt attgtctgtc cgagaagcca aagctgctgc ccctggagct    3000
ggagaagacc gccatccaga actacaccgt gacagagttc cagcccctgt actatgtggc    3060
cgagtctttt aacgatgcca aggagaaggt gagaaatttc gccgccacaa tccctaggcc    3120
cttcagcgtg cggtacgacc cttatcccca gaggatcgag gtgctggata atacacagca    3180
gctgaagatc ctggctgact caatcaatag cgaaatcgga atcctgtgct ccgccctgca    3240
gaaaatcaaa tgaatgcttt atttgtgaaa tttgtgatgc tattgcttta tttgtaacca    3300
ttataagctg caataaacaa gttaacaaca acaattgcat tcattttatg tttcaggttc    3360
agggggaggt gtgggaggtt ttttaaagca tgctggggag agatcgatct gaggaacccc    3420
tagtgatgga gttggccact ccctctctgc gcgctcgctc gctcactgag gccgggcgac    3480
caaaggtcgc ccgacgcccg ggcttcgccc gggcggcctc agtgagcgag cgagcgcgca    3540
gagagggagt ggcccatatg cggtaccaga attcgggtct agacgtcaaa agggcgacac    3600
aaaatttatt ctaaatgcat aataaatact gataacatct tatagtttgt attatatttt    3660
gtattatcgt tgacatgtat aattttgata tcaaaaactg attttcccctt tattattttc    3720 gagatttatt ttcttaattc tctttaacaa actagaaata ttgtatatac aaaaaatcat    3780
aaataataga tgaatagttt aattataggt gttcatcaat cgaaaaagca acgtatctta    3840
tttaaagtgc gttgcttttt tctcatttat aaggttaaat aattctcata tatcaagcaa    3900
agtgacaggc gcccttaaat attctgacaa atgctctttc cctaaactcc ccccataaaa    3960
aaacccgccg aagcgggttt ttacgttatt tgcggattaa cgattactcg ttatcagaac    4020
cgcccagggg gcccgagctt aagactggcc gtcgttttac aacacagaaa gagtttgtag    4080
aaacgcaaaa aggccatccg tcaggggcct tctgcttagt ttgatgcctg gcagttccct    4140
actctcgcct tccgcttcct cgctcactga ctcgctgcgc tcggtcgttc ggctgcggcg    4200
agcggtatca gctcactcaa aggcggtaat acggttatcc acagaatcag ggataacgc    4260
```

```
aggaaagaac atgtgagcaa aaggccagca aaaggccagg aaccgtaaaa aggccgcgtt    4320
gctggcgttt ttccataggc tccgcccccc tgacgagcat cacaaaaatc gacgctcaag    4380
tcagaggtgg cgaaacccga caggactata aagataccag gcgtttcccc ctggaagctc    4440
cctcgtgcgc tctcctgttc cgaccctgcc gcttaccgga tacctgtccg cctttctccc    4500
ttcgggaagc gtggcgcttt ctcatagctc acgctgtagg tatctcagtt cggtgtaggt    4560
cgttcgctcc aagctgggct gtgtgcacga accccccgtt cagcccgacc gctgcgcctt    4620
atccggtaac tatcgtcttg agtccaaccc ggtaagacac gacttatcgc cactggcagc    4680
agccactggt aacaggatta gcagagcgag gtatgtaggc ggtgctacag agttcttgaa    4740
gtggtgggct aactacggct acactagaag aacagtattt ggtatctgcg ctctgctgaa    4800
gccagttacc ttcggaaaaa gagttggtag ctcttgatcc ggcaaacaaa ccaccgctgg    4860
tagcggtggt ttttttgttt gcaagcagca gattacgcgc agaaaaaaag gatctcaaga    4920
agatcctttg atcttttcta cggggtctga cgctcagtgg aacgacgcgc gcgtaactca    4980
cgttaaggga ttttggtcat gagcttgcgc cgtcccgtca gtcagcgta atgctctgct    5040 t                                                                     5041
```

<210> SEQ ID NO 89
<211> LENGTH: 2042
<212> TYPE: DNA
<213> ORGANISM: Artificial Sequence
<220> FEATURE:
<223> OTHER INFORMATION: pHMI-01008 transfer genome

<400> SEQUENCE: 89

```
ccctaaaatg ggcaaacatt gcaagcagca acagcaaac acacagccct ccctgcctgc      60
tgaccttgga gctggggcag aggtcagaga cctctctggg cccatgccac ctccaacatc    120
cactcgaccc cttggaattt cggtggagag gagcagaggt tgtcctggcg tggtttaggt    180
agtgtgagag gggaatgact cctttcggta agtgcagtgg aagctgtaca ctgcccaggc    240
aaagcgtccg ggcagcgtag gcgggcgact cagatcccag ccagtggact tagcccctgt    300
ttgctcctcc gataactggg gtgaccttgg ttaatattca ccagcagcct ccccgttgc    360 ccctctggat ccactgctta aatacggacg aggacagggc cctgtctcct cagcttcagg    420
caccaccact gacctgggac agtgaatcct ctaaggtaaa tataaaattt ttaagtgtat    480
aatgtgttaa actactgatt ctaattgttt ctctcttta gattccaacc tttggaactg    540
accgccacca tgtccaccgc tgtgctggag accctgggc tggggaggaa actgtcagac    600
ttcgggcagg agacttcata cattgaggat aactgtaacc agaatggcgc catctctctg    660
atcttcagcc tgaaggagga agtgggcgcc ctggcaaagg tgctgcgcct gtttgaggag    720
aacgacgtga atctgaccca catcgagtcc ggccttcta gactgaagaa ggacgagtac    780
gagttcttta cccacctgga taagcggtcc ctgccagccc tgacaaacat catcaagatc    840
ctgaggcacg acatcggagc aaccgtgcac gagctgtctc gggacaagaa gaaggatacc    900
gtgccctggt tccctcggac aatccaggag ctggatagat tgccaaccag gatcctgtct    960
tacggagcag agctggacgc agatcaccct ggcttcaagg acccagtgta tcgggcccgg   1020
agaaagcagt ttgccgatat cgcctacaat tataggcacg acagccaat ccctcgcgtg    1080 gagtatatgg aggaggagaa gaagacctgg ggcacagtgt tcaagaccct gaagagcctg    1140
tacaagacac acgcctgcta cgagtataac cacatcttcc cctgctgga gaagtattgt    1200 ggctttcacg aggacaatat ccctcagctg gaggacgtga gccagttcct gcagacctgc    1260
```

```
acaggcttta ggctgaggcc agtggcagga ctgctgagct cccgggactt cctgggagga    1320
ctggccttca gagtgtttca ctgcacccag tacatcaggc acggctccaa gccaatgtat    1380
acaccagagc ccgacatctg tcacgagctg ctgggccacg tgcccctgtt tagcgataga    1440
tccttcgccc agttttccca ggagatcgga ctggcatctc tgggagcacc tgacgagtac    1500
atcgagaagc tggccaccat ctattggttc acagtggagt ttggcctgtg caagcagggc    1560
gatagcatca aggcctacgg agcaggactg ctgtctagct cggcgagctg cagtattgt     1620 ctgtccgaga agccaaagct gctgcccctg agctggaga agaccgccat ccagaactac     1680
accgtgacag agttccagcc cctgtactat gtggccgagc ttttaacga tgccaaggag     1740 aaggtgagaa atttcgccgc cacaatccct aggcccttca gcgtgcggta cgacccttat    1800
acccagagga tcgaggtgct ggataataca cagcagctga agatcctggc tgactcaatc    1860
aatagcgaaa tcggaatcct gtgctccgcc ctgcagaaaa tcaaatgaat gctttatttg    1920
tgaaatttgt gatgctattg ctttatttgt aaccattata agctgcaata acaagttaa     1980 caacaacaat tgcattcatt ttatgtttca ggttcagggg gaggtgtggg aggttttta     2040 aa                                                                     2042

<210> SEQ ID NO 90
<211> LENGTH: 2393
<212> TYPE: DNA
<213> ORGANISM: Artificial Sequence
<220> FEATURE:
<223> OTHER INFORMATION: pHMI-01008 transfer genome

<400> SEQUENCE: 90
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga    120
tctgaattca attcacgcgt ggtacctccc taaaatgggc aaacattgca agcagcaaac    180
agcaaacaca cagccctccc tgcctgctga ccttggagct ggggcagagg tcagagacct    240
ctctgggccc atgccacctc caacatccac tcgacccctt ggaatttcgg tggagaggag    300
cagaggttgt cctggcgtgg tttaggtagt gtgagaggg aatgactcct ttcggtaagt     360
gcagtggaag ctgtacactg cccaggcaaa gcgtccgggc agcgtaggcg ggcgactcag    420
atcccagcca gtggacttag cccctgtttg ctcctccgat aactgggtg accttggtta     480 atattcacca gcagcctccc ccgttgcccc tctggatcca ctgcttaaat acggacgagg    540
acagggccct gtctcctcag cttcaggcac caccactgac ctgggacagt gaatcctcta    600
aggtaaatat aaaatttta agtgtataat gtgttaaact actgattcta attgtttctc      660
tcttttagat tccaaccttt ggaactgacc gccaccatgt ccaccgctgt gctgagaaac    720
cctgggctgg ggaggaaact gtcagacttc gggcaggaga cttcatacat tgaggataac    780
tgtaaccaga atggcgccat ctctctgatc ttcagcctga aggaggaagt gggcgccctg    840
gcaaaggtgc tgcgcctgtt tgaggagaac gacgtgaatc tgacccacat cgagtcccgg    900
ccttctagac tgaagaagga cgagtacgag ttctttaccc acctggataa gcggtccctg    960
ccagccctga caaacatcat caagatcctg aggcacgaca tcgagcaac cgtgcacgag    1020 ctgtctcggg acaagaagaa ggataccgtg ccctggttcc ctcggacaat ccaggagctg    1080
gatagatttg ccaaccagat cctgtcttac ggagcagagc tggacgcaga tcaccctggc    1140
ttcaaggacc cagtgtatcg ggcccggaga aagcagtttg ccgatatcgc ctacaattat    1200
```

```
aggcacggac agccaatccc tcgcgtggag tatatggagg aggagaagaa gacctggggc    1260
acagtgttca agaccctgaa gagcctgtac aagacacacg cctgctacga gtataaccac    1320
atcttccccc tgctggagaa gtattgtggc tttcacgagg acaatatccc tcagctggag    1380
gacgtgagcc agttcctgca gacctgcaca ggctttaggc tgaggccagt ggcaggactg    1440
ctgagctccc gggacttcct gggaggactg gccttcagag tgtttcactg cacccagtac    1500
atcaggcacg gctccaagcc aatgtataca ccagagcccg acatctgtca cgagctgctg    1560
ggccacgtgc ccctgtttag cgatagatcc ttcgcccagt tttcccagga gatcggactg    1620
gcatctctgg gagcacctga cgagtacatc gagaagctgg ccaccatcta ttggttcaca    1680
gtggagtttg gcctgtgcaa gcagggcgat agcatcaagg cctacggagc aggactgctg    1740
tctagcttcg gcgagctgca gtattgtctg tccgagaagc aaagctgct gcccctggag    1800 ctggagaaga ccgccatcca gaactacacc gtgacagagt tccagcccct gtactatgtg    1860
gccgagtctt ttaacgatgc caaggagaag gtgagaaatt cgccgccac aatccctagg    1920 cccttcagcg tgcggtacga cccttatacc cagaggatcg aggtgctgga taatacacag    1980
cagctgaaga tcctggctga ctcaatcaat agcgaaatcg gaatcctgtg ctccgccctg    2040
cagaaaatca aatgaatgct ttatttgtga aatttgtgat gctattgctt tatttgtaac    2100
cattataagc tgcaataaac aagttaacaa caacaattgc attcatttta tgtttcaggt    2160 tcaggggag gtgtgggagg tttttaaag catgctggg agagatcgat ctggtagata    2220
agtagcatgg cgggttaatc attaactaca aggaacccct agtgatggag ttggccactc    2280
cctctctgcg cgctcgctcg ctcactgagg ccgggcgacc aaaggtcgcc cgacgcccgg    2340
gctttgcccg ggcggcctca gtgagcgagc gagcgcgcag agagggagtg gcc           2393
```

<210> SEQ ID NO 91
<211> LENGTH: 5078
<212> TYPE: DNA
<213> ORGANISM: Artificial Sequence
<220> FEATURE:
<223> OTHER INFORMATION: pHMI-01008 full sequence

<400> SEQUENCE: 91

```
agaaaaactc atcgagcatc aaatgaaatt gcaatttatt catatcagga ttatcaatac      60
catatttttg aaaagccgt ttctgtaatg aaggagaaaa ctcaccgagg cagttccata     120
ggatggcaag atcctggtat cggtctgcga ttccgactcg tccaacatca atacaaccta     180
ttaatttccc ctcgtcaaaa ataaggttat caagtgagaa atcaccatga gtgacgactg     240
aatccggtga gaatggcaaa agtttatgca tttctttcca gacttgttca acaggccagc     300
cattacgctc gtcatcaaaa tcactcgcat caaccaaacc gttattcatt cgtgattgcg     360
cctgagcgag gcgaaatacg cgatcgctgt taaaaggaca attacaaaca ggaatcgagt     420
gcaaccggcg caggaacact gccagcgcat caacaatatt ttcacctgaa tcaggatatt     480
cttctaatac ctggaacgct gttttccgg ggatcgcagt ggtgagtaac catgcatcat     540
caggagtacg gataaaatgc ttgatggtcg aagtggcat aaattccgtc agccagttta     600
gtctgaccat ctcatctgta acatcattgg caacgctacc tttgccatgt ttcagaaaca     660
actctggcgc atcgggcttc ccatacaagc gatagattgt cgcacctgat tgcccgacat     720
tatcgcgagc ccatttatac ccatataaat cagcatccat gttggaattt aatcgcggcc     780
tcgacgtttc ccgttgaata tggctcatat tcttcctttt tcaatattat tgaagcattt     840
atcagggtta ttgtctcatg agcggataca tatttgaatg tatttagaaa aataaacaaa     900
```

| | |
|---|---|
| tagggggtcag tgttacaacc aattaaccaa ttctgaacat tatcgcgagc ccatttatac | 960 |
| ctgaatatgg ctcataacac cccttgtttg cctggcggca gtagcgcggt ggtcccacct | 1020 |
| gaccccatgc cgaactcaga agtgaaacgc cgtagcgccg atggtagtgt ggggactccc | 1080 |
| catgcgagag tagggaactg ccaggcatca aataaaacga aaggctcagt cgaaagactg | 1140 |
| ggcctttcgc ccaaaccata tgattgacat gctagttta cgattaccgt tcatcgccct | 1200 |
| gcgcgctcgc tcgctcactg aggccgcccg ggcaaagccc gggcgtcggg cgacctttgg | 1260 |
| tcgcccggcc tcagtgagcg agcgagcgcg cagagaggga gtggaattca cgcgtggatc | 1320 |
| tgaattcaat tcacgcgtgg tacctccta aatgggcaa acattgcaag cagcaaacag | 1380 |
| caaacacaca gccctccctg cctgctgacc ttggagctgg ggcagaggtc agagacctct | 1440 |
| ctgggcccat gccacctcca acatccactc gaccccttgg aatttcggtg gagaggagca | 1500 |
| gaggttgtcc tggcgtggtt taggtagtgt gagaggggaa tgactccttt cggtaagtgc | 1560 |
| agtggaagct gtacactgcc caggcaaagc gtccgggcag cgtaggcggg cgactcagat | 1620 |
| cccagccagt ggacttagcc cctgtttgct cctccgataa ctggggtgac cttggttaat | 1680 |
| attcaccagc agcctccccc gttgcccctc tggatccact gcttaaatac ggacgaggac | 1740 |
| agggccctgt ctcctcagct tcaggcacca ccactgacct gggacagtga atcctctaag | 1800 |
| gtaaatataa aattttaag tgtataatgt gttaaactac tgattctaat tgtttctctc | 1860 |
| ttttagattc caacctttgg aactgaccgc caccatgtcc accgctgtgc tggagaaccc | 1920 |
| tgggctgggg aggaaactgt cagacttcgg gcaggagact tcatacattg aggataactg | 1980 |
| taaccagaat ggcgccatct ctctgatctt cagcctgaag gaggaagtgg gcgccctggc | 2040 |
| aaaggtgctg cgcctgtttg aggagaacga cgtgaatctg acccacatcg agtcccggcc | 2100 |
| ttctagactg aagaaggacg agtacgagtt cttacccac ctggataagc ggtccctgcc | 2160 |
| agccctgaca aacatcatca agatcctgag gcacgacatc ggagcaaccg tgcacgagct | 2220 |
| gtctcgggac aagaagaagg ataccgtgcc ctggttccct cggacaatcc aggagctgga | 2280 |
| tagatttgcc aaccagatcc tgtcttacgg agcagagctg gacgcagatc accctggctt | 2340 |
| caaggaccca gtgtatcggg cccggagaaa gcagtttgcc gatatcgcct acaattatag | 2400 |
| gcacggacag ccaatccctc gcgtggagta tatggaggag gagaagaaga cctggggcac | 2460 |
| agtgttcaag accctgaaga gcctgtacaa gacacacgcc tgctacgagt ataaccacat | 2520 |
| cttccccctg ctggagaagt attgtggctt tcacgaggac aatatccctc agctggagga | 2580 |
| cgtgagccag ttcctgcaga cctgcacagg ctttaggctg aggccagtgg caggactgct | 2640 |
| gagctcccgg gacttcctgg gaggactggc cttcagagtg tttcactgca cccagtacat | 2700 |
| caggcacggc tccaagccaa tgtatacacc agagcccgac atctgtcacg agctgctggg | 2760 |
| ccacgtgccc ctgtttagcg atagatcctt cgcccagttt tcccaggaga tcggactggc | 2820 |
| atctctggga gcacctgacg agtacatcga aagctggcc accatctatt ggttcacagt | 2880 |
| ggagtttggc ctgtgcaagc agggcgatag catcaaggcc tacggagcag gactgctgtc | 2940 |
| tagcttcggc gagctgcagt attgtctgtc cgagaagcca aagctgctgc ccctggagct | 3000 |
| ggagaagacc gccatccaga actacaccgt gacagagttc cagcccctgt actatgtggc | 3060 |
| cgagtctttt aacgatgcca aggagaaggt gagaaatttc gccgccacaa tccctaggcc | 3120 |
| cttcagcgtg cggtacgacc cttataccca gaggatcgag gtgctggata atacacagca | 3180 |
| gctgaagatc ctggctgact caatcaatag cgaaatcgga atcctgtgct ccgccctgca | 3240 |

| | | | | |
|---|---|---|---|---|
| gaaaatcaaa | tgaatgcttt | atttgtgaaa | tttgtgatgc | tattgcttta tttgtaacca | 3300 |
| ttataagctg | caataaacaa | gttaacaaca | acaattgcat | tcattttatg tttcaggttc | 3360 |
| aggggaggt | gtgggaggtt | ttttaaagca | tgctggggag | agatcgatct ggtagataag | 3420 |
| tagcatggcg | ggttaatcat | taactacaag | gaaccctag | tgatggagtt ggccactccc | 3480 |
| tctctgcgcg | ctcgctcgct | cactgaggcc | gggcgaccaa | aggtcgcccg acgcccgggc | 3540 |
| tttgcccggg | cggcctcagt | gagcgagcga | gcgcgcagag | agggagtggc ccatatgcgg | 3600 |
| taccagaatt | cgggtctaga | cgtcaaaagg | gcgacacaaa | atttattcta aatgcataat | 3660 |
| aaatactgat | aacatcttat | agtttgtatt | atattttgta | ttatcgttga catgtataat | 3720 |
| tttgatatca | aaaactgatt | ttcccttat | tattttcgag | atttattttc ttaattctct | 3780 |
| ttaacaaact | agaatattg | tatatacaaa | aaatcataaa | taatagatga atagtttaat | 3840 |
| tataggtgtt | catcaatcga | aaaagcaacg | tatcttattt | aaagtgcgtt gctttttct | 3900 |
| catttataag | gttaaataat | tctcatatat | caagcaaagt | gacaggcgcc cttaaatatt | 3960 |
| ctgacaaatg | ctcttcct | aaactccccc | cataaaaaaa | cccgccgaag cgggtttta | 4020 |
| cgttatttgc | ggattaacga | ttactcgtta | tcagaaccgc | ccaggggcc cgagcttaag | 4080 |
| actggccgtc | gttttacaac | acagaaagag | tttgtagaaa | cgcaaaaagg ccatccgtca | 4140 |
| ggggccttct | gcttagtttg | atgcctggca | gttccctact | ctcgccttcc gcttcctcgc | 4200 |
| tcactgactc | gctgcgctcg | tcgttcggc | tgcggcgagc | ggtatcagct cactcaaagg | 4260 |
| cggtaatacg | gttatccaca | gaatcagggg | ataacgcagg | aaagaacatg tgagcaaaag | 4320 |
| gccagcaaaa | ggccaggaac | cgtaaaaagg | ccgcgttgct | ggcgttttc cataggctcc | 4380 |
| gccccctga | cgagcatcac | aaaaatcgac | gctcaagtca | gaggtggcga accccgacag | 4440 |
| gactataaag | ataccaggcg | tttcccctg | gaagctccct | cgtgcgctct cctgttccga | 4500 |
| ccctgccgct | taccggatac | ctgtccgcct | ttctcccttc | gggaagcgtg gcgctttctc | 4560 |
| atagctcacg | ctgtaggtat | ctcagttcgg | tgtaggtcgt | tcgctccaag ctgggctgtg | 4620 |
| tgcacgaacc | cccgttcag | cccgaccgct | gcgccttatc | cggtaactat cgtcttgagt | 4680 |
| ccaacccggt | aagacacgac | ttatcgccac | tggcagcagc | cactggtaac aggattagca | 4740 |
| gagcgaggta | tgtaggcggt | gctacagagt | tcttgaagtg | gtgggctaac tacggctaca | 4800 |
| ctagaagaac | agtatttggt | atctgcgctc | tgctgaagcc | agttaccttc ggaaaaagag | 4860 |
| ttggtagctc | ttgatccggc | aaacaaacca | ccgctggtag | cggtggtttt tttgtttgca | 4920 |
| agcagcagat | tacgcgcaga | aaaaaaggat | ctcaagaaga | tcctttgatc ttttctacgg | 4980 |
| ggtctgacgc | tcagtggaac | gacgcgcgcg | taactcacgt | taagggattt tggtcatgag | 5040 |
| cttgcgccgt | cccgtcaagt | cagcgtaatg | ctctgctt | | 5078 |

<210> SEQ ID NO 92
<211> LENGTH: 6020
<212> TYPE: DNA
<213> ORGANISM: Artificial Sequence
<220> FEATURE:
<223> OTHER INFORMATION: pHMI-hPAH-TC-025 full sequence

<400> SEQUENCE: 92

| | | | | |
|---|---|---|---|---|
| aacgccagca | acgcggcctt | tttacggttc | ctggcctttt | gctggccttt tgctcacatg | 60 |
| ttctttcctg | cgttatcccc | tgattctgtg | gataaccgta | ttaccgcctt tgagtgagct | 120 |
| gataccgctc | gccgcagccg | aacgaccgag | cgcagcgagt | cagtgagcga ggaagcggaa | 180 |
| gagcgcccaa | tacgcaaacc | gcctctcccc | gcgcgttggc | cgattcatta atgcagcagc | 240 |

```
tggcgtaata gcgaagaggc ccgcaccgat cgcccttccc aacagttgcg cagcctgaat      300
ggcgaatgga attccagacg attgagcgtc aaaatgtagg tatttccatg agcgtttttc      360
ctgttgcaat ggctggcggt aatattgttc tggatattac cagcaaggcc gatagtttga      420
gttcttctac tcaggcaagt gatgttatta ctaatcaaag aagtattgcg acaacggtta      480
atttgcgtga tggacagact cttttactcg gtggcctcac tgattataaa aacacttctc      540
aggattctgg cgtaccgttc ctgtctaaaa tccctttaat cggcctcctg tttagctccc      600
gctctgattc taacgaggaa agcacgttat acgtgctcgt caaagcaacc atagtacgcg      660
ccctgtagcg cgcattaag cgcggcgggt gtggtggtta cgcgcagcgt gaccgctaca      720
cttgccagcg ccctagcgcc cgctcctttc gctttcttcc cttcctttct cgccacgttc      780
gccggctttc cccgtcaagc tctaaatcgg gggctccctt tagggttccg atttagtgct      840
ttacggcacc tcgaccccaa aaaacttgat tagggtgatg gttcacgtag tgggccatcg      900
ccctgataga cggtttttcg ccctttgacg ttggagtcca cgttctttaa tagtggactc      960
ttgttccaaa ctggaacaac actcaaccct atctcggtct attcttttga tttataaggg     1020
attttgccga tttcggccta ttggttaaaa aatgagctga tttaacaaaa atttaacgcg     1080
aattttaaca aaatattaac gcttacaatt taaatatttg cttatacaat cttcctgttt     1140

ttggggcttt tctgattatc aaccggggta catatgattg acatgctagt tttacgatta     1200
ccgttcatcg ccctgcgcgc tcgctcgctc actgaggccg cccgggcaaa gcccggcgt     1260 cgggcgacct ttggtcgccc ggcctcagt agcgagcgag cgcgcagaga gggagtggaa     1320

ttcacgcgtg gatctgaatt caattcacgc gtggtacctc cctaaaatgg gcaaacattg     1380
caagcagcaa acagcaaaca cacagccctc cctgcctgct gaccttggag ctgggcaga     1440 ggtcagagac ctctctgggc ccatgccacc tccaacatcc actcgaccccc ttggaatttc     1500 ggtggagagg agcagaggtt gtcctggcgt ggtttaggta gtgtgagagg ggaatgactc     1560
ctttcggtaa gtgcagtgga agctgtacac tgcccaggca aagcgtccgg gcagcgtagg     1620
cgggcgactc agatcccagc cagtggactt agcccctgtt tgctcctccg ataactgggg     1680

tgaccttggt taatattcac cagcagcctc ccccgttgcc cctctggatc cactgcttaa     1740

atacggacga ggacagggcc ctgtctcctc agcttcaggc accaccactg acctgggaca     1800
gtgaatcctc taaggtaaat ataaaatttt taagtgtata atgtgttaaa ctactgattc     1860

taattgtttc tctcttttag attccaacct ттggaактga ccgccaccat gtccaccgct     1920
gtgctggaga ccctgggct ggggaggaaa ctgtcagact tcgggcagga gacttcatac     1980

attgaggata actgtaacca gaatggcgcc atctctctga тcтткcagcст gaaggaggaa     2040 gtgggcgccc tggcaaaggt gctgcgcctg tttgaggaga cgacgtgaa тстgaccccac     2100 atcgagtccc ggcстткcтag actgaagaag gacgagtacg agttctttac ccacctggat     2160
aagcggtccc tgccagccct gacaaacatc atcaagatcc tgaggcacga catcggagca     2220
accgtgcacg agctgtctcg ggacaagaag aaggataccg tgccctggtt ccctcggaca     2280
atccaggagc tggatagatt tgccaaccag atcctgtctt acggagcaga gctggacgca     2340
gatcaccctg gcttcaagga cccagtgtat cgggccccga aaagcagtt tgccgatatc     2400 gcctacaatt ataggcacgg acagccaatc cctcgcgtgg agtatatgga ggaggagaag     2460
aagacctggg gcacagtgtt caagaccctg aagagcctgt acaagacaca cgcctgctac     2520
gagtataacc acатcтткcc cctgctggag aagtattgtg gctttcacga ggacaatatc     2580
```

```
cctcagctgg aggacgtgag ccagttcctg cagacctgca caggctttag gctgaggcca    2640
gtggcaggac tgctgagctc ccgggacttc ctgggaggac tggccttcag agtgtttcac    2700
tgcacccagt acatcaggca cggctccaag ccaatgtata caccagagcc cgacatctgt    2760
cacgagctgc tgggccacgt gcccctgttt agcgatagac ccttcgccca gttttcccag    2820
gagatcggac tggcatctct gggagcacct gacgagtaca tcgagaagct ggccaccatc    2880
tattggttca cagtggagtt tggcctgtgc aagcagggcg atagcatcaa ggcctacgga    2940
gcaggactgc tgtctagctt cggcgagctg cagtattgtc tgtccgagaa gccaaagctg    3000
ctgcccctgg agctggagaa gaccgccatc cagaactaca ccgtgacaga gttccagccc    3060
ctgtactatg tggccgagtc ttttaacgat gccaaggaga aggtgagaaa tttcgccgcc    3120
acaatcccta ggcccttcag cgtgcggtac gacccttata cccagaggat cgaggtgctg    3180
gataatacac agcagctgaa gatcctggct gactcaatca atagcgaaat cggaatcctg    3240
tgctccgccc tgcagaaaat caaatgaatg ctttatttgt gaaatttgtg atgctattgc    3300
tttatttgta accattataa gctgcaataa acaagttaac aacaacaatt gcattcattt    3360
tatgtttcag gttcaggggg aggtgtggga ggttttttaa agcatgctgg ggagagatcg    3420
atctgaggaa cccctagtga tggagttggc cactccctct ctgcgcgctc gctcgctcac    3480
tgaggccggg cgaccaaagg tcgcccgacg cccgggcttt gcccgggcgg cctcagtgag    3540
cgagcgagcg cgcagagagg gagtggcccc cccccccccc cccccggcg attctcttgt    3600 ttgctccaga ctctcaggca atgacctgat agcctttgta gagacctctc aaaaatagct    3660
accctctccg gcatgaattt atcagctaga acggttgaat atcatattga tggtgatttg    3720
actgtctccg gcctttctca cccgtttgaa tctttaccta cacattactc aggcattgca    3780
tttaaaatat atgagggttc taaaaatttt tatccttgcg ttgaaataaa gcttctccc    3840 gcaaaagtat tacagggtca taatgttttt ggtacaaccg atttagcttt atgctctgag    3900
gctttattgc ttaattttgc taattctttg ccttgcctgt atgatttatt ggatgttgga    3960
atcgcctgat gcggtatttt ctccttacgc atctgtgcgg tatttcacac cgcatatggt    4020
gcactctcag tacaatctgc tctgatgccg catagttaag ccagccccga cacccgccaa    4080
cacccgctga cgcgccctga cgggcttgtc tgctcccggc atccgcttac agacaagctg    4140
tgaccgtctc cgggagctgc atgtgtcaga ggttttcacc gtcatcaccg aaacgcgcga    4200
gacgaaaggg cctcgtgata cgcctatttt tataggttaa tgtcatgata taatggtttt    4260
cttagacgtc aggtggcact tttcggggaa atgtgcgcgg aaccctatt tgtttatttt    4320 tctaaataca ttcaaatatg tatccgctca tgagacaata accctgataa atgcttcaat    4380
aatattgaaa aaggaagagt atgagtattc aacatttccg tgtcgccctt attccctttt    4440
ttgcggcatt ttgccttcct gttttgctc acccagaaac gctggtgaaa gtaaaagatg    4500
ctgaagatca gttgggtgca cgagtgggtt acatcgaact ggatctcaac agcggtaaga    4560
tccttgagag ttttcgcccc gaagaacgtt ttccaatgat gagcactttt aaagttctgc    4620
tatgtggcgc ggtattatcc cgtattgacg ccgggcaaga gcaactcggt cgccgcatac    4680
actattctca gaatgacttg gttgagtact caccagtcac agaaaagcat cttacggatg    4740
gcatgacagt aagagaatta tgcagtgctg ccataaccat gagtgataac actgcggcca    4800
acttacttct gacaacgatc ggaggaccga aggagctaac cgcttttttg cacaacatgg    4860
gggatcatgt aactcgcctt gatcgttggg aaccggagct gaatgaagcc ataccaaacg    4920
acgagcgtga caccacgatg cctgtagcaa tggcaacaac gttgcgcaaa ctattaactg    4980
```

```
gcgaactact tactctagct tcccggcaac aattaataga ctggatggag gcggataaag    5040
ttgcaggacc acttctgcgc tcggcccttc cggctggctg gtttattgct gataaatctg    5100
gagccggtga gcgtgggtct cgcggtatca ttgcagcact ggggccagat ggtaagccct    5160
cccgtatcgt agttatctac acgacgggga gtcaggcaac tatggatgaa cgaaatagac    5220
agatcgctga gataggtgcc tcactgatta agcattggta actgtcagac caagtttact    5280
catatatact ttagattgat ttaaaacttc attttttaatt taaaaggatc taggtgaaga    5340 tccttttttga taatctcatg accaaaatcc cttaacgtga gttttcgttc cactgagcgt    5400 cagacccccgt agaaaagatc aaaggatctt cttgagatcc ttttttttctg cgcgtaatct    5460 gctgcttgca aacaaaaaaa ccaccgctac cagcggtggt ttgtttgccg gatcaagagc    5520
taccaactct ttttccgaag gtaactggct tcagcagagc gcagatacca aatactgtcc    5580
ttctagtgta gccgtagtta ggccaccact tcaagaactc tgtagcaccg cctacatacc    5640
tcgctctgct aatcctgtta ccagtggctg ctgccagtgg cgataagtcg tgtcttaccg    5700
ggttggactc aagacgatag ttaccggata aggcgcagcg gtcgggctga acgggggtt    5760 cgtgcacaca gcccagcttg gagcgaacga cctacaccga actgagatac ctacagcgtg    5820
agctatgaga aagcgccacg cttcccgaag ggagaaaggc ggacaggtat ccggtaagcg    5880
gcagggtcgg aacaggagag cgcacgaggg agcttccagg gggaaacgcc tggtatcttt    5940
atagtcctgt cgggtttcgc cacctctgac ttgagcgtcg attttttgtga tgctcgtcag    6000 ggggggcggag cctatggaaa                                                6020
```

ADENO-ASSOCIATED VIRUS COMPOSITIONS FOR PAH GENE TRANSFER AND METHODS OF USE THEREOF

RELATED APPLICATIONS

This application is a continuation of International Patent Application No. PCT/US2019/016351, filed Feb. 1, 2019, which claims priority to U.S. Provisional Patent Application Ser. No. 62/625,150, filed Feb. 1, 2018, the entire disclosures of which are hereby incorporated herein by reference.

BACKGROUND

Phenylketonuria (PKU) is an autosomal recessive genetic disorder where the majority of cases are caused by mutations in the phenylalanine hydroxylase (PAH) gene. The PAH gene encodes a hepatic enzyme that catalyzes the hydroxylation of L-phenylalanine (Phe) to L-tyrosine (Tyr) upon multimerization. Reduction or loss of PAH activity leads to phenylalanine accumulation and its conversion into phenylpyruvate (also known as phenylketone). This abnormality in phenylalanine metabolism impairs neuronal maturation and the synthesis of myelin, resulting in mental retardation, seizures and other serious medical problems.

Currently, there is no cure for PKU. The standard of care is diet management by minimizing foods that contain high amounts of phenylalanine. Dietary management from birth with a low phenylalanine formula largely prevents the development of the intellectual disability of the disorder. However, even on a low-phenylalanine diet, children still suffer from growth retardation, and adults often have osteoporosis and vitamin deficiencies. Moreover, adherence to life-long dietary treatment is difficult, particularly once children reach school age.

New treatment strategies have recently emerged, including large neutral amino acid (LNAA) supplementation, cofactor tetrahydrobiopterin therapy, enzyme replacement therapy, and genetically modified probiotic therapy. However, these strategies suffer from shortcomings. The LNAA supplementation is suitable only for adults not adhering to a low Phe diet. The cofactor tetrahydrobiopterin can only be used in some mild forms of PKU. Enzyme replacement by administration of a substitute for PAH, e.g., phenylalanine ammonia-lyase (PAL), can lead to immune responses that reduce the efficacy and/or cause side effects. As to genetically modified probiotic therapy, the pathogenicity of PAL-expressing *E. coli* has been a concern.

Gene therapy provides a unique opportunity to cure PKU. Retroviral vectors, including lentiviral vectors, are capable of integrating nucleic acids into host cell genomes, raising safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (SCID) by transducing CD34+ bone marrow precursors with a gammaretroviral vector, four out of ten patients developed leukemia (Hacein-Bey-Abina et al., J Clin Invest. (2008) 118(9):3132-42). Non-integrating vectors, on the other hand, often suffer insufficient expression level or inadequate duration of expression in vivo.

Accordingly, there is a need in the art for improved gene therapy compositions and methods that can efficiently and safely restore PAH gene function in PKU patients.

SUMMARY

Provided herein are adeno-associated virus (AAV) compositions that can restore PAH gene function in cells, and methods for using the same to treat diseases associated with reduction of PAH gene function (e.g., PKU). Also provided are packaging systems for making the adeno-associated virus compositions.

Accordingly, in one aspect, the instant disclosure provides a method for expressing a PAH polypeptide in a cell, the method comprising transducing the cell with a replication-defective adeno-associated virus (AAV) comprising:
(a) an AAV capsid comprising an AAV Clade F capsid protein; and
(b) a transfer genome comprising a transcriptional regulatory element operably linked to a PAH coding sequence.

In certain embodiments, the cell is a hepatocyte, a renal cell, or a cell in the brain, pituitary gland, adrenal gland, pancreas, urinary bladder, gallbladder, colon, small intestine, or breast. In certain embodiments, the cell is in a mammalian subject and the AAV is administered to the subject in an amount effective to transduce the cell in the subject.

In another aspect, the instant disclosure provides a method for treating a subject having a disease or disorder associated with a PAH gene mutation, the method comprising administering to the subject an effective amount of a replication-defective AAV comprising:
(a) an AAV capsid comprising an AAV Clade F capsid protein; and
(b) a transfer genome comprising a transcriptional regulatory element operably linked to a PAH coding sequence.

In certain embodiments, the disease or disorder is phenylketonuria. In certain embodiments, the subject is a human subject.

In another aspect, the instant disclosure provides a replication-defective adeno-associated virus (AAV) comprising:
(a) an AAV capsid comprising an AAV Clade F capsid protein; and
(b) a transfer genome comprising a transcriptional regulatory element operably linked to a PAH coding sequence.

The following embodiments apply to each of the foregoing aspects.

In certain embodiments, the PAH coding sequence encodes an amino acid sequence set forth in SEQ ID NO: 23. In certain embodiments, the PAH coding sequence comprises the nucleotide sequence set forth in SEQ ID NO: 24. In certain embodiments, the PAH coding sequence is silently altered. In certain embodiments, the PAH coding sequence comprises the nucleotide sequence set forth in SEQ ID NO: 25.

In certain embodiments, the transcriptional regulatory element is capable of mediating transcription in a hepatocyte, a renal cell, or a cell in the brain, pituitary gland, adrenal gland, pancreas, urinary bladder, gallbladder, colon, small intestine, or breast. In certain embodiments, the transcriptional regulatory element is capable of mediating transcription in a hepatocyte or renal cell. In certain embodiments, the transcriptional regulatory element comprises one of more of the elements selected from the group consisting of a CAG promoter, a human EF-1α promoter, a human hepatic control region 1 (HCR1), a human α1-antitrypsin (hAAT) promoter, a hepatic specific regulatory module of the hAAT promoter, an SV40 intron, and a minute virus of mouse (MVM) intron. In certain embodiments, the transcriptional regulatory element comprises a nucleotide sequence at least 90% identical to a sequence selected from the group consisting of SEQ ID NOs: 28-30 and 32-41. In certain embodiments, the transcriptional regulatory element comprises a nucleotide sequence selected from the group consisting of SEQ ID NOs: 28-30 and 32-41. In certain embodiments, the transcriptional regulatory element comprises from 5' to 3' the nucleotide sequences set forth in SEQ ID NOs: 29, 30, and 31. In certain embodiments, the transcriptional regulatory element comprises the nucleotide sequences set forth in SEQ ID NO: 32.

In certain embodiments, the transfer genome further comprises an intron operably linked to the PAH coding sequence. In certain embodiments, the intron comprises a nucleotide sequence at least 90% identical to the sequence set forth in SEQ ID NO: 31 or 35. In certain embodiments, the intron comprises the nucleotide sequence set forth in SEQ ID NO: 31 or 35. In certain embodiments, the transfer genome comprises from 5' to 3': a non-coding exon, the intron, and the PAH coding sequence.

In certain embodiments, the transfer genome further comprises a polyadenylation sequence 3' to the PAH coding sequence. In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence comprises a sequence selected from the group consisting of SEQ ID NOs: 42, 43, and 45.

In certain embodiments, the transfer genome comprises a sequence selected from the group consisting of SEQ ID NOs: 46-50, 61, 64, 67, 74, 76, 78, 80, 82, 84, 86, and 89.

In certain embodiments, the transfer genome further comprises a 5' inverted terminal repeat (5' ITR) nucleotide sequence 5' of the genome, and a 3' inverted terminal repeat (3' ITR) nucleotide sequence 3' of the genome. In certain embodiments, the 5' ITR nucleotide sequence has at least 95% sequence identity to SEQ ID NO: 18, and the 3' ITR nucleotide sequence has at least 95% sequence identity to SEQ ID NO: 19. In certain embodiments, the 5' ITR nucleotide sequence has at least 95% sequence identity to SEQ ID NO: 20, and the 3' ITR nucleotide sequence has at least 95% sequence identity to SEQ ID NO: 21. In certain embodiments, the 5' ITR nucleotide sequence has at least 95% sequence identity to SEQ ID NO: 26, and the 3' ITR nucleotide sequence has at least 95% sequence identity to SEQ ID NO: 27.

In certain embodiments, the transfer genome comprises a nucleotide sequence selected from the group consisting of SEQ ID NOs: 51-55, 62, 65, 68, 75, 77, 79, 81, 83, 85, 87, and 90. In certain embodiments, the transfer genome consists of a nucleotide sequence selected from the group consisting of SEQ ID NOs: 51-55, 62, 65, 68, 75, 77, 79, 81, 83, 85, 87, and 90. In certain embodiments, the transfer genome consists of the nucleotide sequence set forth in SEQ ID NO: 52.

In certain embodiments, the AAV Clade F capsid protein comprises an amino acid sequence having at least 95% sequence identity with the amino acid sequence of amino acids 203-736 of SEQ ID NO: 2, 3, 4, 6, 7, 10, 11, 12, 13, 15, 16, or 17. In certain embodiments, the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO: 2, 3, 4, 5, 6, 7, 9, 10, 11, 12, 13, 15, 16, or 17. In certain embodiments, the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 626 of SEQ ID NO: 2 is G, and the amino acid in the capsid protein corresponding to amino acid 718 of SEQ ID NO: 2 is G;
(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(c) the amino acid in the capsid protein corresponding to amino acid 505 of SEQ ID NO: 2 is R, and the amino acid in the capsid protein corresponding to amino acid 687 of SEQ ID NO: 2 is R;
(d) the amino acid in the capsid protein corresponding to amino acid 346 of SEQ ID NO: 2 is A, and the amino acid in the capsid protein corresponding to amino acid 505 of SEQ ID NO: 2 is R; or
(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments, (a) the amino acid in the capsid protein corresponding to amino acid 2 of SEQ ID NO: 2 is T, and the amino acid in the capsid protein corresponding to amino acid 312 of SEQ ID NO: 2 is Q;
(b) the amino acid in the capsid protein corresponding to amino acid 65 of SEQ ID NO: 2 is I, and the amino acid in the capsid protein corresponding to amino acid 626 of SEQ ID NO: 2 is Y;
(c) the amino acid in the capsid protein corresponding to amino acid 77 of SEQ ID NO: 2 is R, and the amino acid in the capsid protein corresponding to amino acid 690 of SEQ ID NO: 2 is K;
(d) the amino acid in the capsid protein corresponding to amino acid 119 of SEQ ID NO: 2 is L, and the amino acid in the capsid protein corresponding to amino acid 468 of SEQ ID NO: 2 is S;
(e) the amino acid in the capsid protein corresponding to amino acid 626 of SEQ ID NO: 2 is G, and the amino acid in the capsid protein corresponding to amino acid 718 of SEQ ID NO: 2 is G;
(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(g) the amino acid in the capsid protein corresponding to amino acid 505 of SEQ ID NO: 2 is R, and the amino acid in the capsid protein corresponding to amino acid 687 of SEQ ID NO: 2 is R;
(h) the amino acid in the capsid protein corresponding to amino acid 346 of SEQ ID NO: 2 is A, and the amino acid in the capsid protein corresponding to amino acid 505 of SEQ ID NO: 2 is R; or
(i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 2, 3, 4, 5, 6, 7, 8, 9, 10, 11, 12, 13, 15, 16, or 17.

In another aspect, the instant disclosure provides a pharmaceutical composition comprising an AAV disclosed herein.

In another aspect, the instant disclosure provides a packaging system for recombinant preparation of an AAV, wherein the packaging system comprises:
(a) a Rep nucleotide sequence encoding one or more AAV Rep proteins;
(b) a Cap nucleotide sequence encoding one or more AAV Clade F capsid proteins as disclosed herein; and
(c) a transfer genome as disclosed herein, wherein the packaging system is operative in a cell for enclosing the transfer genome in the capsid to form the AAV.

In certain embodiments, the packaging system comprises a first vector comprising the Rep nucleotide sequence and the Cap nucleotide sequence, and a second vector comprising the transfer genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins.

In certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E2, E4 and VA. In certain embodiments, the helper virus is herpes simplex virus (HSV). In certain embodiments, the HSV genome comprises one or more of HSV genes selected from the group consisting of UL5/8/52, ICPO, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing a packaging system as described herein into a cell under conditions operative for enclosing the transfer genome or the transfer genome in the capsid to form the AAV.

BRIEF DESCRIPTION OF THE DRAWINGS

FIGS. 1A, 1B, 1C, 1D, and 1E are vector maps of the pHMI-hPAH-TC-004, pHMI-hPAH-TC-025, pHMI-hPAH-TC-010, pHMI-hPAH-TC-011, and pHMI-hPAH-TC-012 vectors, respectively.

FIG. 8A, 8B, 8C are vector maps of pHMI-hPAH-TC-009, pHMI-hPAH-TC-013 and pHMI-hPAH-TC-017 vectors, respectively.

FIG. 10A is a graph showing serum Phe levels over time of male Pah$^{-/-}$ PAH$^{enu2}$ mice. FIG. 10B is a graph showing serum Phe levels over time of female Pah$^{-/-}$ PAH$^{enu2}$ mice. FIG. 10C is a graph showing the average baseline serum Phe levels of the male and female mice in the study (55 mice per group; **** indicates p<0.05).

FIG. 12 depicts the quantification of Western blots of human PAH expression from HEK293 cells transfected with the indicated AAV vectors under the control of a CBA promoter.

DETAILED DESCRIPTION

Figure 1D:
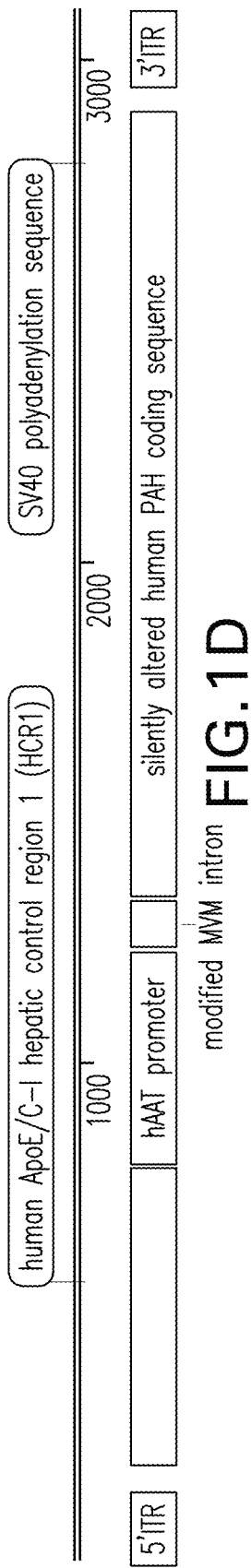

The instant disclosure provided adeno-associated virus (AAV) compositions that can restore PAH gene function in a cell. Also provide are packaging systems for making the adeno-associated virus compositions.

I. DEFINITIONS

As used herein, the term "replication-defective adeno-associated virus" refers to an AAV comprising a genome lacking Rep and Cap genes.

As used herein, the term "PAH gene" refers to the phenylalanine hydroxylase gene. The human PAH gene is identified by Entrez Gene ID 5053. An exemplary nucleotide sequence of a PAH mRNA is provided as SEQ ID NO: 24. An exemplary amino acid sequence of a PAH polypeptide is provided as SEQ ID NO: 23.

As used herein, the term "transfer genome" refers to a recombinant AAV genome comprising a coding sequence operably linked to an exogenous transcriptional regulatory element that mediates expression of the coding sequence when the transfer genome is introduced into a cell. In certain embodiments, the transfer genome does not integrate in the chromosomal DNA of the cell. The skilled artisan will appreciate that the portion of a transfer genome comprising the transcriptional regulatory element operably linked to a PAH coding sequence can be in the sense or antisense orientation relative to direction of transcription of the PAH coding sequence.

As used herein, the term "Clade F capsid protein" refers to an AAV VP1, VP2, or VP3 capsid protein that has at least 90% identity with the VP1, VP2, or VP3 amino acid sequences set forth, respectively, in amino acids 1-736, 138-736, and 203-736 of SEQ ID NO: 1 herein.

As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with a PAH gene mutation" refers to any disease or disorder caused by, exacerbated by, or genetically linked with mutation of a PAH gene. In certain embodiments, the disease or disorder associated with a PAH gene mutation is phenylketonuria (PKU).

As used herein, the term "coding sequence" refers to the portion of a complementary DNA (cDNA) that encodes a polypeptide, starting at the start codon and ending at the stop codon. A gene may have one or more coding sequences due to alternative splicing, alternative translation initiation, and variation within the population. A coding sequence may either be wild-type or codon-altered. An exemplary wild-type PAH coding sequence is set forth in SEQ ID NO: 24.

As used herein, the term "silently altered" refers to alteration of a coding sequence or a stuffer-inserted coding sequence of a gene (e.g., by nucleotide substitution) without changing the amino acid sequence of the polypeptide encoded by the coding sequence or stuffer-inserted coding sequence. Such silent alteration is advantageous in that it may increase the translation efficiency of a coding sequence.

In the instant disclosure, nucleotide positions in a PAH gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. An exemplary nucleotide 1 of the human PAH gene is nucleotide 5,473 of the NCBI Reference Sequence: NG_008690.1, and an exemplary nucleotide 3 of the human PAH gene is nucleotide 5,475 of the NCBI Reference Sequence: NG_008690.1. The nucleotide adjacently 5' to the start codon is nucleotide −1.

In the instant disclosure, exons and introns in a PAH gene are specified relative to the exon encompassing the first nucleotide of the start codon, which is nucleotide 5473 of the NCBI Reference Sequence: NG_008690.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the PAH gene comprises from 5' to 3': exon 1, intron 1, exon 2, intron 2, exon 3, etc. An exemplary exon 1 of the human PAH gene is nucleotides 5001-5532 of the NCBI Reference Sequence: NG_008690.1. An exemplary intron 1 of the human PAH gene is nucleotides 5533-9704 of the NCBI Reference Sequence: NG_008690.1.

As used herein, the term "transcriptional regulatory element" or "TRE" refers to a cis-acting nucleotide sequence, for example, a DNA sequence, that regulates (e.g., controls, increases, or reduces) transcription of an operably linked nucleotide sequence by an RNA polymerase to form an RNA molecule. A TRE relies on one or more trans-acting molecules, such as transcription factors, to regulate transcription. Thus, one TRE may regulate transcription in different ways when it is in contact with different trans-acting molecules, for example, when it is in different types of cells. A TRE may comprise one or more promoter elements and/or enhancer elements. A skilled artisan would appreciate that the promoter and enhancer elements in a gene may be close in location, and the term "promoter" may refer to a sequence comprising a promoter element and an enhancer element. Thus, the term "promoter" does not exclude an enhancer element in the sequence. The promoter and enhancer elements do not need to be derived from the same gene or species, and the sequence of each promoter or enhancer element may be either identical or substantially identical to the corresponding endogenous sequence in the genome.

As used herein, the term "operably linked" is used to describe the connection between a TRE and a coding sequence to be transcribed. Typically, gene expression is placed under the control of a TRE comprising one or more promoter and/or enhancer elements. The coding sequence is "operably linked" to the TRE if the transcription of the coding sequence is controlled or influenced by the TRE. The promoter and enhancer elements of the TRE may be in any orientation and/or distance from the coding sequence, as long as the desired transcriptional activity is obtained. In certain embodiments, the TRE is upstream from the coding sequence.

As used herein, the term "polyadenylation sequence" refers to a DNA sequence that when transcribed into RNA constitutes a polyadenylation signal sequence. The polyadenylation sequence can be native (e.g., from the PAH gene) or exogenous. The exogenous polyadenylation sequence can be a mammalian or a viral polyadenylation sequence (e.g., an SV40 polyadenylation sequence).

As used herein, "exogenous polyadenylation sequence" refers to a polyadenylation sequence not identical or substantially identical to the endogenous polyadenylation sequence of a PAH gene (e.g., human PAH gene). In certain embodiments, an exogenous polyadenylation sequence is a polyadenylation sequence of a non-PAH gene in the same species (e.g., human). In certain embodiments, an exogenous polyadenylation sequence is a polyadenylation sequence of a different species (e.g., a virus).

As used herein, the term "effective amount" in the context of the administration of an AAV to a subject refers to the amount of the AAV that achieves a desired prophylactic or therapeutic effect.

II. ADENO-ASSOCIATED VIRUS COMPOSITIONS

In one aspect, provided herein are novel replication-defective AAV compositions useful for expressing PAH polypeptide in cells with reduced or otherwise defective PAH gene function. In certain embodiments, the AAV disclosed herein comprise: an AAV capsid comprising an AAV Clade F capsid protein; and a transfer genome comprising a transcriptional regulatory element operably linked to a PAH coding sequence, allowing for extrachromosomal expression of PAH.

Any AAV Clade F capsid protein or derivative thereof can be used in the AAV compositions disclosed herein. For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 2, 3, 4, 5, 6, 7, 8, 9, 10, 11, 12, 13, 15, 16, or 17, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 2, 3, 4, 6, 7, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 2, 3, 4, 5, 6, 7, 8, 9, 10, 11, 12, 13, 15, 16, or 17, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 2, 3, 4, 5, 6, 7, 9, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 2, 3, 4, 5, 6, 7, 8, 9, 10, 11, 12, 13, 15, 16, or 17, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 2, 3, 4, 5, 6, 7, 8, 9, 10, 11, 12, 13, 15, 16, or 17.

In certain embodiments, the AAV capsid comprises two or more of: (a) a Clade F capsid protein comprising the amino acid sequence of amino acids 203-736 of SEQ ID NO: 2, 3, 4, 6, 7, 10, 11, 12, 13, 15, 16, or 17; (b) a Clade F capsid protein comprising the amino acid sequence of amino acids 138-736 of SEQ ID NO: 2, 3, 4, 5, 6, 7, 9, 10, 11, 12, 13, 15, 16, or 17; and (c) a Clade F capsid protein comprising the amino acid sequence of amino acids 1-736 of SEQ ID NO: 2, 3, 4, 5, 6, 7, 8, 9, 10, 11, 12, 13, 15, 16, or 17. In certain embodiments, the AAV capsid comprises: (a) a Clade F capsid protein having an amino acid sequence consisting of amino acids 203-736 of SEQ ID NO: 2, 3, 4, 6, 7, 10, 11, 12, 13, 15, 16, or 17; (b) a Clade F capsid protein having an amino acid sequence consisting of amino acids 138-736 of SEQ ID NO: 2, 3, 4, 5, 6, 7, 9, 10, 11, 12, 13, 15, 16, or 17; and (c) a Clade F capsid protein having an amino acid sequence consisting of amino acids 1-736 of SEQ ID NO: 2, 3, 4, 5, 6, 7, 8, 9, 10, 11, 12, 13, 15, 16, or 17.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 8; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 8; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 8. In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 11; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 11; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 11. In certain embodiments, the AAV capsid comprises one or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises two or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises: (a) a Clade F capsid protein having an amino acid sequence consisting of amino acids 203-736 of SEQ ID NO: 11; (b) a Clade F capsid protein having an amino acid sequence consisting of amino acids 138-736 of SEQ ID NO: 11; and (c) a Clade F capsid protein having an amino acid sequence consisting of amino acids 1-736 of SEQ ID NO: 11.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 13; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 13; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 13. In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Transfer genomes useful in the AAV compositions disclosed herein generally comprise a transcriptional regulatory element (TRE) operably linked to a PAH coding sequence. In certain embodiments, the transfer genome comprises a 5' inverted terminal repeat (5' ITR) nucleotide sequence 5' of the TRE and PAH coding sequence, and a 3' inverted terminal repeat (3' ITR) nucleotide sequence 3' of the TRE and PAH coding sequence.

In certain embodiments, the PAH coding sequence comprises all or substantially all of a coding sequence of a PAH gene. In certain embodiments, the transfer genome comprises a nucleotide sequence encoding SEQ ID NO: 23 and can optionally further comprise an exogenous polyadenylation sequence 3' to the PAH coding sequence. In certain embodiments, the nucleotide sequence encoding SEQ ID NO: 23 is wild-type (e.g., having the sequence set forth in SEQ ID NO: 24). In certain embodiments, the nucleotide sequence encoding SEQ ID NO: 23 is codon-altered (e.g., having the sequence set forth in SEQ ID NO: 25). In certain embodiments, the nucleotide sequence encoding SEQ ID NO: 23 is codon-altered (e.g., having the sequence set forth in SEQ ID NO: 69, 70, 71, 72, or 73).

In certain embodiments, the PAH coding sequence encodes a polypeptide comprising all or substantially all of the amino acids sequence of a PAH protein. In certain embodiments, the PAH coding sequence encodes the amino acid sequence of a wild-type PAH protein (e.g., human PAH protein). In certain embodiments, the PAH coding sequence encodes the amino acid sequence of a mutant PAH protein (e.g., human PAH protein), wherein the mutant PAH polypeptide is a functional equivalent of the wild-type PAH polypeptide, i.e., can function as a wild-type PAH polypeptide. In certain embodiments, the functionally equivalent PAH polypeptide further comprises at least one characteristic not found in the wild-type PAH polypeptide, e.g., the ability to stabilize PAH protein (e.g., dimer or tetramer), or the ability to resist protein degradation.

The transfer genome can be used to express PAH in any mammalian cells (e.g., human cells). Thus, the TRE can be active in any mammalian cells (e.g., human cells). In certain embodiments, the TRE is active in a broad range of human cells. Such TREs may comprise constitutive promoter and/or enhancer elements including cytomegalovirus (CMV) promoter/enhancer (e.g., comprising a nucleotide sequence at least 90%, 91%, 92%, 93%, 94%, 95%, 96%, 97%, 98%, 99%, or 100% identical to SEQ ID NO: 58), SV40 promoter, chicken beta actin (CBA) promoter (e.g., comprising a nucleotide sequence at least 90%, 91%, 92%, 93%, 94%, 95%, 96%, 97%, 98%, 99%, or 100% identical to SEQ ID NO: 59), human elongation factor 1 alpha (EF1α) promoter (e.g., comprising a nucleotide sequence at least 90%, 91%, 92%, 93%, 94%, 95%, 96%, 97%, 98%, 99%, or 100% identical to SEQ ID NO: 40), minute virus of mouse (MVM) intron which comprises transcription factor binding sites (e.g., comprising a nucleotide sequence at least 90%, 91%, 92%, 93%, 94%, 95%, 96%, 97%, 98%, 99%, or 100% identical to SEQ ID NO: 35), human phosphoglycerate kinase (PGK1) promoter, human ubiquitin C (Ubc) promoter, human beta actin promoter, human neuron-specific enolase (ENO2) promoter, human beta-glucuronidase (GUSB) promoter, a rabbit beta-globin element (e.g., comprising a nucleotide sequence at least 90%, 91%, 92%, 93%, 94%, 95%, 96%, 97%, 98%, 99%, or 100% identical to SEQ ID NO: 60), and/or human Methyl-CpG Binding Protein 2 (MeCP2) promoter. Any of these TREs can be combined in any order to drive efficient transcription. For example, a transfer genome may comprise a CMV enhancer, a CBA promoter, and the splice acceptor from exon 3 of the rabbit beta-globin gene, collectively called a CAG promoter (e.g., comprising a nucleotide sequence at least 90%, 91%, 92%, 93%, 94%, 95%, 96%, 97%, 98%, 99%, or 100% identical to SEQ ID NO: 28). For example, a transfer genome may comprise a hybrid of CMV enhancer and CBA promoter followed by a splice donor and splice acceptor, collectively called a CASI promoter region (e.g., comprising a nucleotide sequence at least 90%, 91%, 92%, 93%, 94%, 95%, 96%, 97%, 98%, 99%, or 100% identical to SEQ ID NO: 63).

Alternatively, the TRE may be a tissue-specific TRE, i.e., it is active in specific tissue(s) and/or organ(s). A tissue-specific TRE comprises one or more tissue-specific promoter and/or enhancer elements, and optionally one or more constitutive promoter and/or enhancer elements. A skilled artisan would appreciate that tissue-specific promoter and/or enhancer elements can be isolated from genes specifically expressed in the tissue by methods well known in the art. In certain embodiments, the TRE is liver-specific (e.g., hepatocyte-specific). Exemplary liver-specific TREs may comprise one or more elements selected from the group consisting of human albumin promoter, human transthyretin (TTR) promoter (e.g., comprising a nucleotide sequence at least 90%, 91%, 92%, 93%, 94%, 95%, 96%, 97%, 98%, 99%, or 100% identical to SEQ ID NO: 34), human APOE/C-I hepatic control region (HCR) 1 or 2 (e.g., comprising a nucleotide sequence at least 90%, 91%, 92%, 93%, 94%, 95%, 96%, 97%, 98%, 99%, or 100% identical to SEQ ID NO: 29 or 37), human APOH promoter, and human SERPINA1 (hAAT) promoter (e.g., comprising a nucleotide sequence at least 90%, 91%, 92%, 93%, 94%, 95%, 96%, 97%, 98%, 99%, or 100% identical to SEQ ID NO: 30 or 38) or a hepatic specific regulatory module thereof (e.g., comprising a nucleotide sequence at least 90%, 91%, 92%, 93%, 94%, 95%, 96%, 97%, 98%, 99%, or 100% identical to SEQ ID NO: 33). In certain embodiments, an hAAT promoter region comprises a nucleotide sequence at least 90%, 91%, 92%, 93%, 94%, 95%, 96%, 97%, 98%, 99%, or 100% identical to SEQ ID NO: 66. More liver-specific promoter elements are disclosed in WO 2009/130208 and Kramer et al. (Molecular Therapy (2003) 7, 375-385), which are incorporated by reference herein in their entirety.

In certain embodiments, the TRE is kidney-specific (e.g., renal epithelial cell-specific). Exemplary kidney-specific TREs may comprise one or more elements selected from the group consisting of human nephrin promoter, human parathyroid hormone receptor promoter, human uromodulin promoter, and human SLC12A1 promoter. In certain embodiments, the TRE is brain-specific (e.g., neuron-specific, glial cell-specific, astrocyte-specific, oligodendrocyte-specific, microglia-specific and/or central nervous system-specific). Exemplary brain-specific TREs may comprise one or more elements selected from the group consisting of human glial fibrillary acidic protein (GFAP) promoter and human synapsin 1 (SYN1) promoter. More brain-specific promoter elements are disclosed in WO 2016/100575A1, which is incorporated by reference herein in its entirety.

In certain embodiments, the transfer genome comprises two or more TREs, optionally comprising at least one of the TREs disclosed above. A skilled person in the art would appreciate that any of these TREs can be combined in any order, and combinations of a constitutive TRE and a tissue-specific TRE can drive efficient and tissue-specific transcription. For example, in certain embodiments, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29 or 37) and a human EF-1α promoter (e.g., comprising a nucleotide sequence at least 90%, 91%, 92%, 93%, 94%, 95%, 96%, 97%, 98%, or 99% identical to SEQ ID NO: 40), optionally wherein the human HCR1 is 5' to the human EF-1α promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 41. In certain embodiments, the transfer genome comprises a human HCR1 (e.g., comprising the nucleotide sequence set forth in SEQ ID NO: 29 or 37) and a human EF-1α promoter (e.g., comprising the nucleotide sequence set forth in SEQ ID NO: 40), optionally wherein the human HCR1 is 5' to the human EF-1α promoter. In certain embodiments, the transfer genome comprises the sequence set forth in SEQ ID NO: 41.

Similarly, combinations of two or more tissue-specific TREs can drive efficient and tissue-specific transcription. For example, in certain embodiments, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29) and a hAAT promoter (e.g., comprising a nucleotide sequence at least 90%, 91%, 92%, 93%, 94%, 95%, 96%, 97%, 98%, or 99% identical to SEQ ID NO: 30), optionally wherein the human HCR1 is 5' to the hAAT promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 32. In certain embodiments, the transfer genome comprises a human HCR1 (e.g., comprising the nucleotide sequence set forth in SEQ ID NO: 29) and a hAAT promoter (e.g., comprising the nucleotide sequence set forth in SEQ ID NO: 30), optionally wherein the human HCR1 is 5' to the hAAT promoter. In certain embodiments, the transfer genome comprises the nucleotide sequence set forth in SEQ ID NO: 32.

In certain embodiments, the transfer genome comprises a hepatic specific regulatory module of hAAT promoter (e.g., comprising a nucleotide sequence at least 90%, 91%, 92%, 93%, 94%, 95%, 96%, 97%, 98%, or 99% identical to SEQ ID NO: 33) and a human TTR promoter (e.g., comprising a nucleotide sequence at least 90%, 91%, 92%, 93%, 94%, 95%, 96%, 97%, 98%, or 99% identical to SEQ ID NO: 34), optionally wherein the hepatic specific regulatory module is 5' to the human TTR promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 36. In certain embodiments, the transfer genome comprises a hepatic specific regulatory module of hAAT promoter (e.g., comprising the nucleotide sequence set forth in SEQ ID NO: 33) and a human TTR promoter (e.g., comprising the nucleotide sequence set forth in SEQ ID NO: 34), optionally wherein the hepatic specific regulatory module is 5' to the human TTR promoter. In certain embodiments, the transfer genome comprises the nucleotide sequence set forth in SEQ ID NO: 36.

In certain embodiment, the transfer genome comprises a human HCR1 (e.g., comprising a nucleotide sequence at least 90%, 91%, 92%, 93%, 94%, 95%, 96%, 97%, 98%, or 99% identical to SEQ ID NO: 29 or 37) and a hAAT promoter (e.g., comprising a nucleotide sequence at least 90%, 91%, 92%, 93%, 94%, 95%, 96%, 97%, 98%, or 99% identical to SEQ ID NO: 30 or 38), optionally wherein the human HCR1 is 5' to the hAAT promoter. In certain embodiments, the transfer genome comprises a nucleotide sequence at least 90%, 91%, 92%, 93%, 94%, 95%, 96%, 97%, 98%, or 99% identical to the sequence set forth in SEQ ID NO: 39. In certain embodiment, the transfer genome comprises a human HCR1 (e.g., comprising the nucleotide sequence set forth in SEQ ID NO: 29 or 37) and a hAAT promoter (e.g., comprising the nucleotide sequence set forth in SEQ ID NO: 30 or 38), optionally wherein the human HCR1 is 5' to the hAAT promoter. In certain embodiments, the transfer genome comprises the nucleotide sequence set forth in SEQ ID NO: 39.

In certain embodiments, the transfer vector further comprises an intron 5' to or inserted in the PAH coding sequence. Such introns can increase transgene expression, for example, by reducing transcriptional silencing and enhancing mRNA export from the nucleus to the cytoplasm. In certain embodiments, the transfer genome comprises from 5' to 3': a non-coding exon, an intron, and the PAH coding sequence. In certain embodiments, an intron sequence is inserted in the PAH coding sequence, optionally wherein the intron is inserted at an internucleotide bond that links two native exons. In certain embodiments, the intron is inserted at an internucleotide bond that links native exon 1 and exon 2.

The intron can comprise a native intron sequence of the PAH gene, an intron sequence from a different species or a different gene from the same species, and/or a synthetic intron sequence. A skilled worker will appreciate that synthetic intron sequences can be designed to mediate RNA splicing by introducing any consensus splicing motifs known in the art (e.g., in Sibley et al., (2016) Nature Reviews Genetics, 17, 407-21, which is incorporated by reference herein in its entirety). Exemplary intron sequences are provided in Lu et al. (2013) Molecular Therapy 21(5): 954-63, and Lu et al. (2017) Hum. Gene Ther. 28(1): 125-34, which are incorporated by reference herein in their entirety. In certain embodiments, the transfer genome comprises an SV40 intron (e.g., comprising a nucleotide sequence at least 90%, 91%, 92%, 93%, 94%, 95%, 96%, 97%, 98%, or 99% identical to SEQ ID NO: 31) or a minute virus of mouse (MVM) intron (e.g., comprising a nucleotide sequence at least 90%, 91%, 92%, 93%, 94%, 95%, 96%, 97%, 98%, or 99% identical to SEQ ID NO: 35). In certain embodiments, the transfer genome comprises an SV40 intron (e.g., comprising the nucleotide sequence set forth in SEQ ID NO: 31) or a minute virus of mouse (MVM) intron (e.g., comprising the nucleotide sequence set forth in SEQ ID NO: 35).

In certain embodiments, the transfer genome disclosed herein further comprises a transcription terminator (e.g., a polyadenylation sequence). In certain embodiments, the transcription terminator is 3' to the PAH coding sequence. The transcription terminator may be any sequence that effectively terminates transcription, and a skilled artisan would appreciate that such sequences can be isolated from any genes that are expressed in the cell in which transcription of the PAH coding sequence is desired. In certain embodiments, the transcription terminator comprises a polyadenylation sequence. In certain embodiments, the polyadenylation sequence is identical or substantially identical to the endogenous polyadenylation sequence of the human PAH gene. In certain embodiments, the polyadenylation sequence is an exogenous polyadenylation sequence. In certain embodiments, the polyadenylation sequence is an SV40 polyadenylation sequence (e.g., comprising the nucleotide sequence set forth in SEQ ID NO: 42, 43, or 45, or a nucleotide sequence complementary thereto). In certain embodiments, the polyadenylation sequence comprises the sequence set forth in SEQ ID NO: 43.

In certain embodiments, the transfer genome comprises from 5' to 3': a TRE, optionally a non-coding exon and an intron, a PAH coding sequence, and a polyadenylation sequence. In certain embodiments, the TRE has at least 90%, 91%, 92%, 93%, 94%, 95%, 96%, 97%, 98%, or 99% sequence identity to any one of SEQ ID NOs: 28-30 and 32-41; the intron has at least 90%, 91%, 92%, 93%, 94%, 95%, 96%, 97%, 98%, or 99% sequence identity to SEQ ID NO: 31 or 35; the PAH coding sequence has at least 90%, 91%, 92%, 93%, 94%, 95%, 96%, 97%, 98%, or 99% sequence identity to SEQ ID NO: 25; and/or the polyadenylation sequence has at least 90%, 91%, 92%, 93%, 94%, 95%, 96%, 97%, 98%, or 99% sequence identity to any one of SEQ ID NOs: 42, 43, and 45. In certain embodiments, the TRE comprises a nucleotide sequence selected from the group consisting of SEQ ID NOs: 28-30 and 32-41; the intron comprises a nucleotide sequence selected from the group consisting of SEQ ID NOs: 31 and 35; the PAH coding sequence comprises the sequence set forth in SEQ ID NO: 25; and/or the polyadenylation sequence comprises a nucleotide sequence selected from the group consisting of SEQ ID NOs: 42, 43, and 45. In certain embodiments, the TRE comprises the sequence set forth in SEQ ID NO: 28; the PAH coding sequence comprises the sequence set forth in SEQ ID NO: 25; and/or the polyadenylation sequence comprises the sequence set forth in SEQ ID NO: 42. In certain embodiments, the TRE comprises from 5' to 3' the sequence set forth in SEQ ID NO: 29, and the sequence set forth in SEQ ID NO: 30 (e.g., the TRE comprises the sequence set forth in SEQ ID NO: 32); the intron comprises the sequence set forth in SEQ ID NO: 31; the PAH coding sequence comprises the sequence set forth in SEQ ID NO: 25; and/or the polyadenylation sequence comprises the sequence set forth in SEQ ID NO: 43. In certain embodiments, the TRE comprises from 5' to 3' the sequence set forth in SEQ ID NO: 33, and the sequence set forth in SEQ ID NO: 34 (e.g., the TRE comprises the sequence set forth in SEQ ID NO: 36); the intron comprises the sequence set forth in SEQ ID NO: 35; the PAH coding sequence comprises the sequence set forth in SEQ ID NO: 25; and/or the polyadenylation sequence comprises the sequence set forth in SEQ ID NO: 45. In certain embodiments, the TRE comprises from 5' to 3' the sequence set forth in SEQ ID NO: 37, and the sequence set forth in SEQ ID NO: 38 (e.g., the TRE comprises the sequence set forth in SEQ ID NO: 39); the intron comprises the sequence set forth in SEQ ID NO: 35; the PAH coding sequence comprises the sequence set forth in SEQ ID NO: 25; and/or the polyadenylation sequence comprises the sequence set forth in SEQ ID NO: 45. In certain embodiments, the TRE comprises from 5' to 3' the sequence set forth in SEQ ID NO: 37, and the sequence set forth in SEQ ID NO: 40 (e.g., the TRE comprises the sequence set forth in SEQ ID NO: 41); and/or the polyadenylation sequence comprises the sequence set forth in SEQ ID NO: 45.

In certain embodiments, the transfer genome comprises a sequence at least 80%, 85%, 90%, 91%, 92%, 93%, 94%, 95%, 96%, 97%, 98%, or 99% identical to SEQ ID NO: 46, 47, 48, 49, 50, 61, 64, 67, 74, 76, 78, 80, 82, 84, 86, or 89. In certain embodiments, the transfer genome comprises the nucleotide sequence set forth in SEQ ID NO: 46, 47, 48, 49, 50, 61, 64, 67, 74, 76, 78, 80, 82, 84, 86, or 89. In certain embodiments, the transfer genome consists of the nucleotide sequence set forth in SEQ ID NO: 46, 47, 48, 49, 50, 61, 64, 67, 74, 76, 78, 80, 82, 84, 86, or 89. In certain embodiments, the transfer genome comprises the nucleotide sequence set forth in SEQ ID NO: 47. In certain embodiments, the transfer genome consists of the nucleotide sequence set forth in SEQ ID NO: 47.

In certain embodiments, the transfer genomes disclosed herein further comprise a 5' inverted terminal repeat (5' ITR) nucleotide sequence 5' of the TRE, and a 3' inverted terminal repeat (3' ITR) nucleotide sequence 3' of the PAH coding sequence. ITR sequences from any AAV serotype or variant thereof can be used in the transfer genomes disclosed herein. The 5' and 3' ITR can be from an AAV of the same serotype or from AAVs of different serotypes. Exemplary ITRs for use in the transfer genomes disclosed herein are set forth in SEQ ID NOs: 18-21, 26, and 27 herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 90% (e.g., at least 95%, at least 96%, at least 97%, at least 98%, at least 99%, or 100%) sequence identity to SEQ ID NO: 18, or the 3' ITR nucleotide sequence has at least 90% (e.g., at least 95%, at least 96%, at least 97%, at least 98%, at least 99%, or 100%) sequence identity to SEQ ID NO: 19. In certain embodiments, the 5' ITR nucleotide sequence has at least 90% (e.g., at least 95%, at least 96%, at least 97%, at least 98%, at least 99%, or 100%) sequence identity to SEQ ID NO: 18, and the 3' ITR nucleotide sequence has at least 90% (e.g., at least 95%, at least 96%, at least 97%, at least 98%, at least 99%, or 100%) sequence identity to SEQ ID NO: 19. In certain embodiments, the transfer genome comprises a nucleotide sequence set forth in any one of SEQ ID NOs: 46-50, 61, 64, 67, 74, 76, 78, 80, 82, 84, 86, and 89, a 5' ITR nucleotide sequence having the sequence of SEQ ID NO: 18, and a 3' ITR nucleotide sequence having the sequence of SEQ ID NO: 19.

In certain embodiments, the 5' ITR or 3' ITR are from AAV5. In certain embodiments, both the 5' ITR and 3' ITR are from AAV5. In certain embodiments, the 5' ITR nucleotide sequence has at least 90% (e.g., at least 95%, at least 96%, at least 97%, at least 98%, at least 99%, or 100%) sequence identity to SEQ ID NO: 20, or the 3' ITR nucleotide sequence has at least 90% (e.g., at least 95%, at least 96%, at least 97%, at least 98%, at least 99%, or 100%) sequence identity to SEQ ID NO: 21. In certain embodiments, the 5' ITR nucleotide sequence has at least 90% (e.g., at least 95%, at least 96%, at least 97%, at least 98%, at least 99%, or 100%) sequence identity to SEQ ID NO: 20, and the 3' ITR nucleotide sequence has at least 90% (e.g., at least 95%, at least 96%, at least 97%, at least 98%, at least 99%, or 100%) sequence identity to SEQ ID NO: 21. In certain embodiments, the transfer genome comprises a nucleotide sequence set forth in any one of SEQ ID NOs: 46-50, a 5' ITR nucleotide sequence having the sequence of SEQ ID NO: 20, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 26. In certain embodiments, the 5' ITR consists of a nucleotide sequence at least 95%, 96%, 97%, 98%, or 99% identical to SEQ ID NO: 26. In certain embodiments, the 5' ITR consists of the nucleotide sequence set forth in SEQ ID NO: 26. In certain embodiments, the 3' ITR comprises a nucleotide sequence at least 95%, 96%, 97%, 98%, or 99% identical to SEQ ID NO: 27. In certain embodiments, the 5' ITR consists of a nucleotide sequence at least 95%, 96%, 97%, 98%, or 99% identical to SEQ ID NO: 27. In certain embodiments, the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 27. In certain embodiments, the 5' ITR consists of the nucleotide sequence set forth in SEQ ID NO: 26, and the 3' ITR consists of the nucleotide sequence set forth in SEQ ID NO: 19.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR. See, e.g., Savy et al., *Human Gene Therapy Methods* (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 56. In certain embodiments, the 3' ITR comprises a nucleotide sequence at least 95%, 96%, 97%, 98%, or 99% identical to SEQ ID NO: 57. In certain embodiments, the 3' ITR comprises the nucleotide sequence set forth in SEQ ID NO: 57. In certain embodiments, the nucleotide sequence of the 3' ITR consists of a nucleotide sequence at least 95%, 96%, 97%, 98%, or 99% identical to SEQ ID NO: 57. In certain embodiments, the nucleotide sequence of the 3' ITR consists of the nucleotide sequence set forth in SEQ ID NO: 57.

In certain embodiments, the transfer genome comprises from 5' to 3': a 5' ITR; an internal element comprising from 5' to 3': a TRE, optionally a non-coding exon and an intron, a PAH coding sequence, and a polyadenylation sequence, as disclosed herein; a non-resolvable ITR; a nucleotide sequence complementary to the internal element; and a 3' ITR. Such transfer genome can form a self-complementary, double-stranded DNA genome of the AAV after infection and before replication.

In certain embodiments, the transfer genome comprises from 5' to 3': a 5' ITR, a TRE, optionally a non-coding exon and an intron, a PAH coding sequence, a polyadenylation sequence, and a 3' ITR. In certain embodiments, the 5' ITR has at least 90%, 91%, 92%, 93%, 94%, 95%, 96%, 97%, 98%, or 99% sequence identity to SEQ ID: 18, 20, or 26; the TRE has at least 90%, 91%, 92%, 93%, 94%, 95%, 96%, 97%, 98%, or 99% sequence identity to any one of SEQ ID NOs: 28-30 and 32-41; the intron has at least 90%, 91%, 92%, 93%, 94%, 95%, 96%, 97%, 98%, or 99% sequence identity to SEQ ID NO: 31 or 35; the PAH coding sequence has at least 90%, 91%, 92%, 93%, 94%, 95%, 96%, 97%, 98%, or 99% sequence identity to SEQ ID NO: 25; the polyadenylation sequence has at least 90%, 91%, 92%, 93%, 94%, 95%, 96%, 97%, 98%, or 99% sequence identity to any one of SEQ ID NOs: 42, 43, and 45; and/or the 3' ITR has at least 90%, 91%, 92%, 93%, 94%, 95%, 96%, 97%, 98%, or 99% sequence identity to SEQ ID: 19, 21, or 27. In certain embodiments, the 5' ITR comprises or consists of a nucleotide sequence selected from the group consisting of SEQ ID NOs: 18, 20, and 26; the TRE comprises a nucleotide sequence selected from the group consisting of SEQ ID NOs: 28-30 and 32-41; the intron comprises a nucleotide sequence selected from the group consisting of SEQ ID NOs: 31 and 35; the PAH coding sequence comprises the sequence set forth in SEQ ID NO: 25; the polyadenylation sequence comprises a nucleotide sequence selected from the group consisting of SEQ ID NOs: 42, 43, and 45; and/or the 3' ITR comprises or consists of a nucleotide sequence selected from the group consisting of SEQ ID NOs: 19, 21, and 27. In certain embodiments, the 5' ITR comprises or consists of the sequence set forth in SEQ ID NO: 18; the TRE comprises the sequence set forth in SEQ ID NO: 28; the PAH coding sequence comprises the sequence set forth in SEQ ID NO: 25; the polyadenylation sequence comprises the sequence set forth in SEQ ID NO: 42; and/or the 3' ITR comprises or consists of the sequence set forth in SEQ ID NO: 19. In certain embodiments, the 5' ITR comprises or consists of the sequence set forth in SEQ ID NO: 26; the TRE comprises from 5' to 3' the sequence set forth in SEQ ID NO: 29, and the sequence set forth in SEQ ID NO: 30 (e.g., the TRE comprises the sequence set forth in SEQ ID NO: 32); the intron comprises the sequence set forth in SEQ ID NO: 31; the PAH coding sequence comprises the sequence set forth in SEQ ID NO: 25; the polyadenylation sequence comprises the sequence set forth in SEQ ID NO: 43 and/or the 3' ITR comprises or consists of the sequence set forth in SEQ ID NO: 27. In certain embodiments, the 5' ITR comprises or consists of the sequence set forth in SEQ ID NO: 18; the TRE comprises from 5' to 3' the sequence set forth in SEQ ID NO: 33, and the sequence set forth in SEQ ID NO: 34 (e.g., the TRE comprises the sequence set forth in SEQ ID NO: 36); the intron comprises the sequence set forth in SEQ ID NO: 35; the PAH coding sequence comprises the sequence set forth in SEQ ID NO: 25; the polyadenylation sequence comprises the sequence set forth in SEQ ID NO: 45; and/or the 3' ITR comprises or consists of the sequence set forth in SEQ ID NO: 19. In certain embodiments, the 5' ITR comprises or consists of the sequence set forth in SEQ ID NO: 18; the TRE comprises from 5' to 3' the sequence set forth in SEQ ID NO: 37, and the sequence set forth in SEQ ID NO: 38 (e.g., the TRE comprises the sequence set forth in SEQ ID NO: 39); the intron comprises the sequence set forth in SEQ ID NO: 35; the PAH coding sequence comprises the sequence set forth in SEQ ID NO: 25; the polyadenylation sequence comprises the sequence set forth in SEQ ID NO: 45; and/or the 3' ITR comprises or consists of the sequence set forth in SEQ ID NO: 19. In certain embodiments, the 5' ITR comprises or consists of the sequence set forth in SEQ ID NO: 18; the TRE comprises from 5' to 3' the sequence set forth in SEQ ID NO: 37, and the sequence set forth in SEQ ID NO: 40

(e.g., the TRE comprises the sequence set forth in SEQ ID NO: 41); the polyadenylation sequence comprises the sequence set forth in SEQ ID NO: 45; and/or the 3' ITR comprises or consists of the sequence set forth in SEQ ID NO: 19.

In certain embodiments, the transfer genome comprises a sequence at least 80% (e.g., at least 85%, 90%, 91%, 92%, 93%, 94%, 95%, 96%, 97%, 98%, or 99%) identical to the sequence set forth in SEQ ID NO: 51, 52, 53, 54, 55, 62, 65, 68, 75, 77, 79, 81, 83, 85, 87, or 90. In certain embodiments, the transfer genome comprises the sequence set forth in SEQ ID NO: 51, 52, 53, 54, 55, 62, 65, 68, 75, 77, 79, 81, 83, 85, 87, or 90. In certain embodiments, the transfer genome comprises the sequence set forth in SEQ ID NO: 52. In certain embodiments, the transfer genome consists of the sequence set forth in SEQ ID NO: 51, 52, 53, 54, 55, 62, 65, 68, 75, 77, 79, 81, 83, 85, 87, or 90. In certain embodiments, the transfer genome consists of the sequence set forth in SEQ ID NO: 52.

In certain embodiments, the replication-defective AAV comprises: (a) an AAV capsid protein comprising the amino acid sequence of amino acids 203-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27); (b) an AAV capsid protein comprising the amino acid sequence of amino acids 138-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27; and/or (c) an AAV capsid protein comprising the amino acid sequence of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27.

In certain embodiments, the replication-defective AAV comprises: (a) an AAV capsid protein comprising the amino acid sequence of amino acids 203-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; (b) an AAV capsid protein comprising the amino acid sequence of amino acids 138-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; and/or (c) an AAV capsid protein comprising the amino acid sequence of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90.

In another aspect, provided herein is a polynucleotide comprising a nucleic acid sequence that is at least 80% (e.g., at least 85%, 90%, 91%, 92%, 93%, 94%, 95%, 96%, 97%, 98%, or 99%) identical to the nucleic acid sequence set forth in SEQ ID NO: 88, 91, or 92. In certain embodiments, the polynucleotide comprises the nucleic acid sequence set forth in SEQ ID NO: 88, 91, or 92. In certain embodiments, the polynucleotide comprises the nucleic acid sequence set forth in SEQ ID NO: 92. In certain embodiments, the polynucleotide consists of the nucleic acid sequence set forth in SEQ ID NO: 88, 91, or 92. In certain embodiments, the polynucleotide consists of the nucleic acid sequence set forth in SEQ ID NO: 92.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al, 7th ed., Lippincott, Williams, & Wilkins; and Handbook of Pharmaceutical Excipients (2000) A. H. Kibbe et al, 3rd ed. Amer. Pharmaceutical Assoc.

In another aspect, the instant disclosure provides a polynucleotide comprising a coding sequence encoding a human PAH protein or a fragment thereof, wherein the coding sequence has been codon-altered to have less than 100% (e.g., less than 95%, 90%, 85%, 80%, 75%, 70%, 65%, 60%, 55%, or 50%) identical to a wild-type human PAH gene. In certain embodiments, the polynucleotide comprises the sequence set forth in SEQ ID NO: 25. In certain embodiments, the polynucleotide comprises nucleotides 4 to 1359 of the sequence set forth in SEQ ID NO: 25. The polynucleotide can comprise DNA, RNA, modified DNA, modified RNA, or a combination thereof. In certain embodiments, the polynucleotide is an expression vector.

III. METHOD OF USE

In another aspect, the instant disclosure provides methods for expressing a PAH polypeptide in a cell. The methods generally comprise transducing the cell with a replication-defective AAV as disclosed herein. Such methods are highly efficient at restoring PAH expression. Accordingly, in certain embodiments, the methods disclosed herein involve transducing the cell with a replication-defective AAV as disclosed herein.

The methods disclosed herein can be applied to any cell harboring a mutation in the PAH gene. The skilled worker will appreciate that cells that are active in Phe metabolism are of particular interest. Accordingly, in certain embodiments, the method is applied to cells in the liver, kidney, brain, pituitary gland, adrenal gland, pancreas, urinary bladder, gallbladder, colon, small intestine, or breast. In certain embodiments, the method is applied to hepatocytes and/or renal cells.

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with a PAH gene mutation, the method generally comprising administering to the subject an effective amount of a replication-defective AAV as disclosed herein. The subject can be a human subject, a non-human primate subject (e.g., a cynomolgus), or a rodent subject (e.g., a mouse) with a PAH mutation, or a non-human primate subject (e.g., a cynomolgus) or a rodent subject (e.g., a mouse) containing PAH-mutant human liver cells. Suitable mouse subjects include without limitation, mice into which human liver cells (e.g., human hepatocytes) have been engrafted. Any disease or disorder associated with a PAH gene mutation can be treated using the methods disclosed herein. Suitable diseases or disorders include, without limitation, phenylketonuria.

In certain embodiments, the foregoing methods employ a replication-defective AAV comprising: (a) an AAV capsid protein comprising the amino acid sequence of amino acids 203-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27); (b) an AAV capsid protein comprising the amino acid sequence of amino acids 138-736 of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27; and/or (c) an AAV capsid protein comprising the amino acid sequence of SEQ ID NO: 16, and a transfer genome comprising 5' to 3' following genetic elements: a 5' ITR element (e.g., the 5' ITR of SEQ ID NOs: 26), a human HCR1 (e.g., the HCR1 of SEQ ID NOs: 29), an hAAT promoter (e.g., the hAAT promoter of SEQ ID NOs: 30), an SV40 intron (e.g., the SV40 intron of SEQ ID NOs: 31), a silently altered human PAH coding sequence (e.g., the PAH coding sequence of SEQ ID NOs: 25), an SV40 polyadenylation sequence (e.g., the SV40 polyadenylation sequence of SEQ ID NOs: 43), and a 3' ITR element (e.g., the 3' ITR of SEQ ID NOs: 27.

In certain embodiments, the foregoing methods employ a replication-defective AAV comprising: (a) an AAV capsid protein comprising the amino acid sequence of amino acids 203-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; (b) an AAV capsid protein comprising the amino acid sequence of amino acids 138-736 of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90; and/or (c) an AAV capsid protein comprising the amino acid sequence of SEQ ID NO: 16, and a transfer genome comprising the nucleotide sequence set forth in any one of SEQ ID NOs: 24, 25, 46, 47, 48, 49, 50, 51, 52, 53, 54, 55, 61, 62, 64, 65, 67, 68, 74, 75, 76, 77, 78, 79, 80, 81, 82, 83, 84, 85, 86, 87, 89, or 90.

The methods disclosed herein are particularly advantageous in that they are capable of expressing a PAH protein in a cell with high efficiency both in vivo and in vitro. In certain embodiments, the expression level of the PAH protein is at least 10%, 20%, 30%, 40%, 50%, 60%, 70%, 80%, 90%, or 100% of the expression level of the endogenous PAH protein in a cell of the same type that does not have a mutation in the PAH gene. In certain embodiments, the expression level of the PAH protein is at least 1.1, 1.2, 1.3, 1.4, 1.5, 1.6, 1.7, 1.8, 1.9, 2, 3, 4, 5, 6, 7, 8, 9, or 10 fold higher than the expression level of the endogenous PAH protein in a cell of the same type that does not have a mutation in the PAH gene. Any methods of determining the expression level of the PAH protein can be employed including, without limitation, ELISA, Western blotting, immunostaining, and mass spectrometry.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV PACKAGING SYSTEMS

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a transfer genome for expression of the PAH gene as disclosed herein, wherein the packaging system is operative in a cell for enclosing the transfer genome in the capsid to form the AAV.

In certain embodiments, the packaging system comprises a first vector comprising the Rep nucleotide sequence and the Cap nucleotide sequence, and a second vector comprising the transfer genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the transfer genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a transfer genome as described herein being delivered in the form of a transfecting plasmid or a recombinant helper virus).

V. EXAMPLES

The recombinant AAV vectors disclosed herein mediate highly efficient gene transfer in vitro and in vivo. The following examples demonstrate the efficient restoration of the expression of the PAH gene, which is mutated in certain human diseases, such as phenylketonuria, using an AAV-based vector as disclosed herein. These examples are offered by way of illustration, and not by way of limitation.

Example 1: Human PAH Transfer Vector

This example provides human PAH transfer vectors pHMI-hPAH-TC-004, pHMI-hPAH-TC-025, pHMI-hPAH-TC-010, pHMI-hPAH-TC-011, and pHMI-hPAH-TC-012 for expression of human PAH in a human or mouse cell.

a) pHMI-hPAH-TC-004

PAH transfer vector pHMI-hPAH-TC-004, as shown in FIG. 1A, comprises 5' to 3' the following genetic elements: a 5' ITR element, a CAG promoter, a silently altered human PAH coding sequence, an SV40 polyadenylation sequence, and a 3' ITR element. The sequences of these elements are set forth in Table 1. This vector is capable of expressing a human PAH protein in a cell (e.g., a human cell or a mouse cell) to which the vector is transduced.

TABLE 1

Genetic elements in human PAH transfer vector pHMI-hPAH-TC-004

| Genetic Element | SEQ ID NO |
|---|---|
| 5' ITR element | 18 |
| CAG promoter | 28 |
| codon-altered human PAH coding sequence | 25 |
| SV40 polyadenylation sequence | 42 |
| 3' ITR element | 19 |
| Transfer genome (from promoter to polyadenylation sequence) | 46 |
| Transfer genome (from 5' ITR to 3' ITR) | 51 | b) pHMI-hPAH-TC-025

PAH transfer vector pHMI-hPAH-TC-025, as shown in FIG. 1B, comprises 5' to 3' the following genetic elements: a truncated 5' ITR element, a human hepatic control region 1 (HCR1), a human α1-antitrypsin (hAAT) promoter, an SV40 intron, a silently altered human PAH coding sequence, an SV40 polyadenylation sequence, and a modified 3' ITR element. The sequences of these elements are set forth in Table 2. The truncated 5' ITR allows the vector to form a double-stranded AAV genome after transduction into cells. This vector is capable of expressing a human PAH protein in a human hepatocyte to which the vector is transduced.

TABLE 2

Genetic elements in human PAH transfer vector pHMI-hPAH-TC-025

| Genetic Element | SEQ ID NO |
|---|---|
| truncated 5' ITR element | 26 |
| human HCR1 | 29 |

TABLE 2-continued

Genetic elements in human PAH transfer vector
pHMI-hPAH-TC-025

| Genetic Element | SEQ ID NO |
| --- | --- |
| human α1-antitrypsin (hAAT) promoter | 30 |
| SV40 intron | 31 |
| transcriptional regulatory region comprising the human HCR1 and hAAT promoter | 32 |
| codon-altered human PAH coding sequence | 25 |
| SV40 polyadenylation sequence | 43 |
| modified 3' ITR element | 27 |
| Transfer genome (from HCR1 to polyadenylation sequence) | 47 |
| Transfer genome (from 5' ITR to 3' ITR) | 52 |
| Full sequence of transfer vector | 92 | c) pHMI-hPAH-TC-010

PAH transfer vector pHMI-hPAH-TC-010, as shown in FIG. 1C, comprises 5' to 3' the following genetic elements: a 5' ITR element, a hepatic specific regulatory module of hAAT promoter, a human TTR promoter, a modified minute virus of mouse (MVM) intron, a silently altered human PAH coding sequence, an SV40 polyadenylation sequence, and a 3' ITR element. The sequences of these elements are set forth in Table 3. This vector is capable of expressing a human PAH protein in a cell (e.g., a human cell or a mouse cell) to which the vector is transduced, particularly at a high level in a hepatocyte.

TABLE 3

Genetic elements in human PAH transfer vector
pHMI-hPAH-TC-010

| Genetic Element | SEQ ID NO |
| --- | --- |
| 5' ITR element | 18 |
| hepatic specific regulatory module of hAAT promoter | 33 |
| human TTR promoter | 34 |
| modified minute virus of mouse (MVM) intron | 35 |
| transcriptional regulatory region comprising the hepatic specific regulatory module (HSRM) and human TTR promoter | 36 |
| codon-altered human PAH coding sequence | 25 |
| SV40 polyadenylation sequence | 45 |
| 3' ITR element | 19 |
| Transfer genome (from HSRM to polyadenylation sequence) | 48 |
| Transfer genome(from 5' ITR to 3' ITR) | 53 | d) pHMI-hPAH-TC-011

PAH transfer vector pHMI-hPAH-TC-011, as shown in FIG. 1D, comprises 5' to 3' the following genetic elements: a 5' ITR element, a human HCR1, a human α1-antitrypsin (hAAT) promoter, an modified MVM intron, a silently altered human PAH coding sequence, an SV40 polyadenylation sequence, and a 3' ITR element. The sequences of these elements are set forth in Table 4. This vector is capable of expressing a human PAH protein in a human hepatocyte to which the vector is transduced.

TABLE 4

Genetic elements in human PAH transfer vector
pHMI-hPAH-TC-011

| Genetic Element | SEQ ID NO |
| --- | --- |
| truncated 5' ITR element | 18 |
| human HCR1 | 37 |
| human α1-antitrypsin (hAAT) promoter | 38 |

TABLE 4-continued

Genetic elements in human PAH transfer vector
pHMI-hPAH-TC-011

| Genetic Element | SEQ ID NO |
| --- | --- |
| modified minute virus of mouse (MVM) intron | 35 |
| transcriptional regulatory region comprising the human HCR1 and hAAT promoter | 39 |
| codon-altered human PAH coding sequence | 25 |
| SV40 polyadenylation sequence | 45 |
| modified 3' ITR element | 19 |
| Transfer genome (from HCR1 to polyadenylation sequence) | 49 |
| Transfer genome(from 5' ITR to 3' ITR) | 54 | e) pHMI-hPAH-TC-012

Figure 1E:
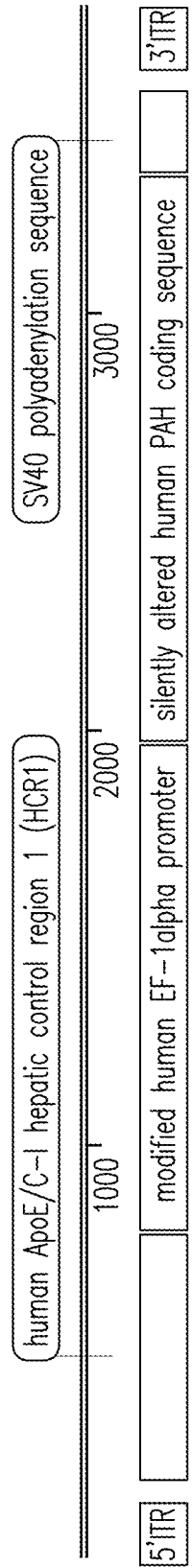

PAH transfer vector pHMI-hPAH-TC-012, as shown in FIG. 1E, comprises 5' to 3' the following genetic elements: a 5' ITR element, a human hepatic control region 1 (HCR1), a modified human EF-1α promoter, a silently altered human PAH coding sequence, an SV40 polyadenylation sequence, and a 3' ITR element. The sequences of these elements are set forth in Table 5. This vector is capable of expressing a human PAH protein in a human hepatocyte to which the vector is transduced.

TABLE 5

Genetic elements in human PAH transfer vector
pHMI-hPAH-TC-012

| Genetic Element | SEQ ID NO |
| --- | --- |
| truncated 5' ITR element | 18 |
| human hepatic control region 1 (HCR1) | 37 |
| modified human EF-1α promoter | 40 |
| transcriptional regulatory region comprising the human HCR1 and modified human EF-1α promoter | 41 |
| codon-altered human PAH coding sequence | 25 |
| SV40 polyadenylation sequence | 45 |
| modified 3' ITR element | 19 |
| Transfer genome (from HCR1 to polyadenylation sequence) | 50 |
| Transfer genome (from 5' ITR to 3' ITR) | 55 |

Figure 2:
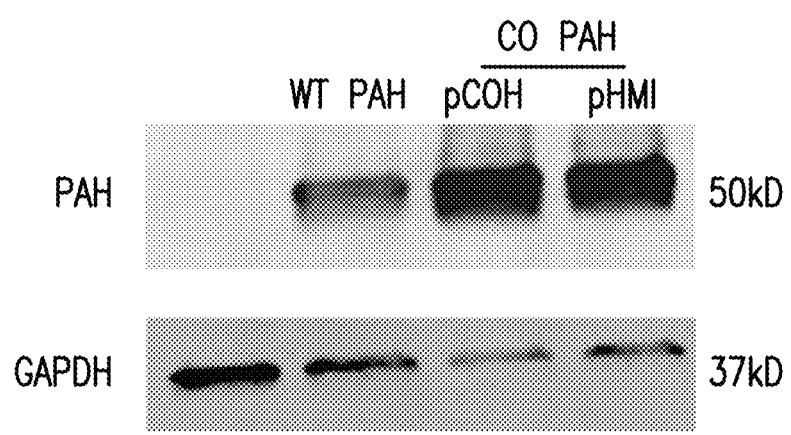
FIG. 2 is an image of Western blot showing the expression of human PAH from the pCOH-WT-PAH ("WT PAH"), pCOH-CO-PAH ("CO PAH pCOH"), and pHMI—CO-PAH ("CO PAH pHMI") vectors. $5 \times 10^5$ HEK 293 cells were transfected with 1 µg of vector. Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was shown as a loading control.

The silent alteration significantly improves the expression of the PAH protein, as demonstrated by comparison of expression vectors pCOH-WT-PAH, pCOH-CO-PAH, and pHMI—CO-PAH. The pCOH-WT-PAH vector comprises a CAG promoter operably linked to a wild-type PAH coding sequence set forth in SEQ ID NO: 24. The pCOH-CO-PAH and pHMI—CO-PAH vectors each comprise a CAG promoter operably linked to a codon-altered human PAH coding sequence as set forth in SEQ ID NO: 25. The pCOH-CO-PAH and pHMI—CO-PAH vectors are highly similar. Each vector was transfected in HEK 293 cells which is naturally deficient in PAH. As shown in FIG. 2, VG-GT-CO-PAH ("CO-hPAH") gave rise to an expression level of human PAH several fold higher than VG-GT-PAH ("WT-hPAH").

The vectors disclosed herein can be packaged in an AAV clade F capsid, such as an AAVHSC5, AAVHSC7, AAVHSC15 or AAVHSC17 capsid. The packaged viral particles can be administered to a wild-type animal, a PAH deficient animal, or a reconstituted animal having human hepatocytes obtained from a patient with phenylketonuria caused by a PAH mutation. The gene transfer efficiency can be measured by collecting liver samples and quantifying the percentage of PAH-positive cells (e.g., cells that have a unique nucleotide sequence from the vector, cells that express a wild-type PAH protein, or cells with a higher PAH activity than in cells from a control animal not receiving the PAH expression vector). The restoration of phenylalanine metabolism, which indicates the efficacy of the PAH expression vectors, can be assessed by measuring the Phe level in the blood and by observing the coat color of the mouse. Safety of the viral particle administration can be evaluated by measuring the aspartate aminotransferase (AST) and alanine aminotransferase (ALT) levels in serum.

Example 2: Mouse PAH Gene Transfer in a Mouse Model

This example provides a mouse PAH transfer vector rAAV-CBA-mPAH that is similar to the human PAH transfer vector pHMI-hPAH-TC-004 described in Example 1 except that a wild-type mouse PAH coding sequence is substituted for the codon-altered human PAH coding sequence. This vector is capable of expressing a mouse PAH protein in a cell (e.g., a human cell or a mouse cell) to which the vector is transduced.

Briefly, Pah$^{-/-}$ (PAH$^{enu2}$) mice were housed in clear polycarbonate cages with contact bedding in an isolator. Picolab Mouse Diet 5058 was provided to the animals ad libitum. Spring or tap water acidified with 1N HCl to a targeted pH of 2.5-3.0 was provided ad libitum. Vectors packaged in AAVHSC15 capsid were prepared in PBS (with Ca and Mg), supplemented with 35 mM NaCl, 1% sucrose, and 0.05% Pluronic F-68. The formulation was injected intravenously via the tail vein.

Blood samples were collected every week after the administration of the PAH transfer vector (0 week: prior to administration) by facial vein puncture or tail snip. The samples were allowed to clot at room temperature for at least 30 minutes, centrifuged at ambient temperature at minimum 1000×g for 10 minutes and the serum samples were extracted. Serum samples were stored at −70° C. Serum phenylalanine and tyrosine levels were measured by tandem mass spectrometry.

For collection of tissue samples, the animals underwent cardiac perfusion with saline. Liver (caudate lobe), kidney (left), brain, heart, and muscle (quadriceps) tissues were snap frozen in liquid nitrogen and stored at −70° C. The snap frozen tissues were ground into powder in liquid nitrogen in a mortar and pestle and divided in to aliquots to test for PAH expression for vector genome biodistribution by qPCR.

The safety of the rAAV-CBA-mPAH vector was assessed by measuring the aspartate aminotransferase (AST) and alanine aminotransferase (ALT) levels in the treated animals. Serum samples were collected pre-dose and one week after administration of the viral particles. The levels of AST and ALT were measured by the Sigma MAK055 and Sigma MAK052 ELISA kits.

Figure 3A:
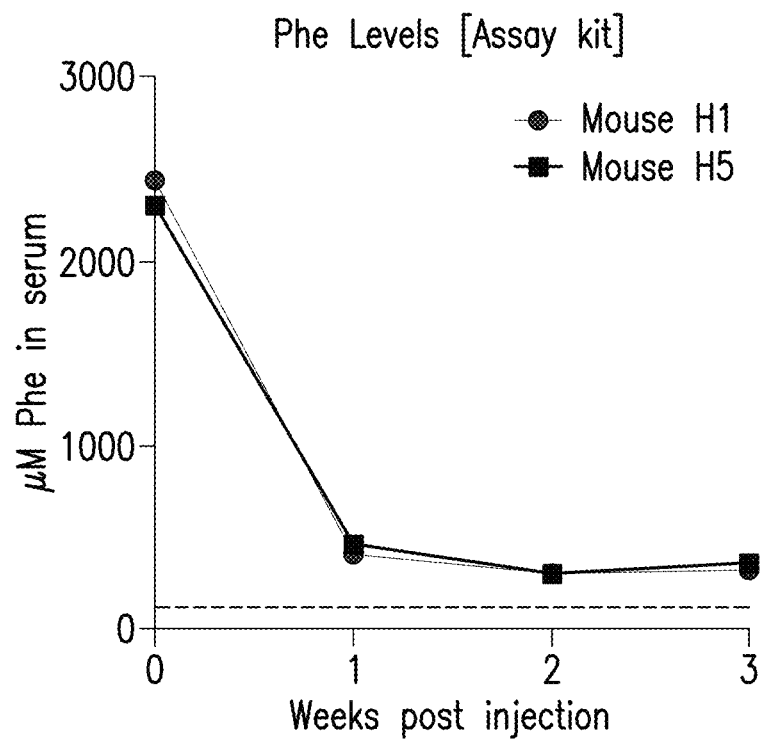
FIGS. 3A and 3B are graphs showing the Phe level in the serum of two pah$^{-/-}$ mice ("Mouse H1" and "Mouse H5") each administered with $5 \times 10^{13}$ vector genomes of the rAAV-CBA-mPAH vector packaged in an AAVHSC capsid per kg of body weight intravenously via the tail vein. Serum samples were collected in a time course. The Phe levels were measured with a BioAssay Systems ELISA kit EPHE-100 (FIG. 3A) or mass spectrometry (FIG. 3B).
Figure 3B:
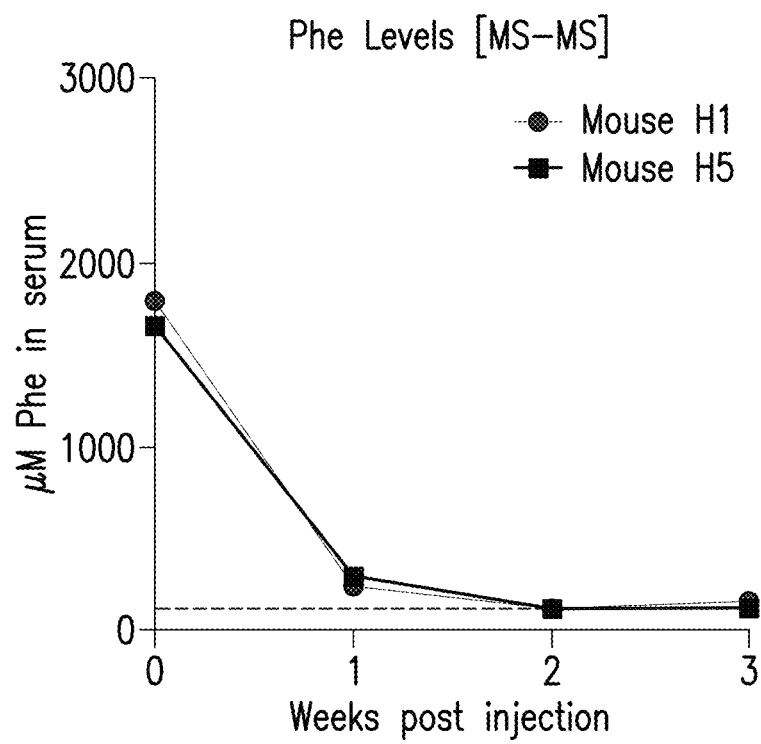

The pah$^{-/-}$ mice manifested phenylketonuria and had lighter coat color than wild-type mice. As shown in FIGS. 3A and 3B, the administration of the rAAV-CBA-mPAH vector lead to significant reduction of Phe levels in the serum within one week, and the Phe levels remained low for four weeks. The coat color also changed from brown to black within one week.

Figure 4:
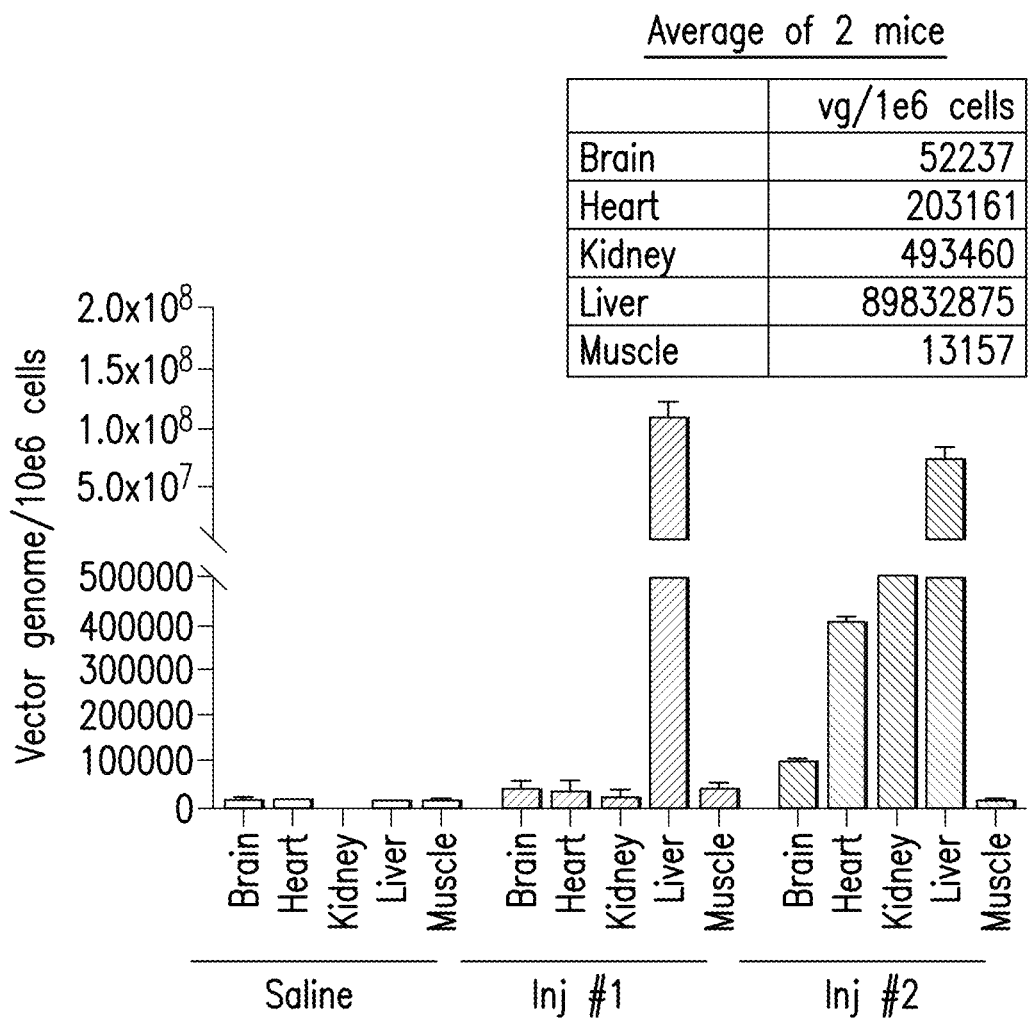
FIG. 4 is a graph and a table showing the numbers of vector genomes per $10^6$ cells detected in major organs. The rAAV-CBA-mPAH vector packaged in an AAVHSC capsid was injected to pah$^{-/-}$ mice intravenously via the tail vein at a dose of $5 \times 10^{13}$ vector genomes per kg of body weight. Organs of the mice were collected 4 weeks after the administration. The numbers of vector genomes per $10^6$ cells were measured by the following method: (1) the weight/volume concentration of the vector genome in a sample was measured by Taqman PCR using a standard curve generated with serial dilutions of the vector plasmid; (2) the mass of a single vector genome was calculated based on the sequence of the vector; (3) the number/volume concentration of the vector genome in the sample was calculated; (4) the weight/volume concentration of genomic DNA in the same sample was measured by Taqman PCR of the apolipoprotein B gene using a standard curve generated with serial dilutions of calculated amounts of genomic DNA isolated from mouse tissues; (5) the number/volume concentration of cell genome in the sample was calculated based on copies of ApoB; and (6) the number of vector genomes per $10^6$ cells was calculated by dividing the number/volume concentration of the vector genome by the number/volume concentration of the cell genome and multiplying the result by $10^6$.

Expression of mPAH was also observed in tissue samples. As shown in FIG. 4, DNA of the rAAV-CBA-mPAH vector was detectable in many organs, wherein the numbers of viral genomes per 10$^6$ cells was the highest in liver, heart, and kidney.

Figure 5A:
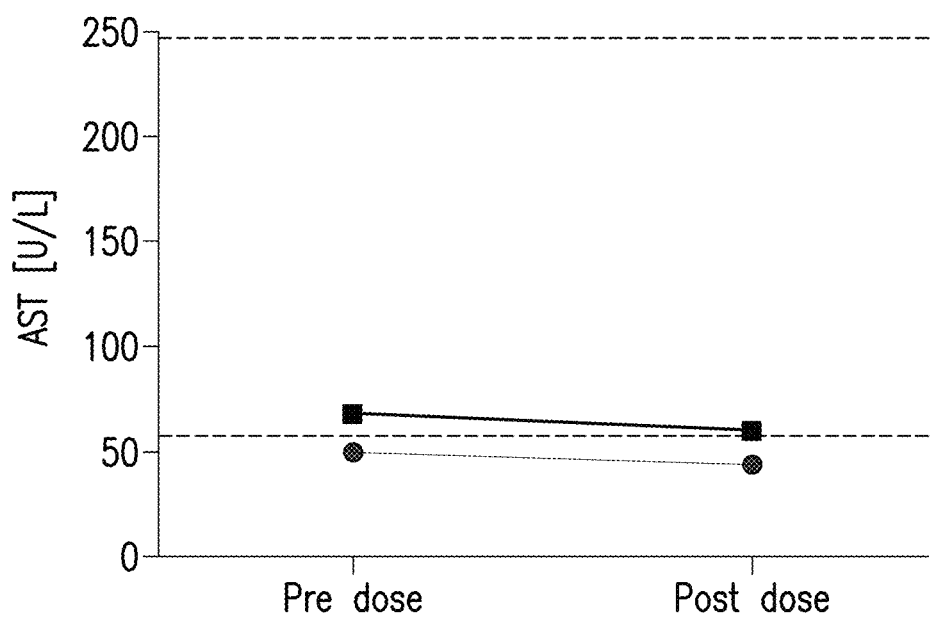
FIGS. 5A and 5B are graphs showing the aspartate aminotransferase (AST) and alanine aminotransferase (ALT) levels in the serum of pah$^{-/-}$ mice administered with the rAAV-CBA-mPAH vector. The rAAV-CBA-mPAH vector packaged in an AAVHSC capsid was injected to pah$^{-/-}$ mice intravenously via the tail vein at a dose of $5 \times 10^{13}$ vector genomes per kg of body weight. Serum samples were collected 4 weeks after the administration. The levels of AST (FIG. 5A) and ALT (FIG. 5B) were measured by ELISA using the Sigma MAK055 and Sigma MAK052 kits, respectively.
Figure 5B:
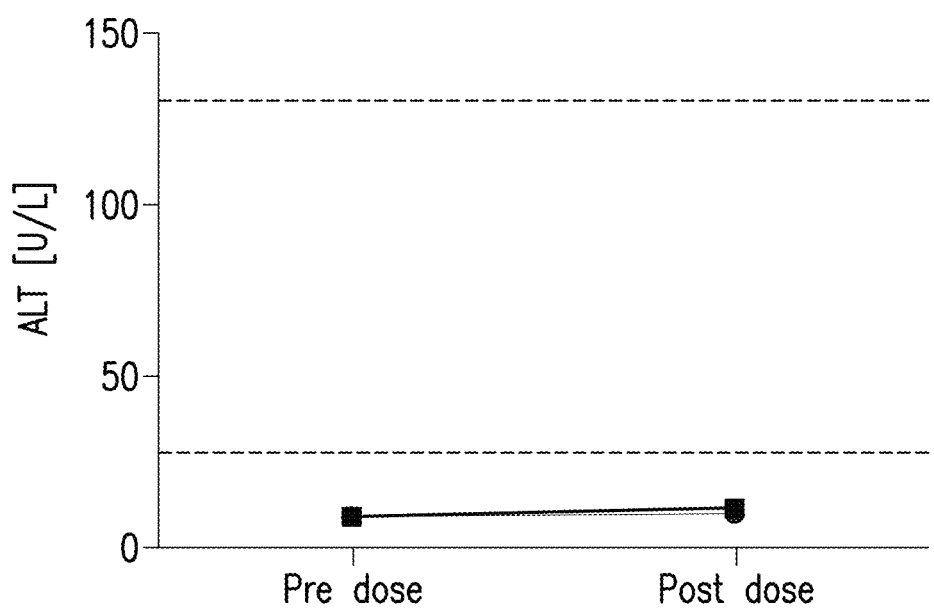

With respect to the safety of the AAV administration, the AST and ALT levels remained low after administration (FIGS. 5A and 5B), suggesting that the rAAV-CBA-mPAH vector was not toxic to the liver.

Example 3: Human PAH Gene Transfer in a Mouse Model

This example demonstrates that the PAH transfer vectors described in Example 1 effectively reversed the phenotype caused by PAH gene deficiency in a mouse model. The mouse model, AAV packaging and formulation, and methods for examining gene transfer efficiency were identical to the ones described in Example 2.

To examine the efficacy of the five PAH transfer vectors in reversing the phenotypes, a single dose of 2.6×10$^{13}$ vector genomes per kg of body weight for male mice, or a dose of 6×10$^{13}$ vector genomes per kg of body weight for female mice. The pah$^{-/-}$ mice manifested increased level of phenylalanine (Phe) and reduced level of tyrosine (Tyr) in the serum. As shown in FIGS. 6A-6H, the administration of any one of the five vectors led to significant reduction of Phe levels and increase of Tyr levels within one week. The efficacy lasted for at least 12 weeks in male mice, and at least 6 weeks in female mice. Other than pHMI-hPAH-TC-004, all the vectors maintained complete reduction of serum Phe levels during the time examined.

Figure 6A:
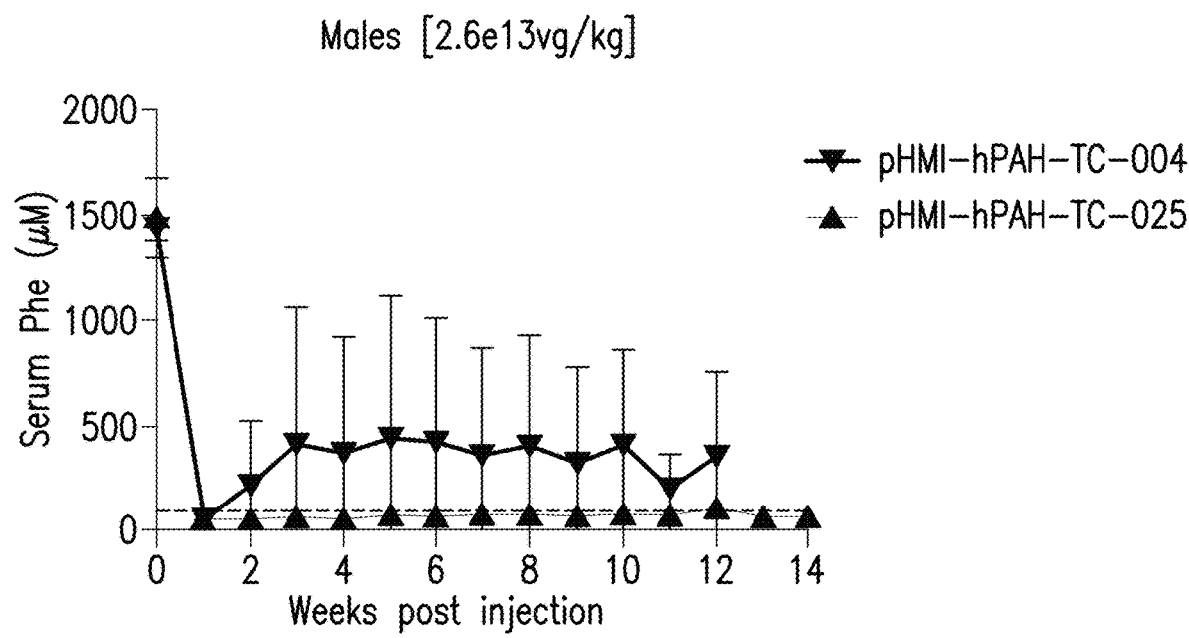
FIGS. 6A-6H are graphs showing the levels of phenylalanine (FIGS. 6A, 6C, 6E, and 6G) or tyrosine (FIGS. 6B, 6D, 6F, and 6H) in the serum of male (FIGS. 6A, 6B, 6E, and 6F) or female (FIGS. 6C, 6D, 6G, and 6H) mice administered with the indicated doses of the pHMI-hPAH-TC-004, pHMI-hPAH-TC-025, pHMI-hPAH-TC-010, pHMI-hPAH-TC-011, or pHMI-hPAH-TC-012 vector.
Figure 6B:
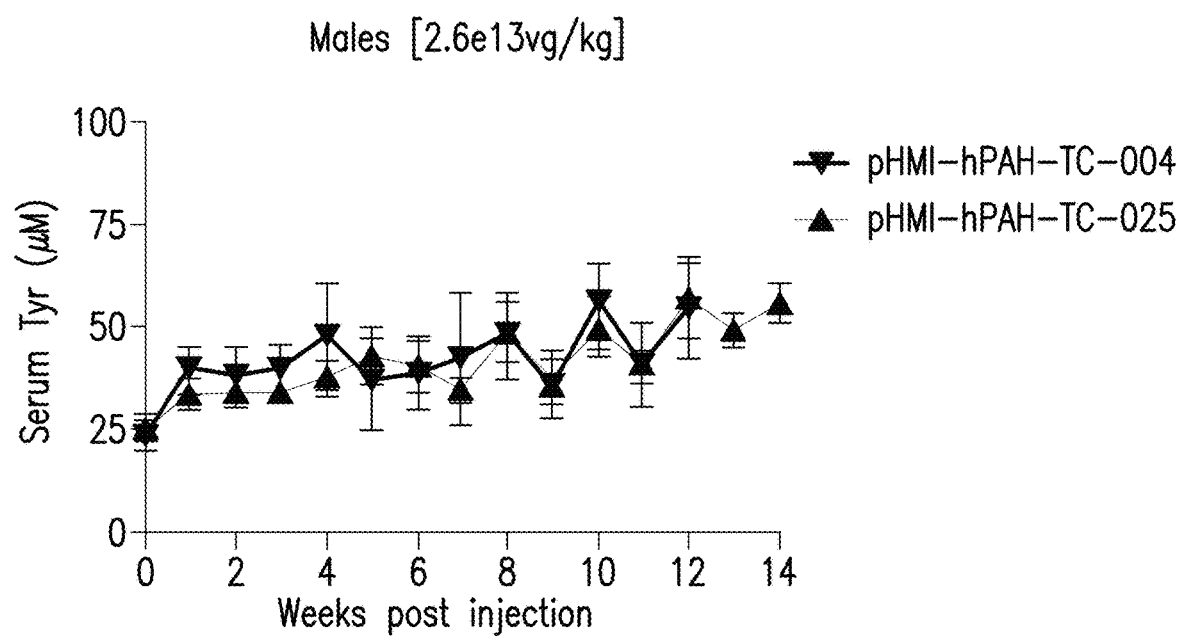
Figure 6C:
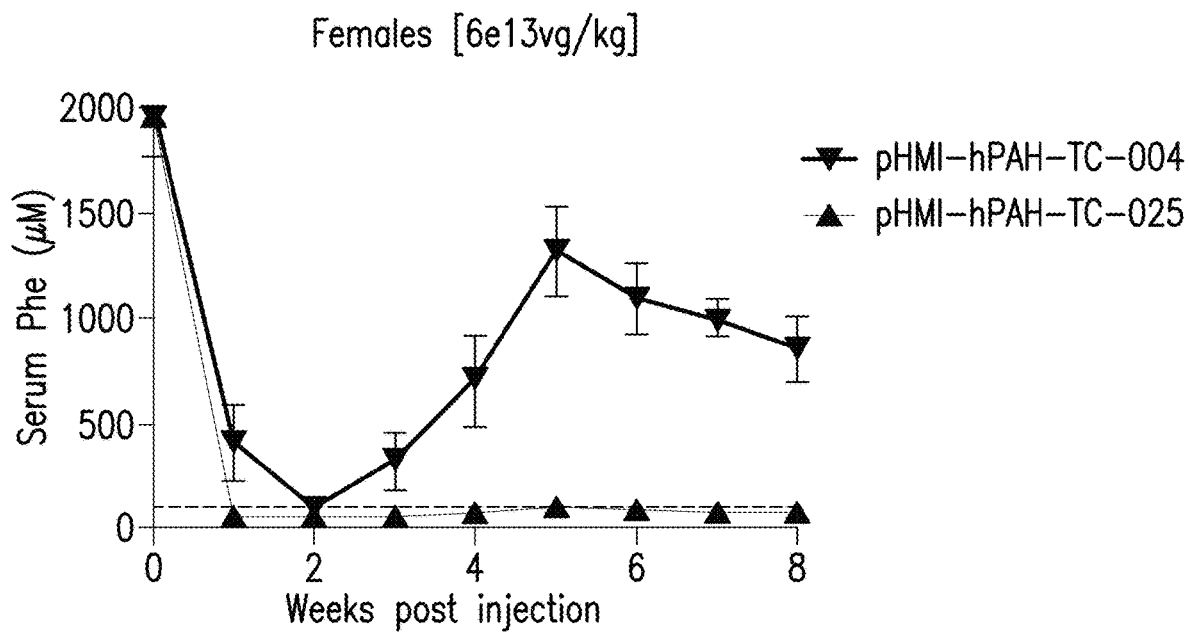
Figure 6D:
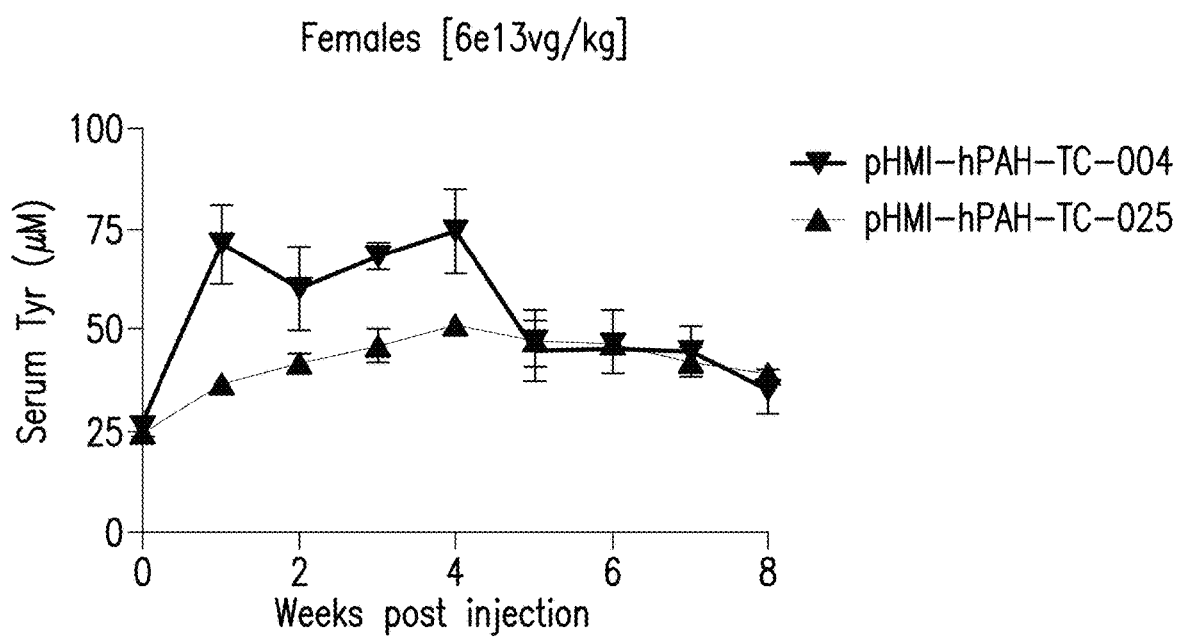
Figure 6E:
Figure 6F:
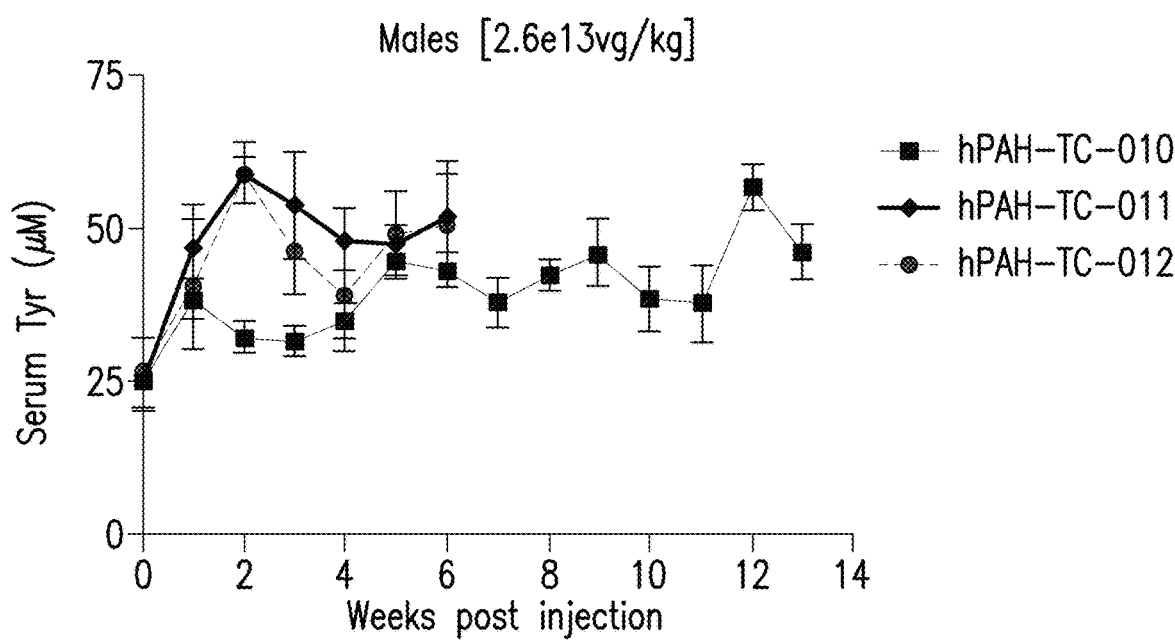
Figure 6G:
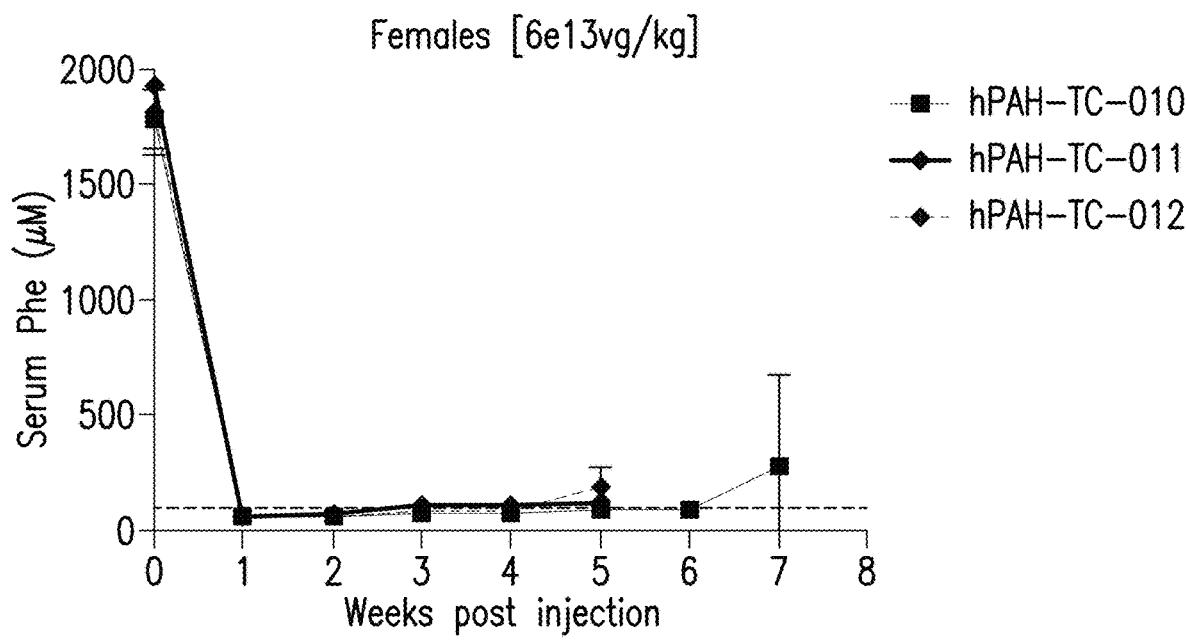
Figure 6H:
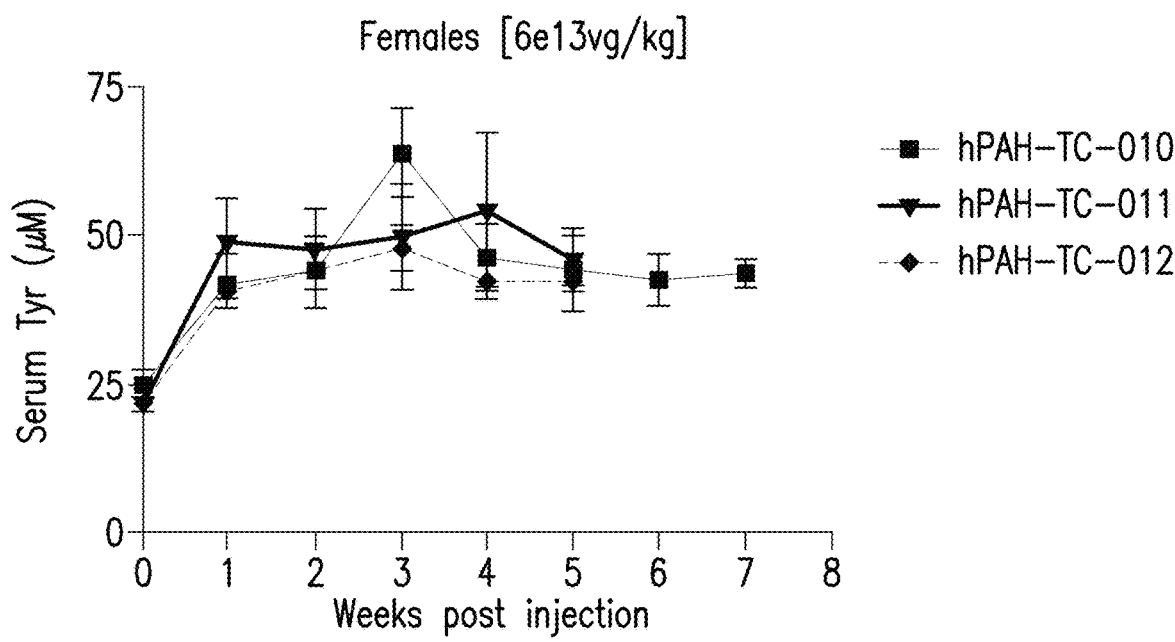
Figure 6I:
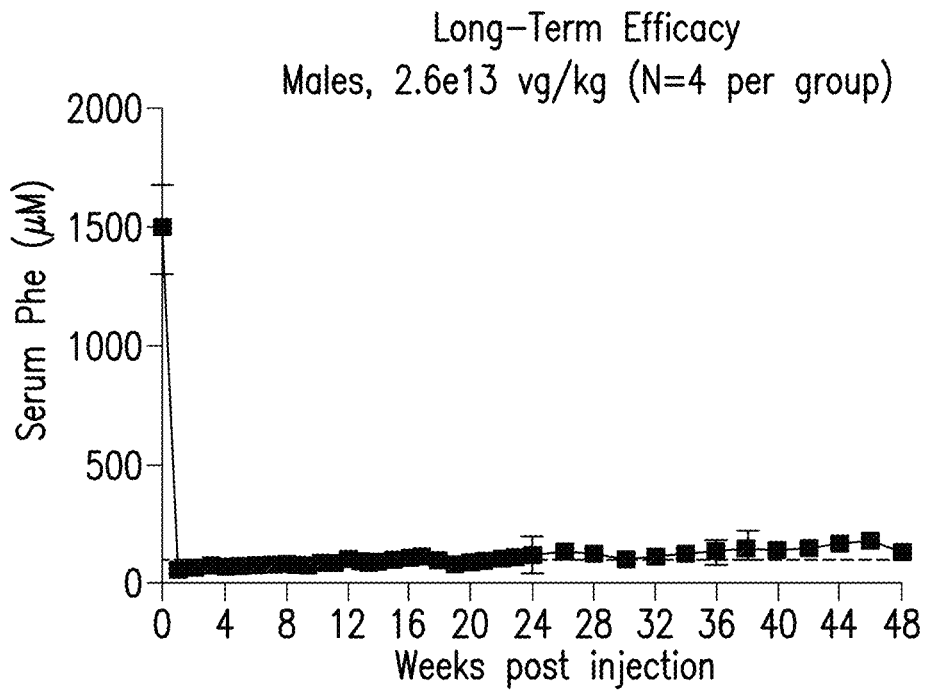
FIGS. 6I-6J are graphs showing the long-term efficacy on levels of phenylalanine in the serum of male (FIG. 6I) or female (FIG. 6J) mice administered the indicated doses of the pHMI-hPAH-TC-025 vector.
Figure 6J:
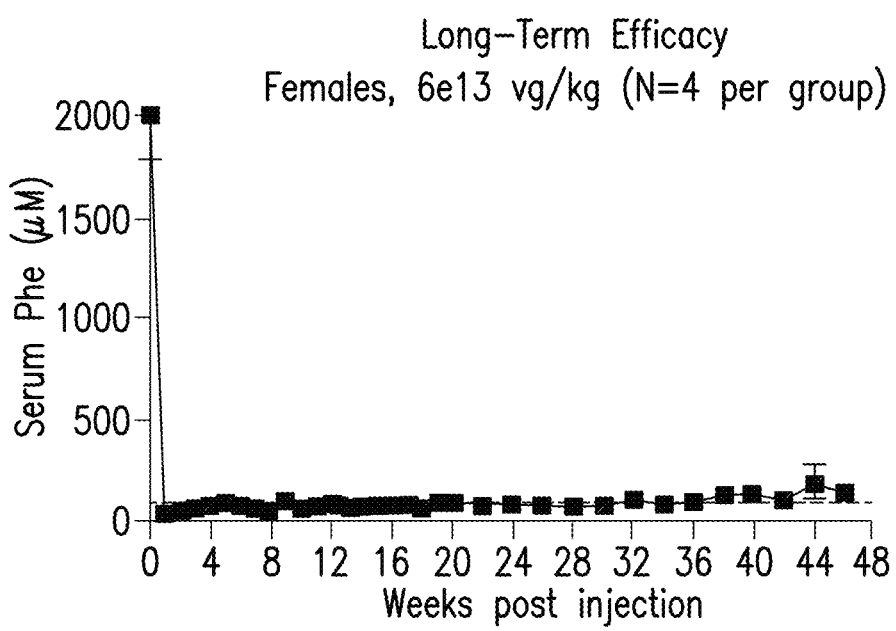
Figure 7A:
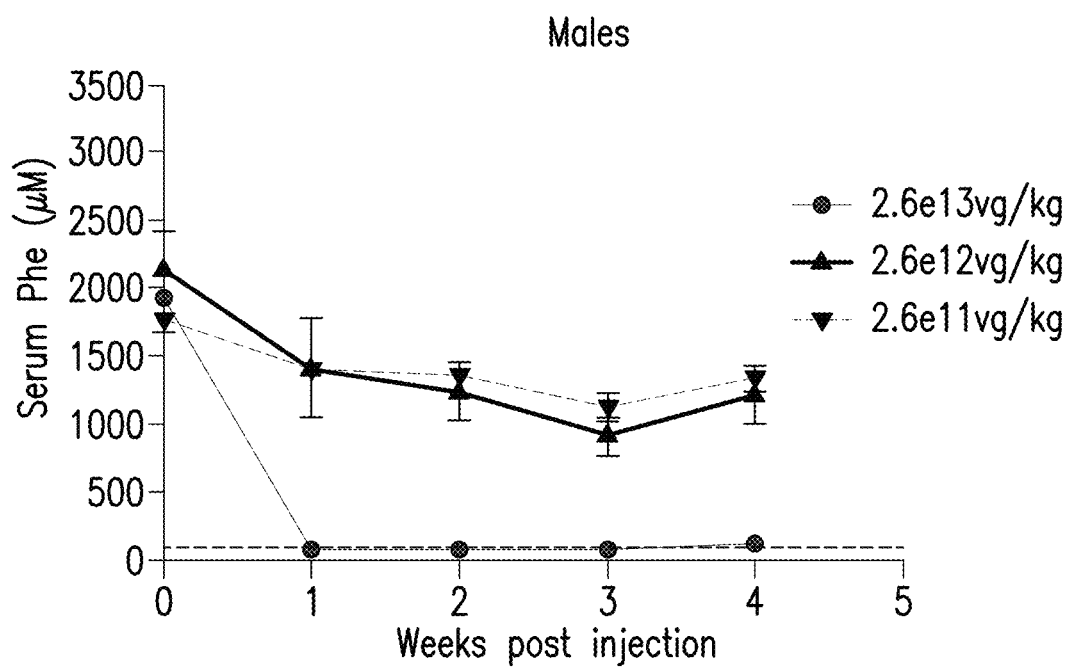
FIGS. 7A-7D are graphs showing the levels of phenylalanine (FIGS. 7A and 7C) or tyrosine (FIGS. 7B and 7D) in the serum of male (FIGS. 7A and 7B) or female (FIGS. 7C and 7D) mice administered with the indicated doses of the pHMI-hPAH-TC-025 vector.
Figure 7B:
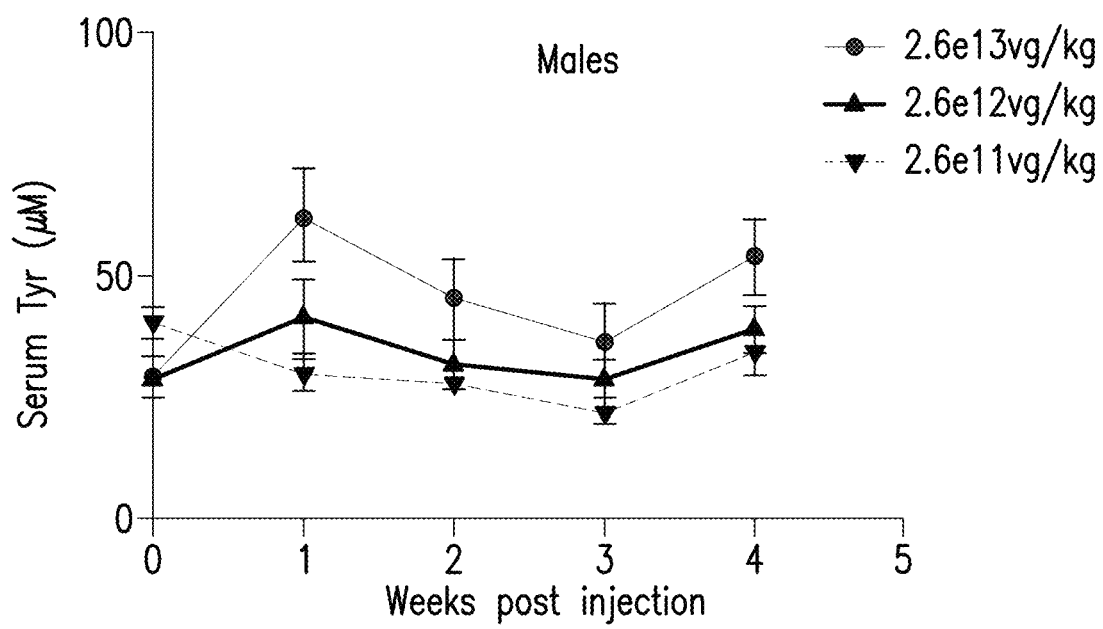
Figure 7C:
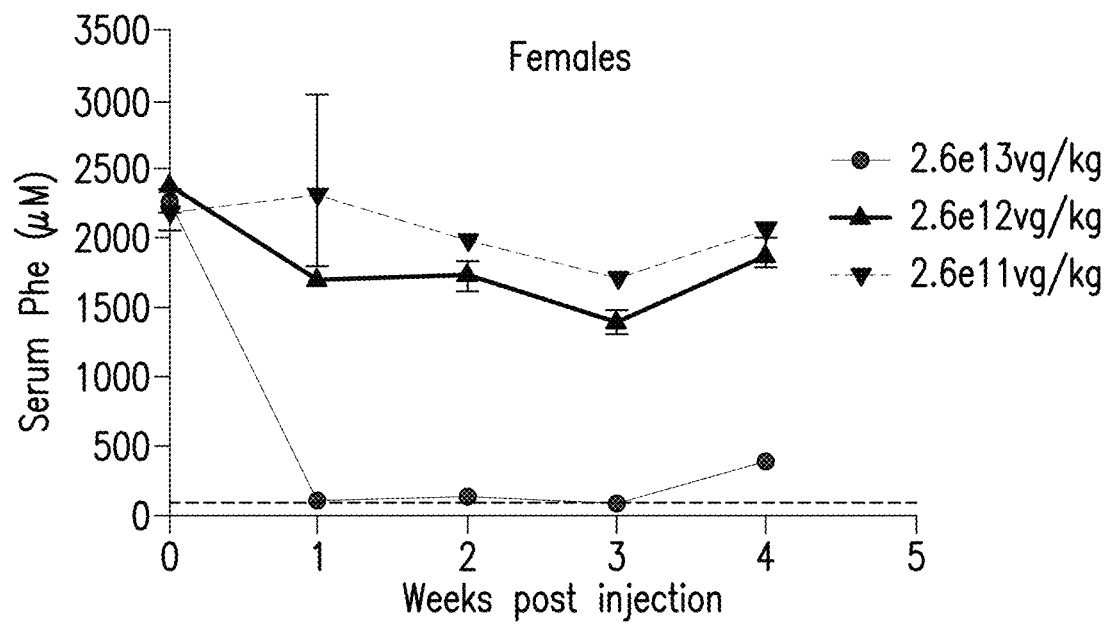
Figure 7D:
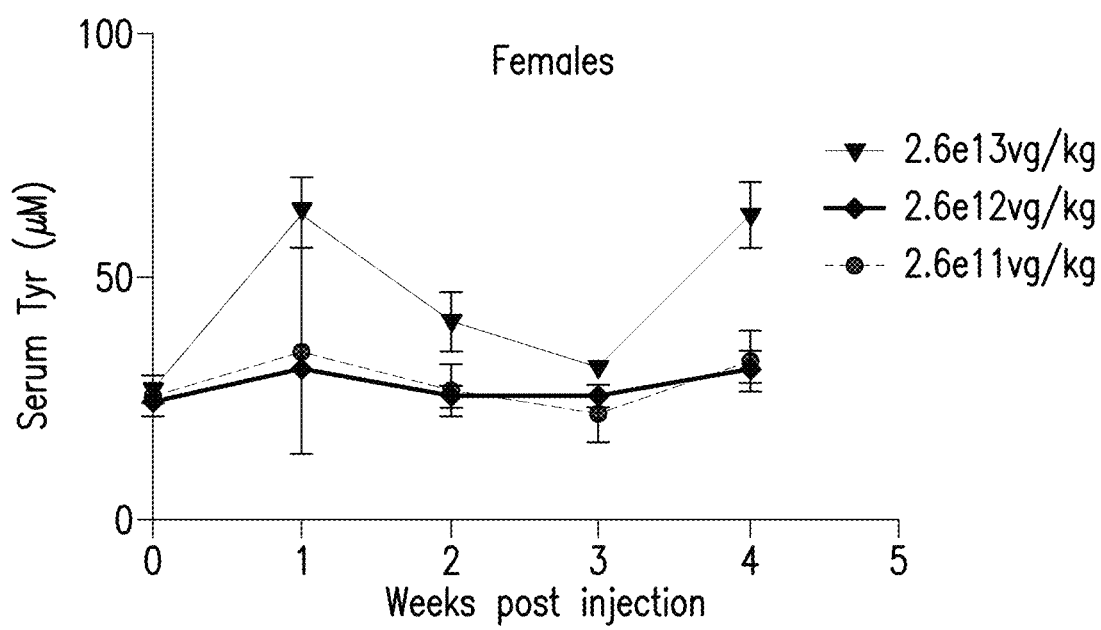

To examine the long-term efficacy of pHMI-hPAH-TC-025 in reversing the phenotype caused by PAH gene deficiency, a single dose of 2.6×10$^{13}$ vector genomes per kg of body weight was administered to male mice, or a single dose of 6×10$^{13}$ vector genomes per kg of body weight was administered to female mice. As shown in FIGS. 6I and 6J, the administration of the pHMI-hPAH-TC-025 vector led to significant reduction of Phe levels within one week. This reduction persisted for at least 48 weeks in male mice, and at least 46 weeks in female mice. Additionally, within two weeks post administration of the AAV, the coat color of the mice administered with pHMI-hPAH-TC-004 changed from brown to black. An increase of PAH mRNA was observed by ddPCR in the liver samples of these mice collected 4 weeks post injection relative to the mice not administered with AAV vectors. An increase of the PAH enzymatic activity was also detected in liver samples by mass spectrometry.

The efficacy of different doses of the pHMI-hPAH-TC-025 vector was further assessed. A single dose of 2.6×10$^{11}$, 2.6×10$^{12}$, or 2.6×10$^{13}$ vector genomes per kg of body weight was administered to male and female mice, and the serum levels of Phe and Tyr were measured. As shown in FIGS. 7A-7D, the dose of 2.6×10$^{13}$ vector genomes per kg of body weight reduced the Phe levels and increased the Tyr levels more significantly than the two lower doses, and maintained complete reduction of serum Phe levels during the time examined in both male and female subjects.

Example 3: Additional Human PAH Transfer Vectors

This example provides human PAH transfer vectors pHMI-hPAH-TC-009, pHMI-hPAH-TC-013, and pHMI-hPAH-TC-017 for expression of human PAH in a human or mouse cell. Vector maps are shown in FIGS. 8A, 8B, and 8C, respectively.

a) pHMI-hPAH-TC-009

PAH transfer vector pHMI-hPAH-TC-009, as shown in FIG. 8A, comprises 5' to 3' the following genetic elements: a 5' ITR element, a CMV enhancer, a CBA promoter, a rabbit β-globin element, a human PAH coding sequence, a polyadenylation sequence, and a 3' ITR element. The sequences of these elements are set forth in Table 6. This vector is capable of expressing a human PAH protein in a cell (e.g., a human cell or a mouse cell) to which the vector is transduced.

TABLE 6

Genetic elements in human PAH transfer vector pHMI-hPAH-TC-009

| Genetic Element | SEQ ID NO |
|---|---|
| 5' ITR element | 18 |
| CMV enhancer | 58 |
| CBA promoter | 59 |
| Rabbit β-globin element | 60 |
| codon-altered human PAH coding sequence | 25 |
| Polyadenylation sequence | 45 |
| 3' ITR element | 19 |
| Transfer genome (from CMV to polyadenylation sequence) | 61 |
| Transfer genome (from 5' ITR to 3' ITR) | 62 | b) pHMI-hPAH-TC-013

PAH transfer vector pHMI-hPAH-TC-013, as shown in FIG. 8B, comprises 5' to 3' the following genetic elements: a 5' ITR element, a CASI promoter region (comprising a CMV enhancer, a CASI promoter, and a ubiquitin C enhancer element (hUBC exon)), a human PAH coding sequence, a polyadenylation sequence, and a 3' ITR element. The sequences of these elements are set forth in Table 7. This vector is capable of expressing a human PAH protein in a cell (e.g., a human cell or a mouse cell) to which the vector is transduced.

TABLE 7

Genetic elements in human PAH transfer vector pHMI-hPAH-TC-013

| Genetic Element | SEQ ID NO |
|---|---|
| 5' ITR element | 18 |
| CAST promoter region | 63 |
| Human PAH coding sequence | 25 |
| Polyadenylation sequence | 45 |
| 3' ITR element | 19 |
| Transfer genome (from promoter region to polyadenylation sequence) | 64 |
| Transfer genome (from 5' ITR to 3' ITR) | 65 | f) pHMI-hPAH-TC-017

PAH transfer vector pHMI-hPAH-TC-017, as shown in FIG. 8C, comprises 5' to 3' the following genetic elements: a 5' ITR element, an hAAT promoter region (comprising an ABMP enhancer (an enhancer region adjacent to a gene on chromosome 9 that expresses highly in liver, 5' to the ATG), a TTR enhancer, an hAAT promoter, and an MVM intron), a human PAH coding sequence, a polyadenylation sequence, and a 3' ITR element. The sequences of these elements are set forth in Table 8. This vector is capable of expressing a human PAH protein in a cell (e.g., a human cell or a mouse cell) to which the vector is transduced.

TABLE 8

Genetic elements in human PAH transfer vector pHMI-hPAH-TC-017

| Genetic Element | SEQ ID NO |
|---|---|
| 5' ITR element | 18 |
| hAAT promoter region | 66 |
| Human PAH coding sequence | 25 |
| Polyadenylation sequence | 45 |
| 3' ITR element | 19 |
| Transfer genome (from promoter region to polyadenylation sequence) | 67 |
| Transfer genome (from 5' ITR to 3' ITR) | 68 |

Figure 9A:
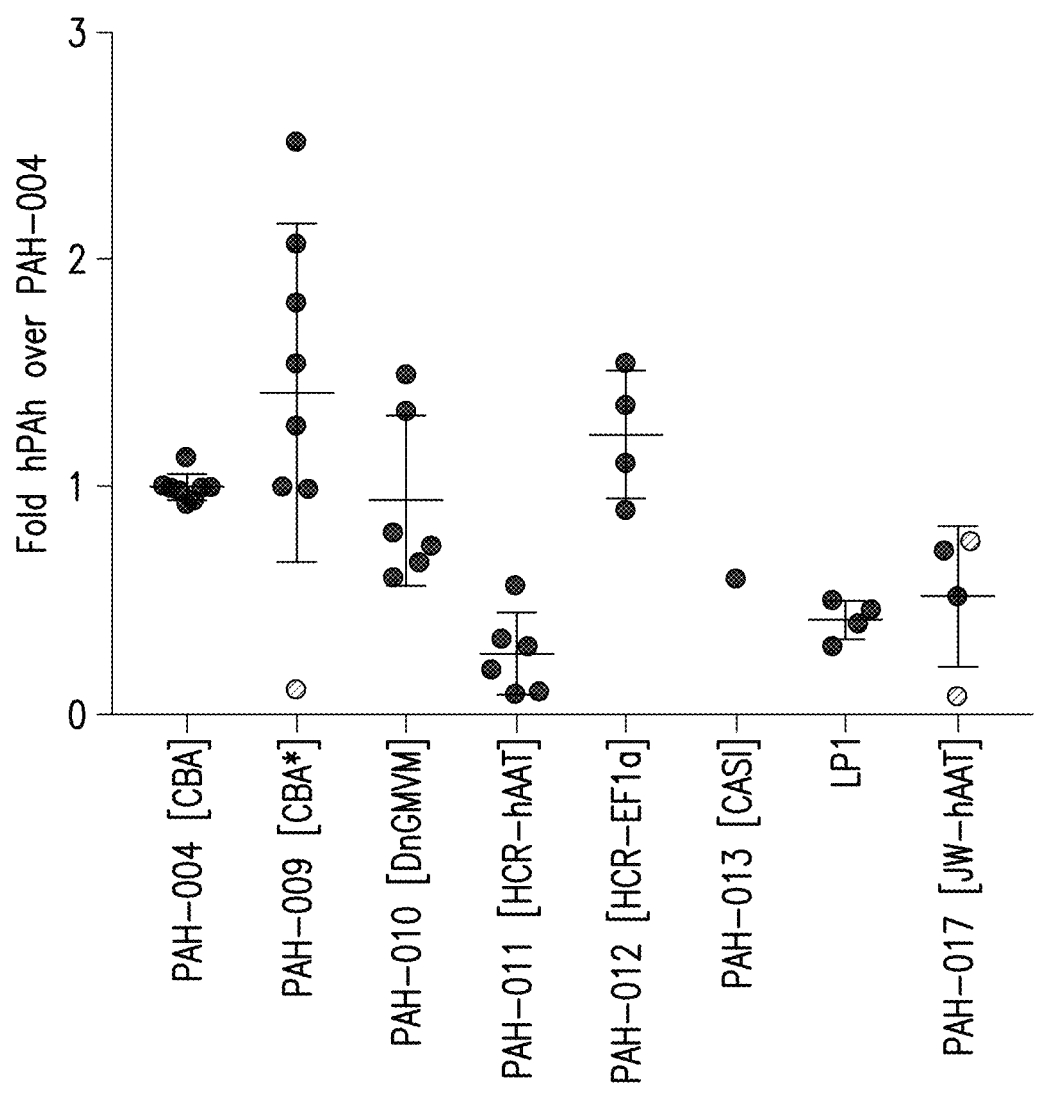
FIG. 9A-9B depict the quantification of Western blots of human PAH expression, from the indicated AAV vectors, in Huh7 cells (FIG. 9A) and HEK293 cells (FIG. 9B).
Figure 9B:
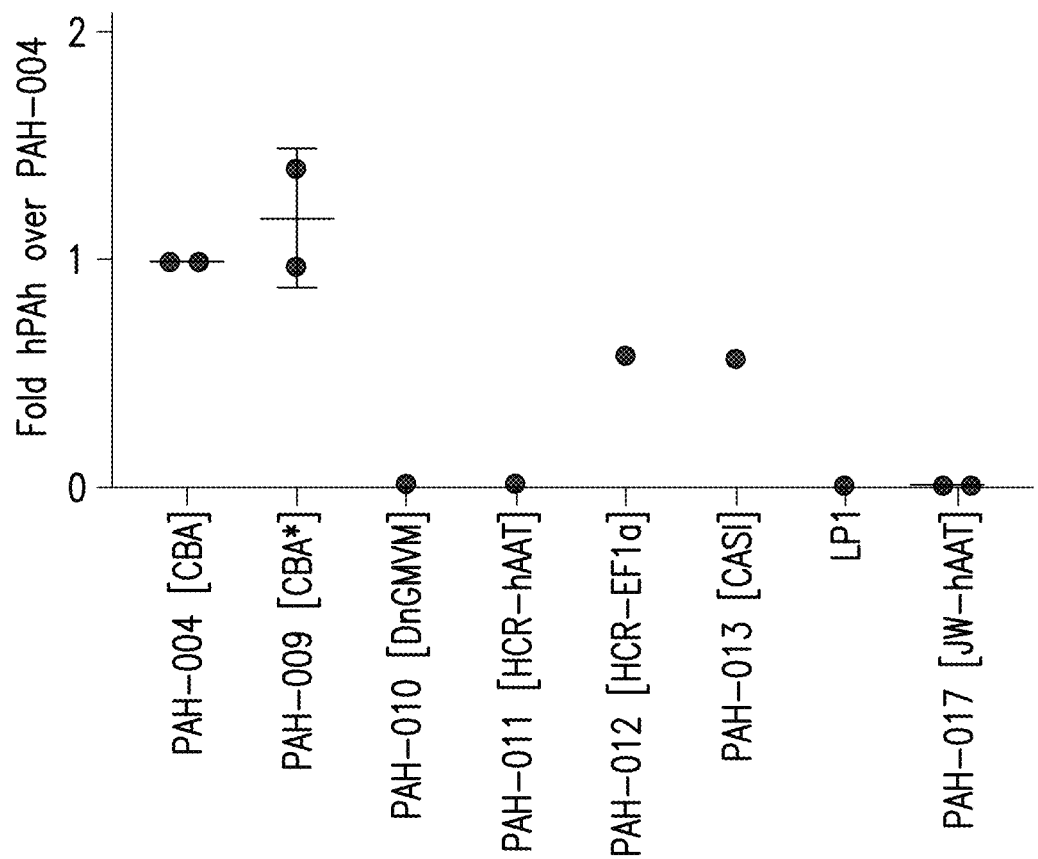

The vectors described in this example were tested for expression in two different cell lines. $5 \times 10^5$ HEK293 cells (kidney; non-liver) and $5 \times 10^5$ Huh7 cells (liver) were transfected with 1 ug each of the following vectors: pHMI-hPAH-TC-004 (PAH-004); pHMI-hPAH-TC-009 (PAH-009); pHMI-hPAH-TC-010 (PAH-010); pHMI-hPAH-TC-011 (PAH-011); pHMI-hPAH-TC-012 (PAH-012); pHMI-hPAH-TC-013 (PAH-013); pHMI-hPAH-TC-025 (LP1); pHMI-hPAH-TC-017 (PAH-017). Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was used as a loading control. PAH expression levels of all vectors were normalized to pHMI-hPAH-TC-004 expression level; data was collected from multiple independent transfections and plotted in FIG. 9. FIG. 9A shows the normalized PAH expression level of the indicated vectors in Huh7 cells. FIG. 9B shows the normalized PAH expression level of the indicated vectors in HEK293 cells.

Figure 10A:
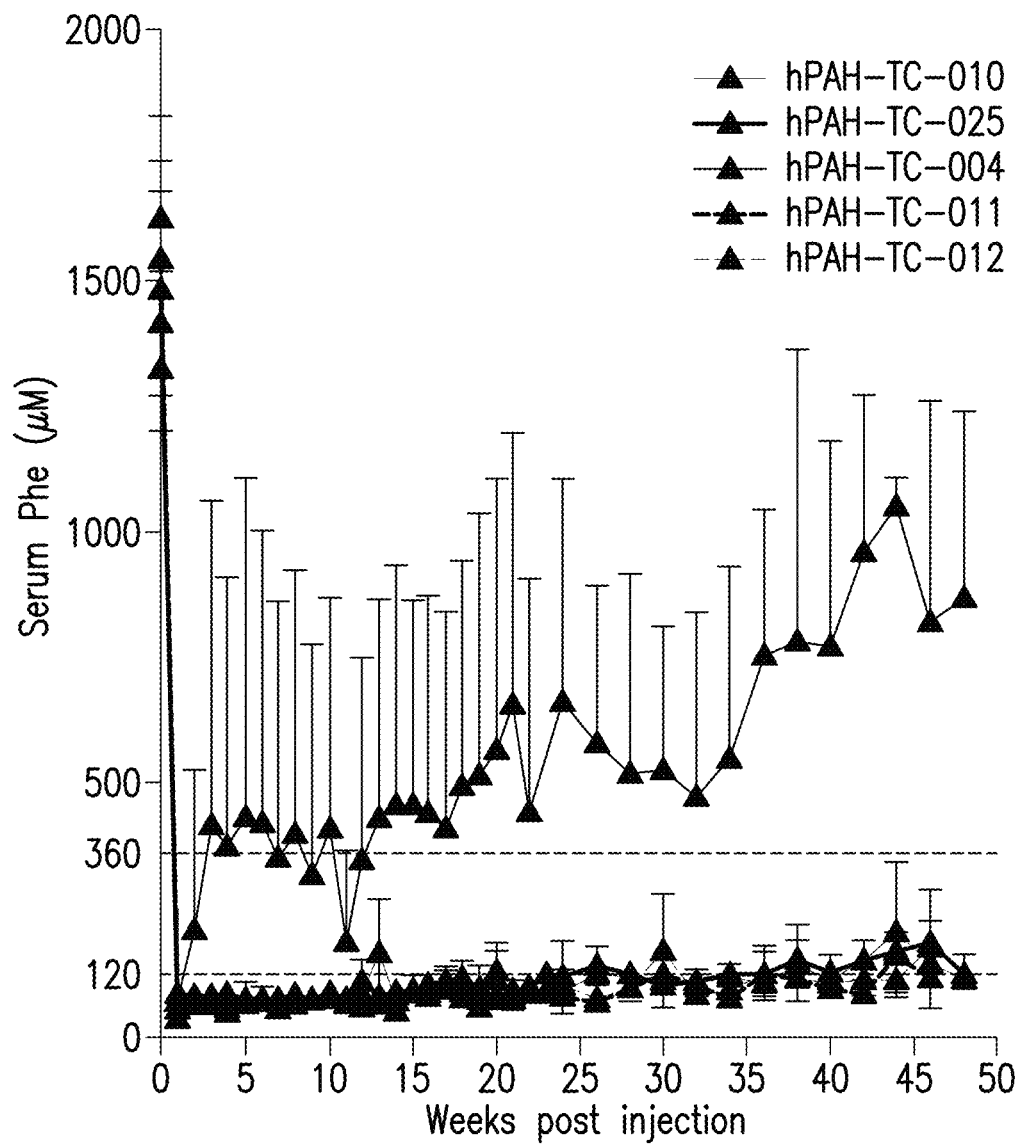
FIG. 10A-10C are graphs showing serum phenylalanine levels in mice that have been administered the indicated AAV vectors.
Figure 10B:
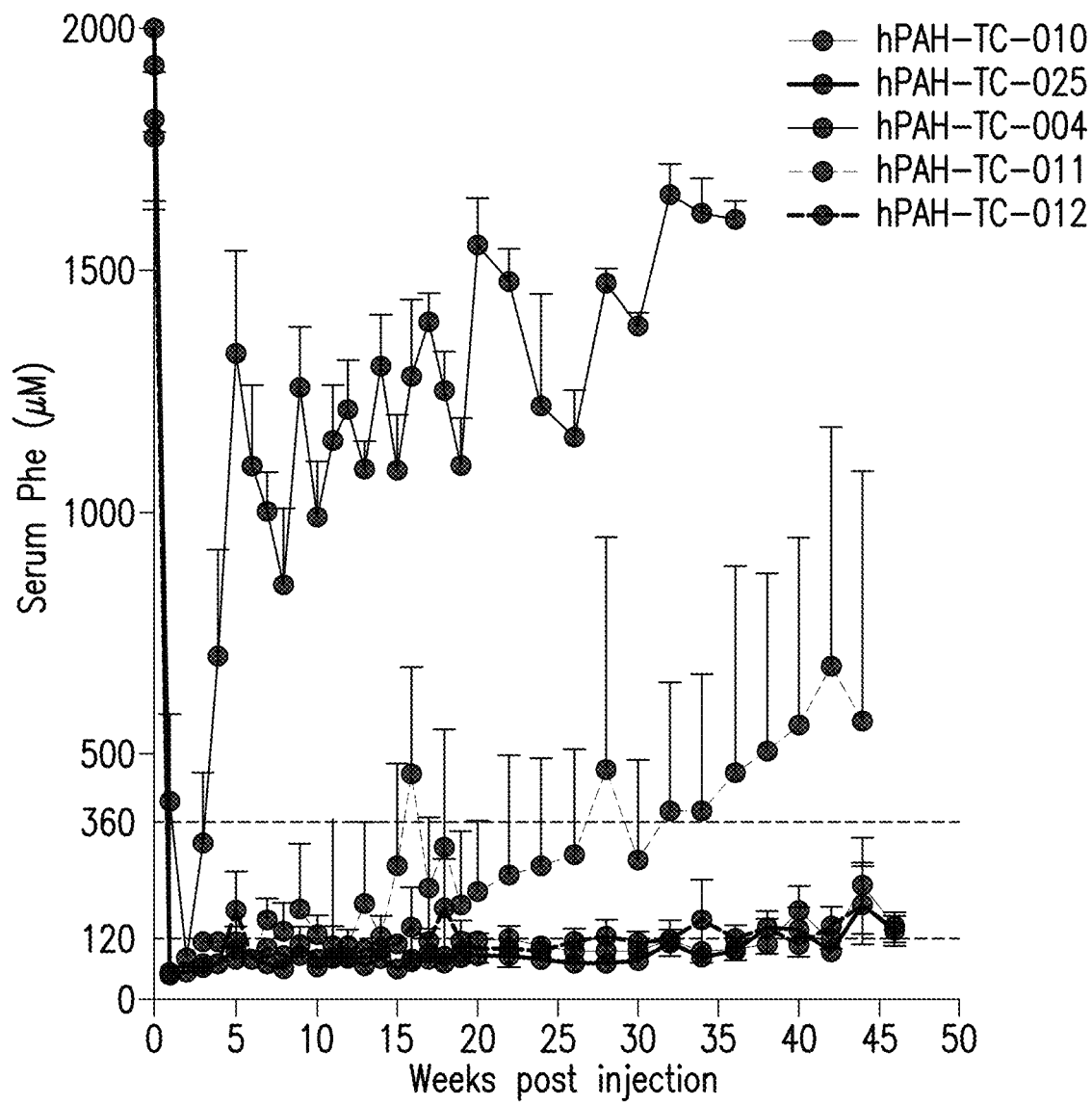
Figure 10C:
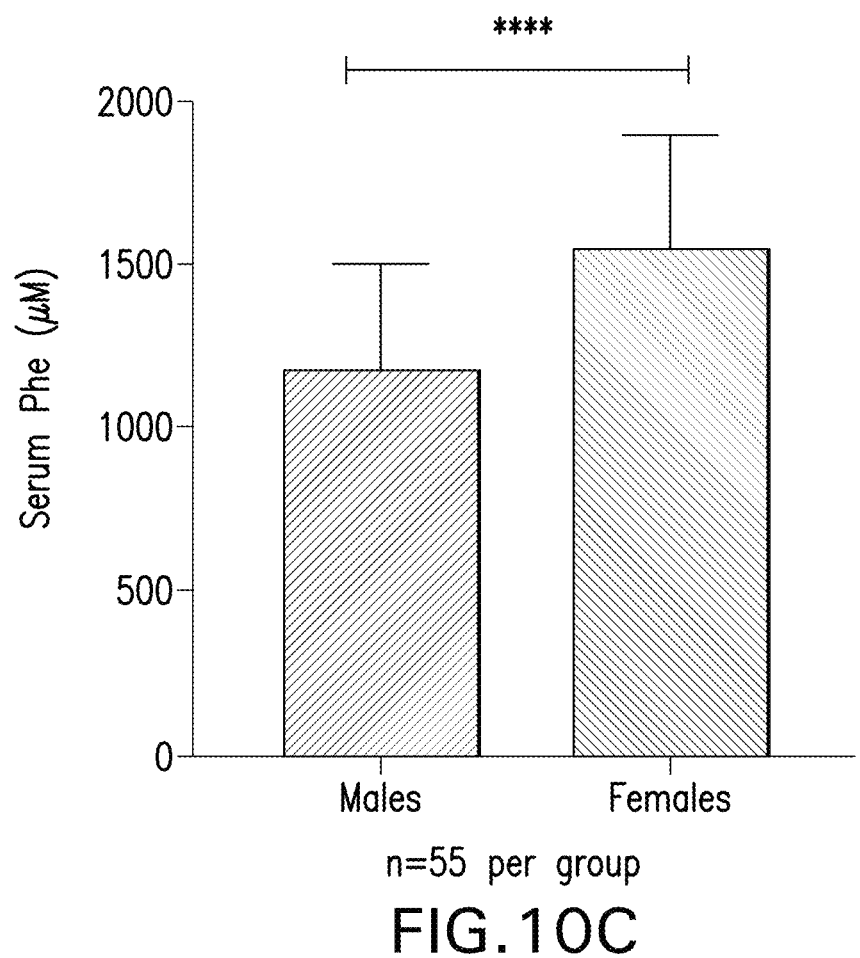
Figure 11A:
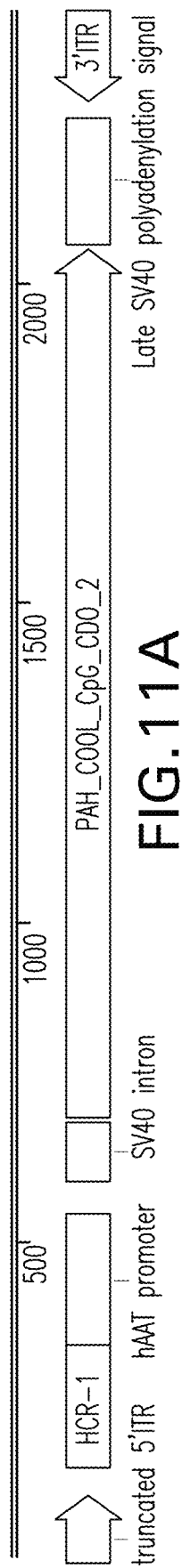
FIGS. 11A, 11B, 11C, 11D, 11E, and 11F are vector maps of pHMI-hPAH-TC-018, pHMI-hPAH-TC-019, pHMI-hPAH-TC-020, pHMI-hPAH-TC-021, pHMI-hPAH-TC-022, and pHMI-hPAH-TC-023 vectors, respectively.
Figure 11B:
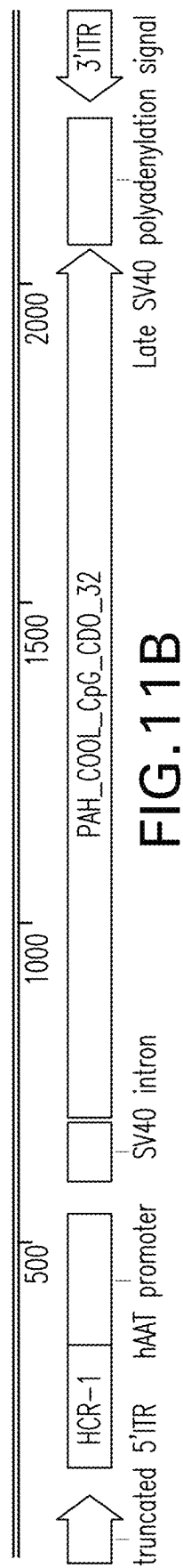
Figure 11C:
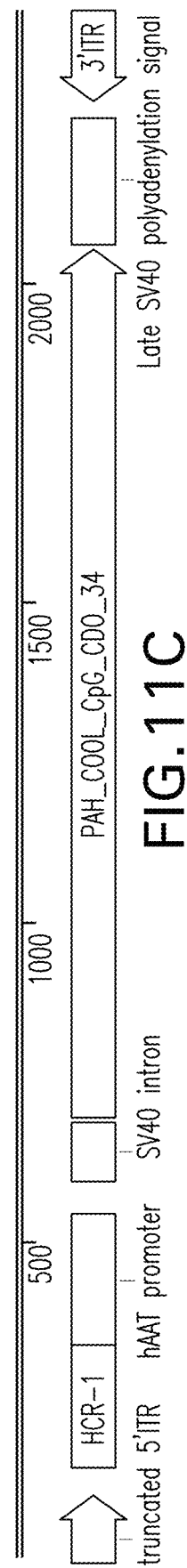
Figure 11D:
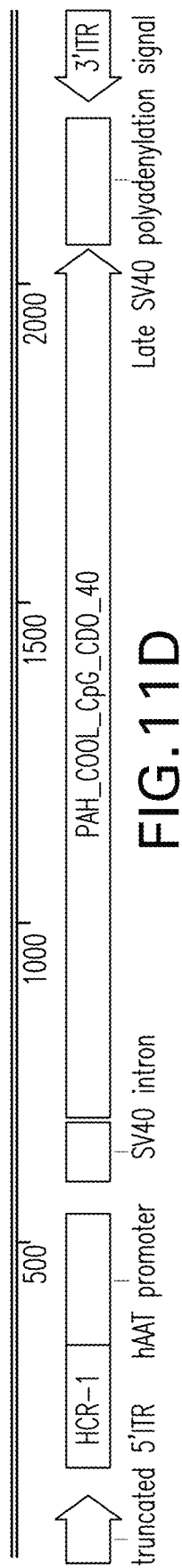
Figure 11E:
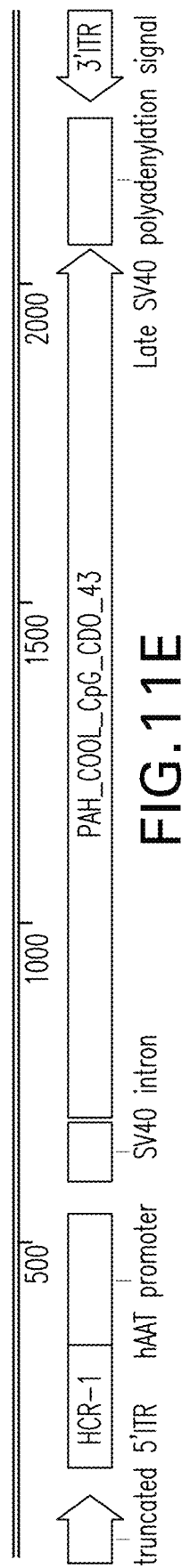
Figure 11F:
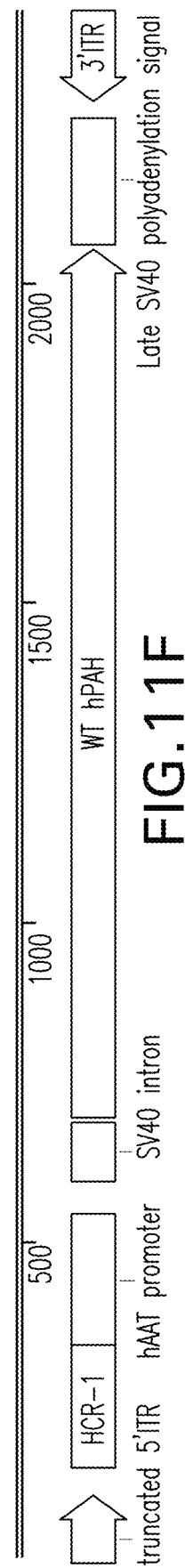

FIGS. 10A and 10B are graphs showing the serum phenylalanine levels over time of male and female homozygous $Pah^{-/-}$ $PAH^{enu2}$ mice respectively. Male and female mice were dosed at 2e13 vg/kg and 6e13 vg/kg respectively with pHMI-hPAH-TC-010 (hPAH-TC-010), pHMI-hPAH-TC-025 (hPAH-TC-025), pHMI-hPAH-TC-004 (hPAH-TC-004), pHMI-hPAH-TC-011 (hPAH-TC-011), or pHMI-hPAH-TC-012 (hPAH-TC-012) vectors packaged in AAVHSC15 capsid. Serum samples were collected weekly then biweekly after the administration. Serum phenylalanine concentrations were assessed by LC-MS/MS. FIG. 10C is a graph showing the average baseline serum phenylalanine level for the male and female homozygous $Pah^{-/-}$ $PAH^{enu2}$ mice in the study. The data represents a total of 55 mice per group.

As shown in FIG. 10, the administration of certain vectors led to significant reduction of Phe levels within one week of administration, and this reduction persisted for at least 45 weeks. FIG. 10 demonstrates that some of the PAH transfer vectors effectively reversed the phenotype caused by PAH gene deficiency in a mouse model. The mouse model, AAV packaging and formulation, and methods for examining gene transfer efficiency were identical to those described in Example 2 herein. The sizes of the AAV vectors were as follows: pHMI-hPAH-TC-010 (hPAH-TC-010): 2391 bp; pHMI-hPAH-TC-025 (hPAH-TC-025): 2351 bp; pHMI-hPAH-TC-004 (hPAH-TC-004): 3781 bp; pHMI-hPAH-TC-011 (hPAH-TC-011): 3158 bp; and pHMI-hPAH-TC-012 (hPAH-TC-012): 3799 bp.

Example 4: Additional Human PAH Transfer Vectors

This example examines the effect of PAH gene CpG content on PAH protein expression, using the PAH transfer vectors pHMI-hPAH-TC-018, pHMI-hPAH-TC-019, pHMI-hPAH-TC-020, pHMI-hPAH-TC-021, pHMI-hPAH-TC-022, and pHMI-hPAH-TC-023. Vector maps are shown in FIGS. 11A, 11B, 11C, 11D, 11E, and 11F, respectively. These PAH transfer vectors comprise the sequences and elements set forth in Table 9.

TABLE 9

Genetic elements in PAH transfer vectors

| Genetic Element | pHMI-hPAH-TC-XXX Vector SEQ ID NO | | | | | |
|---|---|---|---|---|---|---|
| | -018 | -019 | -020 | -021 | -022 | -023 |
| 5' ITR element | 26 | 26 | 26 | 26 | 26 | 26 |
| HCR1 | 29 | 29 | 29 | 29 | 29 | 29 |
| hAAT promoter | 30 | 30 | 30 | 30 | 30 | 30 |
| SV40 intron | 31 | 31 | 31 | 31 | 31 | 31 |
| PAH coding sequence | 69 | 70 | 71 | 72 | 73 | 24 |
| Late SV40 polyadenylation sequence | 45 | 45 | 45 | 45 | 45 | 45 |
| 3' ITR element | 27 | 27 | 27 | 27 | 27 | 27 |
| Transfer genome (from HCR1 to polyadenylation sequence) | 74 | 76 | 78 | 80 | 82 | 84 |
| Transfer genome (from 5' ITR to 3' ITR) | 75 | 77 | 79 | 81 | 83 | 85 |

The vectors described in this example were tested for expression in HEK293 cells but under the control of a CBA promoter. 5×10$^5$ HEK293 cells were transfected with 1 ug each of the following vectors: pHMI-hPAH-TC-004 (PAH-TC-004); pHMI-hPAH-TC-009 (PAH-TC-009); pHMI-hPAH-TC-018 (PAH-TC-018); pHMI-hPAH-TC-019 (PAH-TC-019); pHMI-hPAH-TC-020 (PAH-TC-020); pHMI-hPAH-TC-021 (PAH-TC-021); pHMI-hPAH-TC-022 (PAH-TC-022); pHMI-hPAH-TC-023 (PAH-TC-023). Lysate of the cells was collected 48 hours after transfection. The expression of human PAH was detected by Western blotting with an anti-PAH antibody (Sigma HPA031642). The amount of GAPDH protein as detected by an anti-GAPDH antibody (Millipore MAB 374) was used as a loading control. PAH expression levels of all vectors were normalized to pHMI-hPAH-TC-004 expression level; data was plotted in FIG. 12.

Figure 13:
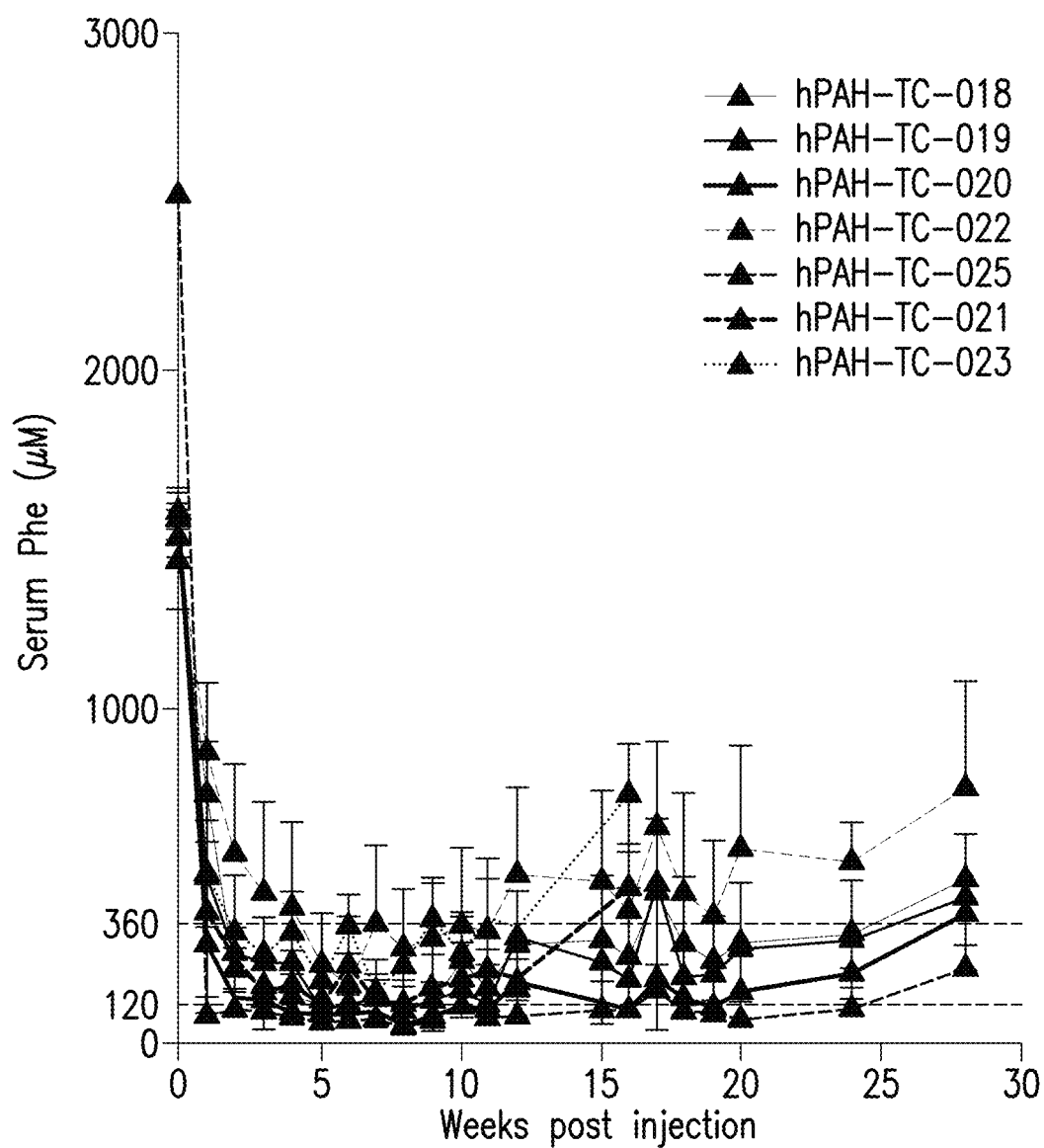
FIG. 13 is a graph showing serum phenylalanine levels over time of male Pah$^{-/-}$ PAH$^{enu2}$ mice administered the indicated AAV vectors.

FIG. 13 is a graph showing the serum phenylalanine levels over time of male homozygous Pah$^{-/-}$ PAH$^{enu2}$ mice. Male mice have been dosed at 2e13 vg/kg with pHMI-hPAH-TC-018 (hPAH-TC-018); pHMI-hPAH-TC-019 (hPAH-TC-019); pHMI-hPAH-TC-020 (hPAH-TC-020); pHMI-hPAH-TC-021 (hPAH-TC-021); pHMI-hPAH-TC-022 (hPAH-TC-022); pHMI-hPAH-TC-023 (hPAH-TC-023); and pHMI-hPAH-TC-025 (hPAH-TC-025) vectors packaged in AAVHSC15 capsid. Serum samples were collected weekly after the administration. Serum phenylalanine concentration was assessed by LC-MS/MS.

As shown in FIG. 13, the administration of certain vectors led to significant reduction of Phe levels within one week of administration, and this reduction persisted for at least 25 weeks. The mouse model, AAV packaging and formulation, and methods for examining gene transfer efficiency were identical to those previously described in Example 2 herein. The CpG content of the vectors were as follows: pHMI-hPAH-TC-018 (hPAH-TC-018): 2; pHMI-hPAH-TC-019 (hPAH-TC-019): 7; pHMI-hPAH-TC-020 (hPAH-TC-020): 22; pHMI-hPAH-TC-021 (hPAH-TC-021): 10; pHMI-hPAH-TC-022 (hPAH-TC-022): 7; pHMI-hPAH-TC-023 (hPAH-TC-023): 23; and pHMI-hPAH-TC-025 (hPAH-TC-025): 60.

Example 5: Alternative ITR Human PAH Transfer Vectors

This example provides human PAH transfer vectors pHMI-01004 and pHMI-01008 for expression of human PAH in a human or mouse cell. Vector maps are shown in FIGS. 14A and 14B, respectively. These PAH transfer vectors comprise the sequences and elements set forth in Table 10.

TABLE 10

Genetic elements in PAH transfer vectors pHMI-01004 and pHMI-01008

| Genetic Element | pHMI-01004 SEQ ID NO | pHMI-01008 SEQ ID NO |
|---|---|---|
| 5' ITR element | 26 | 26 |
| HCR1 | 29 | 29 |
| hAAT promoter region | 30 | 30 |
| SV40 intron | 31 | 31 |
| Human PAH coding sequence | 25 | 25 |
| Polyadenylation sequence | 43 | 43 |
| 3' ITR element | 27 | 57 |
| Transfer genome (from HCR1 to polyadenylation sequence) | 86 | 89 |
| Transfer genome (from 5' ITR to 3' ITR) | 87 | 90 |
| Full sequence of transfer vector | 88 | 91 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A replication-defective adeno-associated virus (AAV) comprising:
   (a) an AAV capsid comprising: a capsid protein comprising the amino acid sequence of amino acids 203-736 of SEQ ID NO: 16; a capsid protein comprising the amino acid sequence of amino acids 138-736 of SEQ ID NO: 16; and/or a capsid protein comprising the amino acid sequence of amino acids 1-736 of SEQ ID NO: 16; and
   (b) a transfer genome comprising a silently altered PAH coding sequence, wherein the silently altered PAH coding sequence comprises the nucleotide sequence set forth in SEQ ID NO: 25.

2. The AAV of claim 1, wherein the transfer genome further comprises a transcriptional regulatory element operably linked to the silently altered PAH coding sequence.

3. The AAV of claim 2, wherein the transcriptional regulatory element mediates transcription in a cell of the liver, the kidney, the brain, the pituitary gland, the adrenal gland, the pancreas, the urinary bladder, the gallbladder, the colon, the small intestine, or the breast.

4. The AAV of claim 2, wherein the transcriptional regulatory element comprises a human hepatic control region 1 (HCR1) comprising the nucleotide sequence set forth in SEQ ID NO: 29.

5. The AAV of claim 2, wherein the transcriptional regulatory element comprises a human α1-antitrypsin (hAAT) promoter comprising the nucleotide sequence set forth in SEQ ID NO: 30.

6. The AAV of claim 2, wherein the transcriptional regulatory element comprises an SV40 intron comprising the nucleotide sequence set forth in SEQ ID NO: 31.

7. The AAV of claim 2, wherein the transcriptional regulatory element comprises the nucleotide sequence set forth in SEQ ID NO: 32.

8. The AAV of claim 1, wherein the transfer genome further comprises an SV40 polyadenylation sequence 3' to the PAH coding sequence, wherein the SV40 polyadenylation sequence comprises the nucleotide sequence set forth in SEQ ID NO: 43.

9. The AAV of claim 1, wherein the transfer genome further comprises a 5' inverted terminal repeat (5' ITR) nucleotide sequence 5' of the genome, and a 3' inverted terminal repeat (3' ITR) nucleotide sequence 3' of the genome.

10. The AAV of claim 9, wherein the 5' ITR nucleotide sequence has at least 95% sequence identity to SEQ ID NO: 26, and the 3' ITR nucleotide sequence has at least 95% sequence identity to SEQ ID NO: 27.

11. The AAV of claim 1, wherein the transfer genome comprises the nucleotide sequence set forth in SEQ ID NO: 47.

12. The AAV of claim 1, wherein the transfer genome comprises the nucleotide sequence set forth in SEQ ID NO: 52.

13. An AAV comprising:
   (a) an AAV capsid comprising: a capsid protein comprising the amino acid sequence of amino acids 203-736 of SEQ ID NO: 16; a capsid protein comprising the amino acid sequence of amino acids 138-736 of SEQ ID NO: 16; and a capsid protein comprising the amino acid sequence of amino acids 1-736 of SEQ ID NO: 16; and
   (b) a transfer genome comprising the nucleotide sequence set forth in SEQ ID NO: 47.

14. An AAV comprising:
   (a) an AAV capsid comprising: a capsid protein comprising the amino acid sequence of amino acids 203-736 of SEQ ID NO: 16; a capsid protein comprising the amino acid sequence of amino acids 138-736 of SEQ ID NO: 16; and a capsid protein comprising the amino acid sequence of amino acids 1-736 of SEQ ID NO: 16; and (b) a transfer genome comprising the nucleotide sequence set forth in SEQ ID NO: 52.

15. An AAV comprising:
(a) an AAV capsid comprising: a capsid protein comprising an amino acid sequence consisting of the amino acid sequence of amino acids 203-736 of SEQ ID NO: 16; a capsid protein comprising an amino acid sequence consisting of amino acids 138-736 of SEQ ID NO: 16; and a capsid protein comprising an amino acid sequence consisting of amino acids 1-736 of SEQ ID NO: 16; and
(b) a transfer genome comprising the nucleotide sequence set forth in SEQ ID NO: 47.

16. An AAV comprising:
(a) an AAV capsid comprising: a capsid protein comprising an amino acid sequence consisting of the amino acid sequence of amino acids 203-736 of SEQ ID NO: 16; a capsid protein comprising an amino acid sequence consisting of amino acids 138-736 of SEQ ID NO: 16; and a capsid protein comprising an amino acid sequence consisting of amino acids 1-736 of SEQ ID NO: 16; and
(b) a transfer genome comprising the nucleotide sequence set forth in SEQ ID NO: 52.

17. A polynucleotide comprising the nucleotide sequence set forth in SEQ ID NO: 25.

18. A polynucleotide comprising the nucleotide sequence set forth in SEQ ID NO: 47.

19. A polynucleotide comprising the nucleotide sequence set forth in SEQ ID NO: 52.

20. A pharmaceutical composition comprising the AAV of claim 1.
21. A pharmaceutical composition comprising the AAV of claim 2.
22. A pharmaceutical composition comprising the AAV of claim 3.
23. A pharmaceutical composition comprising the AAV of claim 4.
24. A pharmaceutical composition comprising the AAV of claim 5.
25. A pharmaceutical composition comprising the AAV of claim 6.
26. A pharmaceutical composition comprising the AAV of claim 7.
27. A pharmaceutical composition comprising the AAV of claim 8.
28. A pharmaceutical composition comprising the AAV of claim 9.
29. A pharmaceutical composition comprising the AAV of claim 10.
30. A pharmaceutical composition comprising the AAV of claim 11.
31. A pharmaceutical composition comprising the AAV of claim 12.
32. A pharmaceutical composition comprising the AAV of claim 13.
33. A pharmaceutical composition comprising the AAV of claim 14.
34. A pharmaceutical composition comprising the AAV of claim 15.
35. A pharmaceutical composition comprising the AAV of claim 16.

* * * * *